(12) United States Patent
Chekler et al.

(10) Patent No.: US 10,328,082 B2
(45) Date of Patent: *Jun. 25, 2019

(54) METHODS OF USE AND COMBINATIONS

(71) Applicant: Pfizer Inc., New York, NY (US)

(72) Inventors: Eugene Lvovich Piatnitski Chekler, Concord, MA (US); Adam Matthew Gilbert, Guilford, CT (US); Rayomand Jal Unwalla, Bedford, MA (US); Patrick Robert Verhoest, Newton, MA (US); James Thomas Anderson, Shaker Heights, OH (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/314,574

(22) PCT Filed: May 18, 2015

(86) PCT No.: PCT/IB2015/053658
§ 371 (c)(1),
(2) Date: Nov. 29, 2016

(87) PCT Pub. No.: WO2015/181676
PCT Pub. Date: Dec. 3, 2015

(65) Prior Publication Data
US 2017/0252352 A1 Sep. 7, 2017

Related U.S. Application Data

(60) Provisional application No. 62/149,881, filed on Apr. 20, 2015, provisional application No. 62/004,979, filed on May 30, 2014.

(51) Int. Cl.
*A61K 31/549* (2006.01)
*A61K 45/06* (2006.01)
(Continued)

(52) U.S. Cl.
CPC .......... *A61K 31/549* (2013.01); *A61K 31/277* (2013.01); *A61K 31/397* (2013.01);
(Continued)

(58) Field of Classification Search
USPC .................................................. 514/210.21
See application file for complete search history.

(56) References Cited

U.S. PATENT DOCUMENTS 3,239,345 A 3/1966 Hodge et al.
3,422,021 A 1/1969 Roy
(Continued)

FOREIGN PATENT DOCUMENTS

EP 0089139 A2 9/1983
EP 0144230 B1 8/1990
(Continued)

OTHER PUBLICATIONS

Almarsson et al, "Crystal engineering of the composition of pharmaceutical phases. Do pharmaceutical co-crystals represent a new path to improved medicines?", ChemComm 17:1889-1896 (2004).
(Continued)

*Primary Examiner* — Marcos L Sznaidman
(74) *Attorney, Agent, or Firm* — Feng Shao

(57) ABSTRACT

The present invention relates to a compound of Formula 1, 2 or 3:

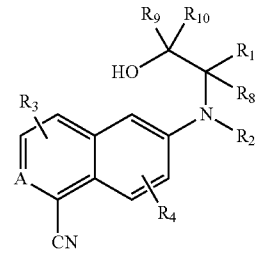

Formula 1

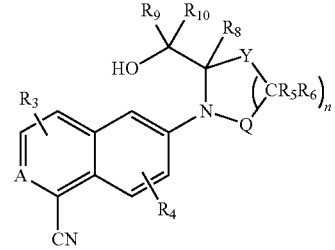

Formula 2

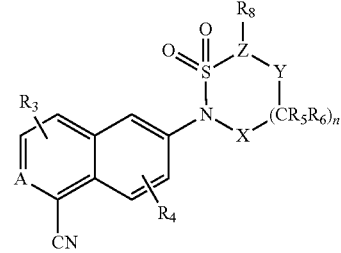

Formula 3 wherein A is N or —$CR_0$—, where $R_0$ is hydrogen, $C_1$-$C_6$ linear or branched chain alkyl, etc., Z is —$CR_e$—, or, —N—, where $R_e$ is hydrogen, $C_1$-$C_6$ linear or branched chain alkyl, etc.; $R_1$ is hydrogen, $C_1$-$C_6$ linear or branched chain alkyl, etc.; $R_2$ are independently hydrogen or $C_1$-$C_6$ linear or branched chain alkyl; $R_3$ and $R_4$ are independently hydrogen, $C_1$-$C_6$ linear or branched chain alkyl, etc.; $R_5$ and $R_6$ are independently hydrogen or $C_1$-$C_6$ linear or branched chain alkyl, etc.; $R_8$ is hydrogen, $C_1$-$C_6$ linear or branched chain alkyl, etc.; $R_9$ and $R_{10}$ are independently hydrogen or (Continued)

$C_1$-$C_6$ linear or branched chain alkyl, etc.; Q is —CO—, —$(CH_2)_q$—, —$(CHR_s)_q$—, or —$(CR_sR_t)_q$—, where $R_s$ and $R_t$ are independently $C_1$-$C_6$ linear or branched chain alkyl, aryl, alkylaryl, heteroaryl or alkylheteroaryl; where q is 0, 1, 2, or 3; and, where n is 0, 1, 2, 3, 4 or 5; or, a pharmaceutically acceptable salt thereof, for the treatment of certain diseases, particularly those affected or mediated by the androgen receptor; to combinations comprising such compounds with a second pharmaceutically active ingredient; to compositions containing such combinations; and to such combinations for the treatment of various diseases, particularly, those affected or mediated by the androgen receptor.

6 Claims, 4 Drawing Sheets

(51) Int. Cl.
| | | |
|---|---|---|
| *A61K 31/277* | (2006.01) | |
| *A61K 31/397* | (2006.01) | |
| *A61K 31/402* | (2006.01) | |
| *A61K 31/433* | (2006.01) | |
| *A61K 31/451* | (2006.01) | |
| *A61K 31/472* | (2006.01) | |
| *A61K 31/4725* | (2006.01) | |

(52) U.S. Cl.
CPC .......... *A61K 31/402* (2013.01); *A61K 31/433* (2013.01); *A61K 31/451* (2013.01); *A61K 31/472* (2013.01); *A61K 31/4725* (2013.01); *A61K 45/06* (2013.01)

(56) References Cited

U.S. PATENT DOCUMENTS

| | | | |
|---|---|---|---|
| 3,865,801 | A | 2/1975 | Chiba et al. |
| 4,036,979 | A | 7/1977 | Asato |
| 4,342,767 | A | 8/1982 | Albers-Schonberg et al. |
| 4,346,227 | A | 8/1982 | Terahara et al. |
| 4,444,784 | A | 4/1984 | Hoffman et al. |
| 4,729,999 | A | 3/1988 | Young |
| 4,761,406 | A | 8/1988 | Flora et al. |
| 4,876,248 | A | 10/1989 | Breliere et al. |
| 4,894,373 | A | 1/1990 | Young |
| 4,922,007 | A | 5/1990 | Kieczykowski et al. |
| 4,927,814 | A | 5/1990 | Gall et al. |
| 4,970,335 | A | 11/1990 | Isomura et al. |
| 5,019,651 | A | 5/1991 | Kieczykowski |
| 5,177,080 | A | 1/1993 | Angerbauer et al. |
| 5,204,350 | A | 4/1993 | Egbertson et al. |
| 5,206,235 | A | 4/1993 | Fisher et al. |
| 5,217,994 | A | 6/1993 | Egbertson et al. |
| 5,260,440 | A | 11/1993 | Hirai et al. |
| 5,273,995 | A | 12/1993 | Roth |
| 5,283,241 | A | 2/1994 | Bochis et al. |
| 5,284,841 | A | 2/1994 | Chu et al. |
| 5,310,737 | A | 5/1994 | Fisher et al. |
| 5,317,017 | A | 5/1994 | Ok et al. |
| 5,354,772 | A | 10/1994 | Kathawala |
| 5,374,721 | A | 12/1994 | Schoen et al. |
| 5,393,763 | A | 2/1995 | Black et al. |
| 5,430,144 | A | 7/1995 | Schoen et al. |
| 5,434,261 | A | 7/1995 | Schoen et al. |
| 5,438,136 | A | 8/1995 | Devita et al. |
| 5,441,868 | A | 8/1995 | Lin |
| 5,492,916 | A | 2/1996 | Morriello et al. |
| 5,494,919 | A | 2/1996 | Morriello et al. |
| 5,494,920 | A | 2/1996 | Glasebrook et al. |
| 5,501,969 | A | 3/1996 | Hastings et al. |
| 5,510,517 | A | 4/1996 | Dauer et al. |
| 5,536,716 | A | 7/1996 | Chen et al. |
| 5,547,933 | A | 8/1996 | Lin |
| 5,612,359 | A | 3/1997 | Murugesan |
| 5,618,698 | A | 4/1997 | Lin |
| 5,621,080 | A | 4/1997 | Lin |
| 5,639,754 | A | 6/1997 | Heeres et al. |
| 5,648,491 | A | 7/1997 | Dauer et al. |
| 5,710,159 | A | 1/1998 | Voss et al. |
| 5,723,480 | A | 3/1998 | Gante et al. |
| 5,736,357 | A | 4/1998 | Brömme et al. |
| 5,741,796 | A | 4/1998 | Hartman et al. |
| 5,760,028 | A | 6/1998 | Jadhav et al. |
| 5,767,115 | A | 6/1998 | Rosenblum et al. |
| 5,773,644 | A | 6/1998 | Chen et al. |
| 5,773,646 | A | 6/1998 | Chandrakumar et al. |
| 5,780,426 | A | 7/1998 | Palladino et al. |
| 5,846,966 | A | 12/1998 | Rosenblum et al. |
| 5,852,210 | A | 12/1998 | Chen et al. |
| 5,919,792 | A | 7/1999 | Duggan et al. |
| 5,925,655 | A | 7/1999 | Duggan et al. |
| 5,929,120 | A | 7/1999 | Hartman et al. |
| 5,952,281 | A | 9/1999 | Mondin et al. |
| 5,952,341 | A | 9/1999 | Duggan et al. |
| 5,981,546 | A | 11/1999 | Duggan et al. |
| 5,990,145 | A | 11/1999 | Wehner et al. |
| 6,005,117 | A | 12/1999 | Wehner et al. |
| 6,008,213 | A | 12/1999 | Bondinell et al. |
| 6,011,045 | A | 1/2000 | Wehner et al. |
| 6,017,925 | A | 1/2000 | Duggan |
| 6,017,926 | A | 1/2000 | Askew et al. |
| 6,028,223 | A | 2/2000 | Ruminski et al. |
| 6,040,311 | A | 3/2000 | Duggan et al. |
| 6,043,265 | A | 3/2000 | Murugesan et al. |
| 6,048,861 | A | 4/2000 | Askew et al. |
| 6,066,648 | A | 5/2000 | Duggan et al. |
| 6,069,158 | A | 5/2000 | Miller et al. |
| 6,106,864 | A | 8/2000 | Dolan et al. |
| 6,159,964 | A | 12/2000 | Ali et al. |
| 6,218,387 | B1 | 4/2001 | Wehner et al. |
| 6,218,415 | B1 | 4/2001 | Wehner et al. |
| 6,221,907 | B1 | 4/2001 | Bernard et al. |
| 6,277,845 | B1 | 8/2001 | Carniato et al. |
| 6,326,403 | B1 | 12/2001 | Holzemann et al. |
| 6,339,082 | B1 | 1/2002 | Carniato et al. |
| 6,399,620 | B1 | 6/2002 | Wehner et al. |
| 6,420,558 | B1 | 7/2002 | Ishikawa et al. |
| 6,559,144 | B2 | 5/2003 | Diefenbach et al. |
| 6,964,973 | B2 | 11/2005 | Zhi et al. |
| 9,328,104 | B2 * | 5/2016 | Anderson ............ C07C 255/58 |
| 2017/0073338 | A1 * | 3/2017 | Chekler ............... C07D 417/04 |

FOREIGN PATENT DOCUMENTS

| | | |
|---|---|---|
| EP | 0513974 B1 | 9/1996 |
| EP | 0668351 B1 | 9/1999 |
| EP | 0928793 B1 | 5/2002 |
| EP | 0928790 B1 | 3/2003 |
| WO | 89/07110 A1 | 8/1989 |
| WO | 89/07111 A1 | 8/1989 |
| WO | 91/05867 A1 | 5/1991 |
| WO | 91/11172 A1 | 8/1991 |
| WO | 93/04081 A1 | 3/1993 |
| WO | 94/02518 A1 | 2/1994 |
| WO | 94/07486 A1 | 4/1994 |
| WO | 94/11012 A1 | 5/1994 |
| WO | 94/13696 A1 | 6/1994 |
| WO | 94/19367 A1 | 9/1994 |
| WO | 95/03289 A1 | 2/1995 |
| WO | 95/03290 A1 | 2/1995 |
| WO | 95/09633 A1 | 4/1995 |
| WO | 95/11029 A1 | 4/1995 |
| WO | 95/12598 A1 | 5/1995 |
| WO | 95/13069 A1 | 5/1995 |
| WO | 95/14666 A1 | 6/1995 |
| WO | 95/16675 A1 | 6/1995 |
| WO | 95/16692 A1 | 6/1995 |
| WO | 95/17422 A1 | 6/1995 |
| WO | 95/17423 A1 | 6/1995 |
| WO | 95/32710 A1 | 12/1995 |
| WO | 95/34311 A1 | 12/1995 |
| WO | 96/00574 A1 | 1/1996 |

(56) References Cited

FOREIGN PATENT DOCUMENTS

| | | |
|---|---|---|
| WO | 96/00730 A1 | 1/1996 |
| WO | 96/02530 A1 | 2/1996 |
| WO | 96/06087 A1 | 2/1996 |
| WO | 96/13523 A1 | 5/1996 |
| WO | 96/26190 A1 | 8/1996 |
| WO | 97/01540 A1 | 1/1997 |
| WO | 97/23200 A1 | 7/1997 |
| WO | 97/24119 A1 | 7/1997 |
| WO | 97/24122 A1 | 7/1997 |
| WO | 97/24124 A1 | 7/1997 |
| WO | 97/37655 A1 | 10/1997 |
| WO | 98/00395 A1 | 1/1998 |
| WO | 98/08840 A1 | 3/1998 |
| WO | 98/14192 A1 | 4/1998 |
| WO | 98/15278 A1 | 4/1998 |
| WO | 98/18460 A1 | 5/1998 |
| WO | 98/18461 A1 | 5/1998 |
| WO | 98/23608 A1 | 6/1998 |
| WO | 98/25892 A1 | 6/1998 |
| WO | 98/30542 A1 | 7/1998 |
| WO | 98/31359 A1 | 7/1998 |
| WO | 98/33798 A1 | 8/1998 |
| WO | 98/55148 A1 | 12/1998 |
| WO | 99/05107 A1 | 2/1999 |
| WO | 99/06049 A1 | 2/1999 |
| WO | 99/11626 A1 | 3/1999 |
| WO | 99/15170 A1 | 4/1999 |
| WO | 99/15178 A1 | 4/1999 |
| WO | 99/15508 A1 | 4/1999 |
| WO | 99/26945 A1 | 6/1999 |
| WO | 99/30709 A1 | 6/1999 |
| WO | 99/30713 A1 | 6/1999 |
| WO | 99/31099 A1 | 6/1999 |
| WO | 99/32457 A1 | 7/1999 |
| WO | 99/33798 A1 | 7/1999 |
| WO | 99/37621 A1 | 7/1999 |
| WO | 99/44994 A1 | 9/1999 |
| WO | 99/45927 A1 | 9/1999 |
| WO | 99/52879 A1 | 10/1999 |
| WO | 99/52896 A1 | 10/1999 |
| WO | 99/59992 A1 | 11/1999 |
| WO | 00/00486 A1 | 1/2000 |
| WO | 00/06169 A1 | 2/2000 |
| WO | 00/09503 A1 | 2/2000 |
| WO | 00/35298 A1 | 6/2000 |
| WO | 01/17562 A1 | 3/2001 |
| WO | 01/49288 A1 | 7/2001 |
| WO | 01/77073 A1 | 10/2001 |
| WO | 2004/110978 A1 | 12/2004 |
| WO | 2009082437 | 7/2009 |
| WO | 2014/087298 A1 | 6/2014 |

OTHER PUBLICATIONS

Aspenberg et al, "The Bone Morphogenetic Proteins Antagonist Noggin Inhibits Membranous Ossification", Journal of Bone and Mineral Research 16(3):497-500 (2001).

Badger et al, "Pharmacological Profile of SB 203580, a Selective Inhibitor of Cytokine Suppressive Binding Protein/P38 Kinase, in Animal Models of Arthritis, Bone Resorption, Endotoxin Shock and Immune Function", The Journal of Pharmacology and Experimental Therapeutics 279(3):1453-1461 (1996).

Brunkow et al, "Bone Dysplasia Sclerosteosis Results from Loss of the SOST Gene Product, a Novel Cysteine Knot-Containing Protein", The American Journal of Human Genetics 68(3):577-589 (2001).

Edwards et al, "Nonsteroidal Androgen Receptor Agonists Based on 4-(Trifluoromethyl)-2H-Pyrano[3,2-g] Quinolin-2-One", Bioorganic & Medicinal Chemistry Letters 9:1003-1008 (1999).

Farina et al, "Selective Inhibitors of the osteoclast vacuolar proton ATPase as novel bone antiresorptive agents", Drug Discovery Today 4(4):163-172 (1999).

Freitag et al, "A synthesis of novel N-sulfonylated β-amino acids", Tetrahedron 62(8):1799-1805 (2006).

Goldstein et al, "A pharmacological review of selective oestrogen receptor modulators", Human Reproduction Update 6(3):212-224 (2000).

Gowen et al, "Antagonizing the parathyroid calcium receptor stimulates parathyroid hormone secretion and bone formation in osteopenic rats", The Journal of Clinical Investigation 105(11):1595-1604 (2000).

Haleblian, "Characterization of Habits and Crystalline Modification of Solids and Their Pharmaceutical Applications", Journal of Pharmaceutical Sciences 64(8):1269-1288 (1975).

Hamann et al, "Discovery of a Potent, Orally Active, Nonsteroidal Androgen Receptor Agonist: 4-Ethyl-1,2,3,4-tetrahyrdo-6-(trifluoromethyl)-8-pyridono[5,6-g]-quinoline (LG121071)", Journal of Medicinal Chemistry 42(2):210-212 (1999).

Keenan et al, "Discovery of Potent Nonpeptide Vitronectin Receptor (av$\beta$3) Antagonists". Journal of Medicinal Chemistry 40(15):2289-2292 (1997).

Keenan et al, "Benzimidazole Derivatives as Arginine Mimetics in 1,4-Benzodiazepine Nonpeptide Vitronectin Receptor (av$\beta$3) Antagonists", Bioorganic & Medicinal Chemistry Letters 8:3165-3170 (1998).

Keenan et al, "Discovery of an Imidazopyridine—Containing 1,4-Benzodiazepine Nonpeptide Vitronectin Receptor (av$\beta$3) Antagonist with Efficacy in a Restenosis Model", Bioorganic & Medicinal Chemistry Letters 8:3171-3176 (1998).

Liang et al, "Fast-dissolving intraoral drug delivery systems", Expert Opinion on Therapeutic Patents 11(6):981-986 (2001).

Lufkin et al, "The Role of Selective Estrogen Receptor Modulators in the Prevention and Treatment of Osteoporosis", Rheumatic Disease Clinics of North America 27(1):163-185 (2001).

Massague et al, "Controlling TGF-$\beta$ signaling", Genes & Development 14:627-644 (2000).

Miller et al, "Chapter 15: Targeting the Estrogen Receptor with SERMs", Section IV. Immunology, Endocrinology and Metabolic Diseases; Annual Reports in Medicinal Chemistry 36:149-158 (2001).

Nakagawa et al, "Vascular endothelial growth factor (VEGF) directly enhances osteoclastic bone resorption and survival of mature osteoclasts", FEBS Letters 473:161-164 (2000).

Ok et al, "Structure-Activity Relationships of the Non-Peptidyl Growth Hormone Secretagogue L-692,429", Bioorganic & Medicinal Chemistry Letters 4(22):2709-2714 (1994).

Patchett et al, "Design and biological activities of L-163,191 (MK-0677): A potent, orally active growth hormone secretagogue", Proc. Natl. Acad. Sci. USA 92:7001-7005 (1995).

PCT International Search Report and Written Opinion for PCT/IB2015/053658 dated Sep. 21, 2015.

Quimby et al, "Tetrasodium Carbonyldiphosphonate. Synthesis, Reactions, and Spectral Properties", Journal of Organic Chemistry 32:4111-4114 (1967).

Shiraki et al, "Vitamin K2 (Menatetrenone) Effectively Prevents Fractures and Sustains Lumbar Bone Mineral Density in Osteoporosis", Journal of Bone and Mineral Research 15(3):515-521 (2000).

Silverman, "Calcitonin", Rheumatic Disease Clinics of North America 27(1):187-196 (2001).

Smith et al, "A Nonpeptidyl Growth Hormone Secretagogue", Science 260(5114):1640-1643 (1993).

Verma et al, "Current Status of Drug Delivery Technologies and Future Directions", Pharmaceutical Technology On-Line 25(2):1-14 (2001).

Ghiron, Luura J., et al, "Effects of Recombinant Insulin-like Growth Factor-I and Growth Factor Hormone on Bone Turnover in Elderly Women", Journal of Bone and Mineral Research, 1995, pp. 1844-1852, 10(12).

Nagata et al., Design and synthesis of tricyclic tetrahydroquinolines as a new series of nonsteroidal selective and androgen receptor modulators (SARMs); Bioorganic & Medicinal Chemistry Letters, vol. 21(6), pp. 1744-1747 (2011).

Nagata et al., "Tetrahydroquinolines as a novel series of nonsteroidal selective androgen receptor modulators: Structural requirements for better physicochemical and biological properties", Bioorganic & Medicinal Chemistry Letters, vol. 21(21), pp. 6310-6313 (2011).

(56) References Cited

OTHER PUBLICATIONS

Huang et al., "The Structure and Function of Androgen Receptor", Sichuan Journal of Zoology, vol. 27(2), pp. 307-310 (2008).

\* cited by examiner

METHODS OF USE AND COMBINATIONS

FIELD OF THE INVENTION

The present invention relates to the use of selective androgen receptor modulators (SARM), or pharmaceutically acceptable salts thereof, for the treatment and/or prevention of certain diseases or disorders that are related to modulation of the androgen receptor. The present invention also relates to a combination of novel heterocyclic compounds, or pharmaceutically active salts thereof, which are effective as selective androgen receptor modulators (SARM) with one or more further pharmaceutically active compounds, or pharmaceutically active salts thereof. Furthermore, the present invention relates to compositions comprising the combination of active agents and to the use of these combinations of active ingredients to treat diseases or disorders that are related to modulation of the androgen receptor. The present invention also relates to a crystalline form of 6-[(4R)-4-methyl-1,1-dioxido-1,2,6-thiadiazinan-2-yl]isoquinoline-1-carbonitrile, compositions thereof and to processes for the preparation thereof. The invention also relates to a crystalline form of 6-[(4R)-4-methyl-, 1,1-dioxido-1,2,6-thiadiazinan-2-yl]isoquinoline-1-carbonitrile for the treatment of diseases and disorders that are related to the modulation of the androgen receptor.

BACKGROUND OF THE INVENTION

The androgen receptor ("AR") is a ligand-activated transcriptional regulatory protein that mediates induction of male sexual development and function through its activity with endogenous androgens. Androgenic steroids play an important role in many physiologic processes, including the development and maintenance of male sexual characteristics such as muscle and bone mass, prostate growth, spermatogenesis, and the male hair pattern. The endogenous steroidal androgens include testosterone and dihydrotestosterone ("DHT"). Steroidal ligands which bind the AR and act as androgens (e.g. testosterone enanthate) or as antiandrogens (e.g. cyproterone acetate) have been known for many years and are used clinically.

New compounds of the following formulae:

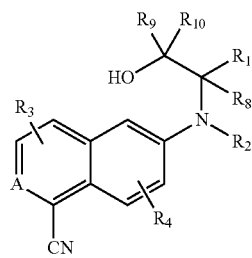

Formula 1

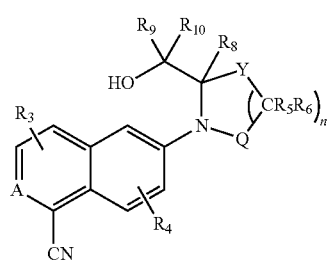

Formula 2

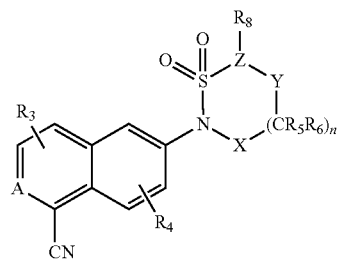

Formula 3 and methods of making the same, are disclosed in co-pending international patent application, PC/IB2013/060381 filed 25 Nov. 2013, and published as WO 2014/087298 on 12 Jun. 2014, assigned to the assignee of the present invention and which is incorporated herein by reference in its entirety. These compounds are known to be active androgen receptor modulators (SARM) and, as such, useful for treating and/or preventing a variety of hormone-related conditions, for example, conditions associated with androgen decline, such as, inter alia, anaemia; anorexia; arthritis; bone disease; musculoskeletal impairment; cachexia; frailty; age-related functional decline in the elderly; growth hormone deficiency; hematopoietic disorders; hormone replacement; loss of muscle strength and/or function; muscular dystrophies; muscle loss following surgery; muscular atrophy; neurodegenerative disease; neuromuscular disease; obesity; osteoporosis; and muscle wasting.

There is an on-going need to provide new therapies for treating and/or preventing a variety of hormone related conditions.

There is an on-going need to provide improved therapies useful for treating and/or preventing a variety of hormone-related conditions, for example, conditions associated with androgen decline, such as, inter alia, anemia; anorexia; arthritis; bone disease; musculoskeletal impairment; cachexia; frailty; age-related functional decline in the elderly; growth hormone deficiency; hematopoietic disorders; hormone replacement; loss of muscle strength and/or function; muscular dystrophies; muscle loss following surgery; muscular atrophy; neurodegenerative diseases; neuromuscular disease; obesity; osteoporosis; and, muscle wasting. Combination therapies as provided herein, compositions thereof, and associated methods of treatment may provide a therapeutic regimen that provides a greater efficacy and/or an improved tolerability to the use of either agent alone.

Identification of new solid forms of a known pharmaceutical active ingredient provide a means of optimising either the physicochemical, stability, manufacturability and/or bioperformance characteristics of the active pharmaceutical ingredient without modifying its chemical structure. Based on a chemical structure, one cannot predict with any degree of certainty whether a compound will crystallise, under what conditions it will crystallise, or the solid state structure of any of those crystalline forms. The specific solid form chosen for drug development can have dramatic influence on the properties of the drug product. The selection of a suitable solid form is partially dictated by yield, rate and quantity of the crystalline structure. In addition, hygroscopicity, stability, solubility and the process profile of the solid form such as compressibility, powder flow and density are important considerations.

As such, there is a need to identify solid forms of compounds known to be active androgen receptor modulators, including 6-[(4R)-4-methyl-1,1-dioxido-1,2,6-thiadiazinan-2-yl]isoquinoline-1-carbonitrile, that exhibit acceptable physicochemical, stability, manufacturability and/or bioperformance properties.

SUMMARY OF THE INVENTION

The present invention relates to a method for treating and/or preventing a disorder or condition in a subject, wherein the disorder or condition is selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy, and stress urinary incontinence comprising administering to said subject an effective amount of a compound of Formula 1, Formula 2 or Formula 3,

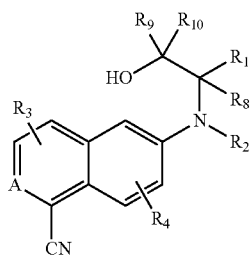

Formula 1

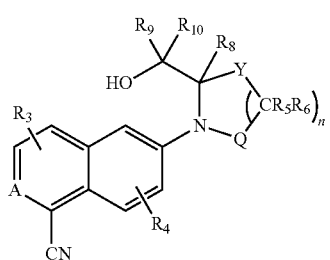

Formula 2

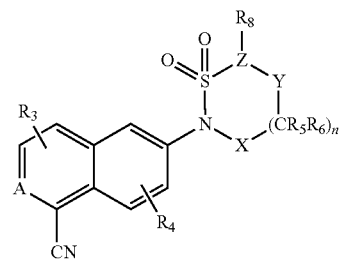

Formula 3 wherein A is N or —$CR_0$—, where $R_0$ is hydrogen, $C_1$-$C_6$ linear or branched chain alkyl, $C_1$-$C_6$ linear or branched chain perfluoroalkyl, aryl, perfluoroaryl, alkylaryl, heteroaryl; or, alkylheteroaryl; X and Y are independently —$CH_2$—, —$CHR_a$—, or, —$CR_aR_b$—, where $R_a$ and $R_b$ are independently $C_1$-$C_6$ linear or branched chain alkyl, aryl, alkylaryl, heteroaryl or, alkylheteroaryl; or, $R_a$ and $R_b$ together form a chain comprising —$(CH_2)_j$—, —$(CHR_c)_j$—, or —$(CR_cR_d)_j$—, where $R_c$ and $R_d$ are independently $C_1$-$C_6$ linear or branched chain alkyl, $C_1$-$C_6$ linear or branched chain perfluoroalkyl, aryl, alkylaryl, heteroaryl or alkylheteroaryl; where j is 2; 3, 4 or 5; Z is —$CR_e$—, or, —N—, where $R_e$ is hydrogen, $C_1$-$C_6$ linear or branched chain alkyl, $C_1$-$C_6$ linear or branched chain perfluoroalkyl, aryl, alkylaryl, heteroaryl or, alkylheteroaryl; $R_1$ is hydrogen, $C_1$-$C_6$ linear or branched chain alkyl, aryl, $C_1$-$C_6$ linear or branched chain perfluoroalkyl, alkylaryl, heteroaryl, alkylheteroaryl, $C_1$-$C_6$ linear or branched chain alkoxylcarbonyl, $C_1$-$C_6$ linear or branched chain alkylamino-carbonylamino, $C_1$-$C_6$ linear or branched chain alkyloxycarbonylamino, $C_1$-$C_6$ linear or branched chain alkylcarbonylamino, or, $C_1$-$C_6$ linear or branched chain alkylaminocarbonyl; $R_2$ are independently hydrogen or $C_1$-$C_6$ linear or branched chain alkyl; $R_3$ and $R_4$ are independently hydrogen, $C_1$-$C_6$ linear or branched chain alkyl, $C_1$-$C_6$ linear or branched chain perfluoroalkyl, $C_1$-$C_6$ linear or branched chain perfluoroalkoxy, halogen, cyano, hydroxyl, amino, carboxy, hydroxyl, aryl, heteroaryl, $C_1$-$C_6$ linear or branched chain alkoxylcarbonyl, $C_1$-$C_6$ linear or branched chain alkylamino-carbonylamino, or, $C_1$-$C_6$ linear or branched chain alkylaminocarbonyl; $R_5$ and $R_6$ are independently hydrogen or $C_1$-$C_6$ linear or branched chain alkyl, $C_1$-$C_6$ linear or branched chain perfluoroalkyl, cyano, hydroxyl, amino, carboxy, hydroxyl, aryl, heteroaryl, or, $R_5$ and $R_6$ together form a chain comprising —$(CH_2)_k$—, —$(CHR_7)_k$—, or —$(CR_{7a}R_{7b})_k$—, where $R_7$, $R_{7a}$, and $R_{7b}$ are independently $C_1$-$C_6$ linear or branched chain alkyl, $C_1$-$C_6$ linear or branched chain perfluoroalkyl, aryl, alkylaryl, heteroaryl or alkylheteroaryl; where k is 2; 3, 4 or 5; $R_8$ is hydrogen, $C_1$-$C_6$ linear or branched chain alkyl, $C_1$-$C_6$ linear or branched chain perfluoroalkyl, aryl, aryl substituted with one, two or three fluorine atoms, perfluoroaryl, alkylaryl, heteroaryl; or, alkylheteroaryl; or, $R_1$ and $R_8$ together form a chain comprising —$(CH_2)_m$—, —$(CHR_f)_m$—, or —$(CR_fR_g)_m$—, where $R_f$ and $R_g$ are independently $C_1$-$C_6$ linear or branched chain alkyl, aryl, alkylaryl, heteroaryl or alkylheteroaryl; where m is 2; 3, 4 or 5; $R_9$ and $R_{10}$ are independently hydrogen or $C_1$-$C_6$ linear or branched chain alkyl, $C_1$-$C_6$ linear or branched chain perfluoroalkyl, cyano, hydroxyl, amino, carboxy, hydroxyl, aryl, heteroaryl, or, $R_9$ and $R_{10}$ together form a chain comprising —$(CH_2)_p$—, —$(CHR_h)_p$—, or —$(CR_hR_i)_p$—, where $R_h$ and $R_i$ are independently $C_1$-$C_6$ linear or branched chain alkyl, aryl, alkylaryl, heteroaryl or alkylheteroaryl; where p is 2; 3, 4 or 5; Q is —CO—, —$(CH_2)_q$—, —(CHR$_s$)$_q$—, or —(CR$_s$R$_t$)$_q$—, where R$_s$ and R$_t$ are independently C$_1$-C$_6$ linear or branched chain alkyl, aryl, alkylaryl, heteroaryl or alkylheteroaryl; where q is 0, 1, 2, or 3; and, where n is 0, 1, 2, 3, 4 or 5; or, a pharmaceutically acceptable salt thereof.

The present invention also relates to a combination of a compound of Formula 1, 2 or 3:

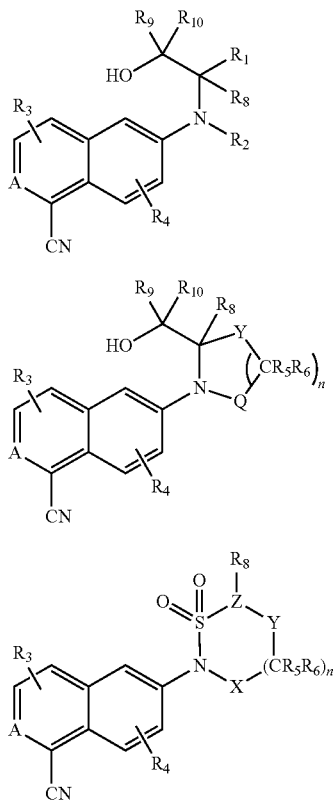

Formula 1

Formula 2

Formula 3 wherein A is N or —CR$_0$—, where R$_0$ is hydrogen, C$_1$-C$_6$ linear or branched chain alkyl, C$_1$-C$_6$ linear or branched chain perfluoroalkyl, aryl, perfluoroaryl, alkylaryl, heteroaryl; or, alkylheteroaryl; X and Y are independently —CH$_2$—, —CHR$_a$—, or, —CR$_a$R$_b$—, where R$_a$ and R$_b$ are independently C$_1$-C$_6$ linear or branched chain alkyl, aryl, alkylaryl, heteroaryl or, alkylheteroaryl; or, R$_a$ and R$_b$ together form a chain comprising —(CH$_2$)$_j$—, —(CHR$_c$)$_j$—, or —(CR$_c$R$_d$)$_j$—, where R$_c$ and R$_d$ are independently C$_1$-C$_6$ linear or branched chain alkyl, C$_1$-C$_6$ linear or branched chain perfluoroalkyl, aryl, alkylaryl, heteroaryl or alkylheteroaryl; where j is 2; 3, 4 or 5; Z is —CR$_e$—, or, —N—, where R$_e$ is hydrogen, C$_1$-C$_6$ linear or branched chain alkyl, C$_1$-C$_6$ linear or branched chain perfluoroalkyl, aryl, alkylaryl, heteroaryl or, alkylheteroaryl; R$_1$ is hydrogen, C$_1$-C$_6$ linear or branched chain alkyl, aryl, C$_1$-C$_6$ linear or branched chain perfluoroalkyl, alkylaryl, heteroaryl, alkylheteroaryl, C$_1$-C$_6$ linear or branched chain alkoxylcarbonyl, C$_1$-C$_6$ linear or branched chain alkylamino-carbonylamino, C$_1$-C$_6$ linear or branched chain alkyloxycarbonylamino, C$_1$-C$_6$ linear or branched chain alkylcarbonylamino, or, C$_1$-C$_6$ linear or branched chain alkylaminocarbonyl; R$_2$ is independently hydrogen or C$_1$-C$_6$ linear or branched chain alkyl; R$_3$ and R$_4$ are independently hydrogen, C$_1$-C$_6$ linear or branched chain alkyl, C$_1$-C$_6$ linear or branched chain perfluoroalkyl, C$_1$-C$_6$ linear or branched chain perfluoroalkoxy, halogen, cyano, hydroxyl, amino, carboxy, hydroxyl, aryl, heteroaryl, C$_1$-C$_6$ linear or branched chain alkoxylcarbonyl, C$_1$-C$_6$ linear or branched chain alkylamino-carbonylamino, or, C$_1$-C$_6$ linear or branched chain alkylaminocarbonyl; R$_5$ and R$_6$ are independently hydrogen or C$_1$-C$_6$ linear or branched chain alkyl, C$_1$-C$_6$ linear or branched chain perfluoroalkyl, cyano, hydroxyl, amino, carboxy, hydroxyl, aryl, heteroaryl, or, R$_5$ and R$_6$ together form a chain comprising —(CH$_2$)$_k$—, —(CHR$_7$)$_k$—, or —(CR$_{7a}$R$_{7b}$)$_k$—, where R$_7$, R$_{7a}$, and R$_{7b}$ are independently C$_1$-C$_6$ linear or branched chain alkyl, C$_1$-C$_6$ linear or branched chain perfluoroalkyl, aryl, alkylaryl, heteroaryl or alkylheteroaryl; where k is 2; 3, 4 or 5; R$_8$ is hydrogen, C$_1$-C$_6$ linear or branched chain alkyl, C$_1$-C$_6$ linear or branched chain perfluoroalkyl, aryl, aryl substituted with one, two or three fluorine atoms, perfluoroaryl, alkylaryl, heteroaryl; or, alkylheteroaryl; or, R$_1$ and R$_8$ together form a chain comprising —(CH$_2$)$_m$—, —(CHR$_f$)$_m$—, or —(CR$_f$R$_g$)$_m$—, where R$_f$ and R$_g$ are independently C$_1$-C$_6$ linear or branched chain alkyl, aryl, alkylaryl, heteroaryl or alkylheteroaryl; where m is 2; 3, 4 or 5; R$_9$ and R$_{10}$ are independently hydrogen or C$_1$-C$_6$ linear or branched chain alkyl, C$_1$-C$_6$ linear or branched chain perfluoroalkyl, cyano, hydroxyl, amino, carboxy, hydroxyl, aryl, heteroaryl, or, R$_9$ and R$_{10}$ together form a chain comprising —(CH$_2$)$_p$—, —(CHR$_h$)$_p$—, or —(CR$_h$R$_i$)$_p$—, where R$_h$ and R$_i$ are independently C$_1$-C$_6$ linear or branched chain alkyl, aryl, alkylaryl, heteroaryl or alkylheteroaryl; where p is 2; 3, 4 or 5; Q is —CO—, —(CH$_2$)$_q$—, —(CHR$_s$)$_q$—, or —(CR$_s$R$_t$)$_q$—, where R$_s$ and R$_t$ are independently C$_1$-C$_6$ linear or branched chain alkyl, aryl, alkylaryl, heteroaryl or alkylheteroaryl; where q is 0, 1, 2, or 3; and, where n is 0, 1, 2, 3, 4 or 5; or, a pharmaceutically acceptable salt thereof with a second pharmaceutically active ingredient, or a pharmaceutically acceptable salt thereof.

In another aspect, this invention relates to a pharmaceutical composition comprising a compound of Formula 1, Formula 2 or Formula 3, as defined herein or pharmaceutically acceptable salt thereof; a second pharmaceutically active ingredient, or a pharmaceutically acceptable salt thereof; and a pharmaceutically acceptable carrier or excipient.

In yet another aspect, this invention relates to a method for treating and/or preventing a disorder or condition in a subject, wherein the disorder or condition is selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy and stress urinary incontinence comprising administering to said subject an effective amount of a compound of Formula 1, Formula 2 or Formula 3 as defined herein, or a pharmaceutical salt thereof, and a second pharmaceutically active agent, thereby treating said disease or condition.

In a yet further aspect, this invention relates to a crystalline form of 6-[(4R)-4-methyl-1,1-dioxido-1,2,6-thiadiazinan-2-yl]isoquinoline-1-carbonitrile.

In another aspect, this invention relates to a pharmaceutical composition comprising a crystalline form of 6-[(4R)-4-methyl-1,1-dioxido-1,2,6-thiadiazinan-2-yl]isoquinoline-1-carbonitrile and a pharmaceutical carrier or excipient.

In another aspect, this invention relates to a method for modulating an activity of an androgen receptor in a subject in need thereof, comprising contacting said androgen receptor with an effective amount of a crystalline form of 6-[(4R)-4-methyl-1,1-dioxido-1,2,6-thiadiazinan-2-yl]isoquinoline-1-carbonitrile, or a pharmaceutical composition thereof, thereby modulating the activity of said androgen receptor.

In yet another aspect, this invention relates to a method for treating and/or preventing a disorder or condition in a subject, wherein the disorder or condition is selected from among anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and muscle wasting comprising administering to said subject an effective amount of a crystalline form of 6-[(4R)-4-methyl-1,1-dioxido-1,2,6-thiadiazinan-2-yl]isoquinoline-1-carbonitrile, or a pharmaceutical composition thereof, thereby treating said disease or condition.

In a further aspect, this invention relates to a method for treating and/or preventing a disorder or condition in a subject, wherein the disorder or condition is selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy and stress urinary incontinence comprising administering to said subject, an effective amount of a crystalline form of 6-[(4R)-4-methyl-1,1-dioxido-1,2,6-thiadiazinan-2-yl]isoquinoline-1-carbonitrile, or a pharmaceutical composition thereof, thereby treating said disease or condition.

In a further aspect, this invention relates to a process for preparing a crystalline form of 6-[(4R)-4-methyl-1,1-dioxido-1,2,6-thiadiazinan-2-yl]isoquinoline-1-carbonitrile.

In particular, the crystalline form of the present invention has been shown to have suitable physicochemical, stability, manufacturability and/or bioperformance properties which render it useful for further development.

DETAILED DESCRIPTION OF THE INVENTION

Figure 1:
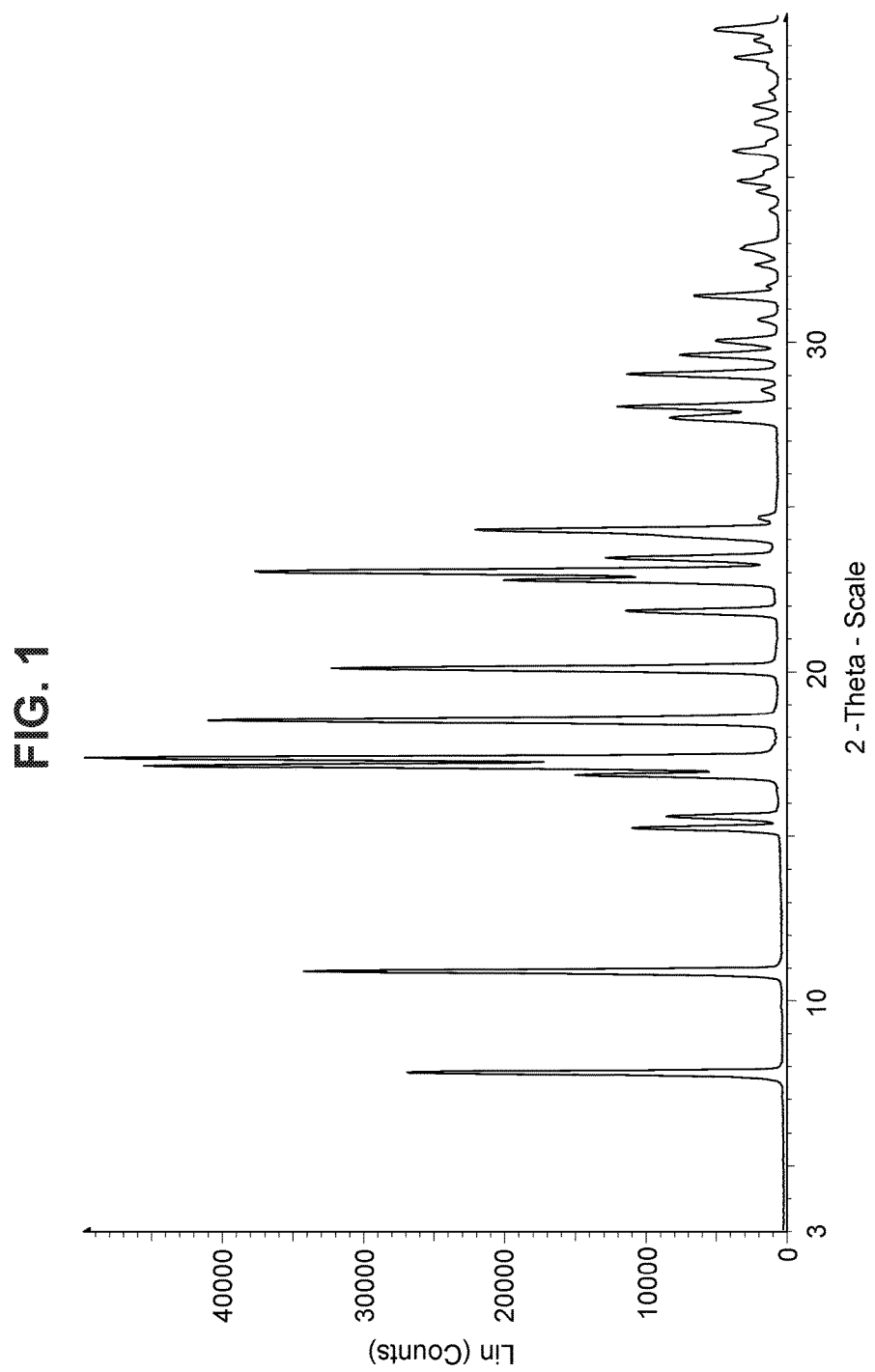
FIG. 1 is a characteristic PXRD X-ray powder diffraction pattern of crystalline 6-[(4R)-4-methyl-1,1-dioxido-1,2,6-thiadiazinan-2-yl]isoquinoline-1-carbonitrile free base (Form (1)). (Vertical axis—intensity (counts); horizontal axis: 2-theta (degrees)).

The present invention relates to a method for treating and/or preventing a disorder or condition in a subject, wherein the disorder or condition is selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy, and stress urinary incontinence comprising administering to said subject an effective amount of a compound of Formula 1, Formula 2 or Formula 3,

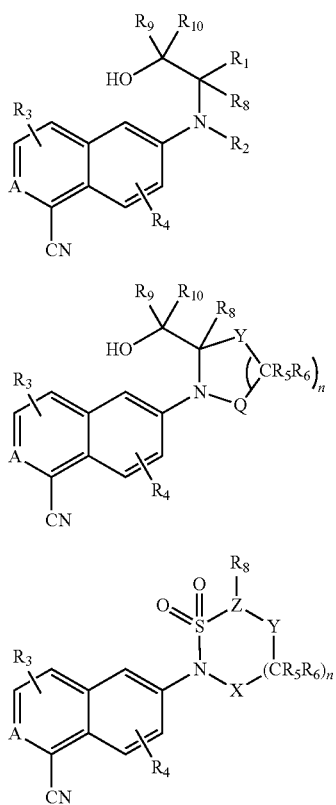

Formula 1

Formula 2

Formula 3 wherein A is N or —$CR_0$—, where $R_0$ is hydrogen, $C_1$-$C_6$ linear or branched chain alkyl, $C_1$-$C_6$ linear or branched chain perfluoroalkyl, aryl, perfluoroaryl, alkylaryl, heteroaryl; or, alkylheteroaryl; X and Y are independently —$CH_2$—, —$CHR_a$—, or, —$CR_aR_b$—, where $R_a$ and $R_b$ are independently $C_1$-$C_6$ linear or branched chain alkyl, aryl, alkylaryl, heteroaryl or, alkylheteroaryl; or, $R_a$ and $R_b$ together form a chain comprising —$(CH_2)_j$—, —$(CHR_c)_j$—, or —$(CR_cR_d)_j$—, where $R_c$ and $R_d$ are independently $C_1$-$C_6$ linear or branched chain alkyl, $C_1$-$C_6$ linear or branched chain perfluoroalkyl, aryl, alkylaryl, heteroaryl or alkylheteroaryl; where j is 2; 3, 4 or 5; Z is —$CR_e$—, or, —N—, where $R_e$ is hydrogen, $C_1$-$C_6$ linear or branched chain alkyl, $C_1$-$C_6$ linear or branched chain perfluoroalkyl, aryl, alkylaryl, heteroaryl or, alkylheteroaryl; $R_1$ is hydrogen, $C_1$-$C_6$ linear or branched chain alkyl, aryl, $C_1$-$C_6$ linear or branched chain perfluoroalkyl, alkylaryl, heteroaryl, alkylheteroaryl, $C_1$-$C_6$ linear or branched chain alkoxylcarbonyl, $C_1$-$C_6$ linear or branched chain alkylamino-carbonylamino, $C_1$-$C_6$ linear or branched chain alkyloxycarbonylamino, $C_1$-$C_6$ linear or branched chain alkylcarbonylamino, or, $C_1$-$C_6$ linear or branched chain alkylaminocarbonyl; $R_2$ are independently hydrogen or $C_1$-$C_6$ linear or branched chain alkyl; $R_3$ and $R_4$ are independently hydrogen, $C_1$-$C_6$ linear or branched chain alkyl, $C_1$-$C_6$ linear or branched chain perfluoroalkyl, $C_1$-$C_6$ linear or branched chain perfluoroalkoxy, halogen, cyano, hydroxyl, amino, carboxy, hydroxyl, aryl, heteroaryl, $C_1$-$C_6$ linear or branched chain alkoxylcarbonyl, $C_1$-$C_6$ linear or branched chain alkylamino-carbonylamino, or, $C_1$-$C_6$ linear or branched chain alkylaminocarbonyl; $R_5$ and $R_6$ are independently hydrogen or $C_1$-$C_6$ linear or branched chain alkyl, $C_1$-$C_6$ linear or branched chain perfluoroalkyl, cyano, hydroxyl, amino, carboxy, hydroxyl, aryl, heteroaryl, or, $R_5$ and $R_6$ together form a chain comprising —$(CH_2)_k$—, —$(CHR_7)_k$—, or —$(CR_{7a}R_{7b})_k$—, where $R_7$, $R_{7a}$, and $R_{7b}$ are independently $C_1$-$C_6$ linear or branched chain alkyl, $C_1$-$C_6$ linear or branched chain perfluoroalkyl, aryl, alkylaryl, heteroaryl or alkylheteroaryl; where k is 2; 3, 4 or 5; $R_8$ is hydrogen, $C_1$-$C_6$ linear or branched chain alkyl, $C_1$-$C_6$ linear or branched chain perfluoroalkyl, aryl, aryl substituted with one, two or three fluorine atoms, perfluoroaryl, alkylaryl, heteroaryl; or, alkylheteroaryl; or, $R_1$ and $R_8$ together form a chain comprising —$(CH_2)_m$—, —$(CHR_f)_m$—, or —$(CR_fR_g)_m$—, where $R_f$ and $R_g$ are independently $C_1$-$C_6$ linear or branched chain alkyl, aryl, alkylaryl, heteroaryl or alkylheteroaryl; where m is 2; 3, 4 or 5; $R_9$ and $R_{10}$ are independently hydrogen or $C_1$-$C_6$ linear or branched chain alkyl, $C_1$-$C_6$ linear or branched chain perfluoroalkyl, cyano, hydroxyl, amino, carboxy, hydroxyl, aryl, heteroaryl, or, $R_9$ and $R_{10}$ together form a chain comprising —$(CH_2)_p$—, —$(CHR_h)_p$—, or —$(CR_hR_i)_p$—, where $R_h$ and $R_i$ are independently $C_1$-$C_6$ linear or branched chain alkyl, aryl, alkylaryl, heteroaryl or alkylheteroaryl; where p is 2; 3, 4 or 5; Q is —CO—, —$(CH_2)_q$—, —$(CHR_s)_q$—, or —$(CR_sR_t)_q$—, where $R_s$ and $R_t$ are independently $C_1$-$C_6$ linear or branched chain alkyl, aryl, alkylaryl, heteroaryl or alkylheteroaryl; where q is 0, 1, 2, or 3; and, where n is 0, 1, 2, 3, 4 or 5; or, a pharmaceutically acceptable salt thereof.

Compounds of Formula 1, Formula 2 and Formula 3 are described below in more detail, including preferred embodiments thereof and derivatives thereof. Unless otherwise specified, the definitions, descriptions, derivatives and preferred embodiments of compounds of Formula 1, Formula 2 and Formula 3 set out below, are to be considered equally useful and applicable to all embodiments set out herein which comprise compounds of Formula 1, Formula 2 and/or Formula 3 or their derivatives.

In one embodiment, the compound of Formula 1 is such that $R_1$ and $R_2$ are independently $C_1$-$C_6$ linear or branched chain alkyl; and, $R_3$ and $R_4$ are both hydrogen.

In a particular embodiment, the compound of Formula 1 is such that $R_1$ and $R_2$ are independently methyl, ethyl or propyl.

In another embodiment, the compound of Formula 2 is such that Q is —$(CH_2)_q$—, —$(CHR_s)_q$—, or —$(CR_sR_t)_q$—, where $R_s$ and $R_t$ are independently $C_1$-$C_6$ linear or branched chain alkyl; and, q is 1 or 2. In yet another embodiment of the compound having Formula 2, Q is —CO—.

In a particular embodiment, the compound of Formula 3, is such that X and Y are independently —$CH_2$—, —$CHR_a$—, or, —$CR_aR_b$—, where $R_a$ and $R_b$ are independently $C_1$-$C_6$ linear or branched chain alkyl, aryl, alkylaryl, heteroaryl or, alkylheteroaryl. In another embodiment of the present invention, the compound of Formula 3 is such that, X and Y are independently —$CH_2$—, —$CHR_a$—, or, —$CR_aR_b$—, where $R_a$ and $R_b$ are independently methyl or ethyl.

In certain specific embodiments, the compound of Formula 1, Formula 2 or Formula 3 is selected from the group consisting of:

6-[(3S)-3-methyl-1,1-dioxido-1,2,5-thiadiazolidin-2-yl]isoquinoline-1-carbonitrile;
6-[(3S)-3-ethyl-1,1-dioxido-1,2,5-thiadiazolidin-2-yl]isoquinoline-1-carbonitrile
6-[(3R)-1,1-dioxido-3-(2,2,2-trifluoroethyl)-1,2,5-thiadiazolidin-2-yl]isoquinoline-1-carbonitrile;
6-[(3R)-1,1-dioxido-3-(2-phenylethyl)-1,2,5-thiadiazolidin-2-yl]isoquinoline-1-carbonitrile;

6-[1-methyl-(3S)-3-methyl-1,1-dioxido-1,2,5-thiadiazolidin-2-yl]isoquinoline-1-carbonitrile;
6-{(3R)-1,1-dioxido-3-[3-(trifluoromethyl)phenyl]-1,2,5-thiadiazolidin-2-yl}isoquinoline-1-carbonitrile;
6-[(3S)-3-(4-chlorophenyl)-1,1-dioxido-1,2,5-thiadiazolidin-2-yl]isoquinoline-1-carbonitrile;
6-[(3S)-3-methyl-1,1-dioxido-1,2-thiazolidin-2-yl]isoquinoline-1-carbonitrile;
6-[(3S)-3-methyl-1,1-dioxido-1,2,5-thiadiazolidin-2-yl]naphthalene-1-carbonitrile;
6-[(4R)-4-methyl-1,1-dioxido-1,2,6-thiadiazinan-2-yl]isoquinoline-1-carbonitrile;
6-[(4S)-4-methyl-1,1-dioxido-1,2,6-thiadiazinan-2-yl]isoquinoline-1-carbonitrile;
6-{(3R)-1,1-dioxido-3-(3-phenyl)-1,2,5-thiadiazolidin-2-yl}isoquinoline-1-carbonitrile;
6-(4,4-dimethyl-1,1-dioxido-1,2,6-thiadiazinan-2-yl)isoquinoline-1-carbonitrile;
6-(6,6-dioxido-6-thia-5,7-diazaspiro[2.5]oct-5-yl)isoquinoline-1-carbonitrile;
6-[(4R)-4-(3-methylbenzyl)-1,1-dioxido-1,2,6-thiadiazinan-2-yl]isoquinoline-1-carbonitrile;
6-[(4R)-6-ethyl-4-methyl-1,1-dioxido-1,2,6-thiadiazinan-2-yl]isoquinoline-1-carbonitrile;
6-(5-methyl-1,1-dioxido-1,2,6-thiadiazinan-2-yl)isoquinoline-1-carbonitrile;
6-[(4S)-4-(4-methylphenyl)-1,1-dioxido-1,2,6-thiadiazinan-2-yl]isoquinoline-1-carbonitrile;
6-[(4R)-4-(4-methylphenyl)-1,1-dioxido-1,2,6-thiadiazinan-2-yl]isoquinoline-1-carbonitrile;
6-[(4S)-4-(3-methylphenyl)-1,1-dioxido-1,2,6-thiadiazinan-2-yl]isoquinoline-1-carbonitrile;
6-[(4S)-4-ethyl-1,1-dioxido-1,2,6-thiadiazinan-2-yl]isoquinoline-1-carbonitrile; and,
6-(1,1-dioxido-4-propyl-1,2,6-thiadiazinan-2-yl)isoquinoline-1-carbonitrile, or a pharmaceutically acceptable salt thereof.

In certain specific embodiments, the compound of the present invention is selected from the group consisting of:
6-{[(2R,3S)-4,4,4-trifluoro-3-hydroxybutan-2-yl]amino}isoquinoline-1-carbonitrile;
6-{(2R)-2-[(1R)-2,2,2-trifluoro-1-hydroxyethyl]azetidin-1-yl}isoquinoline-1-carbonitrile;
6-{(2S)-2-[(1S)-2,2,2-trifluoro-1-hydroxyethyl]azetidin-1-yl}isoquinoline-1-carbonitrile;
6-{methyl[(2R,3R)-4,4,4-trifluoro-3-hydroxybutan-2-yl]amino}isoquinoline-1-carbonitrile;
6-{methyl[(2R,3S)-4,4,4-trifluoro-3-hydroxybutan-2-yl]amino}isoquinoline-1-carbonitrile;
6-{(2R)-2-[(1R)-2,2,2-trifluoro-1-hydroxyethyl]piperidin-1-yl}isoquinoline-1-carbonitrile;
6-{(2R)-2-[(1S)-2,2,2-trifluoro-1-hydroxyethyl]piperidin-1-yl}isoquinoline-1-carbonitrile;
6-{(2R,5R)-2-methyl-5-[(1R)-2,2,2-trifluoro-1-hydroxyethyl]pyrrolidin-1-yl}isoquinoline-1-carbonitrile;
6-{(2R,5R)-2-[(1R)-1-hydroxyethyl]-5-methylpyrrolidin-1-yl}isoquinoline-1-carbonitrile;
6-{(5R)-2-oxo-5-[(1S)-2,2,2-trifluoro-1-hydroxyethyl]pyrrolidin-1-yl}isoquinoline-1-carbonitrile;
6-{(5S)-2-oxo-5-[(1S)-2,2,2-trifluoro-1-hydroxyethyl]pyrrolidin-1-yl}isoquinoline-1-carbonitrile;
6-{(2R)-2-[(1R)-2,2,2-trifluoro-1-hydroxyethyl]pyrrolidin-1-yl}isoquinoline-1-carbonitrile;
6-{(2R)-2-[(1S)-2,2,2-trifluoro-1-hydroxyethyl]pyrrolidin-1-yl}isoquinoline-1-carbonitrile;
6-{(2S)-2-[(1S)-2,2,2-trifluoro-1-hydroxyethyl]pyrrolidin-1-yl}isoquinoline-1-carbonitrile;
6-{(2S)-2-[(1R)-2,2,2-trifluoro-1-hydroxyethyl]pyrrolidin-1-yl}isoquinoline-1-carbonitrile;
6-{(2S,5S)-2-methyl-5-[(1S)-2,2,2-trifluoro-1-hydroxyethyl]pyrrolidin-1-yl}isoquinoline-1-carbonitrile;
6-{(2R,5R)-2-[(1S)-1-hydroxyethyl]-5-methylpyrrolidin-1-yl}isoquinoline-1-carbonitrile;
6-((2R,3S)-4,4,4-trifluoro-3-hydroxybutan-2-ylamino)-1-naphthonitrile;
6-((R)-2-((R)-2,2,2-trifluoro-1-hydroxyethyl)azetidin-1-yl)-1-naphthonitrile;
6-((S)-2-((S)-2,2,2-trifluoro-1-hydroxyethyl)azetidin-1-yl)-1-naphthonitrile
6-(methyl((2R,3R)-4,4,4-trifluoro-3-hydroxybutan-2-yl)amino)-1-naphthonitrile;
6-(methyl((2R,3S)-4,4,4-trifluoro-3-hydroxybutan-2-yl)amino)-1-naphthonitrile;
6-((R)-2-((R)-2,2,2-trifluoro-1-hydroxyethyl)piperidin-1-yl)-1-naphthonitrile;
6-((R)-2-((S)-2,2,2-trifluoro-1-hydroxyethyl)piperidin-1-yl)-1-naphthonitrile;
6-((2R,5R)-2-methyl-5-((R)-2,2,2-trifluoro-1-hydroxyethyl)pyrrolidin-1-yl)-1-naphthonitrile;
6-((2R,5R)-2-((R)-1-hydroxyethyl)-5-methylpyrrolidin-1-yl)-1-naphthonitrile;
6-((R)-2-oxo-5-((S)-2,2,2-trifluoro-1-hydroxyethyl)pyrrolidin-1-yl)-1-naphthonitrile;
6-((S)-2-oxo-5-((S)-2,2,2-trifluoro-1-hydroxyethyl)pyrrolidin-1-yl)-1-naphthonitrile;
6-((R)-2-((R)-2,2,2-trifluoro-1-hydroxyethyl)pyrrolidin-1-yl)-1-naphthonitrile;
6-((R)-2-((S)-2,2,2-trifluoro-1-hydroxyethyl)pyrrolidin-1-yl)-1-naphthonitrile;
6-((S)-2-((S)-2,2,2-trifluoro-1-hydroxyethyl)pyrrolidin-1-yl)-1-naphthonitrile;
6-((S)-2-((R)-2,2,2-trifluoro-1-hydroxyethyl)pyrrolidin-1-yl)-1-naphthonitrile;
6-((2S,5S)-2-methyl-5-((S)-2,2,2-trifluoro-1-hydroxyethyl)pyrrolidin-1-yl)-1-naphthonitrile; and,
6-((2R,5R)-2-((S)-1-hydroxyethyl)-5-methylpyrrolidin-1-yl)-1-naphthonitrile, or, a pharmaceutically acceptable salt thereof.

Particularly preferred embodiments include those where the compound of Formula 1, Formula 2 or Formula 3 is selected from the group consisting of 6-[(3R)-3-methyl-1,1-dioxido-1,2,5-thiadiazolidin-2-yl]isoquinoline-1-carbonitrile, 6-[(3S)-3-methyl-1,1-dioxido-1,2,5-thiadiazolidin-2-yl]isoquinoline-1-carbonitrile, 6-[(4R)-4-methyl-1,1-dioxido-1,2,6-thiadiazinan-2-yl]isoquinoline-1-carbonitrile, 6-[(4S)-4-methyl-1,1-dioxido-1,2,6-thiadiazinan-2-yl]isoquinoline-1-carbonitrile, and 6-(methyl-((2R,3R)-4,4,4-trifluoro-3-hydroxybutan-2-yl)amino)-1-naphthonitrile, or a pharmaceutically acceptable salt thereof.

In a more particularly preferred embodiment, the compound of Formula 1, Formula 2 or Formula 3 is 6-[(4R)-4-methyl-1,1-dioxido-1,2,6-thiadiazinan-2-yl]isoquinoline-1-carbonitrile.

The term "alkyl", alone or in combination, means an acyclic, saturated hydrocarbon group of the formula $C_nH_{2n+1}$ which may be linear or branched. Examples of such groups include methyl, ethyl, n-propyl, isopropyl, n-butyl, isobutyl, sec-butyl, tert-butyl, pentyl, iso-amyl and hexyl. Unless otherwise specified, an alkyl group comprises from 1 to 6 carbon atoms. The carbon atom content of alkyl and various other hydrocarbon-containing moieties is indicated by a prefix designating a lower and upper number of carbon atoms in the moiety, that is, the prefix $C_i$-$C_j$ indicates a moiety of the integer "i" to the integer "j" carbon atoms, inclusive. Thus, for example, $C_1$-$C_6$ alkyl refers to alkyl of one to six carbon atoms, inclusive.

The term "hydroxy," as used herein, means an OH radical. The term "heterocyclic" refers to a saturated or partially saturated (i.e. non aromatic) heterocycle which may be attached via a ring nitrogen atom (when the heterocycle is attached to a carbon atom) or a ring carbon atom (in all cases). Equally, when substituted, the substituent may be located on a ring nitrogen atom (if the substituent is joined through a carbon atom) or a ring carbon atom (in all cases). Specific examples include oxiranyl, aziridinyl, oxetanyl, azetidinyl, tetrahydrofuranyl, pyrrolidinyl, tetrahydropyranyl, piperidinyl, 1,4-dioxanyl, morpholinyl, piperazinyl, azepanyl, oxepanyl, oxazepanyl and diazepinyl.

The term "heteroaryl" refers to an aromatic heterocycle which may be attached via a ring carbon atom (in all cases) or a ring nitrogen atom with an appropriate valency (when the heterocycle is attached to a carbon atom). Equally, when substituted, the substituent may be located on a ring carbon atom (in all cases) or a ring nitrogen atom with an appropriate valency (if the substituent is joined through a carbon atom). Specific examples include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridyl, pyridazinyl, pyrimidinyl and pyrazinyl. The term "cycloalkyl" means a means a monocyclic, saturated hydrocarbon group of the formula $C_nH_{2n-1}$. Examples include cyclopropyl, cyclobutyl, cyclopentyl, cyclohexyl, and cycloheptyl. Unless otherwise specified, a cycloalkyl group comprises from 3 to 8 carbon atoms.

The term "oxo" means a double-bonded oxygen. The term "alkoxy" means a radical comprising an alkyl radical that is bonded to an oxygen atom, such as a methoxy radical. Examples of such radicals include methoxy, ethoxy, propoxy, isopropoxy, butoxy and tert-butoxy. The term "halo" means, fluoro, chloro, bromo or iodo.

Compounds of Formula 1, Formula 2 or Formula 3 can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given; other process conditions can also be used unless otherwise stated. Optimum reaction conditions can vary with the particular reactants or solvent used. Those skilled in the art will recognize that the nature and order of the synthetic steps presented can be varied for the purpose of optimizing the formation of the compounds described herein.

Accordingly, the general reaction schemes provided herein illustrate the preparation of the compounds of Formula 1, formula 2 or Formula 3. Unless otherwise indicated, the substituent variables used in the reaction schemes and the accompanying discussion are defined as indicated above.

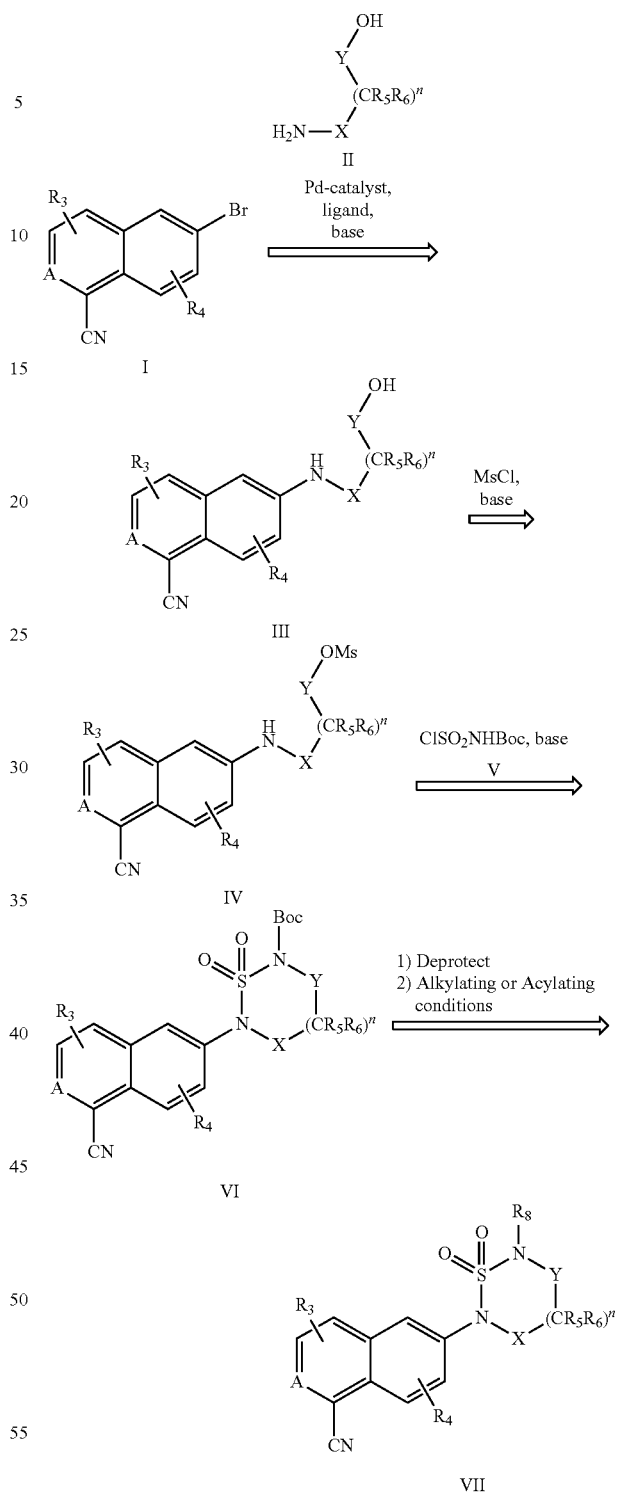

Bromides of general formula I are coupled with aminoalcohols II under coupling conditions such as Pd-catalyzed coupling conditions. The hydroxyl groups of compounds III are activated as leaving groups by mesylate formation among other methods in the presence of a base to generate compounds IV. The treatment of compounds IV with the reagent V produces Boc-protected intermediates VI. Boc-group de-protection followed by alkylation or acylation of intermediate NH compounds culminates the synthesis of a chemical class of compounds of general formula VII. The preparation of products VII with $R_3$ and $R_4$ being unprotected amino, hydroxyl or carboxylic acid groups would require protection of the corresponding functionality using standard methods of organic chemistry and de-protection in the appropriate point in the synthetic sequence.

The preparation of compounds with A being carbon is exemplified by the synthesis of 6-[(3S)-3-methyl-1,1-dioxido-1,2-thiazolidin-2-yl]isoquinoline-1-carbonitrile (Example 8).

When Z (Formula 3) is not equal to N, an alternative procedure to the one described above should be applied. The preparation of compounds with A being carbon is exemplified by the synthesis of 6-[(3S)-3-(4-chlorophenyl)-1,1-dioxido-1,2,5-thiadiazolidin-2-yl]isoquinoline-1-carbonitrile (Example 7).

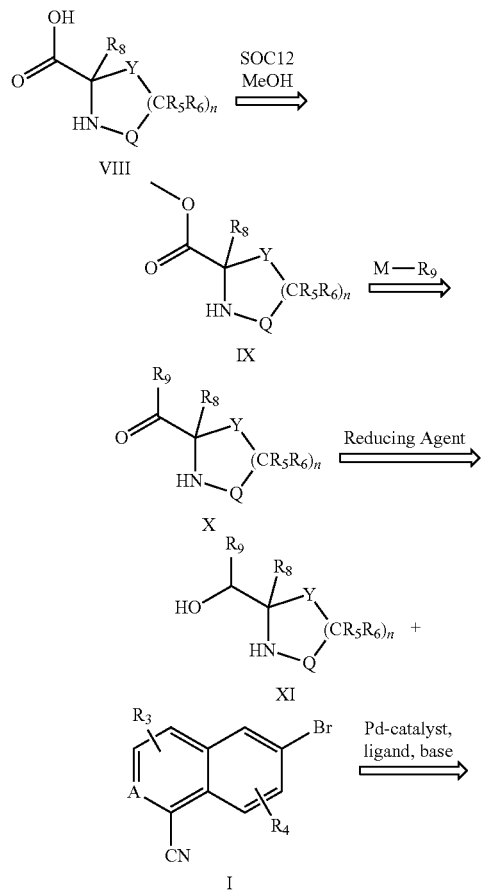

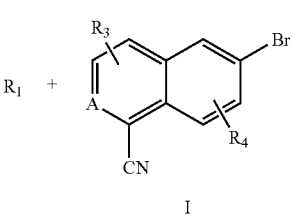

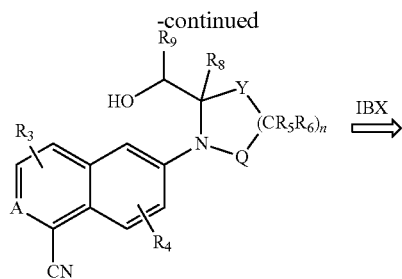

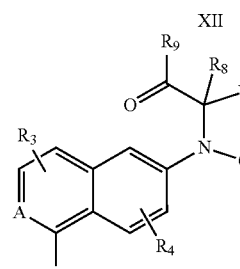

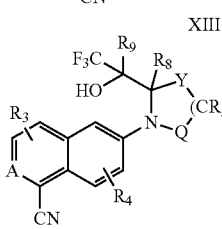

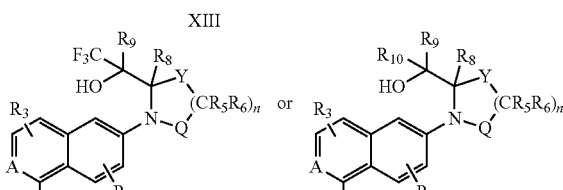

Aminoacids VIII are converted into methyl esters IX via a standard acid chloride formation protocols. The esters IX undergo transformations into a corresponding ketones (or aldehydes) X using a nucleophilic reagents M-$R_9$ that deliver fragments $R_9$. An alternative approach to produce ketones X would be to employ functional equivalents such as Weinreb amides that are described in the organic chemistry literature. The keto or aldehyde groups are reduced to produce aminoalcohols XI which are coupled with bromide I under Pd-catalyzed conditions. The hydroxyl groups of compounds XII are oxidized to yield a keto or aldehyde compounds XIII which are treated with either $CF_3$-group delivering reagents or with a nucleophilic reagents M-$R_{10}$ that contains fragments $R_{10}$. The product XIV contains $R_{10}$ functionality where $R_{10}$ may be represented by $CF_3$ or another group described in claims. The preparation of products XIV with $R_3$, $R_4$, $R_5$, $R_6$, $R_8$, $R_9$, and $R_{10}$ that contain unprotected NH, OH or COOH groups would require protection of the corresponding functionality using standard methods of organic chemistry and de-protection in the appropriate point in the synthetic sequence.

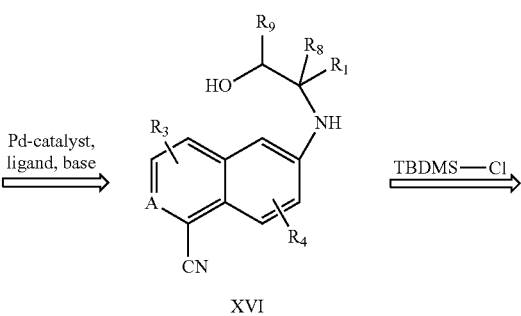

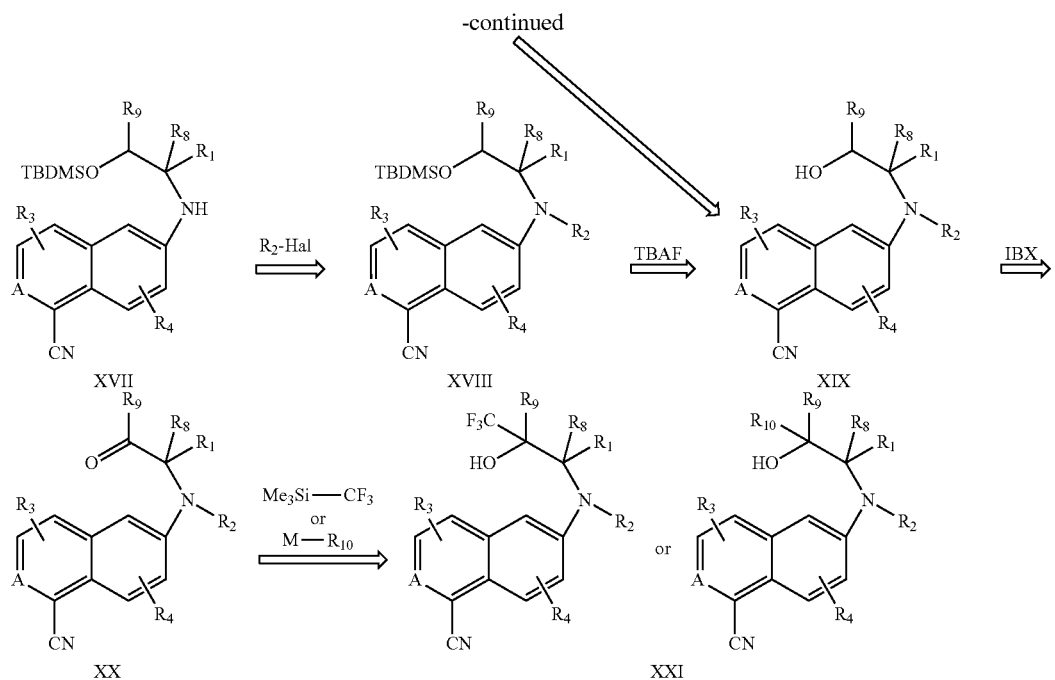

Aminoalcohols XV are coupled with bromides I under coupling conditions such as Pd-catalyzed amide coupling conditions. The hydroxyl groups of XVI are protected with TBDMS or like groups, and NH group of XVII may be modified by incorporation of $R_2$. The protecting groups in XVIII are removed to result in aminoalcohol XIX. The hydroxyl groups of XIX is oxidized to yield a keto or aldehyde compounds XX which are treated with either a $CF_3$-group containing reagent or with nucleophilic reagents $M-R_{10}$ that contains fragments $R_{10}$. The products XXI contain $R_{10}$ functionality where $R_{10}$ may be represented by $CF_3$ or another group described in claims. The preparation of products XXIII with $R_1$, $R_2$, $R_3$, $R_8$, $R_9$, and $R_{10}$ that contain unprotected NH, OH or COOH groups would require protection of the corresponding functionality using standard methods of organic chemistry and de-protection in the appropriate point in the synthetic sequence.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatography such as high-performance liquid chromatography (HPLC), gas chromatography (GC), gel-permeation chromatography (GPC), or thin layer chromatography (TLC).

Preparation of the compounds of Formula 1, Formula 2 or Formula 3 can involve protection and de-protection of various chemical groups. The chemistry of protecting groups can be found, for example, in Greene et al., *Protective Groups in Organic Synthesis*, 4th. Ed. (John Wiley & Sons, 2007), the entire disclosure of which is incorporated by reference herein for all purposes.

References to compounds of Formula 1, 2 or 3 are taken to include the compounds themselves and prodrugs thereof. As such, references to compounds of Formula 1, Formula 2 or Formula 3 includes references to compounds of Formula 1, 2 or 3 as well as pharmaceutically acceptable salts of such compounds, and prodrugs of such compounds and pharmaceutically acceptable salts of such prodrugs, and to pharmaceutically acceptable solvates of said compounds, slats thereof, prodrugs thereof and salts of prodrugs thereof.

Included within the scope of a compound of Formula 1, 2 or 3 as described herein is that compound in the form of a prodrug. Thus, certain derivatives of a compound of Formula 1, 2 or 3 which may have little or no pharmacological activity themselves can, when administered into or onto the body, be converted into a compound of Formula 1, 2 or 3 having the desired activity, for example by hydrolytic cleavage, particularly hydrolytic cleavage promoted by an esterase or peptidase enzyme. Such derivatives are referred to as 'prodrugs'. Further information on the use of prodrugs may be found in 'Pro-drugs as Novel Delivery Systems', Vol. 14, ACS Symposium Series (T. Higuchi and W. Stella) and 'Bioreversible Carriers in Drug Design', Pergamon Press, 1987 (Ed. E. B. Roche, American Pharmaceutical Association). Reference can also be made to Nature Reviews/Drug Discovery, 2008, 7, 355 and Current Opinion in Drug Discovery and Development, 2007, 10, 550.

Prodrugs of the compound of Formula 1, 2 or 3 as described herein can, for example, be produced by replacing appropriate functionalities present in the compounds of Formula 1, 2 or 3 with certain moieties known to those skilled in the art as 'pro-moieties' as described, for example, in 'Design of Prodrugs' by H. Bundgaard (Elsevier, 1985).

Thus, a prodrug of the compound of Formula 1, 2 or 3 as described herein is (a) an ester or amide derivative of a carboxylic acid in a compound of Formula 1, 2 or 13; (b) an ester, carbonate, carbamate, phosphate or ether derivative of a hydroxyl group in a compound of Formula 1, 2 or 3; (c) an amide, imine, carbamate or amine derivative of an amino group in a compound form Formula 1, 2 or 3; (d) a thioester, thiocarbonate, thiocarbamate or sulphide derivatives of a thiol group in a compound of Formula 1, 2 or 3; or (e) an oxime or imine derivative of a carbonyl group in a compound of Formula 1, 2 or 3.

Some specific examples of prodrugs of the compound of Formula 1, 2 or 3 as described herein include:

(i) where the compound of Formula 1, 2 or 3 contains a carboxylic acid functionality (—COOH), an ester thereof, such as a compound wherein the hydrogen of the carboxylic acid functionality of the compound of Formula 1, 2 or 3 is replaced by $C_1$-$C_8$ alkyl (e.g. ethyl) or $(C_1$-$C_8$ alkyl)C(=O)OCH$_2$— (e.g. $^tBuC(=O)OCH_2$—);

(ii) where the compound of Formula 1, 2 or 3 contains an alcohol functionality (—OH), an ester thereof, such as a compound wherein the hydrogen of the alcohol functionality of the compound of Formula 1, 2 or 3 is replaced by —CO($C_1$-$C_8$ alkyl) (e.g. methylcarbonyl) or the alcohol is esterified with an amino acid;

(iii) where the compound of Formula 1, 2 or 3 contains an alcohol functionality (—OH), an ether thereof, such as a compound wherein the hydrogen of the alcohol functionality of the compound of Formula 1, 2 or 3 is replaced by $(C_1$-$C_8$ alkyl)C(=O)OCH$_2$— or —CH$_2$OP(=O)(OH)$_2$;

(iv) where the compound of Formula 1, 2 or 3 contains an alcohol functionality (—OH), a phosphate thereof, such as a compound wherein the hydrogen of the alcohol functionality of the compound of Formula 1, 2 or 3 is replaced by —P(=O)(OH)$_2$ or —P(=O)(ONa)$_2$ or —P(=O)(O$^-$)$_2$Ca$^{2+}$;

(v) where the compound of Formula 1, 2 or 3 contains a primary or secondary amino functionality (—NH$_2$ or —NHR where R≠H), an amide thereof, for example, a compound wherein, as the case may be, one or both hydrogens of the amino functionality of the compound of Formula 1, 2 or 3 is/are replaced by $(C_1$-$C_{10})$alkanoyl, —COCH$_2$NH$_2$ or the amino group is derivatized with an amino acid; or, (vi) where the compound of Formula 1, 2 or 3 contains a primary or secondary amino functionality (—NH$_2$ or —NHR where R≠H), an amine thereof, for example, a compound wherein, as the case may be, one or both hydrogens of the amino functionality of the compound of Formula 1, 2 or 3 is/are replaced by —CH$_2$OP(=O)(OH)$_2$.

Certain compounds of Formula 1, 2 or 3 may themselves act as prodrugs of other compounds of Formula 1, 2 or 3. It is also possible for two compounds of Formula 1, 2 or 3 to be joined together in the form of a prodrug. In certain circumstances, a prodrug of a compound of Formula 1, 2 or 3 may be created by internally linking two functional groups in a compound of Formula 1, 2 or 3, for instance by forming a lactone.

Pharmaceutically acceptable salts of the compounds of Formula 1, 2 or 3 include acid addition and base salts. Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, naphthalene-1,5-disulfonic acid and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see Handbook of Pharmaceutical Salts: Properties, Selection, and Use by Stahl and Wermuth (Wiley-VCH, 2002).

Pharmaceutically acceptable salts of compounds of Formula 1, 2 or 3 may be prepared by one or more of three methods:

(i) by reacting the compound of Formula 1, 2 or 3 with the desired acid or base;

(ii) by removing an acid- or base-labile protecting group from a suitable precursor of the compound of Formula 1, 2 or 3 or by ring-opening a suitable cyclic precursor, for example, a lactone or lactam, using the desired acid or base; or, (iii) by converting one salt of the compound of Formula 1, 2 or 3 to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

The compounds of Formula 1, 2 or 3, and pharmaceutically acceptable salts thereof, may exist in unsolvated and solvated forms. The term 'solvate' is used herein to describe a molecular complex comprising the compound of Formula 1, 2 or 3, or a pharmaceutically acceptable salt thereof, and one or more pharmaceutically acceptable solvent molecules, for example, ethanol. The term 'hydrate' may be employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the definition of compounds of Formula 1, Formula 2 or Formula 3 as described herein are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

Hereinafter, all references to compounds of Formula 1, 2 or 3 are to be considered to include references to pharmaceutically acceptable salts, solvates, multi-component complexes and liquid crystals thereof and to solvates, multi-component complexes and liquid crystals of pharmaceutically acceptable salts thereof.

The compounds of Formula 1, 2 or 3 may exhibit polymorphism and/or one or more kinds of isomerism (e.g. optical, geometric or tautomeric isomerism). The compounds of Formula 1, 2 or 3 may also be isotopically labelled. Such variation is implicit to the compounds of Formula 1, 2 or 3 defined as they are by reference to their structural features and therefore within the scope of the invention.

Compounds of Formula 1, 2 or 3 containing one or more asymmetric carbon atoms can exist as two or more stereoisomers. Where a compound of Formula 1, 2 or 3 contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula 1, 2 or 3 containing, for example, an imino, keto, or oxime group, or so-called valence tautomerism in compounds which contain an aromatic moiety. It follows that a single compound may exhibit more than one type of isomerism.

The pharmaceutically acceptable salts of compounds of Formula 1, 2 or 3 may also contain a counterion which is optically active (e.g. d-lactate or l-lysine) or racemic (e.g. dl-tartrate or dl-arginine). Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of Formula 1, Formula 2 or Formula 3 contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of Formula 1, Formula 2 or Formula 3 (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. Chiral chromatography using sub- and supercritical fluids may be employed. Methods for chiral chromatography useful in some embodiments of the present invention are known in the art (see, for example, Smith, Roger M., Loughborough University, Loughborough, UK; Chromatographic Science Series (1998), 75 (Supercritical Fluid Chromatography with Packed Columns), pp. 223-249 and references cited therein). In some relevant examples herein, columns were obtained from Chiral Technologies, Inc, West Chester, Pa., USA, a subsidiary of Daicel® Chemical Industries, Ltd., Tokyo, Japan.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. While both of the crystal forms present in a racemic mixture have identical physical properties, they may have different physical properties compared to the true racemate. Racemic mixtures may be separated by conventional techniques known to those skilled in the art. *Stereochemistry of Organic Compounds* by E. L. Eliel and S. H. Wilen (Wiley, 1994).

As used herein, the term compounds of Formula 1, Formula 2 or Formula 3 also includes all pharmaceutically acceptable isotopically-labelled compounds of Formula 1, Formula 2 or Formula 3 wherein one or more atoms are replaced by atoms having the same atomic number, but an atomic mass or mass number different from the atomic mass or mass number which predominates in nature. Isotopically-labelled compounds of Formula 1, Formula 2 or Formula 3 can generally be prepared by conventional techniques known to those skilled in the art or by processes analogous to those described in the accompanying Examples and Preparations using an appropriate isotopically-labelled reagent in place of the non-labelled reagent previously employed. In particular, hydrogen atoms may be replaced by deuterium atoms since such deuterated compounds are sometimes more resistant to metabolism.

As defined herein compounds of Formula 1, Formula 2 or Formula 3 also include within their scope active metabolites of compounds of Formula 1, Formula 2 or Formula 3, that is, compounds formed in vivo upon administration of the drug, often by oxidation or dealkylation.

Some examples of metabolites in accordance with the invention include:
(i) where the compound of Formula 1, 2 or 3 contains a methyl group, an hydroxymethyl derivative thereof (—CH$_3$→—CH$_2$OH);
(ii) where the compound of Formula 1, 2 or 3 contains an alkoxy group, an hydroxy derivative thereof (—OR→—OH);
(iii) where the compound of Formula 1, 2 or 3 contains a tertiary amino group, a secondary amino derivative thereof (—NRR'→—NHR or —NHR');
(iv) where the compound of Formula 1 contains a secondary amino group, a primary derivative thereof (—NHR→—NH$_2$);
(v) where the compound of Formula 1, 2 or 3 contains a phenyl moiety, a phenol derivative thereof (-Ph→-PhOH); and,
(vi) where the compound of Formula 1, 2 or 3 contains an amide group, a carboxylic acid derivative thereof (—CONH$_2$→COOH).

In an even more particularly preferred embodiment, the compound of Formula 1, Formula 2 or Formula 3 is a crystalline form of 6-[(4R)-4-methyl-1,1-dioxido-1,2,6-thiadiazinan-2-yl]isoquinoline-1-carbonitrile, wherein 6-[(4R)-4-methyl-1,1-dioxido-1,2,6-thiadiazinan-2-yl]isoquinoline-1-carbonitrile is in it's free base form.

There are a number of analytical methods one of ordinary skill in the art can use to analyze solid forms, in particular crystalline solid forms. The term "analyze" as used herein shall be taken to mean to obtain information about the solid state structure of solid forms. For example, X-ray powder diffraction is one such suitable technique for differentiating amorphous solid forms from crystalline solid forms and for characterizing and identifying crystalline solid forms since different crystalline forms exhibit different X-ray powder patterns. A discussion of the theory of X-ray powder diffraction patterns can be found in Clearfield, Reibenspies and Bhuvanesh (Editors), Principles and Applications of Powder Diffraction: Edition 1, Wiley, John & Sons, Incorporated (2008), which is incorporated by reference in its entirety.

Due to differences in instruments, samples and sample preparation, minor variation in peak values in spectroscopic techniques can occur. In an X-ray powder diffraction pattern typical precision of a 2-theta x-axis value of an x-ray powder pattern is of the order of plus or minus 0.2° 2-theta. As such, a peak value reported to be at 9.2° 2-theta could occur at anywhere between 9.0° 2-theta and 9.4° 2-theta when measured on most x-ray diffractometers under most conditions. In a FT-Raman spectra typical precision of a Raman shift is of the order of plus or minus 2 cm$^{-1}$. In a solid state NMR the typical precision of a $^{13}$C peak shift is of the order of plus or minus 0.2 ppm.

In a further preferred embodiment, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9 and 15.2.

In a yet further preferred embodiment, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, and 15.2 and one or more additional characteristic peaks expressed in degrees 2-theta (±0.2° 2-theta) selected from the group consisting of 17.1, 17.3, and 18.5.

In another embodiment, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2 and 17.1.

In another embodiment, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2 and 17.3.

In another embodiment, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2 and 18.5.

In another embodiment, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2, 17.1 and 17.3.

In another embodiment, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2, 17.1, and 18.5.

In another embodiment, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2, 17.3, and 18.5.

In a still further preferred embodiment, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2, 17.1, 17.3, and 18.5.

In an even further preferred embodiment, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) as depicted in Table 1.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in cm$^{-1}$ (±2 cm$^{-1}$) at 708, 1555 and 2230.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in cm$^{-1}$ (±2 cm$^{-1}$) as depicted in Table 2.

In another embodiment of the present invention, the crystalline form of 6-[(4R)-4-methyl-1,1-dioxido-1,2,6-thiadiazinan-2-yl]isoquinoline-1-carbonitrile Form (1) exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a solid state NMR spectra having characteristic peaks expressed in ppm (±0.2 ppm) at 15.3, 136.6 and 143.2.

In another embodiment of the present invention, the crystalline form of 6-[(4R)-4-methyl-1,1-dioxido-1,2,6-thiadiazinan-2-yl]isoquinoline-1-carbonitrile Form (1) exhibits a solid state NMR spectra having characteristic peaks expressed in ppm (±0.2 ppm) as depicted in Table 3.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9 and exhibits a FT-Raman spectra having one or more characteristic peaks expressed in cm$^{-1}$ (±2 cm$^{-1}$) selected from the group consisting of 708, 1555 and 2230.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9 and exhibits a FT-Raman spectra having a characteristic peak expressed in cm$^{-1}$ (±2 cm$^{-1}$) at 708.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9 and 15.2 and exhibits a FT-Raman spectra having characteristic peaks expressed in cm$^{-1}$ (±2 cm$^{-1}$) at 708, 1555 and 2230.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9 and exhibits a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9 and 15.2 and exhibits a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9 and 15.2 and exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in $cm^{-1}$ (±2 $cm^{-1}$) at 708 and 2230 and exhibits a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in $cm^{-1}$ (±2 $cm^{-1}$) at 708 and 2230 and exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in $cm^{-1}$ (±2 $cm^{-1}$) at 708, 1555 and 2230 and exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9, a FT-Raman spectra having characteristic peaks expressed in $cm^{-1}$ (±2 $cm^{-1}$) at 708 and 2230 and exhibits a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9, a FT-Raman spectra having characteristic peaks expressed in $cm^{-1}$ (±2 $cm^{-1}$) at 708 and 2230 and exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9 and 15.2, a FT-Raman spectra having characteristic peaks expressed in $cm^{-1}$ (±2 $cm^{-1}$) at 708, 1555 and 2230 and exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9 and exhibits either a FT-Raman spectra having one or more characteristic peaks expressed in $cm^{-1}$ (±2 $cm^{-1}$) selected from the group consisting of 708, 1555 and 2230; and/or a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in $cm^{-1}$ (±2 $cm^{-1}$) at 708 and 2230 and exhibits either an X-ray powder diffraction pattern having one or more characteristic peaks expressed in degrees 2-theta (±0.2° 2-theta) selected from the group consisting of 7.8, 10.9, 15.2, 17.1, 17.3, and 18.5; and/or a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a solid state NMR spectra having a characteristic peak expressed in ppm (±0.2 ppm) at 136.6 and exhibits either an X-ray powder diffraction pattern having one or more characteristic peaks expressed in degrees 2-theta (±0.2° 2-theta) selected from the group consisting of 7.8, 10.9, 15.2, 17.1, 17.3, and 18.5; and/or exhibits a FT-Raman spectra having one or more characteristic peaks expressed in $cm^{-1}$ (±2 $cm^{-1}$) selected from the group consisting of 708, 1555 and 2230.

In a preferred embodiment, the crystalline form of 6-[(4R)-4-methyl-1,1-dioxido-1,2,6-thiadiazinan-2-yl]isoquinoline-1-carbonitrile is anhydrous.

As used herein, the term "anhydrous" shall be taken to mean that the crystalline form contains less than about 5% w/w, more preferably less than about 1% w/w and even more preferably less than about 0.5% w/w of the solvent of crystallization or water. In another embodiment the term "anhydrous" shall be taken to mean that the crystalline form contains less than about 1% w/w of the solvent of crystallization or water.

A crystalline form of 6-[(4R)-4-methyl-1,1-dioxido-1,2,6-thiadiazinan-2-yl]isoquinoline-1-carbonitrile, including crystalline 6-[(4R)-4-methyl-1,1-dioxido-1,2,6-thiadiazinan-2-yl]isoquinoline-1-carbonitrile Form (1), can be prepared by crystallization of 6-[(4R)-4-methyl-1,1-dioxido-1,2,6-thiadiazinan-2-yl]isoquinoline-1-carbonitrile from a solvent, preferably a solvent comprising acetone or, in an alternative embodiment, from a solvent comprising acetone and water. In one embodiment the solvent is acetone. In another embodiment the solvent is acetone and water. The crystalline form so prepared can be further dried, preferably under vacuum, to form the anhydrous form.

The method of the present invention relates to a method for treating and/or preventing a disorder or condition in a subject, wherein the disorder or condition is related to dysregulation of the androgen receptor in a subject, which method comprises administering to said subject an effective amount of a compound of Formula 1, Formula 2 or Formula 3, as defined herein, or a pharmaceutically acceptable salt thereof.

As used herein, throughout the application, the term "therapeutically effective" is intended to qualify the amount of compound or pharmaceutical compositions, or the combined amount of active ingredients in the case of combination therapy. This amount, or combined amount, will achieve the goal of treating the relevant condition.

As used herein throughout the application, the term "treat," "treatment" or "treating" shall be taken to mean administration of the compound, pharmaceutical composition or combination to effect preventative, palliative, supportive, restorative or curative treatment. The term "treatment" encompasses any objective or subjective improvement in a subject with the relevant condition or disease.

As used herein throughout the application, the term "preventative treatment", "prevent", "preventing" or "prevention" shall be taken to mean that the compound, pharmaceutical composition or combination is administered to a subject to inhibit or stop the relevant condition from occurring in a subject, particularly in a subject or member of a population that is significantly predisposed to the relevant condition.

In some embodiments, the compound of Formula 1, Formula 2 or Formula 3, or pharmaceutically acceptable salts thereof, possess in vivo tissue selective androgenic and anabolic activity, which is accordingly utilized for particular applications, as will be appreciated by one skilled in the art.

In one embodiment, the methods of this invention are useful for treating a subject which is a human. In another embodiment, the subject is a mammal. In another embodiment the subject is an animal. In another embodiment the subject is an invertebrate. In another embodiment the subject is a vertebrate. In one embodiment, the subject is male. In another embodiment, the subject is female. In some embodiments, while the methods as described herein may be useful for treating either males or females, females may respond more advantageously to administration of certain compounds, for certain methods, as described and exemplified herein.

Disorders or conditions related to dysregulation of the androgen receptor can be appreciated by one skilled in the art. These disorders or conditions include, but are not limited to, those described herein in further detail. Each disorder or condition described herein is considered to be a separate embodiment of the invention and disclosure. Unless otherwise specified, the definitions, descriptions, derivatives and preferred embodiments of disorders or conditions related to the dysregulation of the androgen receptor set out below, are to be considered equally useful and applicable to all embodiments set out herein which comprise disorders or conditions related to dysregulation of the androgen receptor.

In one aspect, the disorder or condition is associated with a subject having anemia. In one embodiment, "anemia" refers to the condition of having less than the normal number of red blood cells or less than the normal quantity of hemoglobin in the blood, reduced hematocrit or reduced mean corpuscular volume, or reduced corpuscular size. The oxygen-carrying capacity of the blood is decreased in anemia. In some embodiments, treating anemia may also refer herein to treating underlying factors resulting in anemia, such as for example: a) hemorrhage (bleeding); b) hemolysis (excessive destruction of red blood cells); c) underproduction of red blood cells; and d) not enough normal hemoglobin. In some embodiments, treating anemia in this invention refers to treating any form thereof, including aplastic anemia, benzene poisoning, Fanconi anemia, hemolytic disease of the newborn, hereditary spherocytosis, iron deficiency anemia, osteoporosis, pernicious anemia, sickle cell disease, aplastic anemia, hemolytic anemia, sickle cell anemia, renal anemia, thalassemia, myelodysplastic syndrome, and a variety of bone marrow diseases.

In another embodiment, the disorder or condition is one or more of the following a) treating a bone related disorder; b) preventing a bone related disorder; c) suppressing a bone related disorder; d) inhibiting a bone related disorder; e) increasing a strength of a bone of a subject; f) increasing a bone mass in a subject; or g) use for osteoclastogenesis inhibition. In particular, one embodiments provides for a) accelerate bone repair; b) treating bone disorders; c) treating bone density loss; d) treating low bone mineral density (BMD); e) treating reduced bone mass; f) treating metabolic bone disease; g) promoting bone growth or regrowth; h) promoting bone restoration; i) promoting bone fracture repair; j) promoting bone remodeling; k) treating bone damage following reconstructive surgery including of the face, hip, or joints; l) enhancing of bone strength and function; m) increasing cortical bone mass; or n) increasing trabecular connectivity.

In one embodiment, the bone related disorder is a genetic disorder, or in another embodiment, is induced as a result of a treatment regimen for a given disease. For example, and in one embodiment, the compounds of Formula 1, Formula 2 or Formula 3, or pharmaceutically acceptable salts thereof, as herein described are useful in treating a bone-related disorder that arises as a result of cancer metastasis to bone, or in another embodiment, as a result of androgen-deprivation therapy, for example, given in response to prostate carcinogenesis in the subject. In one embodiment, the bone-related disorder is osteoporosis. In another embodiment, the bone-related disorder is osteopenia. In another embodiment, the bone-related disorder is increased bone resorption. In another embodiment, the bone-related disorder is bone fracture. In another embodiment, the bone-related disorder is bone frailty. In another embodiment, the bone-related disorder is a loss of bone mineral density (BMD). In another embodiment, the bone-related disorder is any combination of osteoporosis, osteopenia, increased bone resorption, bone fracture, bone frailty and loss of BMD. Each disorder represents a separate embodiment of the present invention.

"Osteoporosis" refers, in one embodiment, to a thinning of the bones with reduction in bone mass due to depletion of calcium and bone protein. In another embodiment, osteoporosis is a systemic skeletal disease, characterized by low bone mass and deterioration of bone tissue, with a consequent increase in bone fragility and susceptibility to fracture. In osteoporotic patients, bone strength is abnormal, in one embodiment, with a resulting increase in the risk of fracture. In another embodiment, osteoporosis depletes both the calcium and the protein collagen normally found in the bone, in one embodiment, resulting in either abnormal bone quality or decreased bone density. In another embodiment, bones that are affected by osteoporosis can fracture with only a minor fall or injury that normally would not cause a bone fracture. The fracture can be, in one embodiment, either in the form of cracking (as in a hip fracture) or collapsing (as in a compression fracture of the spine). The spine, hips, and wrists are common areas of osteoporosis-induced bone fractures, although fractures can also occur in other skeletal areas. Unchecked osteoporosis can lead, in another embodiment, to changes in posture, physical abnormality, and decreased mobility.

Osteoporosis may result from androgen deprivation. Accordingly, in another embodiment, the osteoporosis follows androgen deprivation. In another embodiment, the osteoporosis is primary osteoporosis. In another embodiment, the osteoporosis is secondary osteoporosis. In another embodiment, the osteoporosis is postmenopausal osteoporosis. In another embodiment, the osteoporosis is juvenile osteoporosis. In another embodiment, the osteoporosis is idiopathic osteoporosis. In another embodiment, the osteoporosis is senile osteoporosis.

"Sarcopenia" in one embodiment refers to the degenerative loss of skeletal muscle mass, quality and strength associated with aging, In one embodiment sarcopenia is a component of the fraility syndrome, It may be characterized by attributes such as muscle atrophy alone or in conjunction with one or more additional attributes such as was reduction in muscle tissue quality characterized by such factors such as replacement of muscle fibres with fat, an increase in fibrosis, changes in muscle metabolism, oxidative stress and degeneration of the neuromuscular junction, one or more of which can lead to progressive loss of muscle function and frailty. In one embodiment the sarcopenia is in chronic obstructive pulmonary disease.

In another aspect, the disorder or condition relates to reducing the incidence, delaying the onset or progression, or reducing and/or abrogating the symptoms associated with a musculoskeletal disease in a subject.

In one embodiment, the skeletal-related events treated using the methods provided herein provided herein, are fractures, which in one embodiment, are pathological fractures, non-traumatic fractures, vertebral fracture, non-vertebral fractures, morphometric fractures, or a combination thereof. In some embodiments, fractures may be simple, compound, transverse, greenstick, or comminuted fractures. In one embodiment, fractures may be to any bone in the body, which in one embodiment, is a fracture in any one or more bones of the arm, wrist, hand, finger, leg, ankle, foot, toe, hip, collar bone, or a combination thereof. In another embodiment, the methods and/or compounds or compositions provided herein, are effective in treatment, prevention, suppression, inhibition or reduction of the risk of skeletal-related events such as pathologic fractures, spinal cord compression, hypercalcemia, bone-related pain, or their combination.

In another embodiment, the skeletal-related events sought to be treated using the methods provided herein and/or utilizing the compositions provided herein, comprise the necessity for bone surgery and/or bone radiation, which in some embodiments, is for the treatment of pain resulting in one embodiment from bone damage, or nerve compression. In another embodiment, the skeletal-related events sought to be treated using the methods provided herein and/or utilizing the compositions provided herein, comprise spinal cord compression, or the necessity for changes in antineoplastic therapy, including changes in hormonal therapy, in a subject. In some embodiments, skeletal-related events sought to be treated using the methods provided herein and/or utilizing the compositions provided herein, comprise treating, suppressing, preventing, reducing the incidence of, or delaying progression or severity of bone metastases, or bone loss. In one embodiment, bone loss may comprise osteoporosis, osteopenia, or a combination thereof. In one embodiment, skeletal-related events may comprise any combination of the embodiments listed herein.

In one embodiment, the skeletal-related events are a result of cancer therapy. In one embodiment, the skeletal-related events are a result of hormone deprivation therapy, while in another embodiment, they are a product of androgen deprivation therapy (ADT). In some embodiments, musculoskeletal diseases comprise achondroplasia, acquired hyperostosis syndrome, acrocephalosyndactylia, arthritis, arthrogryposis, arthropathy, neurogenic bursitis, cartilage diseases, cleidocranial dysplasia, clubfoot, compartment syndromes, craniofacial dysostosis, craniosynostoses, dermatomyositis, Dupuytren's contracture, dwarfism, Ellis Van Creveld syndrome, enchondromatosis, eosinophilia-myalgia syndrome, exostoses, fasciitis, fatigue syndrome, fibromyalgia, fibrous dysplasia of bone, fibrous dysplasia, polyostotic, flatfoot, foot deformities, Freiberg's disease, funnel chest, Goldenhar syndrome, gout, hallux valgus, hip dislocation, hyperostosis, intervertebral disk displacement, kabuki make-up syndrome, Klippel-Feil syndrome, Langer-Giedion syndrome, Legg-Perthes disease, lordosis, mandibulofacial dysostosis, melorheostosis, mitochondrial myopathies, muscle cramp, muscle spasticity, muscular dystrophies, musculoskeletal abnormalities, musculoskeletal diseases, myositis, myositis ossificans, myotubular myopathy, osteitis deformans, osteoarthritis, osteochondritis, osteogenesis imperfecta, osteomyelitis, osteonecrosis, osteopetrosis, osteoporosis, poland syndrome, polychondritis, relapsing, polymyalgia rheumatica, polymyositis, rhabdomyolysis, rheumatic diseases, Russell silver syndrome, Scheuermann's disease, scoliosis, Sever's disease/calceneal apophysitis, spinal diseases, spinal osteophytosis, spinal stenosis, spondylitis, ankylosing, spondylolisthesis, sprengel's deformity, synovitis, tendinopathy, tennis elbow, tenosynovitis, thanatophoric dysplasia, or Tietze's syndrome.

A muscle is a tissue of the body that primarily functions as a source of power. There are three types of muscles in the body: a) skeletal muscle—the muscle responsible for moving extremities and external areas of the bodies; b) cardiac muscle—the heart muscle; and c) smooth muscle—the muscle that is in the walls of arteries and bowel. A wasting condition or disorder is defined herein as a condition or disorder that is characterized, at least in part, by an abnormal, progressive loss of body, organ or tissue mass. A wasting condition can occur as a result of a pathology such as, for example, cancer, or an infection, or it can be due to a physiologic or metabolic state, such as disuse deconditioning that can occur, for example, due to prolonged bed rest or when a limb is immobilized, such as in a cast. A wasting condition can also be age associated. The loss of body mass that occurs during a wasting condition can be characterized by a loss of total body weight, or a loss of organ weight such as a loss of bone or muscle mass due to a decrease in tissue protein.

In another aspect, the disorder or condition is muscle atrophy or a wasting condition or disorder. In one embodiment, therefore, the invention provides for the treatment of wasting diseases, including but not limited to, muscle injury, bed rest, immobility, nerve injury, neuropathy, diabetic neuropathy, alcoholic neuropathy, anorexia, anorexia nervosa, anorexia associated with cachexia, anorexia associated with aging, subacute combined degeneration of the spinal cord, diabetes, rheumatoid arthritis, motor neurone diseases, Duchenne muscular dystrophy, carpal tunnel syndrome, chronic infection, tuberculosis, Addison's disease, adult sma, limb muscle atrophy, back tumour, dermatomyositis, hip cancer, inclusion body myositis, incontinentia pigmenti, intercostal neuralgia, juvenile rheumatoid arthritis, Legg-Calve-Perthes disease, muscle atrophy, multifocal motor neuropathy, nephrotic syndrome, osteogenesis imperfecta, post-polio syndrome, rib tumor, spinal muscular atrophy, reflex sympathetic dystrophy syndrome, or Tay-Sachs.

In one embodiment, the terms "muscle wasting" or "muscular wasting", refer to the progressive loss of muscle mass and/or to the progressive weakening and degeneration of muscles, including the skeletal or voluntary muscles which control movement, cardiac muscles which control the heart, and smooth muscles. In one embodiment, the muscle wasting condition or disorder is a chronic muscle wasting condition or disorder. "Chronic muscle wasting" is defined herein as the chronic (i.e. persisting over a long period of time) progressive loss of muscle mass and/or to the chronic progressive weakening and degeneration of muscle. Muscle wasting can occur as a result of a pathology, disease, condition or disorder. In one embodiment, the pathology, illness, disease or condition is chronic. In another embodiment, the pathology, illness, disease or condition is genetic.

The loss of muscle mass that occurs during muscle wasting can be characterized by a muscle protein breakdown or degradation, by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass and to muscle wasting. The term "catabolism" has its commonly known meaning in the art, specifically an energy burning form of metabolism.

In a particular aspect, the disorder or condition associated with the present invention is muscle atrophy or wasting associated with disuse, trauma, immobilization, spinal cord injury, or stroke comprising administering to a patient in need thereof an effective amount of a compound of the present invention. Even more particularly, the disorder or condition associated with the present invention is muscle atrophy associated with hip or knee replacement, hip fracture, spinal cord injury, or stroke.

In another embodiment, the pathology, illness, disease or condition of muscle wasting or muscular wasting is neurological. In another embodiment, the pathology, illness, disease or condition is infectious. As described herein, the pathologies, diseases, conditions or disorders for which the compounds and compositions of the present invention are administered are those that directly or indirectly produce a wasting (i.e. loss) of muscle mass, that is a muscle wasting disorder.

In one embodiment, muscle wasting in a subject is a result of the subject having a muscular dystrophie; muscle atrophy; X-linked spinal-bulbar muscular atrophy (SBMA). In some embodiments, muscle loss or muscle wasting or cachexia in a subject results in reduced protein reserves, decreased strength and functional capacity, frailty, falls, reduced aerobic capacity, reduced energy requirements or increased mortality in patients and the methods of this invention serve to treat these conditions, as well. In some embodiments, muscle loss or muscle wasting or cachexia in a subject results in increased dietary protein needs, inflammation (accelerated muscle protein breakdown), loss of motor units (aging CNS), reduced rate of muscle protein synthesis (post-prandial), and/or changing endocrine function (testosterone, estrogen, growth hormone, insulin resistance) and the methods of this invention serve to treat these conditions, as well.

If the condition or disorder is a muscular dystrophy, it includes, but is not limited to, genetic diseases characterized by progressive weakness and degeneration of the skeletal or voluntary muscles that control movement. The muscles of the heart and some other involuntary muscles are also affected in some forms of muscular dystrophy. The major forms of muscular dystrophy (MD) are: duchenne muscular dystrophy, myotonic dystrophy, duchenne muscular dystrophy, becker muscular dystrophy, limb-girdle muscular dystrophy, facioscapulhumeral muscular dystrophy, congenital muscular dystrophy, oculopharyngeal muscular dystrophy, distal muscular dystrophy and emery-dreifuss muscular dystrophy. Muscular dystrophy can affect people of all ages. Although some forms first become apparent in infancy or childhood, others may not appear until middle age or later. Duchenne MD is the most common form, typically affecting children. Myotonic dystrophy is the most common of these diseases in adults. Muscle atrophy (MA) is characterized by wasting away or diminution of muscle and a decrease in muscle mass. For example, Post-Polio MA is a muscle wasting that occurs as part of the post-polio syndrome (PPS). The atrophy includes weakness, muscle fatigue, and pain.

In another aspect the disorder or condition is a muscular atrophy. Muscular atrophy includes, but is not limited to, those muscular atrophies which are X-linked spinal-bulbar muscular atrophy (SBMA—also known as Kennedy's Disease). This disease arises from a defect in the androgen receptor gene on the X chromosome, affects only males, and its onset is in adulthood. Because the primary disease cause is an androgen receptor mutation, androgen replacement is not a current therapeutic strategy. There are some investigational studies where exogenous testosterone propionate is being given to boost the levels of androgen with hopes of overcoming androgen insensitivity and perhaps provide an anabolic effect. Still, use of supraphysiological levels of testosterone for supplementation will have limitations and other potentially serious complications.

Sarcopenia a debilitating disease that afflicts the elderly and chronically ill patients and is characterized by loss of muscle mass and function. Further, increased lean body mass is associated with decreased morbidity and mortality for certain muscle-wasting disorders. In addition, other circumstances and conditions are linked to, and can cause muscle wasting disorders. For example, studies have shown that in severe cases of chronic lower back pain, there is paraspinal muscle wasting.

Muscle wasting and other tissue wasting is also associated with advanced age. It is believed that general weakness in old age is due to muscle wasting. As the body ages, an increasing proportion of skeletal muscle is replaced by fibrous tissue. The result is a significant reduction in muscle power, performance and endurance.

Long term hospitalization due to illness or injury, or disuse deconditioning that occurs, for example, when a limb is immobilized, can also lead to muscle wasting, or wasting of other tissue. Studies have shown that in patients suffering injuries, chronic illnesses, burns, trauma or cancer, who are hospitalized for long periods of time, there is a long-lasting unilateral muscle wasting, and a decrease in body mass.

Injuries or damage to the central nervous system (CNS) are also associated with muscle wasting and other wasting disorders. Injuries or damage to the CNS can be, for example, caused by diseases, trauma or chemicals. Examples are central nerve injury or damage, peripheral nerve injury or damage and spinal cord injury or damage. In one embodiment CNS damage or injury comprise Alzheimer's diseases (AD); anger (mood); anorexia, anorexia nervosa, anorexia associated with aging and/or assertiveness (mood).

In another embodiment, the disorder or condition is muscle wasting or other tissue wasting which occurs as a result of alcoholism. In one embodiment, the wasting disease, disorder or condition being treated is associated with chronic illness. In some embodiments, wasting diseases or disorders, such as cachexia; malnutrition, tuberculosis, leprosy, diabetes, renal disease, chronic obstructive pulmonary disease (COPD), cancer, end stage renal failure, sarcopenia, emphysema, osteomalacia, or cardiomyopathy, may be treated by the methods of this invention. In some embodiments, wasting is due to infection with enterovirus, Epstein-Ban virus, herpes zoster, HIV, trypanosomes, influenze, coxsackie, rickettsia, trichinella, schistosoma or mycobacteria, and this invention, in some embodiments, provides methods of treatment thereof.

Cachexia is weakness and a loss of weight caused by a disease or as a side effect of illness. Cardiac cachexia, i.e. a muscle protein wasting of both the cardiac and skeletal muscle, is a characteristic of congestive heart failure. Cancer cachexia is a syndrome that occurs in patients with solid tumors and hematological malignancies and is manifested by weight loss with massive depletion of both adipose tissue and lean muscle mass. Cachexia is also seen in acquired immunodeficiency syndrome (AIDS), human immunodeficiency virus (HIV)-associated myopathy and/or muscle weakness/wasting is a relatively common clinical manifestation of AIDS. Individuals with HIV-associated myopathy or muscle weakness or wasting typically experience significant weight loss, generalized or proximal muscle weakness, tenderness, and muscle atrophy.

Accordingly, in one particular aspect, the disorder or condition which is treated or prevented in methods of the present invention includes treating and/or reducing the severity of, reducing the incidence of, or reducing pathogenesis of cachexia and/or cachexia associated with cancer in a subject. In another embodiment, the cancer is selected from, but not limited to, adrenocortical carcinoma anal cancer, bladder cancer, brain tumor, brain stem glioma, brain tumor, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, ewings family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, small cell lung cancer, non small cell lung cancer, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof.

In a further aspect, the disorder or condition of the method of the present invention is cancer in a subject, including, but not limited to, reduction of incidence or severity or pathogenesis of a cancer in a subject, delaying progression, prolonging remission or delaying onset of cancer in a subject. In some embodiments, such cancers are hormone-dependent or associated with reproductive tissue in males or females, such as cancer of the prostate, ovary, breast, uterus, testicle, or others. In one embodiment, the method provides for the treatment of a precancerous precursor or lesion in a subject and/or reduction of incidence of precancerous precursors or lesions in a subject. In some embodiments, such precancerous precursors are found in hormone-responsive tissue or are associated with reproductive tissue in males or females, such as in the prostate, ovary, breast, uterus, testicle, or others. In some embodiments, such precancerous precursors comprise any local intraepithelial neoplasia, for example, of the prostate, the cervix, etc. In some embodiments, such methods are useful in treating neoplasia or pre-neoplasia, dysplasia or hyperplasia in a tissue, such as in reproductive tissue in males or females. In one embodiment, the cancer is prostate cancer.

In one embodiment, the method provides for treating and/or preventing, including reducing the severity of, reducing the incidence of, delaying the onset of, lung cancer, which in one preferred embodiment is non-small cell lung cancer. In another aspect, the method provides for treating and/or preventing, including reducing the severity of, reducing the incidence of, delaying the onset of, cachexia or other conditions arising as a result of lung cancer in the subject, which in one preferred embodiment is non-small cell lung cancer. In another aspect, the method provides for treating and/or preventing, including reducing the severity of, reducing the incidence of, or reducing pathogenesis of, cancer. In another embodiment, the cancer, includes but is not limited to, androgen AR dependent tumors (malignant or benign) such as prostate cancer, breast cancer (male or female, operable or inoperable), bladder cancers; brain cancers; bone tumors, colon cancer, endometrial cancer, liver cancer, lung cancer, lymphatic cancer, kidney cancer, osteosarcoma cancer, ovarian cancer, pancreas cancer, penis cancer, skin cancer, thyroid cancer; and/or hormone-dependent cancers.

In one embodiment, the disorder or condition associated with the methods provided herein are reducing cancer metastases to the bone, such as in terms of number of foci, the size of foci, or a combination thereof.

In another aspect, the disorder or condition associated with the methods herein is benign prostate hyperplasia (BPH). "BPH (benign prostate hyperplasia)" is a nonmalignant enlargement of the prostate gland, and is the most common non-malignant proliferative abnormality found in any internal organ and the major cause of morbidity in the adult male. BPH occurs in over 75% of men over 50 years of age, reaching 88% prevalence by the ninth decade. BPH frequently results in a gradual squeezing of the portion of the urethra which traverses the prostate (prostatic urethra). This causes patients to experience a frequent urge to urinate because of incomplete emptying of the bladder and urgency of urination. The obstruction of urinary flow can also lead to a general lack of control over urination, including difficulty initiating urination when desired, as well as difficulty in preventing urinary flow because of the inability to empty urine from the bladder, a condition known as overflow urinary incontinence, which can lead to urinary obstruction and to urinary failure. Accordingly, an embodiment of the invention includes the method for treating and/or preventing benign prostate hyperplasia (BPH) in a subject. Another embodiment includes a method for treating and/or preventing, including all embodiments encompassed by the term, prostatitis.

According to a further aspect, the disorder or condition of the methods of treatment and/or prevention herein is one or more symptoms associated with a respiratory tract disease in a subject. Such respiratory tract diseases include, but are not limited to, airway obstruction, apnea, asbestosis, asthma, atelectasis, berylliosis, bronchial diseases, bronchiectasis, bronchiolitis, bronchiolitis obliterans organizing pneumonia, bronchitis, bronchopulmonary dysplasia, common cold, cough, empyema, pleural, epiglottitis, hemoptysis, hypertension, pulmonary, hyperventilation, Kartagener syndrome, lung abscess, lung diseases, meconium aspiration syndrome, pleural effusion, pleurisy, pneumonia, pneumothorax, pulmonary alveolar proteinosis, pulmonary disease, chronic obstructive, pulmonary edema, pulmonary embolism, pulmonary emphysema, pulmonary fibrosis, respiratory distress syndrome, newborn-respiratory hypersensitivity, respiratory tract infections, rhinoscleroma, scimitar syndrome, severe acute respiratory syndrome, silicosis, sleep apnea, central stridor, tracheal stenosis, Wegener's granulomatosis, or whooping cough.

According to another aspect, the disorder or condition of the methods of treatment and/or prevention, including reducing the incidence, delaying the onset or progression, or reducing and/or abrogating, is the symptoms associated with an otorhinolaryngologic disease in a subject, such otorhinolaryngologic diseases, include, but are not limited to, cholesteatoma, middle ear, croup, deafness, epistaxis, hearing loss, hyperacusis, labyrinthitis, laryngitis, laryngomalacia, laryngostenosis, mastoiditis, Meniere's disease, nasal obstruction, nasal polyps, otitis, otorhinolaryngologic diseases, otosclerosis, pharyngitis, presbycusis, retropharyngeal abscess, rhinitis, sinusitis, tinnitus, tonsillitis, tympanic membrane perforation, vestibular neuronitis, vocal cord paralysis, or voice disorders.

According to a further aspect, the disorder or condition associated with the methods of the invention herein is the treatment or prevention of diseases or disorders caused by, or associated with a hormonal disorder, disruption or imbalance. In particular, in one embodiment, the hormonal disorder, disruption or imbalance comprises an excess of a hormone. In another embodiment, the hormonal disorder, disruption or imbalance comprises a deficiency of a hormone. In one embodiment, the hormone is a steroid hormone. In another embodiment, the hormone is an estrogen. In another embodiment, the hormone is an androgen. In another embodiment, the hormone is a glucocorticoid. In another embodiment, the hormone is a cortico-steroid. In another embodiment, the hormone is Luteinizing Hormone (LH). In another embodiment, the hormone is Follicle Stimulating Hormone (FSH). In another embodiment, the hormone is any other hormone known in the art. In another embodiment, the hormonal disorder, disruption or imbalance is associated with menopause. In another embodiment, the hormonal disorder, disruption or imbalance is associated with andropause, andropausal vasomotor symptoms, andropausal gynecomastia, muscle strength and/or function, bone strength and/or function and anger. In another embodiment, hormone deficiency is a result of specific manipulation, as a byproduct of treating a disease or disorder in the subject. For example, the hormone deficiency may be a result of androgen depletion in a subject, as a therapy for prostate cancer in the subject. Each possibility represents a separate embodiment of the present invention.

According to another aspect, the disorder or condition associated with the methods of the invention herein is the treatment or prevention of, including reversing the adverse effects of, androgen deprivation therapy (ADT). The present invention further provides a method for the reversal, treatment, or prevention of the adverse effects of ADT in a patient comprising administering to a patient in need of such treatment or prevention an effective amount of a compound of the present invention, or a pharmaceutically acceptable salt thereof.

In one embodiment of this invention, a method is provided for hormone replacement therapy in a patient (i.e., one suffering from an androgen-dependent condition). For example, androgen-dependent conditions which may be treated with the compounds and/or compositions as herein described, comprising the methods of the present invention include those conditions which are associated with aging, hypogonadism, sarcopenia, diminished erythropoiesis, osteoporosis, and any other conditions dependent upon low androgen (e.g., testosterone) or estrogen levels. In one embodiment, the Androgen-dependent conditions that may be treated with the compounds and/or compositions as herein described, may comprise conditions characterized by elevated androgen or estrogen levels, including hirsutism, infertility, polycystic ovarian syndrome, endometrial carcinoma, breast cancer, male pattern baldness, prostate cancer, testicular cancer, and others, as will be known to one skilled in the art. For such conditions, the subject may be administered a SARM as herein described, alone or in combination with another therapeutic agent, as will be appreciated by one skilled in the art.

Studies involving patients with spinal cord injuries (SCI) have shown that central neurotransmitters may be altered after SCI causing hypothalamus-pituitary-adrenal axis dysfunction, whose disruption led to a significant decrease in testosterone and other hormone levels. SCI or other acute illness or trauma characteristically includes heightened catabolism in conjunction with the lowered anabolic activity resulting in a condition that is prone to loss of lean body tissue, which is often accompanied by disturbed nutrient utilization. The effects of the loss of lean body mass include the development of wounds and impaired healing mechanisms, further compounding the problem. Because of poor nutrition and protein combined with immobilization, patients with spinal cord injury are at high risk for bed sores.

In another aspect, the disorder or condition associated with the methods herein is the treatment of a wide variety of injuries of the CNS. CNS injury may refer, in one embodiment, to a breakdown of the membrane of a nerve cell, or, in another embodiment, to the inability of the nerve to produce and propagate nerve impulses, or in another embodiment, to the death of the cell. An injury includes damage that directly or indirectly affects the normal functioning of the CNS. The injury may be a structural, physical, or mechanical impairment and may be caused by physical impact, as in the case of a crushing, compression, or stretching of nerve fibers. Alternatively, the cell membrane may be destroyed by or degraded by an illness, a chemical imbalance, or a physiological malfunction such as anoxia (e.g., stroke), aneurysm, or reperfusion. A CNS injury includes, for example and without limitation, damage to retinal ganglion cells, a traumatic brain injury, a stroke-related injury, a cerebral aneurism-related injury, a spinal cord injury, including monoplegia, diplegia, paraplegia, hemiplegia and quadriplegia, a neuroproliferative disorder, or neuropathic pain syndrome. With injury to the spinal cord of a mammal, connections between nerves in the spinal cord are broken. Such injuries block the flow of nerve impulses for the nerve tracts affected by the injury, with a resulting impairment to both sensory and motor function. Injuries to the spinal cord may arise from compression or other contusion of the spinal cord, or a crushing or severing of the spinal cord. A severing of the spinal cord, also referred to herein as a "transection," may be a complete severing or, may be an incomplete severing of the spinal cord. In some embodiments, injuries or damage to the CNS may be associated with muscle wasting disorders. Injuries or damage to the CNS can be, for example, caused by diseases, trauma or chemicals. Examples are central nerve injury or damage, peripheral nerve injury or damage and spinal cord injury or damage. These include, but are not limited to, cranial nerve diseases such as bell palsy, cranial nerve diseases, facial hemiatrophy, facial neuralgia, glossopharyngeal nerve diseases, Moebius syndrome, or trigeminal neuralgia.

In some embodiments, demyelinating diseases comprise adrenoleukodystrophy, alexander disease, canavan disease, demyelinating disease, diffuse cerebral sclerosis of schilder, leukodystrophy-globoid cell, leukodystrophy-metachromatic, multiple sclerosis, or neuromyelitis optica. In some embodiments, nervous system malformations comprise Arnold-Chiari malformation, Charcot-Marie-Tooth disease, encephalocele, hereditary motor and sensory neuropathies, septo-optic dysplasia, spina bifida occulta, or spinal dysraphism. In some embodiments, neurologic manifestations comprise agnosia, amnesia, anomia, aphasia, apraxias, back pain, Brown-Sequard syndrome, cerebellar ataxia, chorea, communication disorders, confusion, dizziness, dyslexia, dystonia, facial paralysis, fasciculation, gait disorders, neurologic-headache, hemiplegia, memory disorders, mental retardation, mutism, myoclonus, neck pain, nonverbal learning disorder, olfaction disorders, pain, paralysis, phantom limb, prosopagnosia, quadriplegia, seizures, spasm, speech disorders, synesthesia tardive dyskinesia, taste disorders, torticollis, tremor, trismus, unconsciousness, or vertigo. In some embodiments, neuromuscular diseases comprise. amyotrophic lateral sclerosis, brachial plexus neuritis, brachial plexus neuropathies, bulbar palsy, carpal tunnel syndrome, cubital tunnel syndrome, diabetic neuropathies, dysautonomia, guillain, barre syndrome, hereditary sensory and autonomic neuropathies, miller fisher syndrome, motor neuron disease, muscular atrophy, spinal, myasthenia gravis, myopathies, structural, congenital, nerve compression syndromes, neuralgia, neuromuscular diseases, paralyses, familial periodic, peripheral nervous system diseases, poems syndrome, polyneuropathies, polyradiculopathy, refsum disease, sciatica, spinal muscular atrophies of childhood, stiff-person syndrome, thoracic outlet syndrome, or ulnar nerve compression syndromes.

In a further aspect, the disorder or condition associated with the methods of the present invention includes treating and/or preventing, including reducing the incidence, delaying the onset or progression, or reducing and/or abrogating the symptoms associated with, an ophthalmic disease in a subject.

In some embodiments ophthalmic disease comprise acute zonal occult outer retinopathy, Adie syndrome, albinism, ocular-amaurosis, fugax, amblyopia, aniridia, anisocoria, anophthalmos, aphakia, astigmatism, blepharitis, blepharoptosis, blepharospasm, blindness, cataract, chalazion, chorioretinitis, choroideremia, coloboma, color vision defects, conjunctivitis, corneal diseases, corneal dystrophies, corneal edema, corneal ulcer, diabetic retinopathy, diplopia, distichiasis, dry eye syndromes, Duane retraction syndrome, ectropion, entropion, esotropia, exfoliation syndrome, exotropia, eye hemorrhage, eye neoplasms, eyelid diseases, floaters, general fibrosis syndrome, glaucoma, gyrate atrophy, hemianopsia, Hermanski-Pudlak syndrome, hordeolum, Horner syndrome, hyperopia, hyphema, iritis, Kearns-Sayer syndrome, keratitis, keratoconus, lacrimal apparatus diseases, lacrimal duct obstruction, lens diseases, macular degeneration, microphthalmos, myopia, nystagmus, pathologic, ocular motility disorders, oculomotor nerve diseases, ophthalmoplegia, optic atrophies, optic nerve diseases, optic neuritis, optic neuropathy, orbital cellulitis, papilledema, peter's anomaly, presbyopia, pterygium, pupil disorders, refractive errors, retinal detachment, retinal diseases, retinal vein occlusion, retinitis pigmentosa, retinopathy of prematurity, retinoschisis, scleritis, scotoma, strabismus, Thygeson's superficial punctate keratitis, trachoma, uveitis, white dot syndrome, vision disorders, or vitreous disorders.

In another aspect, the disorder or condition associated with the methods of the present invention includes treating and/or preventing, including reducing the incidence, delaying the onset or progression, or reducing and/or abrogating the symptoms associated with a nervous system disease in a subject, such nervous system diseases, including but not limited to, autonomic nervous system diseases, central nervous system diseases, cranial nerve diseases, demyelinating diseases, nervous system malformations, neurologic manifestations, or neuromuscular diseases. In another embodiment, autonomic nervous system diseases comprise causalgia, or reflex sympathetic dystrophy. In another embodiment, central nervous system diseases comprise Alzheimer's disease, arachnoiditis, brain abscess, brain ischemia, central nervous system infections, cerebral palsy, cerebrovascular disorders, corticobasal ganglionic degeneration (CBGD), Creutzfeldt-Jakob syndrome, Dandy-Walker syndrome, dementia, encephalitis, encephalomyelitis, epilepsy, epilepsy induced hypogonadal and/or hypermetabolic state, essential tremor, Friedreich ataxia, Gerstmann-Straussler-Scheinker disease, Hallervorden-Spatz syndrome, Huntington disease, hydrocephalus, hypoxia, insomnia, ischemic attack, kuru, Landau-Kleffner syndrome, Lewy Body disease, Machado-Joseph disease, meige syndrome, meningitis, bacterial meningitis, viral, migraine disorders, movement disorders, multiple system atrophy, myelitis, olivopontocerebellar atrophies, Parkinson's disease, parkinsonian disorders, poliomyelitis, post-poliomyelitis syndrome, prion diseases, pseudotumor cerebri, Shy-Drager syndrome, spasms, infantile, spinal cord diseases, supranuclear palsy, syringomyelia, thalamic diseases, tic disorders, tourette syndrome, or uveomeningoencephalitic syndrome. In some embodiments, the central nervous system disease is cystic fibrosis induced hypogonadal state. In one embodiment, methods of treating a subject with a nervous system disease encompass treating any secondary conditions in the subject, which arise due to the subject having a nervous system disease, some of which are described herein.

In a further aspect, the disorder or condition associated with methods of the invention includes treating hair loss, alopecia, androgenic alopecia, alopecia greata, alopecia secondary to chemotherapy, alopecia secondary to radiation therapy, alopecia induced by scarring or alopecia induced by stress. In one embodiment, "hair loss", or "alopecia", refers to baldness as in the very common type of male-pattern baldness. Baldness typically begins with patch hair loss on the scalp and sometimes progresses to complete baldness and even loss of body hair. Hair loss affects both males and females.

In another aspect, the disorder or condition associated with methods of the invention includes treating and/or preventing, including reducing the incidence, delaying the onset or progression, or reducing and/or abrogating the symptoms associated with, an infection in a subject. In some embodiments, infections comprise actinomycosis, anaplasmosis, anthrax, aspergillosis, bacteremia, bacterial mycoses, *bartonella* infections, botulism, brucellosis, *burkholderia* infections, *campylobacter* infections, candidiasis, cat-scratch disease, *chlamydia* infections, cholera, *clostridium* infections, coccidioidomycosis, cross infection, cryptococcosis, dermatomycoses, diphtheria, ehrlichiosis, *Escherichia coli* infections, fasciitis, necrotizing, *Fusobacterium* infections, gas gangrene, gram-negative bacterial infections, gram-positive bacterial infections, histoplasmosis, impetigo, *Klebsiella* infections, legionellosis, leprosy, leptospirosis, *Listeria* infections, lyme disease, maduromycosis, melioidosis, *mycobacterium* infections, *mycoplasma* infections, mycoses, *nocardia* infections, onychomycosis, plague, pneumococcal infections, *pseudomonas* infections, psittacosis, q fever, rat-bite fever, relapsing fever, rheumatic fever, *Rickettsia* infections, rocky mountain spotted fever, *salmonella* infections, scarlet fever, scrub typhus, sepsis, sexually transmitted diseases, Staphylococcal infections, Streptococcal infections, tetanus, tick-borne diseases, tuberculosis, tularemia, typhoid fever, typhus, louse-borne, *vibrio* infections, yaws, *yersinia* infections, zoonoses, zygomycosis, acquired immunodeficiency syndrome, adenoviridae infections, alphavirus infections, arbovirus infections, borna disease, bunyaviridae infections, caliciviridae infections, chickenpox, coronaviridae infections, coxsackievirus infections, cytomegalovirus infections, dengue, DNA virus infections, eethyma, contagious, encephalitis, arbovirus, Epstein-barr virus infections, erythema infectiosum, hantavirus infections, hemorrhagic fevers, viral hepatitis, viral human herpes simplex, herpes zoster, herpes zoster oticus, herpesviridae infections, infectious mononucleosis, human-lassa fever, measles, molluscum, contagiosum, mumps, paramyxoviridae infections, phlebotomus fever, polyomavirus infections, rabies, respiratory syncytial virus infections, rift valley fever, RNA virus infections, rubella, slow virus diseases, smallpox, subacute sclerosing panencephalitis, tumor virus infections, warts, west nile fever, virus diseases, yellow fever, amebiasis, anisakiasis, ascariasis, babesiosis, *blastocystis hominis* infections, bug bite, cestode infections, chagas disease, cryptosporidiosis, cyclosporiasis, cysticercosis, dientamoebiasis, diphyllobothriasis, dracunculiasis, echinococcosis, ectoparasitic infestations, filariasis, giardiasis, helminthiasis, hookworm infections, larva migrans, leishmaniasis, lice infestations, loiasis, malaria, mite infestations, myiasis, onchocerciasis, protozoan infections, scabies, schistosomiasis, skin diseases, parasitic, strongyloidiasis, taeniasis, toxocariasis, toxoplasmosis, trichinosis, *trichomonas* infections, trypanosomiasis, trypanosomiasis, african, or whipworm infections.

In another aspect, the disorder or condition associated with methods of the invention includes treating and/or preventing, including reducing the incidence, delaying the onset or progression, or reducing and/or abrogating the symptoms associated with a digestive system disease in a subject, including, but not limited to, gastrointestinal disease. In some embodiments, gastrointestinal diseases comprise adenomatous polyposis coli, Alagille syndrome, anus diseases, appendicitis, barrett esophagus, biliary atresia, biliary tract diseases, Caroli disease, celiac disease, cholangitis, cholecystitis, cholelithiasis, colitis, ulcerative, Crohn's disease, deglutition disorders, duodenal ulcer, dysentery, enterocolitis, pseudomembranous, esophageal achalasia, esophageal atresia, esophagitis, exocrine pancreatic insufficiency, fatty liver, fecal incontinence, gastritis, gastritis, hypertrophic, gastroenteritis, gastroesophageal reflux, gastroparesis, hemorrhoids, hepatic vein thrombosis, hepatitis, hepatitis, chronic, hernia, diaphragmatic, hernia, hiatal, Hirschsprung disease, hypertension, portal, inflammatory bowel diseases, intestinal diseases, intestinal neoplasms, intestinal neuronal dysplasia, intestinal obstruction, irritable bowel syndrome, lactose intolerance, liver cirrhosis, liver diseases, meckel diverticulum, pancreatic diseases, pancreatic neoplasms, pancreatitis, peptic ulcer, Peutz-Jeghers syndrome, proctitis, rectal diseases, rectal prolapse, short bowel syndrome, tracheoesophageal fistula, whipple disease, or Zollinger-Ellison syndrome.

In some embodiments, stomatognathic diseases comprise ankyloglossia, bruxism, burning mouth syndrome, cheilitis, cherubism, cleft lip, dentigerous cyst, gingivitis, glossitis, benign migratory, herpes labialis, Ludwig's angina, macroglossia, Melkersson-Rosenthal syndrome, periodontal diseases, Pierre Robin syndrome, prognathism, salivary gland diseases, sialorrhea, stomatitis, aphthous, temporomandibular joint disorders, temporomandibular joint dysfunction syndrome, or xerostomia.

In a further aspect, the disorder or condition associated with methods of the invention includes treating and/or preventing, including reducing the incidence, delaying the onset or progression, or reducing and/or abrogating the symptoms associated with an urologic and/or male genital disease in a subject. In some embodiments, an urologic and/or male genital diseases comprise anti-glomerular basement membrane disease, balanitis, bladder exstrophy, bladder neoplasms, cryptorchidism, cystitis, interstitial, diabetes insipidus, nephrogenic, epididymitis, fournier gangrene, glomerulonephritis, Goodpasture syndrome, hematospermia, hematuria, hemolytic-uremic syndrome, hydronephrosis, hypospadias, impotence, infertility, kidney calculi, kidney failure, acute, kidney failure, chronic, kidney tubular necrosis, acute, medullary sponge kidney, multicystic dysplastic kidney, nephritis, hereditary, nephrosis, nephrotic syndrome, nocturia, oliguria, penile diseases, penile induration, penile neoplasms, phimosis, priapism, prostatic diseases, benign prostate hyperplasia, prostatic neoplasms, proteinuria, pyelonephritis, Reiter disease, renal artery obstruction, spermatic cord torsion, testicular diseases, urethral stricture, urethritis, urinary retention, urinary tract infections, urination disorders, urologic and male genital diseases, urologic diseases, varicocele, vesico, or urethral reflux.

In another aspect, the disorder or condition associated with methods of the invention includes treating and/or preventing, including reducing the incidence, delaying the onset or progression, or reducing and/or abrogating the symptoms associated with, a dermatological disorder in a subject. In some embodiments, dermatological disorders comprise acne, actinic keratosis, alopecia, androgenic alopecia, alopecia greata, alopecia secondary to chemotherapy, alopecia secondary to radiation therapy, alopecia induced by scarring, alopecia induced by stress, angioma, athlete's foot, aquagenic pruritus, atopic dermatitis, baldness, basal cell carcinoma, bed sore, Behcet's disease, blepharitis, boil, Bowen's disease, bullous pemphigoid, canker sore, carbuncles, cellulitis, chloracne, chronic dermatitis of the hands and feet, dyshidrosis, cold sores, contact dermatitis, creeping eruption, dandruff, dermatitis, dermatitis herpetiformis, dermatofibroma, diaper rash, eczema, epidermolysis bullosa, erysipelas, erythroderma, friction blister, genital wart, hidradenitis, suppurativa, hives, hyperhidrosis, ichthyosis, impetigo, jock itch, Kaposi's sarcoma, keloid, keratoacanthoma, keratosis pilaris, lice infection, lichen planus, lichen simplex chronicus, lipoma, lymphadenitis, malignant melanoma, melasma, miliaria, molluscum contagiosum, nummular dermatitis, paget's disease of the nipple, pediculosis, pemphigus, perioral dermatitis, photoallergy, photosensitivity, *pityriasis rosea, pityriasis rubra* pilaris, psoriasis, raynaud's disease, ring worm, rosacea, scabies, scleroderma, sebaceous cyst, seborrheic keratosis, seborrhoeic dermatitis, shingles, skin cancer, skin tags, spider veins, squamous cell carcinoma, stasis dermatitis, tick bite, *tinea barbae, tinea capitis, tinea corporis, tinea cruris, tinea pedis, tinea unguium, tinea versicolor, tinea*, tungiasis, vitiligo, or warts.

In another aspect, the invention provides for the treatment and/or prevention of a dermatological disorder, such as a wound or a burn. In some embodiments, wounds and/or ulcers are found protruding from the skin or on a mucosal surface or as a result of an infarction in an organ. A wound may be a result of a soft tissue defect or a lesion or of an underlying condition. In one embodiment, the term "wound" denotes a bodily injury with disruption of the normal integrity of tissue structures. The term is also intended to encompass the terms "sore", "lesion", "necrosis" and "ulcer". In one embodiment, the term "sore" refers to any lesion of the skin or mucous membranes and the term "ulcer" refers to a local defect, or excavation, of the surface of an organ or tissue, which is produced by the sloughing of necrotic tissue. Lesion generally relates to any tissue defect. Necrosis is related to dead tissue resulting from infection, injury, inflammation or infarctions. All of these are encompassed by the term "wound", which denotes any wound at any particular stage in the healing process including the stage before any healing has initiated or even before a specific wound like a surgical incision is made (prophylactic treatment).

Examples of wounds which can be prevented and/or treated in accordance with the present invention are, e.g., aseptic wounds, contused wounds, incised wounds, lacerated wounds, non-penetrating wounds (i.e. wounds in which there is no disruption of the skin but there is injury to underlying structures), open wounds, penetrating wounds, perforating wounds, puncture wounds, septic wounds, subcutaneous wounds, etc. Examples of sores are bed sores, canker sores, chrome sores, cold sores, pressure sores etc. Examples of ulcers are, e.g., peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, veneral ulcer, e.g. caused by gonorrhoea (including urethritis, endocervicitis and proctitis). Conditions related to wounds or sores which may be successfully treated according to the invention are burns, anthrax, tetanus, gas gangrene, scalatina, erysipelas, sycosis barbae, folliculitis, impetigo contagiosa, or impetigo bullosa, etc. There is often a certain overlap between the use of the terms "wound" and "ulcer" and "wound" and "sore" and, furthermore, the terms are often used at random. Therefore as mentioned above, in the present context the term "wounds" encompasses the term "ulcer", "lesion", "sore" and "infarction", and the terms are indiscriminately used unless otherwise indicated.

The kinds of wounds to be treated according to the invention also include, but are not limited to, i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions. Another way of classifying wounds is as i) small tissue loss due to surgical incisions, minor abrasions and minor bites, or as ii) significant tissue loss. The latter group includes ischemic ulcers, pressure sores, fistulae, lacerations, severe bites, thermal burns and donor site wounds (in soft and hard tissues) and infarctions. In other aspects of the invention, the wound to be prevented and/or treated is selected from the group consisting of aseptic wounds, infarctions, contused wounds, incised wounds, lacerated wounds, non-penetrating wounds, open wounds, penetrating wounds, perforating wounds, puncture wounds, septic wounds and subcutaneous wounds. Other wounds which are of importance in connection with the present invention are wounds like ischemic ulcers, pressure sores, fistulae, severe bites, thermal burns and donor site wounds.

In another aspect, the invention provides for the use of the SARM compounds as described herein and/or compositions are useful in wound healing as an adjunct to physical therapy/rehabilitation, as an anabolic agent. In another embodiment, the methods and compositions as described herein are useful in promoting healing of anterior cruciate ligament (ACL) or medial cruciate ligament (MCL) injuries, or accelerating recovery after ACL or MCL surgery. In another embodiment, the methods and compositions as described herein are useful in enhancing athletic performance. In another embodiment, the methods and compositions as described herein are useful in treating burns. In another embodiment, the methods and compositions as described herein are useful in stimulating cartilage regrowth. In another embodiment, the methods and compositions as described herein are useful in preventing, treating, or reversing of catabolism associated with prolonged critical illness, pulmonary dysfunction, ventilator dependency, aging, AIDS, trauma, surgery, congestive heart failure, cardiac myopathy, burns, cancer, COPD. In another embodiment, the methods and compositions as described herein are useful in preventing or reversing protein catabolism due to trauma. In another embodiment, the methods and compositions as described herein are useful as a) adjunct to cauterization therapy (laser or radio) as is used in surgery to promote wound healing, b) adjunct to cryotherapy to promote wound healing, c) adjunct to chemotherapy to prevent side effects such as alopecia, hypogonadism, muscle wasting, osteopenia, osteoporosis, sarcopenia, increased LDL, TG or total cholesterol, decreased HDL. In another embodiment, the compositions as described herein are useful in chronic catabolic state (coma, wasting conditions, starvation, eating disorders); concomitant bone fracture and muscle damage; critical illness in which muscle or bone wasting are apparent; and/or connective tissue diseases and disorders Ischemic ulcers and pressure sores are wounds, which normally only heal very slowly and especially in such cases an improved and more rapid healing is of course of great importance for the patient. Furthermore, the costs involved in the treatment of patients suffering from such wounds are markedly reduced when the healing is improved and takes place more rapidly.

Donor site wounds are wounds which e.g. occur in connection with removal of hard tissue from one part of the body to another part of the body e.g. in connection with transplantation. The wounds resulting from such operations are very painful and an improved healing is therefore most valuable. The term "skin" is used in a very broad sense embracing the epidermal layer of the skin and in those cases where the skin surface is more or less injured also the dermal layer of the skin. Apart from the stratum corneum, the epidermal layer of the skin is the outer (epithelial) layer and the deeper connective tissue layer of the skin is called the dermis.

In some embodiments, the present invention provides a method for promoting healing of anterior cruciate ligament (ACL) or medial cruciate ligament (MCL) injuries, or accelerating recovery after ACL or MCL surgery. In some embodiments, burns are associated with reduced testosterone levels, and hypgonadism is associated with delayed wound healing. In one embodiment, the methods of this invention, provide for treating a subject suffering from a wound or a burn.

In another aspect, the disorder or condition associated with methods of the invention includes treating and/or preventing, including reducing the incidence, delaying the onset or progression, or reducing and/or abrogating the symptoms associated with an endocrine disorder.

In some embodiments, endocrine disorders comprise acromegaly, Addison disease, adrenal gland diseases, adrenal hyperplasia, congenital, androgen-insensitivity syndrome, congenital hypothyroidism, Cushing syndrome, diabetes insipidus, diabetes mellitus, diabetes mellitus-type 1, diabetes mellitus-type 2, diabetic, ketoacidosis, empty Sella syndrome, endocrine gland neoplasms, endocrine system diseases, gigantism, gonadal disorders, graves disease, hermaphroditism, hyperaldosteronism, hyperglycemic hyperosmolar nonketotic coma, hyperpituitarism, hyperprolactinemia, hyperthyroidism, hypogonadism, hypopituitarism, hypothyroidism, Kallmann syndrome, Nelson syndrome, parathyroid diseases, pituitary diseases, polyendocrinopathies, autoimmune, puberty, delayed, puberty, precocious, renal osteodystrophy, thyroid diseases, thyroid hormone resistance syndrome, thyroid neoplasms, thyroid nodule, thyroiditis, thyroiditis, autoimmune, thyroiditis, subacute, or Wolfram syndrome.

"Hypogonadism" is a condition resulting from or characterized by abnormally decreased functional activity of the gonads, with retardation of growth and sexual development. In one embodiment, the invention provides for the treating, reducing the incidence, delaying the onset or progression, or reducing and/or abrogating the symptoms associated with urogenital disease and/or fertility in a subject. In some embodiments, urogenital diseases and/or fertility diseases comprise abortion, spontaneous-adhesions-pelvic, candidiasis, vulvovaginal, depression-postpartum, diabetes, gestational, dyspareunia, dystocia, eclampsia, endometriosis, fetal death, fetal growth retardation, fetal membranes, premature rupture, genital diseases, female, genital neoplasms, female, hydatidiform mole, hyperemesis gravidarum, infertility, ovarian cysts, ovarian torsion, pelvic inflammatory disease, placenta diseases, placental insufficiency, polycystic ovary syndrome, polyhydramnios, postpartum hemorrhage, pregnancy complications, pregnancy, ectopic, pruritus vulvae, puerperal disorders, puerperal infection, salpingitis, trophoblastic neoplasms, uterine cervix incompetence, uterine inversion, uterine prolapse, vaginal diseases, vulvar diseases, vulvar lichen sclerosis.

In one embodiment, therefore, the invention is directed to reducing and/or abrogating the symptoms associated with a hypogonadal state in a subject. In some embodiments, hypogonadism is caused by treatments which alter the secretion of hormones from the sex glands in both women and men. In some embodiments, hypogonadism may be "primary" or "central." In primary hypogonadism, the ovaries or testes themselves do not function properly. In some embodiments, hypogonadism may be induced by surgery, radiation, genetic and developmental disorders, liver and kidney disease, infection, or certain autoimmune disorders. In some embodiments, menopause is a form of hypogonadism. Menopause may cause, in some embodiments, amenorrhea, hot flashes, vaginal dryness, or irritability due to woman's estrogen levels fall. Accordingly, another aspect of the invention is the treatment of or reduction in symptoms of menopause.

In another embodiment, the invention is directed to the treatment of cystic fibrosis and induced hypogonadal states as a result of cystic fibrosis; epilepsy and induced hypogonadal and/or hypermetabolic states as a result of the same; hereditary angioedema, lupus erythematosus and decreased BMD as a result of the same; as well as other hypogonadal states.

In a further aspect, the disorder or condition associated with methods of the invention includes treating and/or preventing, including reducing the incidence, delaying the onset or progression, or reducing and/or abrogating the symptoms associated with hemic and/or lymphatic disease in a subject. In some embodiments, hemic and/or lymphatic diseases comprise afibrinogenemia, anemia, aplastic anemia, hemolytic anemia, congenital nonspherocytic anemia, megaloblastic anemia, pernicious anemia, sickle cell anemia, angiolymphoid hyperplasia with eosinophilia, antithrombin III deficiency, Bernard-Soulier syndrome, blood coagulation disorders, blood platelet disorders, blue rubber bleb nevus syndrome, Chediak-Higashi syndrome, cryoglobulinemia, disseminated intravascular coagulation, eosinophilia, Erdheim-Chester disease, erythroblastosis, fetal, evans syndrome, factor V deficiency, factor VII deficiency, factor X deficiency, factor XI deficiency, factor XII deficiency, fanconi anemia, giant lymph node hyperplasia, hematologic diseases, hemoglobinopathies, hemoglobinuria, paroxysmal, hemophilia a, hemophilia b, hemorrhagic disease of newborn, histiocytosis, histiocytosis, langerhans-cell, histiocytosis, non-langerhans-cell, job's syndrome, leukopenia, lymphadenitis, lymphangioleiomyomatosis, lymphedema, methemoglobinemia, myelodysplastic syndromes, myelofibrosis, myeloid metaplasia, myeloproliferative disorders, neutropenia, paraproteinemias, platelet storage pool deficiency, polycythemia vera, protein c deficiency, protein s deficiency, purpura, thrombocytopenic, purpura, thrombotic thrombocytopenic, RH-isoimmunization, sarcoidosis, sarcoidosis, spherocytosis, splenic rupture, thalassemia, thrombasthenia, thrombocytopenia, Waldenstrom macroglobulinemia, or Von Willebrand disease.

In another aspect, the disorder or condition associated with methods of the invention includes treating and/or preventing, including reducing the incidence, delaying the onset or progression, or reducing and/or abrogating the symptoms associated with, a congenital, hereditary, or neonatal disease in a subject. In some embodiments, congenital, hereditary, and neonatal diseases comprise Aicardi syndrome, amniotic band syndrome, anencephaly, Angelman syndrome, ataxia telangiectasia, Bannayan-Zonana syndrome, Barth syndrome, basal cell nevus syndrome, Beckwith-Wiedemann syndrome, bloom syndrome, branchio-oto-renal syndrome, cat eye syndrome, cerebral gigantism-charge syndrome, chromosome 16 abnormalities, chromosome 18 abnormalities, chromosome 20 abnormalities, chromosome 22 abnormalities, Costello syndrome, cri-du-chat syndrome, Currarino syndrome, cystic fibrosis, de-Lange syndrome, distal trisomy 10q, down syndrome, ectodermal dysplasia, fetal alcohol syndrome, fetal diseases, fetofetal transfusion, fragile x syndrome, Freeman-Sheldon syndrome, gastroschisis, genetic diseases, inborn, hernia, umbilical, holoprosencephaly, incontinentia pigmenti, Ivemark syndrome, Jacobsen syndrome, jaundice, Klinefelter syndrome, Larsen syndrome, Laurence-moon syndrome, lissencephaly, microcephaly, monosomy 9p, nail-patella syndrome, neurofibromatoses, neuronal ceroid-lipofuscinosis, Noonan syndrome, ochoa syndrome (urofacial syndrome, hydronephrosis with peculiar facial expression), oculocerebrorenal syndrome, Pallister-Killian syndrome, Prader-Willi syndrome, proteus syndrome, prune belly syndrome, Rett syndrome, Robinow syndrome, Rubinstein-Taybi syndrome, schizencephaly, situs inversus, Smith-Lemli-Opitz syndrome, Smith-Magenis syndrome, Sturge- Weber syndrome, syphilis, congenital, trichothiodystrophy, triple-x females, trisomy 13 (Patau syndrome), trisomy 9, turner syndrome, twins, conjoined, Usher syndrome, Waardenburg's syndrome, Werner syndrome, or Wolf-Hirschhorn syndrome.

In another aspect, the disorder or condition associated with methods of the invention includes treating and/or preventing, including reducing the incidence, delaying the onset or progression, or reducing and/or abrogating the symptoms associated with a connective tissue disease in a subject. In some embodiments, connective tissue diseases comprise ankylosing spondylitis, Ehlers-Danlos syndrome, Henoch-Schonlein purpura, Kawasaki disease, Marfan syndrome, polyarteritis nodosa, polymyositis, psoriatic arthritis, reactive arthritis, rheumatoid arthritis, scleroderma, Sjogren's syndrome, Still's disease, systemic lupus erythematosus, Takayasu disease, or Wegener's granulomatosis.

In a further aspect, the disorder or condition associated with methods of the invention includes treating and/or preventing, including reducing the incidence, delaying the onset or progression, or reducing and/or abrogating the symptoms associated with, a metabolic disease in a subject. In some embodiments, metabolic diseases comprise acid-base imbalance, acidosis, alkalosis, alkaptonuria, alpha-mannosidosis, amino acid metabolism inborn errors, amyloidosis, iron-deficiency anemia, ascorbic acid deficiency, avitaminosis, beriberi, biotimidase deficiency, carbohydrate-deficient glycoprotein syndrome, carnitine disorders, cystinosis, cystinuria, dehydration, fabry disease, fatty acid oxidation disorders, fucosidosis, galactosemias, Gaucher disease, Gilbert disease, glucosephosphate dehydrogenase deficiency, glutaric acidemia, glycogen storage disease, Hartnup disease, hemochromatosis, hemosiderosis, hepatolenticular degeneration, histidinemia, homocystinuria, hyperbilirubinemia, hypercalcemia, hyperinsulinism, hyperkalemia, hyperlipidemia, hyperoxaluria, hypervitaminosis A, hypocalcemia, hypoglycemia, hypokalemia, hyponatremia, hypophosphatasia, insulin resistance, iodine deficiency, iron overload, jaundice, chronic idiopathic, leigh disease, lesch-nyhan syndrome, leucine metabolism disorders, lysosomal storage diseases, magnesium deficiency, maple syrup urine disease, Melas syndrome, Menkes kinky hair syndrome, metabolic diseases, metabolic syndrome x, metabolism, inborn errors, mitochondrial diseases, mucolipidoses, mucopolysaccharidoses, Niemann-Pick diseases, obesity, ornithine carbamoyltransferase deficiency disease, osteomalacia, pellagra, peroxisomal disorders, phenylketonurias, porphyria, erythropoietic, porphyrias, progeria, pseudo, gaucher disease, refsum disease, Reye syndrome, rickets, Sandhoff disease, starvation, tangier disease, Tay-Sachs disease, tetrahydrobiopterin deficiency, trimethylaminuria, tyrosinemias, urea cycle disorders, water-electrolyte imbalance, Wernicke encephalopathy, vitamin A deficiency, vitamin B 12 deficiency, vitamin B deficiency, Wolman disease, or Zellweger syndrome.

In another aspect, the disorder or condition associated with methods of the invention includes treating and/or preventing, including reducing the incidence, delaying the onset or progression, or reducing and/or abrogating the symptoms associated with, a disorder of environmental origin in a subject. In some embodiments, disorders of environmental origin comprise barotrauma, bites and stings, brain concussion, burns, central cord syndrome, craniocerebral trauma, electric injuries, fractures, bone, frostbite, heat stress disorders, motion sickness, occupational diseases, poisoning, shaken baby syndrome, shoulder injuries, space motion sickness, spinal cord injuries, tick paralysis, or wounds (penetrating and non-penetrating).

In a further aspect, the disorder or condition associated with methods of the invention includes treating and/or preventing, including reducing the incidence, delaying the onset or progression, or reducing and/or abrogating the symptoms associated with, a behavior mechanism in a subject. In some embodiments, behavior mechanisms comprise aggression, attitude to death, codependency, self-injurious behavior, sexual behavior, or social behavior.

In another aspect, the disorder or condition associated with methods of the invention includes treating and/or preventing, including reducing the incidence, delaying the onset or progression, or reducing and/or abrogating the symptoms associated with, a mental disorder in a subject. In some embodiments, mental disorders comprise Asperger syndrome, attention deficit disorder with hyperactivity, autistic disorder, bipolar disorder, borderline personality disorder, capgras syndrome, child behavior disorders, combat disorders, cyclothymic disorder, dependent personality disorder, depressive disorder, dissociative disorders, dysthymic disorder, eating disorders, firesetting behavior, hypochondriasis, impulse control disorders, Kleine-Levin syndrome, mental disorders, mental disorders diagnosed in childhood, multiple personality disorder, Munchausen syndrome, Munchhausen syndrome, narcissistic personality disorder, narcolepsy, obsessive-compulsive disorder, paraphilias, phobic disorders, psychotic disorders, restless legs syndrome, schizophrenia, seasonal affective disorder, sexual and gender disorders, sexual dysfunctions, psychological, sleep disorders, somatoform disorders, stress disorders, post-traumatic, substance-related disorders, suicidal behavior, or trichotillomania.

"Depression" refers to an illness that involves the body, mood and thoughts that affects the way a person eats, sleeps and the way one feels about oneself, and thinks about things. The signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain. "Cognition" refers to the process of knowing, specifically the process of being aware, knowing, thinking, learning and judging. Cognition is related to the fields of psychology, linguistics, computer science, neuroscience, mathematics, ethology and philosophy. In one embodiment, "mood" refers to a temper or state of the mind. As contemplated herein, alterations mean any change for the positive or negative, in cognition and/or mood.

In one embodiment the mental disorder is depression.

In one embodiment the mental disorder is an alteration in cognition or a cognitive disorder.

In a further aspect, the disorder or condition associated with methods of the invention includes treating and/or preventing, including reducing the incidence, delaying the onset or progression, or reducing and/or abrogating the symptoms associated with, a liver disease in a subject. In some embodiments, liver diseases comprise liver cancer, primary biliary cirrhosis, autoimmune hepatitis, chronic liver disease, cirrhosis of the liver, hepatitis, viral hepatitis (hepatitis a, hepatitis b, chronic hepatitis b, hepatitis c, chronic hepatitis c, hepatitis d, hepatitis e, hepatitis x), liver failure, jaundice, neonatal jaundice, hepatoma, liver cancer, liver abscess, alcoholic liver disease, hemochromatosis, Wilson's disease, portal hypertension, primary sclerosing cholangitis, sarcoidosis, tapeworms, alveolar hydatid disease, fascioliasis, schistosomiasis, gaucher disease, Zellweger syndrome, alcoholism, food poisoning, pneumococcal pneumonia or *vibrio vulnificus*.

In another aspect, the disorder or condition associated with methods of the invention includes treating and/or preventing, including reducing the incidence, delaying the onset or progression, or reducing and/or abrogating the symptoms associated with, a kidney disease in a subject. In some embodiments, kidney diseases comprise acromegaly, acute renal failure (ARF) amyloidosis, autosomal dominant polycystic kidney disease, kidney stones, kidney cysts, autosomal recessive polycystic kidney disease, chronic renal failure (CRF), chronic renal disease, chronic kidney disease (CKD), coffin-Lowry syndrome, cor pulmonale, cryoglobulinemia, diabetic nephropathy, dyslipidemia, Gaucher disease, glomerulonephritis, goodpasture syndrome, hemolytic uremic syndrome, hepatitis, kidney cancer, kidney stones, leukemia, lipoproteinemia, lupus, multiple myeloma, nephritis, polyartekidney cysts, post streptococcal glomerulonephritis, glomerulonephritis, kidney pain, preeclampsia, renal tuberculosis, pyelonephritis, renal tubular acidosis kidney disease, streptococcal toxic shock syndrome, thromboembolism, toxoplasmosis, urinary tract infections, uremia, vesicoureteral reflux, or williams syndrome. In some embodiments, the kidney disease being treatment comprises kidney metabolic syndrome. In one embodiment, the kidney disease or disorder is acute, or in another embodiment, chronic. In one embodiment, clinical indications of a kidney disease or disorder, wherein the methods of treatment may be useful include urinary casts, measured GFR, or other markers of renal function. In one embodiment, the kidney disease or disorder is a chronic kidney disease (CKD). In some embodiments treating CKD patients includes treating those with advanced disease (uremia), and may comprise treating muscle wasting, repetitive catabolic stimuli (chronic infections, dialysis), anorexia, or other associated conditions, which will comprise what is meant by treating the disease.

CKD predisposes the subject to functional impairment, which in turn may result in the presence of a chronic inflammatory state, local and systemic inflammatory effects, increased adiposity (e.g. visceral adipose tissue), decreased LBM and/or any adverse effects of adipose tissue. In some embodiments, conventional therapies such as the administration of anabolic hormones lose efficacy in such subjects, as a result of resistance to the anabolic hormones resulting in decreased levels and resistance to actions (for example due to uremic toxins), however, the compounds/compositions of this invention may in some embodiments be effective in such a scenario. In one embodiment, the invention is useful in improving Stage 3 and 4 CKD, by, inter alia, and in some embodiments, increasing lean body mass (LBM), improving physical performance, increasing quality of life, decreasing adiposity, improving physical performance, decreasing muscle catabolism, improving or treating renal metabolic syndrome, decreasing risk for development of insulin resistance and/or decreasing the risk for heart disease.

In another aspect, the invention provides for improving muscle wasting and physical performance in end-stage renal disease (dialysis) patients. In some embodiments, the treatment methods of this invention are useful in treating uremic cachexia and/or complications, diseases and/or conditions associated thereto. The compounds of the invention are anticipated to be useful in subjects predisposed to kidney diseases or disorders. In one embodiment, the phrase "predisposed to a kidney disease or disorder" with respect to a subject is synonymous with the phrase "subject at risk", and includes a subject at risk of acute or chronic renal failure, or at risk of the need for renal replacement therapy, if the subject is reasonably expected to suffer a progressive loss of renal function associated with progressive loss of functioning nephron units. Whether a particular subject is at risk is a determination which may routinely be made by one of ordinary skill in the relevant medical or veterinary art.

In particular, in one embodiment, the method provides for the treatment of subjects with kidney disease, in particular male subjects with end-stage renal disease (ESRD) suffer from hypogonadism, with some having concomitant moderate to severe protein-energy malnutrition (PEM), which leads to higher required doses of EPO, lower QOL scores, and higher mortality. Many have other symptoms associated with hypogonadism, including fatigue, lack of apetite, muscle weakness, etc. In some embodiments, the treatment methods of this invention are useful in treating symptoms associated with hypogonadism, brought about in the subject by the kidney disease or disorder. In another embodiment, the invention is directed to female patients having an androgen deficiency (ADIF); androgen deficiency in aging male (ADAM), including fatigue, depression, decreased libido, erectile dysfunction, decreased cognition, decreased mood; androgen insufficiency (male or female), androgen deficiency (male or female).

Diabetic nephropathy is a complication of diabetes that evolves early, typically before clinical diagnosis of diabetes is made. The earliest clinical evidence of nephropathy is the appearance of low but abnormal levels (>30 mg/day or 20 .mu.g/min) of albumin in the urine (microalbuminuria), followed by albuminuria (>300 mg/24 h or 200 .mu.g/min) that develops over a period of 10-15 years. In patients with type 1 diabetes, diabetic hypertension typically becomes manifest early on, by the time that patients develop microalbuminuria. Once overt nephropathy occurs, the glomerular filtration rate (GFR) falls over a course of times, which may be several years, resulting in End Stage Renal Disease (ESRD) in diabetic individuals. Accordingly, in one embodiment, the invention provides for the treatment of renal disease. Muscle wasting can occur as a result of pathology, disease, condition or disorders, including disorders for treatment via the methods of this invention, such as, for example, end stage renal failure.

The term "diabetes", in one embodiment, refers to a relative or absolute lack of insulin leading to uncontrolled carbohydrate metabolism. Most patients can be clinically classified as having either insulin-dependent diabetes mellitus (IDDM or Type-I diabetes) or non-insulin-dependent diabetes mellitus (NIDDM or Type-II diabetes). The term "increased blood pressure" or "hypertension" refers, in other embodiments, to a repeatedly high blood pressure above 140 over 90 mmHg. Chronically-elevated blood pressure can cause blood vessel changes in the back of the eye, thickening of the heart muscle, kidney failure, and brain damage. The term "stroke" refers, in other embodiments, to damage to nerve cells in the brain due to insufficient blood supply often caused by a bursting blood vessel or a blood clot. The term "heart disease", in other embodiments, refers to a malfunction in the heart normal function and activity, including heart failure.

In another aspect, the disorder or condition associated with the method described herein is stress urinary incontinence. Urinary incontinence is commonly defined as the unintentional passing of urine. Urinary incontinence is usually divided into two sub-categories, stress incontinence and urge incontinence. In general, stress incontinence is associated with symptoms of unintentional passing of urine, even small amounts of urine, when intra-abdominal pressure is increased, or when the bladder is placed under increased pressure, for example, but not limited to, when the patients coughs, sneezes, exercises, laughs or lifts something heavy. In one aspect, the disorder or condition associated with the methods described herein includes stress urinary incontinence in female patients. In one embodiment, the present invention provides a method for the treatment of stress urinary incontinence. In one embodiment, the present invention provides a method for the treatment of stress urinary incontinence in a female patient.

In some embodiments, the present invention provides a method for prevention of statin induced rhabdomyolysis. In some embodiments, the present invention provides a method for prevention of statin induced rhabdomyolysis, organ failure or insufficiency. In some embodiments, the present invention provides a method for prevention of statin induced kidney or liver failure or insufficiency.

In another aspect, the disorder or condition associated with methods of the invention includes treating and/or preventing, promoting or speeding recovery following a surgical procedure, reducing a fat mass in a subject, for treating abdominal fat accumulation; improving body composition; lowering body fat content; lowering fat mass; improving blood lipid profile, increasing muscle mass/strength/function; increasing bone mass/BMD/strength/function; congenital hyperinsulinemia; cushing's disease (hypercortisolemia); obesity, diabetes or other diseases or conditions associated with a metabolic syndrome in a subject in need thereof.

The term "obesity" is defined, in one embodiment, as an increase in body weight beyond the limitation of skeletal and physical requirement, as the result of excessive accumulation of fat in the body. The term "obesity-associated metabolic disorder" refers, in one embodiment, to a disorder which results from, is a consequence of, is exacerbated by or is secondary to obesity. Non-limiting examples of such a disorder are osteoarthritis, Type II diabetes mellitus, increased blood pressure, stroke, and heart disease.

The phrase "treating atherosclerosis and its associated diseases," means diseases such as, for example, cardiovascular disorders, cerebrovascular disorders, peripheral vascular disorders, or intestinal vascular disorders in a subject improving the dexterity and movement in a subject, for example, by treating arthritis in the subject. The term "arthritis" refers, in another embodiment, to a non-inflammatory degenerative joint disease occurring chiefly in older people, characterized by degeneration of the articular cartilage, hypertrophy of bones and the margins, changes in the synovial membrane, etc. It is accompanied, in other embodiments, by pain and stiffness, particularly after prolonged activity.

In one embodiment, the present invention relates to a method for treating and/or preventing anemia in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing anorexia in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing arthritis in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing bone disease in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing benign prostate hyperplasia in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing musculoskeletal impairment in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing cachexia in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing cachexia associated with cancer in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing cancer in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing frailty in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing age-related functional decline in the elderly in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing growth hormone deficiency in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing hematopoietic disorders in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing hormone replacement in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing hypergonadism in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing loss of muscle strength and/or function in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing muscular dystrophies in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing muscle loss following surgery in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing muscular atrophy in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing neurodegenerative diseases in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing neuromuscular disease in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing obesity in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing osteoporosis in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing sarcopenia including sarcopenia in chronic obstructive pulmonary disease, in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing a method of improving dexterity and movement in a subject in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing atherosclerosis and its associated diseases in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing dysmenorrhea in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing dysspermtogenic sterility in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing muscle wasting in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing respiratory tract disease in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing otorhinolaryngologic disease in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing hormonal disorder/disruption or imbalance in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing androgen deprivation therapy in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing injuries of the central nervous system in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing hair loss in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing an infection in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing digestive system disease in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing urologic or male genital disease in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing dermatological disorder in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing endocrine disorder in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing hemic or lymphatic disorder in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing congenital/hereditary or neonatal disease in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing connective tissue disease in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing metabolic disease in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing disorder of environmental origin in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing a behavior mechanism in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing a mental disorder in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing a cognitive disorder in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing liver disease in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing kidney disease in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing diabetic nephropathy in a subject, which method comprises administering to said subject an effective amount of a compound of Formula 1, Formula 2 or Formula 3, as defined herein, or a pharmaceutically acceptable salt thereof.

In one embodiment, the present invention relates to a method for treating and/or preventing stress urinary incontinence in a subject, which method comprises administering to said subject an effective amount of a compound of Formula 1, Formula 2 or Formula 3, as defined herein, or a pharmaceutically acceptable salt thereof.

This invention also relates to a compound of Formula 1, Formula 2 or Formula 3, as defined herein, or a pharmaceutically acceptable salt thereof for use in the treatment of a disorder or condition selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy and stress urinary incontinence.

This invention also relates to the use of compound of Formula 1, Formula 2 or Formula 3, as defined herein, or a pharmaceutically acceptable salt thereof for the manufacture of a medicament for the treatment of a disorder or condition selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy; and stress urinary incontinence.

This invention also relates to a pharmaceutical composition comprising a compound of Formula 1, Formula 2 or Formula 3, as defined herein, or a pharmaceutically acceptable salt thereof, for treating a disorder or condition selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy; and stress urinary incontinence.

The present invention also relates to a combination of a compound of Formula 1, Formula 2 or Formula 3

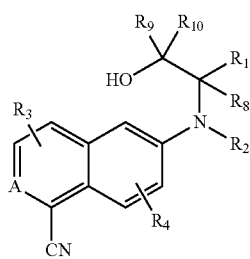

Formula 1

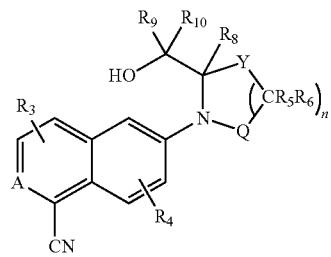

Formula 2

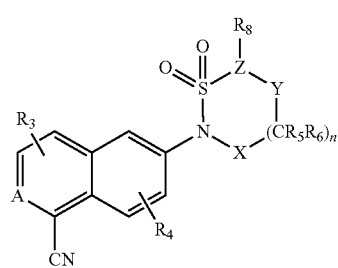

Formula 3 wherein A is N or —$CR_0$—, where $R_0$ is hydrogen, $C_1$-$C_6$ linear or branched chain alkyl, $C_1$-$C_6$ linear or branched chain perfluoroalkyl, aryl, perfluoroaryl, alkylaryl, heteroaryl; or, alkylheteroaryl; X and Y are independently —$CH_2$—, —$CHR_a$—, or, —$CR_aR_b$—, where $R_a$ and $R_b$ are independently $C_1$-$C_6$ linear or branched chain alkyl, aryl, alkylaryl, heteroaryl or, alkylheteroaryl; or, $R_a$ and $R_b$ together form a chain comprising —$(CH_2)_j$—, —$(CHR_c)_j$—, or —$(CR_cR_d)_j$—, where $R_c$ and $R_d$ are independently $C_1$-$C_6$ linear or branched chain alkyl, $C_1$-$C_6$ linear or branched chain perfluoroalkyl, aryl, alkylaryl, heteroaryl or alkylheteroaryl; where j is 2; 3, 4 or 5; Z is —$CR_e$—, or, —N—, where $R_e$ is hydrogen, $C_1$-$C_6$ linear or branched chain alkyl, $C_1$-$C_6$ linear or branched chain perfluoroalkyl, aryl, alkylaryl, heteroaryl or, alkylheteroaryl; $R_1$ is hydrogen, $C_1$-$C_6$ linear or branched chain alkyl, aryl, $C_1$-$C_6$ linear or branched chain perfluoroalkyl, alkylaryl, heteroaryl, alkylheteroaryl, $C_1$-$C_6$ linear or branched chain alkoxylcarbonyl, $C_1$-$C_6$ linear or branched chain alkylamino-carbonylamino, $C_1$-$C_6$ linear or branched chain alkyloxycarbonylamino, $C_1$-$C_6$ linear or branched chain alkylcarbonylamino, or, $C_1$-$C_6$ linear or branched chain alkylaminocarbonyl; $R_2$ are independently hydrogen or $C_1$-$C_6$ linear or branched chain alkyl; $R_3$ and $R_4$ are independently hydrogen, $C_1$-$C_6$ linear or branched chain alkyl, $C_1$-$C_6$ linear or branched chain perfluoroalkyl, $C_1$-$C_6$ linear or branched chain perfluoroalkoxy, halogen, cyano, hydroxyl, amino, carboxy, hydroxyl, aryl, heteroaryl, $C_1$-$C_6$ linear or branched chain alkoxylcarbonyl, $C_1$-$C_6$ linear or branched chain alkylamino-carbonylamino, or, $C_1$-$C_6$ linear or branched chain alkylaminocarbonyl; $R_5$ and $R_6$ are independently hydrogen or $C_1$-$C_6$ linear or branched chain alkyl, $C_1$-$C_6$ linear or branched chain perfluoroalkyl, cyano, hydroxyl, amino, carboxy, hydroxyl, aryl, heteroaryl, or, $R_5$ and $R_6$ together form a chain comprising —$(CH_2)_k$—, —$(CHR_7)_k$—, or —$(CR_{7a}R_{7b})_k$—, where $R_7$, $R_{7a}$, and $R_{7b}$ are independently $C_1$-$C_6$ linear or branched chain alkyl, $C_1$-$C_6$ linear or branched chain perfluoroalkyl, aryl, alkylaryl, heteroaryl or alkylheteroaryl; where k is 2; 3, 4 or 5; $R_8$ is hydrogen, $C_1$-$C_6$ linear or branched chain alkyl, $C_1$-$C_6$ linear or branched chain perfluoroalkyl, aryl, aryl substituted with one, two or three fluorine atoms, perfluoroaryl, alkylaryl, heteroaryl; or, alkylheteroaryl; or, $R_1$ and $R_8$ together form a chain comprising —(CH$_2$)$_m$—, —(CHR$_f$)$_m$—, or —(CR$_f$R$_g$)$_m$—, where R$_f$ and R$_g$ are independently C$_1$-C$_6$ linear or branched chain alkyl, aryl, alkylaryl, heteroaryl or alkylheteroaryl; where m is 2; 3, 4 or 5; R$_9$ and R$_{10}$ are independently hydrogen or C$_1$-C$_6$ linear or branched chain alkyl, C$_1$-C$_6$ linear or branched chain perfluoroalkyl, cyano, hydroxyl, amino, carboxy, hydroxyl, aryl, heteroaryl, or, R$_9$ and R$_{10}$ together form a chain comprising —(CH$_2$)$_p$—, —(CHR$_h$)$_p$—, or —(CR$_h$R$_i$)$_p$—, where R$_h$ and R$_i$ are independently C$_1$-C$_6$ linear or branched chain alkyl, aryl, alkylaryl, heteroaryl or alkylheteroaryl; where p is 2; 3, 4 or 5; Q is —CO—, —(CH$_2$)$_q$—, —(CHR$_s$)$_q$—, or —(CR$_s$R$_t$)$_q$—, where R$_s$ and R$_t$ are independently C$_1$-C$_6$ linear or branched chain alkyl, aryl, alkylaryl, heteroaryl or alkylheteroaryl; where q is 0, 1, 2, or 3; and, where n is 0, 1, 2, 3, 4 or 5; or, a pharmaceutically acceptable salt thereof with a second pharmaceutically active ingredient, or a pharmaceutically acceptable salt thereof.

In one embodiment, the invention relates to a combination of a compound of Formula 1, Formula 2 or Formula 3

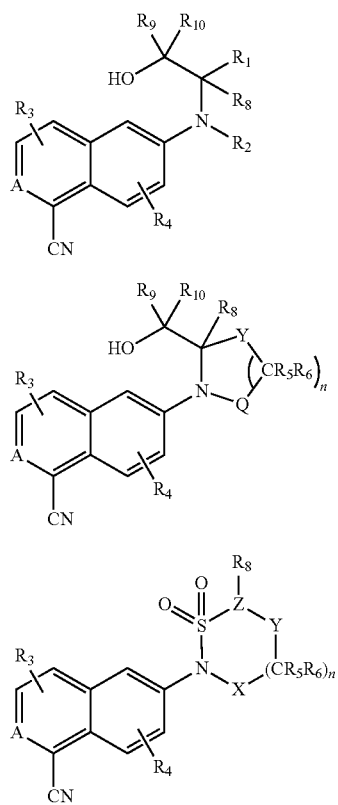

Formula 1

Formula 2

Formula 3 wherein A is N or —CR$_0$—, where R$_0$ is hydrogen, C$_1$-C$_6$ linear or branched chain alkyl, C$_1$-C$_6$ linear or branched chain perfluoroalkyl, aryl, perfluoroaryl, alkylaryl, heteroaryl; or, alkylheteroaryl; X and Y are independently —CH$_2$—, —CHR$_a$—, or, —CR$_a$R$_b$—, where R$_a$ and R$_b$ are independently C$_1$-C$_6$ linear or branched chain alkyl, aryl, alkylaryl, heteroaryl or, alkylheteroaryl; or, R$_a$ and R$_b$ together form a chain comprising —(CH$_2$)$_j$—, —(CHR$_c$)$_j$—, or —(CR$_c$R$_d$)$_j$—, where R$_c$ and R$_d$ are independently C$_1$-C$_6$ linear or branched chain alkyl, C$_1$-C$_6$ linear or branched chain perfluoroalkyl, aryl, alkylaryl, heteroaryl or alkylheteroaryl; where j is 2; 3, 4 or 5; Z is —CR$_e$—, or, —N—, where R$_e$ is hydrogen, C$_1$-C$_6$ linear or branched chain alkyl, C$_1$-C$_6$ linear or branched chain perfluoroalkyl, aryl, alkylaryl, heteroaryl or, alkylheteroaryl; R$_1$ is hydrogen, C$_1$-C$_6$ linear or branched chain alkyl, aryl, C$_1$-C$_6$ linear or branched chain perfluoroalkyl, alkylaryl, heteroaryl, alkylheteroaryl, C$_1$-C$_6$ linear or branched chain alkoxylcarbonyl, C$_1$-C$_6$ linear or branched chain alkylamino-carbonylamino, C$_1$-C$_6$ linear or branched chain alkyloxycarbonylamino, C$_1$-C$_6$ linear or branched chain alkylcarbonylamino, or, C$_1$-C$_6$ linear or branched chain alkylaminocarbonyl; R$_2$ are independently hydrogen or C$_1$-C$_6$ linear or branched chain alkyl; R$_3$ and R$_4$ are independently hydrogen, C$_1$-C$_6$ linear or branched chain alkyl, C$_1$-C$_6$ linear or branched chain perfluoroalkyl, C$_1$-C$_6$ linear or branched chain perfluoroalkoxy, halogen, cyano, hydroxyl, amino, carboxy, hydroxyl, aryl, heteroaryl, C$_1$-C$_6$ linear or branched chain alkoxylcarbonyl, C$_1$-C$_6$ linear or branched chain alkylamino-carbonylamino, or, C$_1$-C$_6$ linear or branched chain alkylaminocarbonyl; R$_5$ and R$_6$ are independently hydrogen or C$_1$-C$_6$ linear or branched chain alkyl, C$_1$-C$_6$ linear or branched chain perfluoroalkyl, cyano, hydroxyl, amino, carboxy, hydroxyl, aryl, heteroaryl, or, R$_5$ and R$_6$ together form a chain comprising —(CH$_2$)$_k$—, —(CHR$_7$)$_k$—, or —(CR$_{7a}$R$_{7b}$)$_k$—, where R$_7$, R$_{7a}$, and R$_{7b}$ are independently C$_1$-C$_6$ linear or branched chain alkyl, C$_1$-C$_6$ linear or branched chain perfluoroalkyl, aryl, alkylaryl, heteroaryl or alkylheteroaryl; where k is 2; 3, 4 or 5; R$_8$ is hydrogen, C$_1$-C$_6$ linear or branched chain alkyl, C$_1$-C$_6$ linear or branched chain perfluoroalkyl, aryl, aryl substituted with one, two or three fluorine atoms, perfluoroaryl, alkylaryl, heteroaryl; or, alkylheteroaryl; or, R$_1$ and R$_8$ together form a chain comprising —(CH$_2$)$_m$—, —(CHR$_f$)$_m$—, or —(CR$_f$R$_g$)$_m$—, where R$_f$ and R$_g$ are independently C$_1$-C$_6$ linear or branched chain alkyl, aryl, alkylaryl, heteroaryl or alkylheteroaryl; where m is 2; 3, 4 or 5; R$_9$ and R$_{10}$ are independently hydrogen or C$_1$-C$_6$ linear or branched chain alkyl, C$_1$-C$_6$ linear or branched chain perfluoroalkyl, cyano, hydroxyl, amino, carboxy, hydroxyl, aryl, heteroaryl, or, R$_9$ and R$_{10}$ together form a chain comprising —(CH$_2$)$_p$—, —(CHR$_h$)$_p$—, or —(CR$_h$R$_i$)$_p$—, where R$_h$ and R$_i$ are independently C$_1$-C$_6$ linear or branched chain alkyl, aryl, alkylaryl, heteroaryl or alkylheteroaryl; where p is 2; 3, 4 or 5; Q is —CO—, —(CH$_2$)$_q$—, —(CHR$_s$)$_q$—, or —(CR$_s$R$_t$)$_q$—, where R$_s$ and R$_t$ are independently C$_1$-C$_6$ linear or branched chain alkyl, aryl, alkylaryl, heteroaryl or alkylheteroaryl; where q is 0, 1, 2, or 3; and, where n is 0, 1, 2, 3, 4 or 5; or, a pharmaceutically acceptable salt thereof with a second pharmaceutically active ingredient, or a pharmaceutically acceptable salt thereof, with the proviso that the compound of Formula 1, Formula 2 or Formula 3 is not crystalline 6-[(4R)-4-methyl-1,1-dioxido-1,2,6-thiadiazinan-2-yl]isoquinoline-1-carbonitrile.

As used herein, the term "combinations of the invention" refers to a combination of one or more compounds of Formula 1, Formula 2 or Formula 3 as defined herein, or, a pharmaceutically acceptable salt thereof, with one or more additional pharmaceutically active ingredients, or pharmaceutically acceptable salts thereof.

As used herein, the terms "combination", "co-administration", "co-administered" and "in combination with", refer to a combination of a compound of Formula 1, 2 or 3 and one or more other therapeutic agents, or pharmaceutically active ingredients, includes the following:

a. simultaneous administration of such a combination of a compound of Formula 1, 2 or 3 and a further therapeutic agent to a patient in need of treatment, when such components are formulated together into a single dosage form which releases said components at substantially the same time to said patient, b. substantially simultaneous administration of such a combination of a compound of Formula 1, 2 or 3 and a further therapeutic agent to a patient in need of treatment, when such components are formulated apart from each other into separate dosage forms which are taken at substantially the same time by said patient, whereupon said components are released at substantially the same time to said patient, c. sequential administration of such a combination of a compound of Formula 1, 2 or 3 and a further therapeutic agent to a patient in need of treatment, when such components are formulated apart from each other into separate dosage forms which are taken at consecutive times by said patient with a significant time interval between each administration, whereupon said components are released at substantially different times to said patient; and, d. sequential administration of such a combination of a compound of Formula 1, 2 or 3 and a further therapeutic agent to a patient in need of treatment, when such components are formulated together into a single dosage form which releases said components in a controlled manner.

Examples of second pharmaceutically active ingredients, one or more of which may be administered in combination with a compound of Formula 1, Formula 2 or Formula 3, or a pharmaceutically acceptable salt thereof, include, but are not limited to:

(i) estrogen and estrogen derivatives (such as conjugated estrogens and synthetic estrogens) including, but not limited to, steroidal compounds having estrogenic activity such as, for example, 17.beta.-estradiol, estrone, conjugated estrogen (PREMARIN®), equine estrogen, 17.beta.-ethynyl estradiol, and the like. The estrogen or estrogen derivative can be employed alone or in combination with a progestin or progestin derivative. Nonlimiting examples of progestin derivatives are norethindrone and medroxy-progesterone acetate;

(ii) a bisphosphonate compound, including, but not limited to:

(a) alendronate (also known as alendronic acid, 4-amino-1-hydroxybutylidene-1,1-bisphosphonic acid, alendronate sodium, alendronate monosodium trihydrate or 4-amino-1-hydroxybutylidene-1,1-bisphosphonic acid monosodium trihydrate. Alendronate is described in U.S. Pat. No. 4,922,007, to Kieczykowski et al., issued May 1, 1990; U.S. Pat. No. 5,019,651, to Kieczykowski, issued May 28, 1991; U.S. Pat. No. 5,510,517, to Dauer et al., issued Apr. 23, 1996; U.S. Pat. No. 5,648,491, to Dauer et al., issued Jul. 15, 1997;

(b) [(cycloheptylamino)-methylene]-bis-phosphonate (incadronate), which is described in U.S. Pat. No. 4,970,335, to Isomura et al., issued Nov. 13, 1990;

(c) (dichloromethylene)-bis-phosphonic acid (clodronic acid) and the disodium salt (clodronate), which are described in Belgium Patent 672,205 (1966) and J. Org. Chem 32, 4111 (1967);

(d) [1-hydroxy-3-(1-pyrrolidinyl)-propylidene]-bis-phosphonate (EB-1053);

(e) (1-hydroxyethylidene)-bis-phosphonate (etidronate);

(f) [1-hydroxy-3-(methylpentylamino)propylidene]-bis-phosphonate (ibandronate), which is described in U.S. Pat. No. 4,927,814, issued May 22, 1990;

(g) (6-amino-1-hydroxyhexylidene)-bis-phosphonate (neridronate);

(h) [3-(dimethylamino)-1-hydroxypropylidene]-bis-phosphonate (olpadronate);

(i) (3-amino-1-hydroxypropylidene)-bis-phosphonate (pamidronate);

(j) [2-(2-pyridinyl)ethylidene]-bis-phosphonate (piridronate), which is described in U.S. Pat. No. 4,761,406;

(k) [1-hydroxy-2-(3-pyridinyl)-ethylidene]-bis-phosphonate (risedronate);

(l) {[(4-chlorophenyl)thio]methylene}-bis-phosphonate (tiludronate), which is described in U.S. Pat. No. 4,876,248, to Breliere et al., Oct. 24, 1989;

(m) [1-hydroxy-2-(1H-imidazol-1-yl)ethylidene]-bis-phosphonate (zoledronate); and (n) [1-hydroxy-2-imidazopyridin-(1,2-a)-3-ylethylidene]-bis-phosphonate (minodronate).

(iii) a selective estrogen receptor modulator (SERM), including, but not limited to tamoxifen, 4-hydroxytamoxifen, raloxifene (see, e.g., U.S. Pat. No. 5,393,763), lasofoxifene, ospemifene, tesmilifene, toremifene, azorxifene, EM-800, EM-652, TSE 424, pipendoxifene, clomiphene, zuclomiphene, enclomiphene, droloxifene, idoxifene, levormeloxifene, nafoxidene, zindoxifene, RU 58,688, EM 139, ICI-164,384, ICI-182,780, CI-680, CI-628, CN-55, 945-27, Mer-25, U-11,555A, U-100A, bazedoxifene, miproxifene phosphate, PPT (1,3,5-tris(4-hydroxyphenyl)-4-propyl-1H-pyrazole), diarylpropionitrile (DPN), diethylstibestrol, coumestrol, genistein, GW5638, LY353581, delmadinone acetate, tibolone, DPPE, (N,N-diethyl-2-{4-(phenylmethyl)-phenoxy}ethanamine), TSE-424, WAY-070, WAY-292, WAY-818, cyclocommunol, prinaberel, ERB-041, WAY-397, WAY-244, ERB-196, WAY-169122, MF-101, ERb-002, ERB-037, ERB-017, BE-1060, BE-380, BE-381, WAY-358, [18F]FEDNP, LSN-500307, AA-102, CT-101, CT-102, or VG-101 and salts thereof, and the like (see, e.g., U.S. Pat. Nos. 4,729,999 and 4,894,373) [Goldstein, et al., "A pharmacological review of selective estrogen receptor modulators," Human Reproduction Update, 6: 212-224 (2000); Lufkin, et al., Rheumatic Disease Clinics of North America, 27: 163-185 (2001), and "Targeting the Estrogen Receptor with SERMs," Ann. Rep. Med. Chem. 36: 149-158 (2001)]. PSK-3471;

(iv) calcitonin and analogue thereof, including, but not limited to, salmon, Elcatonin, SUN-8577 or TJN-135, wherein if the calcitonin analogue is salmon it is optionally dosed as a nasal spray (for example as disclosed in Azra et al., Calcitonin. 1996. In: J. P. Bilezikian, et al., Ed., Principles of Bone Biology, San Diego: Academic Press; and Silverman, "Calcitonin," Rheumatic Disease Clinics of North America. 27: 187-196, 2001);

(v) a cysteine protease cathepsin K, formerly known as cathepsin O.sub.2, for example as described in PCT International Application Publication No. WO 96/13523; U.S. Pat. Nos. 5,501,969 and 5,736,357, and which include those which at an acidic pH degrade type-I collagen. Examples of cathepsin K include, but are not limited to, those disclosed in WO 01/49288, and WO 01/77073. Examples of cathepsin K inhibitors include, but are not limited to AAE581 and Odanacatib;

(vi) alpha.v.beta.3 Integrin receptor antagonists peptidyl as well as peptidomimetic antagonists of the .alpha.v.beta.3 integrin receptor which indluce, but are not limited to those disclosed in the following publications W. J. Hoekstra and B. L. Poulter, Curr. Med. Chem. 5: 195-204 (1998) and references cited therein; WO 95/32710; WO 95/37655; WO 97/01540; WO 97/37655; WO 98/08840; WO 98/18460; WO 98/18461; WO 98/25892; WO 98/31359; WO 98/30542; WO 99/15506; WO 99/15507; WO 00/03973; EP 853084; EP 854140; EP 854145; U.S. Pat. Nos. 5,204,350; 5,217,994; 5,639,754; 5,741,796; 5,780,426; 5,929,120; 5,952,341; 6,017,925; and 6,048,861. Other .alpha.v.beta.3 antagonists are described in R. M. Keenan et al., J. Med. Chem. 40: 2289-2292 (1997); R. M. Keenan et al., Bioorg. Med. Chem. Lett. 8: 3165-3170 (1998); and R. M. Keenan et al., Bioorg. Med. Chem. Lett. 8: 3171-3176 (1998). Other non-limiting representative examples of published patent and patent applications that describe various .alpha.v.beta.3 integrin receptor antagonists include: those comprising benzazepine and benzocycloheptene-PCT Patent Application Nos. WO 96/00574, WO 96/00730, WO 96/06087, WO 96/26190, WO 97/24119, WO 97/24122, WO 97/24124, WO 98/14192, WO 98/15278, WO 99/05107, WO 99/06049, WO 99/15170, WO 99/15178, WO 97/34865, WO 99/15506, and U.S. Pat. No. 6,159,964; those comprising dibenzpcyclohepthene, and dibenzoxapine—PCT Patent Application Nos. WO 97/01540, WO 98/30542, WO 99/11626, WO 99/15508, and U.S. Pat. Nos. 6,008,213 and 6,069,158; those having a phenol constraint—PCT Patent Application Nos. WO 98/00395, WO 99/32457, WO 99/37621, WO 99/44994, WO 99/45927, WO 99/52872, WO 99/52879, WO 99/52896, WO 00/06169, European Patent Nos. EP 0 820,988, EP 0 820,991, and U.S. Pat. Nos. 5,741,796, 5,773,644, 5,773,646, 5,843,906, 5,852,210, 5,929,120, 5,952,281, 6,028,223 and 6,040,311; those having a monocyclic ring constraint—PCT Patent Application Nos. WO 99/26945, WO 99/30709, WO 99/30713, WO 99/31099, WO 99/59992, WO 00/00486, WO 00/09503, European Patent Nos. EP 0 796,855, EP 0 928,790, EP 0 928,793, and U.S. Pat. Nos. 5,710,159, 5,723,480, 5,981, 546, 6,017,926, and 6,066,648; and those having a bicyclic ring constraint—PCT Patent Application Nos. WO 98/23608, WO 98/35949, and WO 99/33798, European Patent No. EP 0 853,084, and U.S. Pat. Nos. 5,760,028, 5,919,792, and 5,925,655

(vii) osteoclast vacuolar ATPase inhibitors, also called proton pump inhibitors, due to the role they play in the bone resorptive process [see C. Farina et al., DDT, 4: 163-172 (1999)], including, but not limited to, omeprazole, lansoprazole, pantoprazole, rebeprazole, or esomeprazole;

(viii) angiogenic factor VEGF, due to the role they play in stimulating bone-resorbing activity of isolated mature rabbit osteoclasts via binding to its receptors on osteoclasts [see M. Nakagawa et al., FEBS Letters, 473: 161-164 (2000)] including, but not limited to KDR/Flk-1 and Flt-1;

(ix) HMG-CoA reductase inhibitors, also known as the "statins", including, but not limited to, statins in their lactonized or dihydroxy open acid forms and pharmaceutically acceptable salts and esters thereof, including but not limited to lovastatin (see U.S. Pat. No. 4,342,767); simvastatin (see U.S. Pat. No. 4,444,784); dihydroxy open-acid simvastatin, particularly the ammonium or calcium salts thereof; pravastatin, particularly the sodium salt thereof (see U.S. Pat. No. 4,346,227); fluvastatin, particularly the sodium salt thereof (see U.S. Pat. No. 5,354,772); atorvastatin, particularly the calcium salt thereof (see U.S. Pat. No. 5,273,995); cerivastatin, particularly the sodium salt thereof (see U.S. Pat. No. 5,177,080), rosuvastatin, also known as ZD4522 (see U.S. Pat. No. 5,260,440) and pitavastatin, also referred to as NK-104, itavastatin, lovastatin, pravastatin sodium, or nisvastatin (see PCT international application publication number WO 97/23200);

(x) osteoanabolic agents including, but not limited to, parathyroid hormone (PTH) and fragments thereof, such as naturally occurring PTH (1-84), PTH (1-34), analogs thereof, native or with substitutions and particularly parathyroid hormone subcutaneous injection, for example Forteo (teriparatide);

(xi) protein kinase inhibitors including, but not limited to, those disclosed in WO 01/17562 and which are in one embodiment selected from inhibitors of p38, non-limiting example of which include SB 203580 [Badger et al., J. Pharmacol. Exp. Ther., 279: 1453-1461 (1996)];

(xii) activators of peroxisome proliferator-activated receptor-.gamma. (PPAR.gamma.), including, but not limited to, those compounds included within the structural class known as thiazolidinediones, those compounds outside the thiazolidinedione structural class, and glitazones, such as, for example, darglitazone, isaglitazone, rivoglitazone, netoglitazone, troglitazone, pioglitazone, rosiglitazone, and BRL 49653;

(xiii) activators of peroxisome proliferator-activated receptor-.alpha (PPAR.alpha. agonists), including, but not liited to, bezafibrate, clofibrate, fenofibrate including micronized fenofibrate, and gemiibrozil;

(xiv) dual acting peroxisome proliferator-activated alpha./.gamma. agonists including, but not limited to, muraglitazar, naveglitazar, farglitazar, tesaglitazar, ragaglitazar, oxeglitazar, PN-2034, PPAR.delta., such as for example, GW-501516;

(xv) the polypeptide osteoprotegerin, and derivatives or analogues thereof, including, but not limited to mammalian osteoprotegerin and human osteoprotegerin;

(xvi) calcium receptor antagonists which induce the secretion of PTH as described by Gowen et al., J. Clin. Invest. 105: 1595-604 (2000);

(xvii) growth hormone and its analogs, including, but not limited to, human growth hormone, such as, for example, somatotropin or analogues, nutropin A; growth promoting agents such as, for example, TRH, diethylstilbesterol, theophylline, enkephalins, E series prostaglandins, such as, for example, Ep1, EP2, EP4, FP, IP and derivatives thereof, prostanoids, compounds disclosed in U.S. Pat. No. 3,239, 345, e.g., zeranol, and compounds disclosed in U.S. Pat. No. 4,036,979, e.g., sulbenox or peptides disclosed in U.S. Pat. No. 4,411,890; growth hormone secretagogues such as, for example, anamorelin, pralmorelin, examorelin, tabimorelin, capimorelin, capromorelin, ipamorelin, EP-01572, EP-1572, or JMV-1843, GHRP-6, GHRP-1 (as described in U.S. Pat. No. 4,411,890 and publications WO 89/07110 and WO 89/07111), GHRP-2 (as described in WO 93/04081), NN.sub.7O.sub.3 (Novo Nordisk), LY444711 (Lilly), MK-677 (Merck), CP424391 (Pfizer) and B-HT920 and other representative examples disclosed in U.S. Pat. Nos. 3,239,345, 4,036,979, 4,411,890, 5,206,235, 5,283,241, 5,284,841, 5,310,737, 5,317,017, 5,374,721, 5,430,144, 5,434,261, 5,438,136, 5,494,919, 5,494,920, 5,492,916 and 5,536,716; European Patent Pub. Nos. 0,144,230 and 0,513, 974; PCT Patent Pub. Nos. WO 94/07486, WO 94/08583, WO 94/11012; WO 94/13696, WO 94/19367, WO 95/03289, WO 95/03290, WO 95/09633, WO 95/11029, WO 95/12598, WO 95/13069, WO 95/14666, WO 95/16675, WO 95/16692, WO 95/17422, WO 95/17423, WO 95/34311, and WO 96/02530; articles, Science, 260 1640-1643 (Jun. 11, 1993); Ann. Rep. Med. Chem., 28: 177-186 (1993); Bioorg. Med. Chem. Lett., 4: 2709-2714 (1994); and Proc. Natl. Acad. Sci. USA, 92: 7001-7005 (1995); and growth hormone releasing factor and its analogues such as, for example (a) epidermal growth factor (EGF);

(b) transforming growth factor-.alpha. (TGF-.alpha.);

(c) platelet derived growth factor (PDGF);

(d) fibroblast growth factors (FGFs) including acidic fibroblast growth factor (.alpha.-FGF) and basic fibroblast growth factor (.beta.-FGF), including, but not limited to aFGF, bFGF and related peptides with FGF activity [Hurley Florkiewicz, "Fibroblast growth factor and vascular endothelial growth factor families," 1996. In: J. P. Bilezikian, et al., Ed. Principles of Bone Biology, San Diego: Academic Press];

(e) transforming growth factor-.beta. (TGF-.beta.)

(f) insulin like growth factors (IGF-1 and IGF-2) selected from, but not limited to, Insulin-like Growth Factor I, alone or in combination with IGF binding protein 3 and IGF II [See Johannson and Rosen, "The IGFs as potential therapy for metabolic bone diseases," 1996, In: Bilezikian, et al., Ed., Principles of Bone Biology, San Diego: Academic Press; and Ghiron et al., J. Bone Miner. Res. 10: 1844-1852 (1995)] IGF-1, IGF-1 analogues and secretagogue IGF-1

(xviii) a bone morphogenetic protein (BMP), including, but not limited to, chordin, fetuin, BMP 2, 3, 5, 6, 7, as well as related molecules TGF beta and GDF 5 [Rosen et al., "Bone morphogenetic proteins," 1996. In: J. P. Bilezikian, et al., Ed., Principles of Bone Biology, San Diego: Academic Press; and Wang E A, Trends Biotechnol., 11: 379-383 (1993)];

(xix) an inhibitor of BMP antagonism including, but not limited to, sclerostin, SOST, noggin, chordin, gremlin, and dan [see Massague and Chen, "Controlling TGF-beta signaling," Genes Dev., 14: 627-644, 2000; Aspenberg et al., J. Bone Miner. Res. 16: 497-500, 2001; and Brunkow et al., Am. J. Hum. Genet. 68: 577-89 (2001)];

(xx) Vitamin D, vitamin D derivatives, vitamin D analogs, including, but not limited to, D.sub.3 (cholecaciferol), D.sub.2 (ergocalciferol), 25-OH-vitamin D.sub.3, 1.alpha., 25(OH).sub.2 vitamin D.sub.3, 1.alpha.-OH-vitamin D.sub.3, 1.alpha.-OH-vitamin D.sub.2, dihydrotachysterol, 26,27-F6-1.alpha.,25(OH).sub.2 vitamin D.sub.3, 19-nor-1.alpha.,25(OH).sub.2 vitamin D.sub.3, 22-oxacalcitriol, calcipotriol, 1.alpha.,25(OH).sub.2-16-ene-23-yne-vitamin D.sub.3 (Ro 23-7553), EB1089, 20-epi-1.alpha., 25(OH).sub.2 vitamin D.sub.3, KH1060, ED71, 1.alpha.,24 (S)—(OH).sub.2 vitamin D.sub.3, 1.alpha.,24(R)—(OH) .sub.2 vitamin D.sub.3 [See, Jones G., "Pharmacological mechanisms of therapeutics: vitamin D and analogs," 1996. In: J. P. Bilezikian, et al. Ed. Principles of Bone Biology, San Diego: Academic Press] and vitamin D receptor ligand and analogues such as calcitriol, topitriol, ZK-150123, TEI-9647, BXL-628, Ro-26-9228, BAL-2299, Ro-65-2299 or DP-035;

(xxi) Vitamin K and Vitamin K derivatives, including, but not limited to, menatetrenone (vitamin K2) [see Shiraki et al., J. Bone Miner. Res., 15: 515-521 (2000)];

(xxii) soy isoflavones, including ipriflavone;

(xxiii) dietary calcium supplements including, but not limited to, calcium carbonate, calcium citrate, and natural calcium salts (Heaney. Calcium. 1996. In: J. P. Bilezikian, et al., Ed., Principles of Bone Biology, San Diego: Academic Press);

(xxiv) fluoride salts, including, but not limited to, sodium fluoride (NaF) and monosodium fluorophosphate (MFP);

(xxv) androgen receptor modulators, such as those disclosed in Edwards, J. P. et. al., Bio. Med. Chem. Let., 9, 1003-1008 (1999) and Hamann, L. G. et. al., J. Med. Chem., 42, 210-212 (1999); a steroidal or nonsteroidal androgen receptor antagonist, including, but not limited to, enzalutamide, ARN-509, flutamide, hydroxyflutamide, bicalutamide, nilutamide, or hydroxysteroid dehydrogenase inhibitor or abiraterone; a reversible antiandrogen; or another SARM agent, including, but not limited to those disclosed herein, RU-58642, RU-56279, WS9761 A and B, RU-59063, RU-58841, bexlosteride, LG-2293, L-245976, LG-121071, LG-121091, LG-121104, LGD-2226, LGD-2941, LGD-3303, LGD-4033, YM-92088, YM-175735, LGD-1331, BMS-357597, BMS-391197, S-40542, S-40503, BMS-482404, EM-4283, EM-4977, BMS-564929, BMS-391197, BMS-434588, BMS-487745, BMS-501949, SA-766, YM-92088, YM-580, LG-123303, LG-123129, PMCol, YM-175735, BMS-591305, BMS-591309, BMS-665139, BMS-665539, CE-590, 116BG33, 154BG31, arcarine, or ACP-105;

(xxvi) an antiemetic drug including, but not limited to, a dopamine antagonist such as, for example, domperidone droperidol, chlorpromazine, promethazine, or metoclopramide; or an antihistamine such as, for example, cyclizine, diphenhydramine, dimenhydrinate, or meclizine; or tropisetron;

(xxvii) erythropoietin, including obtained by natural sources (e.g., urinary erythropoietin; See U.S. Pat. No. 3,865,801), or recombinantly produced protein and analogs thereof, for example, as described in U.S. Pat. Nos. 5,441, 868, 5,547,933, 5,618,698 and 5,621,080 as well as human erythropoietin analogs with increased glycosylation and/or changes in the amino acid sequence as those described in European Patent Publication No. EP 668351 and the hyperglycosylated analogs having 1-14 sialic acid groups and changes in the amino acid sequence described in PCT Publication No. WO 91/05867, including erythropoietin-like polypeptides comprise darbepoietin (from Amgen; also known as Aranesp and novel erthyropoiesis stimulating protein (NESP));

(xxviii) an immunomodulating agent, including, but not limited to, immunosuppressive cytotoxic drugs, such as, for example, mechlorethamine, chlorambucil; immunosuppressive agent such as, for example, mycophenolate motefil or 6-thioguanine, including those which can optionally be administered topically such as tacrolimus, pimecrolimus, imiquimod, 5-fluorouracil, or mechlorethamin; immunostimulatory agents such as, for example, a non-specificimmunostimulator for example Freund's complete adjuvant, Freund's incomplete adjuvant, a montanide ISA adjuvant, a Ribi's adjuvant, a Hunter's TiterMax, an aluminum salt adjuvant, a nitrocellulose-adsorbed protein, a Gerbu Adjuvant;

(xxix) a retinoid, including, but not limited to, isotretinoin, acitretin, tretinoin, adapalene, tazarotene, bexarotene, alitretinoin, or beta-carotene;

(xxx) an antacid agent;

(xxxi) a 17-beta hydroxysteroid dehydrogenase inhibitor;

(xxxii) an anti-rheumatic drug, including, but not limited to, chloroquine, hydroxychloroquine, sulfasalazine, cyclosporine, sulfasalazine, aurothioglucose, gold sodium thiomalate, or auranofin;

(xxxiii) a gene therapy agent, including but not limited to, an antisense agent such as, for example, anti-sense oligonucleotides; or a replacement gene;

(xxxiv) a PDE5 inhibitor, for example sildenafil, tadalafil or vardenafil;

(xxxv) strontium ranelate (xxxvi) a chemotherapeutic agent and/or therapy, including but not limited to, ifosfamide, adriamycin, doxorubicin, cyclosporine;

(xxxvii) an MMP inhibitor;

(xxxviii) an anti-thyroid agent, including, but not limited to, thyroid hormone supplement thyroxine, L-thyroxine;

(xxxix) an angiotensin converting enzyme (ACE) inhibitor, including, but not limited to, benazepril, captopril, cilazapril, enalapril, fosinopril, lisinopril, moexipril, perindopril, quinapril, ramipril, trandolapril, or enalaprilat; or angiotensin II antagonists such as, for example, losartan;

(xl) a neurodegenerative disorder medication including, but not limited to, acetylcholinesterase inhibitor such as, for example, tacrine, donepezil, galanthamine, or rivastigmine; N-methyl-D-aspartate (NMDA) antagonist such as, for example, memantine; dopaminergic agonist; AMPA regulator; cholinesterase inhibitor; dopaminergic drugs such as, for example, amantadine, biperiden, bromocriptine, entacapone, selegiline/deprenyl, iphenhydramine, pergolide, procyclidine, selegiline, or trihexyphenidyl; gamma secretase inhibitor; or A beta lowering drug; riluzole; an agent which silences the gene that causes the progression of the disease; or a cholinesterase inhibitor, including but not limited to a quaternary ammonium agent, such as, for example, edrophonium or ambenonium;

(xli) an anti-hypercholesterolemic agent including, but not limited to, a cholesterol absorption inhibitors, such as, for example, SCH-58235, also known as ezetimibe; 1-(4-fluorophenyl)-3(R)-[3(S)-(4-fluorophenyl-)-3-hydroxypropyl)]-4(S)-(4-hydroxyphenyl)-2-azetidinone, described in U.S. Pat. Nos. 5,767,115 and 5,846,966; niacin-lovastatin; colestipol HCl; sodium, gemfibrozil; cholestyramine; cholestyramine light; colesevelam HCl;

(xlii) an adrenomimetic drug, such as a beta-adrenoceptor agonist, alpha-adrenoceptor agonist, In one embodiment, the adrenomimetic drug is a catecholamine. In one embodiment, adrenomimetic drugs include but are not limited to isoproterenol, norepinephrine, epinephrine, ephedrine, or dopamine. In one embodiment, the adrenomimetic drug is a directly acting adrenomimetic drug. In some embodiments, directly acting adrenomimetic drugs include but are not limited to phenylephrine, metaraminol, or methoxamine;

(xliii) an appetite stimulants such as megestrol acetate, cyproheptadine;

(xliv) a luteinizing hormone releasing hormone (LHRH), a LHRH analog or derivative, a luteinizing hormone agonists or antagonists including, but not limited to, letrozole, anastrazole, atamestane, fadrozole, minamestane, exemestane, plomestane, liarozole, NKS-01, vorozole, YM-511, finrozole, 4-hydroxyandrostenedione, aminogluethimide, or rogletimide;

(xlv) a vitronectin receptor antagonist;

(xlvi) a Src SH2 antagonists or a Src kinase inhibitors;

(xlvii) a protein synthesis inhibitor including, but not limited to, abrin, aurintricarboxylic acid, colicin E3, cycloheximide, diphtheria toxin, edeine A, emetine, erythromycin, ethionine, 5-fluorotryptophan, fusidic acid, guanylyl methylene diphosphonate and guanylyl imidodiphosphate, kanamycin, kasugamycin, kirromycin, and O-methyl threonine, modeccin, neomycin, norvaline, pactamycin, paromomycine, puromycin, ricin, .alpha.-sarcin, shiga toxin, showdomycin, sparsomycin, spectinomycin, streptomycin, thiostrepton;

(xlviii) an inhibitor of an enzyme involved in the androgen biosynthetic pathway, including, but not limited to, 17-ketoreductase inhibitor, a 17-aldoketoreductase inhibitor, a3-.DELTA.H4,6-isomerase inhibitor, a 3-.DELTA.H4,5-isomerase inhibitor, a 17,20 desmolase inhibitor, a p450c17 inhibitor, a p450ssc inhibitor, a 17.beta.-hydroxysteroid dehydrogenase inhibitor, or a 17,20-lyase inhibitor such as abiraterone;

(xlix) an anti-inflammatory agent, including, but not limited to, non-steroidal anti-inflammatory agents such as salsalate, diflunisal, ibuprofen, fenoprofen, flubiprofen, fenamate, ketoprofen, nabumetone, piroxicam, naproxen, diclofenac, indomethacin, sulindac, tolmetin, etodolac, ketorolac, oxaprozin, or celecoxib, cyclooxygenase-2 inhibitors, such as rofecoxib and celecoxib; 5-amino-salicylate, corticosteroid, metronidazole, ciprofloxacin, infiximab, budesonide, or anti-TNF alpha antibody;

(l) an anti-diabetic agent, including, but not limited to, a sulfonylurea, such as, for example tolbutamide, acetohexamide, tolazamide, chlorpropamide, glipizide, glyburide, glimepiride, or gliclazide; a meglitinide, for example prandin or nateglinide; a biguanide, such as, for example metformin; a thiazolidinedione such as, for example rosiglitazone, pioglitazone, or troglitazone;

(lii) an analgesic agent, including, but not limited to, paracetamol;

(liii) an expectorant, including, but not limited to a mucolytic agent;

(liv) an anti-estrogen;

(lv) an antiviral agent, including, but not limited to, abacavir, acyclovir, amantadine, didanosine, emtricitabine, enfuvirtide, entecavir, lamivudine, nevirapine, oseltamivir, ribavirin, rimantadine, stavudine, valaciclovir, vidarabine, zalcitabine, or zidovudine; nucleotide analog reverse transcriptase inhibitor such as, for example, otenofovir or adefovir; or interferon alpha; a protease inhibitor include but are not limited to saquinavir, ritonavir, indinavir, nelfinavir, amprenavir, lopinavir, fosamprenavir, or tipranavir;

(lvi) a cortisone, cortisol, icortisone, corticosterone, corticosteroid, glucocorticosteroid including, but not limited to, including glucocorticoid or analogues thereof, corticotrophin, cyclosporine, cyclophosphamide, tacrolimus-FK-506, anti-thymocyte globulin, mycophenylate prednisone or dexamethasone moeftil, betamethasone dipropionate, clobetasol, diflorasone, amcinonide, desoximetasone, fluocinonide, aclometasone, desonide triamcinolone, fluticasone, halobetasol, mometasone, or hydrocortisone, prednisone; or steroidal or nonsteroidal glucocorticoid receptor ligands, such as, ZK-216348, ZK-243149, ZK-243185, LGD-5552, mifepristone, RPR-106541, ORG-34517, GW-215864.times., Sesquicillin, CP-472555, CP-394531, A-222977, AL-438, A-216054, A-276575, CP-394531, CP-409069, UGR-07;

(lvii) somatostatin analogue or agents which inhibit somatostatin or its release, including, but not limited to, physostigmine and pyridostigmine;

(lviii) a Bax activity modulator such as alisol B acetate;

(lix) a cytokine, including, but not limited to, IL-3, IL-7, GM-CSF, anticytokine antibodies, cytokine inhibitors;

(lx) an insulin, including but not limited to, short-, intermediate-, and long acting formulations;

(lxi) insulin-sensitizers, including but not limited to, biguanides such as, for example, metformin;

(lxii) gonadotropin; gonadotropin-releasing hormone or analogue or derivatives thereof; gonadotropin-releasing hormone agonists or antagonists, including, but not limited to, leuprolide, goserelin, triptorelin, alfaprostol, histrelin, detirelix, ganirelix, antide iturelix, cetrorelix, ramorelix, ganirelix, antarelix, teverelix, abarelix, ozarelix, sufugolix, prazarelix, degarelix, NBI-56418, TAK-810, acyline;

(lxiii) a ghrelin, a ghrelin receptor ligand or analogs thereof, including, but not limited to, human ghrelin, CYT-009-GhrQb, L-692429, GHRP-6, SK&F-110679, or U-75799E, leptin, metreleptin, pegylated leptin; a leptin receptor agonist, such as LEP(116-130), OB3, [D-Leu4]-OB3, rAAV-leptin, AAV-hOB, rAAVhOB; or a steroidal or nonsteroidal GR ligand;

(lxiv) a 5a-Reductase Inhibitor, including, but not limited to, finasteride, dutasteride, izonsteride;

(lxv) an aromatase inhibitor, including, but not limited to, letrozole, anastrazole, atamestane, fadrozole, minamestane, exemestane, plomestane, liarozole, NKS-01, vorozole, YM-511, finrozole, 4-hydroxyandrostenedione, aminogluethimide, rogletimide;

(lxvi) an agent for treating an ophthalmic disease, including, but not limited to, betagan, betimol, timoptic, betoptic, betoptic, ocupress, optipranolol, xalatan, alphagan, azopt, trusopt, cospot, pilocar, pilagan, propine, opticrom, acular, livostin, alomide, emadine, patanol, alrex, poly-pred, pred-g, dexacidin, erythromycin, maxitrol, FML, ocufen, voltaren, profenal, pred forte, betadine, gramicidin, prednisolone, betaxolol, humorsol, proparacaine, betoptic, hylartin, flurbiprofen, methazolamide, timolol, terramycin, ciprofloxacin, miostat, triamcinolone, miconazole, tobramycin, physostimine, gentamicin, pilocarpine, goniosol, oxytetracycline, viroptic, suprofen, celluvisc, ciloxan, ocuflox, brinzolamide, cefazolin, tobrex, latanoprost, indocycanine, trifluridine, phenylephrine, demecarium, neomycin, tropicamide, dexamethasone, neptazane, dipivefrin, vidarabine, dorzolamide, ofloxacin, epinephrine, acyclovir, carbonic anhydrase inhibitor, vitamin A, zinc, copper, atropine, flarex, eflone, illotycin, or garamycin;

(lxvii) an adrenoceptor antagonist including, but not limited to, a haloalkylamine, such as, for example, phenoxybenzamine; imidazoline, such as, for example, phentolamine or tolazoline; quinazoline such as, for example, prazosin, terazosin, doxazosin, or trimazosin; or an agent with combined alpha and blocking activity, such as, for example, labetalol, bucindolol, carvedilol, or medroxalol;

(lxviii) a progestin, a progestin deriviative or analog, a synthetic progestin, progesterone, progesterone receptor agonists ("PRA"), such as levonorgestrel, medroxyprogesterone acetate (MPA) prostaglandins (for osteo) or steroidal or nonsterodial progesterone receptor ligands;

(lxix) an alpha glucosidase inhibitor such as acarbose, miglitol;

(lxx) an anti-arrhythmic agent including, but not limited to, a sodium channel blocker such as, for example, quinidine, procainamide, disopyramide, lidocaine, tocamide, mexiletine, encamide, or flecamide; a beta-adrenergic blocker, such as, for example acebutolol, esmolol, or sotalol; or an agent that prolong repolarization, such as, for example, amiodarone; adenosine or digoxin;

(lxxi) an agent wich interferes with tumor necrosis factore, including, but not limited to, etanercept;

(lxxii) a beta-blocker, including, but not limited to, acebutolol, atenolol, betaxolol hydrochloride, bisoprolol fumarate, carteolol hydrochloride, carvedilol, celiprolol hydrochloride, esmolol hydrochloride, labetalol hydrochloride, levobunolol, metoprolol tartrate, metipranolol, nadolol, nebivolol, oxprenolol hydrochloride, pindolol, sotalol hydrochloride, or timolol maleate;

(lxxiii) a photochemotherapy agent including, but not limited to, PUVA or psoralen such as oxsoralen;

(lxxiv) a photodynamic agent, including, but not limited to, porphyrin;

(lxxv) an anti-diuretic hormone or antidiuretic hormone analogue;

(lxxvi) a steroidal or nonsteroidal AR antagonists such as flutamide, hydroxyflutamide, bicalutamide, nilutamide, enzalutamide, ARN-509;

(lxxxvii) a myostatin antibody or a myostatin analog;

(lxxxviii) a RANK ligand monoclonal antibody (mAb), including, but not limited to, denosumab (Prolia™) formerly AMG162 (Amgen)

(lxxxix) a diuretic, including, but not limited to thiazide diuretic, such as, for example, bendrofluazide, bendroflumethiazide, benzthiazide, chlorothiazide, chlorthalidone, cyclopenthiazide, Diucardin®, Diuril®, Enduron®, Esidrix®, Exna®, HCTZ, Hydrochlorothiazide, HydroDIURIL®, hydroflumethiazide, Hydromox®, Hygroton®, indapamide, Lozol®, methyclothiazide, metolazone, Mykrox®, Naqua®, Naturetin®, Oretic®, polythiazide, quinethazone, Renese®, trichlormethiazide, xipamide, or Zaroxolyn®; a loop diuretic such as, for example, furosemide, bumetanide, or torsemide; a potassium-sparing diuretic such as, for example, amiloride, triamterene, aldosterone antagonists, or spironolactone; organomercurial, ethacrynic acid, furosemide, bumetanide, piretanide, muzolimine, chlorothiazide and thiazide, phthalimidine, chlorthalidone, clorexolone, quinazolinone, quinethazone, metolazone ilenzenesulphonamide, mefruside, chlorobenzamide, clopamidesalicylamide, xipamide, xanthine, aminophylline, carbonic anhydrase inhibitor, acetazolamide mannitol, potassium-sparing compound, aldosterone antagonist, spironolactone;

(xc) a steroid, including, but not limited to, an androgenic/anabolic steroid such as testosterone/oxandrolone;

(xci) a proteasome inhibitor;

(xcii) a melanocortin 4 receptor agonist, including, but not limited to, bremelanotide;

(xciii) a squalene epoxidase inhibitor or a squalene synthetase inhibitors (also known as squalene synthase inhibitors);

(xciv) a calcium channel blocker, including but not limited to, verapamil, diltiazem, or mebefradil;

(xcv) a mineral, including, but not limited to, selenium, magnesium, zinc, chromium, calcium, potassium, platinum or derivatives or salts thereof;

(xcvi) a calcium receptor antagonist;

(xcvii) a beta-2 agonist;

(xcviii) an anti-cholinergic bronchodilator, including, but not limited to, theophylline, aminophylline;

(xcix) a vasoactive agent or an inotrope including, but not limited to, digoxin, dopamine, dobutamine, hydralazine, prazosin, carvedilol, nitroprusside, nitroglycerin, lisinopril, diltiazem, hydrochlorothiazide, furosemide, spironolactone, AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), or nitrates;

(c) an anticancer agent including, but not limited to, (a) a monoclonal antibody, which antibody may be optionally used for diagnosis, monitoring, or treatment of cancer, including monoclonal antibodies which react against specific antigens on cancer cells such as the monoclonal antibody acts as a cancer cell receptor antagonist, those which monoclonal antibodies enhance the patient's immune response, those which act against cell growth factors, thus blocking cancer cell growth, those which are conjugated or linked to anti-cancer drugs, radioisotopes, other biologic response modifiers, other toxins, or a combination thereof;

(b) a selective tyrosine kinase inhibitor including those embodiments where the selective tyrosine kinase inhibitor inhibits catalytic sites of cancer promoting receptors thereby inhibiting tumor growth; the selective tyrosine kinase inhibitor modulates growth factor signaling; the selective tyrosine kinase inhibitor targets EGFR (ERB B/HER) family members; the selective tyrosine kinase inhibitor is a BCR-ABL tyrosine kinase inhibitor; the selective tyrosine kinase inhibitor is an epidermal growth factor receptor tyrosine kinase inhibitor; the selective tyrosine kinase inhibitor is a vascular endothelial growth factor tyrosine kinase inhibitor; the selective tyrosine kinase inhibitor is a Platelet Derived Growth Factor (PDGF) inhibitor;

(c) an alkylating agent (d) a vinca alkaloid, including, but not limited to, vindesine (e) platinum compounds, including, but not limited to, carboplatin (f) taxanes, including, but not limited to, docetaxel (g) antineoplastic agents, including, but not limited to, alkylating agents such as, for example, alkyl sulfonates such as busulfan, improsulfan and piposulfan; aziridines, carboquone, meturedepa and uredepa; ethylenimines and methylmelamines such as altretamine, triethylenemelamine, triethylenephosphoramide, triethylenethiophosphoramide and trimethylol melamine; nitrogen mustards such as chlorambucil, chlomaphazine, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, ranimustine, dacarbazine, mannomustine, mitobronitol, mitolactol and pipobroman, hormonal antineoplastics and antimetabolites;

(h) inhibitors of DNA synthesis, including alkylating agents such as dimethyl sulfate, mitomycin C, nitrogen and sulfur mustards, MNNG and NMS; intercalating agents such as acridine dyes, actinomycins, adriamycin, anthracenes, benzopyrene, ethidium bromide, propidium diiodide-intertwining, and agents such as distamycin and netropsin;

(i) DNA base analogs such as acyclovir, adenine, .beta.-1-D-arabinoside, amethopterin, aminopterin, 2-aminopurine, aphidicolin, 8-azaguanine, azaserine, 6-azauracil, 2'-azido-2'-deoxynucliosides, 5-bromodeoxycytidine, cytosine, .beta.-1-D-arabinoside, diazooxynorleucine, dideoxynucleosides, 5-fluorodeoxycytidine, 5-fluorodeoxyuridine, 5-fluorouracil, hydroxyurea and 6-mercaptopurine;

(j) topoisomerase inhibitors, such as coumermycin, nalidixic acid, novobiocin and oxolinic acid, inhibitors of cell division, including colcemide, vinblastine and vincristine; and RNA synthesis inhibitors including actinomycin D, .alpha.-amanitine and other fungal amatoxins, cordycepin (3'-deoxyadenosine), dichlororibofuranosyl benzimidazole, rifampicine, streptovaricin and streptolydigin;

(k) an ER antagonist, including, but not limited to, fulvestrant;

(l) a cancer vaccine, including a therapeutic vaccine thus, treating an existing cancer; a a prophylactic vaccine thus, preventing the development of cancer, which vaccine may be a antigen/adjuvant vaccine, or a whole cell tumor vaccine, or a dendritic cell vaccine. In one embodiment, the cancer vaccine comprises viral vectors and/or DNA vaccines, including those embodiments where the cancer vaccine is an idiotype vaccine;

(ci) a cholesterol acyltransferase (ACAT) inhibitors including selective inhibitors of ACAT-1 or ACAT-2 as well as dual inhibitors of ACAT-1 and -2;

(cii) an amylin analogue such as pramlintide;

(ciii) a cholesteryl ester transfer protein or CETP Inhibitor, including, but not limited to, JTT-705, CETi-1;

(civ) a vasodilator;

(cv) an anti-anginal agent including, but not limited to, nifedipine;

(cvi) a glucagon-like peptide-1 (GLP-1) and analogues, including, but not limited to, exenatide or liraglutide;

(cvii) a H.sub.2-receptor antagonist, including, but not limited to, cimetidine and ranitidine, famotidine, or nizatidine (cviii) a hypocholesterolemic agent;

(cix) an anti-hypertensive including, but not limited to, methyldopa, reserpine, clonidine, and verapamil;

(cx) a AR partial antagonists, including, but not limited to, spironolactone, eplerenone;

(cxi) an endothelin antagonist;

(cxii) a vacuolar-H.sup.+-ATPase inhibitor;

(cxiii) a alpha.nu.beta.3 Integrin receptor antagonist;

(cxiv) an agent to decrease prostate (benign or malignant) hypertrophy;

(cxv) a microsomal triglyceride transfer protein (MTP) inhibitor;

(cxvi) a FSH agonist/antagonist;

(cxvii) a colchicine;

(cxviii) a LDL (low density lipoprotein) receptor inducer;

(cxix) an agent such as a LXR ligand that enhances ABC1 gene expression;

(cxx) a steroidal or nonsterodial PR ligand;

(cxxi) a cytotoxic antibiotic;

(cxxii) an antimetabolite;

(cxxiii) an analgesic agent;

(cxxiv) a cholinomimetic agent, including, but not limited to, a direct-acting parasympathomimetic drug such as, for example, methacholine, pilocarpine, carbachol, or bethanechol (cxxv) a selective serotonin receptor inhibitor;

(cxxvi) a serotonin norepinephrine receptor inhibitor;

(cxxvii) an anti-infective agent;

(cxxviii) a AT-II receptor antagonist, including, but not limited to, valsartan or telmisartan;

(cxxix) an agent treating neuromuscular transmission, a nervous system stimulant;

(cxxx) androgen deprevation therapy;

(cxxxi) a muscarinic blocking agent, including, but not limited to, belladonna alkaloid such as, for example, atropine or scopolamine;

(cxxxii) a 5-HT.sub.3 receptor antagonist including, but not limited to, dolasetron, granisetron, ondansetron;

(cxxxiii) a beta-3 adrenergic agonist;

(cxxxiv) a DPP-IV inhibitor, including, but not limited to, vildagliptin or sitagliptin;

(cxxxv) a pancreatic lipase inhibitor, including, but not limited to, orlistat, cetilistat;

(cxxxvi) a muscle relaxant including but not limited to methocarbamol, baclofen, carisoprodol, chlorzoxazone, cyclobenzaprine, dantrolene, metaxalone, orphenadrine, amyl nitrite, pancuronium, tizanidine, clonidine, or gabapentin;

(cxxxvii) a vasoconstrictor agent including, but not limited to, adrenalin dimethylarginine, caffeine, cannabis, catecholamines, decongestants, pseudoephedrinse, norepinephrines, tetrahydrozoline, or thromboxane;

(cxxxviii) a fusion inhibitor such as enfuvirtide;

(cxxxix) a SGLT (sodium-dependent glucose transporter 1) inhibitor;

(cxl) a FBPase (fructose 1,6-bisphosphatase) inhibitor;

(cxli) a dipeptidyl peptidase IV (DPP4) inhibitors such as those disclosed in WO 01/68603;

(cxlii) a fibrinogen receptor antagonist;

(cxliii) coenzyme Q10;

(cxliv) folic antioxidants;

(cxlv) one or more nucleic acids which encode bone-stimulating compounds;

(cxlvi) acyl-coenzyme A; or (cxlvii) an HDL-elevating agent including, but not limited to, 1-hydroxyalkyl-3-phenylthiourea, and analogs thereof;

(cxlviii) an antimuscarinic agent including, but not limited to, tolterodine or fesoteridine, or (cxlix) an alpha 2 delta agent including, but not limited to, gabapentin or pregablin;

or pharmaceutically acceptable salts or derivatives thereof.

A compound of Formula 1, Formula 2 or Formula 3 as defined herein, or a pharmaceutically acceptable salt thereof, can also be combined with one or more of the following pharmaceutically active agents, osteocalcin, osteonectin; osteoprotegerin; gallium maltolate; metyrapone; mitotane; mifepristone; thiazolidinedione; folic acid; carnitine; inflamase forte; inflamase mild; melatonin; clenbuterol; methotrexate; probucol; HCT-1026; aminolevulinic acid; canrenoate; pteridines; pyrazine; carboxamide-triamterene; or amiloride; propranolol; follistatin; creatinine; green tea cachecins; saw palmetto; lycopene; genistein; pentoxifylline; hydrazine sulfate; nicardipin; econpred plus; lotemax; vexol; blephamide; tobradex; polytrim or pharmaceutically acceptable salts or derivatives thereof.

In a preferred embodiment, the second pharmaceutically active ingredient is selected from the group consisting of estrogens and estrogen derivatives, bisphosphonates, SERMs, calcitonin, cathepsin K inhibitors, alpha.v.beta.3 integrin receptor antagonists, vacuolar ATPase inhibitors, antagonists of VEGF, HMG-CoA reductase inhibitors, osteoanabolic agents, protein kinase inhibitors, activators of the peroxisome proliferator-activated receptor-.gamma. (PPAR.gamma.), the polypeptide osteoprotegerin, calcium receptor antagonists, growth hormone secretagogues, growth hormone releasing hormone, insulin-like growth factor, bone morphogenetic protein (BMP), inhibitors of BMP antagonism, fibroblast growth factors, vitamin D and derivatives thereof, vitamin K and derivatives thereof, soy isoflavones, calcium salts, fluoride salts, all as described herein, or pharmaceutically acceptable salts thereof.

In a preferred embodiment, the second pharmaceutically active ingredient is an estrogen or estrogen derivative, or pharmaceutically acceptable salts thereof.

In another preferred embodiment, the second pharmaceutically active ingredient is a bisphosphonate, or pharmaceutically acceptable salts thereof. In a further preferred embodiment, the bisophsophonate is selected from the group consisting of alendronate, clodronate, etidronate, ibandronate, incadronate, minodronate, neridronate, olpadronate, pamidronate, piridronate, risedronate, tiludronate, zoledronate, pharmaceutically acceptable salts of these bisphosphonates, and pharmaceutically acceptable salts thereof.

In a further preferred embodiment, the second pharmaceutically active ingredient is a SERM, or pharmaceutically acceptable salt thereof.

In a further preferred embodiment, the second pharmaceutically active ingredient is a calcitonin, or pharmaceutically acceptable salt thereof.

In a further preferred embodiment, the second pharmaceutically active ingredient is a cathepsin K inhibitor, or pharmaceutically acceptable salt thereof.

In a further preferred embodiment, the second pharmaceutically active ingredient is an alpha.v.beta.3 integrin receptor antagonists, or pharmaceutically acceptable salt thereof.

In a further preferred embodiment, the second pharmaceutically active ingredient is a vacuolar ATPase inhibitor, or pharmaceutically acceptable salt thereof.

In a further preferred embodiment, the second pharmaceutically active ingredient is an antagonists of VEGF, or pharmaceutically acceptable salt thereof.

In a further preferred embodiment, the second pharmaceutically active ingredient is an HMG-CoA reductase inhibitor, or pharmaceutically acceptable salt thereof.

In a further preferred embodiment, the second pharmaceutically active ingredient is an osteoanabolic agent, or pharmaceutically acceptable salt thereof.

In a further preferred embodiment, the second pharmaceutically active ingredient is a protein kinase inhibitor, or pharmaceutically acceptable salt thereof.

In a further preferred embodiment, the second pharmaceutically active ingredient is an activator of the peroxisome proliferator-activated receptor-.gamma. (PPAR.gamma.), or pharmaceutically acceptable salt thereof.

In a further preferred embodiment, the second pharmaceutically active ingredient is the polypeptide osteoprotegerin, or pharmaceutically acceptable salt thereof.

In a further preferred embodiment, the second pharmaceutically active ingredient is a calcium receptor antagonist, or pharmaceutically acceptable salt thereof.

In a further preferred embodiment, the second pharmaceutically active ingredient is a growth hormone secretagogue, or pharmaceutically acceptable salt thereof.

In a further preferred embodiment, the second pharmaceutically active ingredient is a growth hormone releasing hormone, or pharmaceutically acceptable salt thereof.

In a further preferred embodiment, the second pharmaceutically active ingredient is an insulin-like growth factor, or pharmaceutically acceptable salt thereof.

In a further preferred embodiment, the second pharmaceutically active ingredient is a bone morphogenetic protein, or pharmaceutically acceptable salt thereof.

In a further preferred embodiment, the second pharmaceutically active ingredient is an inhibitors of BMP antagonism, or pharmaceutically acceptable salt thereof.

In a further preferred embodiment, the second pharmaceutically active ingredient is a fibroblast growth factor, or pharmaceutically acceptable salt thereof.

In a further preferred embodiment, the second pharmaceutically active ingredient is an antimuscarinic agent, or a pharmaceutically acceptable salt thereof.

In a further preferred embodiment, the second pharmaceutically active ingredient is an alpha 2 delta agent, or a pharmaceutically acceptable salt thereof.

In one embodiment, the present invention provides combined preparations. In one embodiment, the term "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art. Thus, a kit of the invention comprises two or more separate pharmaceutical compositions, at least one of which contains a compound of Formula 1, 2 or 3, or a pharmaceutically acceptable salt thereof, at least a second of which comprises a second pharmaceutically active ingredient, or a pharmaceutically acceptable salt thereof, and means for separately retaining said compositions, such as a container, divided bottle, or divided foil packet. An example of such a kit is the familiar blister pack used for the packaging of tablets, capsules and the like. Such a kit is particularly suitable for administering different dosage forms, for example, oral and parenteral, for administering separate compositions at different dosage intervals, or for titrating the separate compositions against one another. To assist compliance, the kit typically comprises directions for administration and may be provided with a so-called memory aid.

In one embodiment, this invention relates to a kit comprising:

(i) a pharmaceutical dosage form comprising a compound of Formula 1, Formula 2 or Formula 3, as defined herein, or pharmaceutically acceptable salt thereof, and a pharmaceutically acceptable excipient; and (ii) a pharmaceutical dosage form comprising a second pharmaceutically active ingredient, and a pharmaceutically acceptable excipient.

Second pharmaceutically active ingredients useful in the kits of the present invention include those embodiments and preferred embodiments of second pharmaceutically active ingredients disclosed herein.

In one embodiment the invention is a kit comprising:

(i) a pharmaceutical dosage form comprising a compound of Formula 1, Formula 2 or Formula 3,

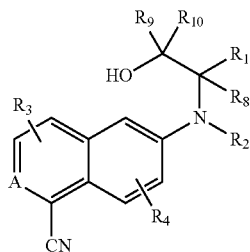

Formula 1

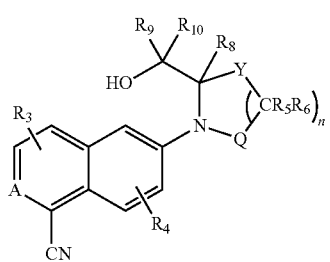

Formula 2

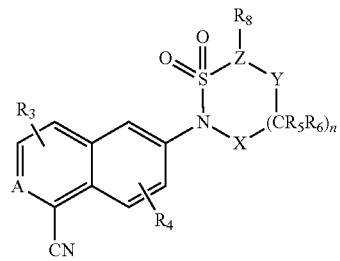

Formula 3 wherein A is N or —$CR_0$—, where $R_0$ is hydrogen, $C_1$-$C_6$ linear or branched chain alkyl, $C_1$-$C_6$ linear or branched chain perfluoroalkyl, aryl, perfluoroaryl, alkylaryl, heteroaryl; or, alkylheteroaryl X and Y are independently —$CH_2$—, —$CHR_a$—, or, —$CR_aR_b$—, where $R_a$ and $R_b$ are independently $C_1$-$C_6$ linear or branched chain alkyl, aryl, alkylaryl, heteroaryl or, alkylheteroaryl; or, $R_a$ and $R_b$ together form a chain comprising —$(CH_2)_j$—, —$(CHR_c)_j$—, or —$(CR_cR_d)_j$—, where $R_c$ and $R_d$ are independently $C_1$-$C_6$ linear or branched chain alkyl, $C_1$-$C_6$ linear or branched chain perfluoroalkyl, aryl, alkylaryl, heteroaryl or alkylheteroaryl; where j is 2; 3, 4 or 5

Z is —$CR_e$—, or, —N—, where $R_e$ is hydrogen, $C_1$-$C_6$ linear or branched chain alkyl, $C_1$-$C_6$ linear or branched chain perfluoroalkyl, aryl, alkylaryl, heteroaryl or, alkylheteroaryl;

$R_1$ is hydrogen, $C_1$-$C_6$ linear or branched chain alkyl, aryl, $C_1$-$C_6$ linear or branched chain perfluoroalkyl, alkylaryl, heteroaryl, alkylheteroaryl, $C_1$-$C_6$ linear or branched chain alkoxylcarbonyl, $C_1$-$C_6$ linear or branched chain alkylamino-carbonylamino, $C_1$-$C_6$ linear or branched chain alkyloxycarbonylamino, $C_1$-$C_6$ linear or branched chain alkylcarbonylamino, or, $C_1$-$C_6$ linear or branched chain alkylaminocarbonyl;

$R_2$ are independently hydrogen or $C_1$-$C_6$ linear or branched chain alkyl;

$R_3$ and $R_4$ are independently hydrogen, $C_1$-$C_6$ linear or branched chain alkyl, $C_1$-$C_6$ linear or branched chain perfluoroalkyl, $C_1$-$C_6$ linear or branched chain perfluoroalkoxy, halogen, cyano, hydroxyl, amino, carboxy, hydroxyl, aryl, heteroaryl, $C_1$-$C_6$ linear or branched chain alkoxylcarbonyl, $C_1$-$C_6$ linear or branched chain alkylamino-carbonylamino, or, $C_1$-$C_6$ linear or branched chain alkylaminocarbonyl;

$R_5$ and $R_6$ are independently hydrogen or $C_1$-$C_6$ linear or branched chain alkyl, $C_1$-$C_6$ linear or branched chain perfluoroalkyl, cyano, hydroxyl, amino, carboxy, hydroxyl, aryl, heteroaryl, or, $R_5$ and $R_6$ together form a chain comprising —$(CH_2)_k$—, —$(CHR_7)_k$—, or —$(CR_{7a}R_{7b})_k$—, where $R_7$, $R_{7a}$, and $R_{7b}$ are independently $C_1$-$C_6$ linear or branched chain alkyl, $C_1$-$C_6$ linear or branched chain perfluoroalkyl, aryl, alkylaryl, heteroaryl or alkylheteroaryl; where k is 2; 3, 4 or 5;

$R_8$ is hydrogen, $C_1$-$C_6$ linear or branched chain alkyl, $C_1$-$C_6$ linear or branched chain perfluoroalkyl, aryl, aryl substituted with one, two or three fluorine atoms, perfluoroaryl, alkylaryl, heteroaryl; or, alkylheteroaryl; or, $R_1$ and $R_8$ together form a chain comprising —$(CH_2)_m$—, —$(CHR_f)_m$—, or —$(CR_fR_g)_m$—, where $R_f$ and $R_g$ are independently $C_1$-$C_6$ linear or branched chain alkyl, aryl, alkylaryl, heteroaryl or alkylheteroaryl; where m is 2; 3, 4 or 5;

$R_9$ and $R_{10}$ are independently hydrogen or $C_1$-$C_6$ linear or branched chain alkyl, $C_1$-$C_6$ linear or branched chain perfluoroalkyl, cyano, hydroxyl, amino, carboxy, hydroxyl, aryl, heteroaryl, or, $R_9$ and $R_{10}$ together form a chain comprising —(CH$_2$)$_p$—, —(CHR$_h$)$_p$—, or —(CR$_h$R$_i$)$_p$—, where R$_h$ and R$_i$ are independently C$_1$-C$_6$ linear or branched chain alkyl, aryl, alkylaryl, heteroaryl or alkylheteroaryl; where p is 2; 3, 4 or 5;

Q is —CO—, —(CH$_2$)$_q$—, —(CHR$_s$)$_q$—, or —(CR$_s$R$_t$)$_q$—, where R$_s$ and R$_t$ are independently C$_1$-C$_6$ linear or branched chain alkyl, aryl, alkylaryl, heteroaryl or alkylheteroaryl; where q is 0, 1, 2, or 3; and, where n is 0, 1, 2, 3, 4 or 5; or pharmaceutically acceptable salt thereof, and a pharmaceutically acceptable excipient; and (ii) a pharmaceutical dosage form comprising a second pharmaceutically active ingredient, and a pharmaceutically acceptable excipient.

In one embodiment this kit is for use in the treatment of a disorder or condition selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy and stress urinary incontinence.

This invention also relates to a pharmaceutical composition comprising a compound of Formula 1, Formula 2 or Formula 3, as defined herein or pharmaceutically acceptable salt thereof as defined above; a second pharmaceutically active ingredient, or pharmaceutically acceptable salt thereof; and a pharmaceutically acceptable carrier or excipient.

Second pharmaceutically active ingredients useful in the compositions of the present invention include those embodiments and preferred embodiments of second pharmaceutically active ingredients disclosed herein.

As used herein the term "excipient" is taken to mean any ingredient in the pharmaceutical composition other than the compound of Formula 1, Formula 2 or Formula 3, or pharmaceutically acceptable salt thereof as defined above; a second pharmaceutically active ingredient, or pharmaceutically acceptable salt thereof. The choice of excipient will depend to a large extent on factors such as the particular mode of administration, the effect of the excipient on solubility and stability, and the nature of the dosage form, which factors are well known to the person skilled in the art. The term "excipient" encompasses diluent, carrier or adjuvant.

Pharmaceutical compositions suitable for the delivery of a compound of Formula 1, Formula 2 or Formula 3, as defined herein, or pharmaceutically acceptable salt thereof as defined above; a second pharmaceutically active ingredient, or pharmaceutically acceptable salt thereof and methods for their preparation can be readily determined by one skilled in the art. Such compositions and methods for preparation may be found, for example, in Remington's Pharmaceutical Sciences, 19$^{th}$ Edition (Mack Publishing Company, 1995).

Preferred pharmaceutical compositions of the present invention are those suitable for oral administration. Oral administration may involve swallowing, so that the pharmaceutically active ingredient enters the gastrointestinal tract, or alternatively, oral administration may involve buccal or sublingual administration by which the pharmaceutically active ingredient enters the blood stream directly from the mouth. Formulations suitable for oral administration include solid formulations such as tablets, capsules containing particulates, liquids, or powders, lozenges (including liquid filled), chews, multi- and nano-particulates, gels, solid solution, liposomes, films, ovules, sprays and liquid formulations.

Tablet formulations suitable for oral administration usually comprise from about 0.1% w/w to about 80% w/w of the active pharmaceutical ingredient, dependent on dose, more typically from 5% w/w to about 60% w/w of the dosage form. One of ordinary skill will appreciate that one of the factors to consider when determining the level of active pharmaceutical ingredient suitable for inclusion in a tablet for oral administration is that needed to ensure adequate patient dosing. For example, when dealing with an active ingredient which is potent or highly potent, tablet formulations suitable for oral administration may comprise a lower amount of active pharmaceutical ingredient, for example from about 0.1% w/w to about 20% w/w of the active pharmaceutical ingredient.

In addition to the active pharmaceutical ingredient, tablets suitable for oral administration also comprise one or more of the following excipients. Tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from about 1% w/w to about 25% w/w. In one embodiment of the present invention, the disintegrant will comprise from about 5% w/w to about 20% w/w of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from about 0.2% w/w to about 5% w/w of the tablet, and glidants may comprise from about 0.2% w/w to about 1% w/w of the tablet. Tablets also generally contain lubricants such as magnesium stearate, calcium stearate, zinc stearate, sodium stearyl fumarate, and mixtures of magnesium stearate with sodium lauryl sulfate. Lubricants generally comprise from about 0.25% w/w to about 10% w/w. In one embodiment of the present invention, lubricants comprise from about 0.5% w/w to about 3% w/w of the tablet. Other possible ingredients include anti-oxidants, colorants, flavoring agents, preservatives and taste-masking agents.

For example, exemplary tablet formulations comprise up to about 80% w/w of the active pharmaceutical ingredient, from about 0% w/w to about 90% w/w binder, from about 0% w/w to about 95% w/w diluent, from about 1% w/w to about 25% w/w disintegrant, and from about 0.25% w/w to about 10% w/w lubricant.

Tablet blends may be compressed directly or by roller to form tablets. Tablet blends, or portions of blends, may alternatively be wet-, dry-, or melt-granulated, melt congealed, or extruded before tableting. The final formulation may comprise one or more layers, and may be coated or uncoated; it may even be encapsulated. Formulations of tablets are discussed in Pharmaceutical Dosage Forms: Tablets, Vol. 1, by H. Lieberman and L. Lachman (Marcel Dekker, New York, 1980).

When preparing pharmaceutical compositions of the present invention, it may be necessary to adjust the particle volume mean diameter and/or the particle size distribution of the crystalline active pharmaceutical ingredient to further optimise its physicochemical properties or other properties such as stability manufacturability and/or bioperformance. For example, in some cases there may be a desire to reduce the particle size to increase the rate of dissolution. Particle size reduction is also sometimes used to ensure content uniformity for formulations which have very low loading of active pharmaceutical ingredients. For the present invention it is preferred that the crystalline form of the active pharmaceutical ingredient has a volume mean diameter of no more than 50 µm and a particle size distribution such that 95% of the sample volume particles have a diameter of no more than 130 µm, as measured by laser diffraction, with dry dispersion, using standard techniques.

Formulations suitable for oral administration also include fast-dissolving or fast-disintegrating dose forms such as those described in Expert Opinion in Therapeutic Patents, 11(6), 981-986 by Lang and Chen (2001).

Solid formulations for oral administration may be formulated to be immediate and/or modified release. Modified release includes delayed, sustained, pulsed, controlled, targeted and programmed release. Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al. (2001). The use of chewing gum to achieve controlled release is described in WO-A-00/35298.

Other pharmaceutical compositions of the present invention suitable for oral administration include consumable oral films. These are typically pliable water-soluble or water-swellable thin film dosage forms which may be rapidly dissolving or mucoadhesive and typically comprise a film-forming polymer, a binder, a solvent, a humectant, a plasticizer, a stabilizer or emulsifier, a viscosity-modifying agent and a solvent. Some components of the formulation may perform more than one function. The film-forming polymer may be selected from natural polysaccharides, proteins, or synthetic hydrocolloids and, when included in a composition, the film forming polymer is typically present in the range of about 0.01% w/w to about 99% w/w, more typically in the range of about 30% w/w to about 80% w/w. Other possible ingredients include anti-oxidants, colorants, flavorings and flavor enhancers, preservatives, salivary stimulating agents, cooling agents, co-solvents (including oils), emollients, bulking agents, anti-foaming agents, surfactants and taste-masking agents. Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Other suitable pharmaceutical compositions of the present invention also include liquid formulations. Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Pharmaceutical compositions of the present invention may also be adapted for administration of the active directly into the blood stream, into muscle, or into an internal organ. Such parenteral administration includes intravenous, intraarterial, intraperitoneal, intrathecal, intraventricular, intraurethral, intrasternal, intracranial, intramuscular and subcutaneous administration. Suitable devices for parenteral administration include needle (including microneedle) injectors, needle-free injectors and infusion techniques. Suitable pharmaceutical compositions also include those for topical administration to the skin or mucosa, that is, dermally or transdermally.

Yet another suitable pharmaceutical composition of the present invention are those adapted for intranasal administration or for inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin. The pressurized container, pump, spray, atomizer, or nebulizer contains a solution or suspension of the pharmaceutically active ingredient, which solution or suspension also comprises for example, ethanol, aqueous ethanol, or a suitable alternative agent for dispersing, solubilizing, or extending release of the compound, a propellant as solvent and an optional surfactant, such as sorbitan trioleate, oleic acid, or an oligolactic acid. Prior to use in a dry powder or suspension formulation, the drug product is micronized to a size suitable for delivery by inhalation (typically less than 5 µm). This may be achieved by any appropriate comminuting method, such as spiral jet milling, fluid bed jet milling, supercritical fluid processing to form nanoparticles, high pressure homogenization, or spray drying. Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as I-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose. Formulations for intranasal administration may be formulated to be immediate and/or modified release using, for example, PGLA. Modified release includes delayed, sustained, pulsed, controlled, targeted and programmed release.

Pharmaceutical compositions of the present invention also include those formulated to be administered directly to the eye or ear, typically in the form of drops of a micronized suspension or solution in isotonic, pH-adjusted, sterile saline.

Pharmaceutical compositions of the present invention optionally comprise flavors. Suitable flavors, such as menthol and levomenthol, or sweeteners, such as saccharin or saccharin sodium, may be added.

Pharmaceutical compositions of the present invention optionally also comprise soluble macromolecular entities, such as cyclodextrin and suitable derivatives thereof or polyethylene glycol-containing polymers, in order to improve the solubility, dissolution rate, taste, bioavailability and/or stability of the active ingredient when using any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e., as a carrier, diluent, or solubilizer. Most commonly used for these purposes are alpha-, beta- and gamma-cyclodextrins, examples of which may be found in international patent publications WO-A-91/11172, WO-A-94/02518 and WO-A-98/55148.

Preferred pharmaceutical compositions of the present invention are those which are suitable for oral administration. More preferably pharmaceutical compositions of the present invention are suitable for oral administration and are in the form of a tablet or a capsule.

It is to be understood that this invention is directed to combined therapies and compositions thereof as described herein, for treatment and/or prevention of any disease, disorder or condition, as appropriate, as will be appreciated by one skilled in the art, and include in particular those embodiments and preferred embodiments of disorders and conditions disclosed herein.

In another aspect this invention relates to a method for modulating an activity of an androgen receptor in a subject in need thereof, comprising contacting said androgen receptor with an effective amount of a combination of a compound of Formula 1, Formula 2 or Formula 3, as defined herein, or a pharmaceutically acceptable salt thereof and a second pharmaceutically active ingredient, as defined herein, or a pharmaceutically acceptable salt thereof, thereby modulating the activity of said androgen receptor.

This invention also relates to a method of treating a disorder or condition relating to dysregulation of an androgen receptor in a subject, comprising administering to the subject a therapeutically effective amount of a combination of a compound of Formula 1, Formula 2 or Formula 3, as defined herein, or a pharmaceutically acceptable salt thereof and a second pharmaceutically active ingredient, as defined herein, or a pharmaceutically acceptable salt thereof.

In yet another aspect, this invention relates to a method for treating a disorder or condition in a subject, wherein the disorder or condition is selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy, and stress urinary incontinence comprising administering to said subject an effective amount of a combination of a compound of Formula 1, Formula 2 or Formula 3, as defined herein, or a pharmaceutically acceptable salt thereof and a second pharmaceutically active ingredient, as defined herein, or a pharmaceutically acceptable salt thereof, thereby treating said disease or condition.

This invention also relates to a combination of a compound of Formula 1, Formula 2 or Formula 3, as defined herein, or a pharmaceutically acceptable salt thereof and a second pharmaceutically active ingredient, as defined herein, or a pharmaceutically acceptable salt thereof, for use as a medicament.

This invention also relates to a combination of a compound of Formula 1, Formula 2 or Formula 3, as defined herein, or a pharmaceutically acceptable salt thereof and a second pharmaceutically active ingredient, as defined herein, or a pharmaceutically acceptable salt thereof, for use in the treatment of a disorder or condition relating to dysregulation of an androgen receptor.

This invention also relates to a combination of a compound of Formula 1, Formula 2 or Formula 3, as defined herein, or a pharmaceutically acceptable salt thereof and a second pharmaceutically active ingredient, as defined herein, or a pharmaceutically acceptable salt thereof, for use in the treatment of a disorder or condition wherein the disorder or condition is selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy and stress urinary incontinence.

This invention also relates to the use of a combination of a compound of Formula 1, Formula 2 or Formula 3, as defined herein, or a pharmaceutically acceptable salt thereof and a second pharmaceutically active ingredient, as defined herein, or a pharmaceutically acceptable salt thereof, for the manufacture of a medicament for the treatment of a disorder or condition relating to dysregulation of an androgen receptor.

This invention also relates to the use of a combination of a compound of Formula 1, Formula 2 or Formula 3, as defined herein, or a pharmaceutically acceptable salt thereof and a second pharmaceutically active ingredient, as defined herein, or a pharmaceutically acceptable salt thereof, for the manufacture of a medicament for the treatment of a disorder or condition wherein the disorder or condition is selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy and stress urinary incontinence.

This invention also relates to a pharmaceutical composition comprising a combination of a compound of Formula 1, Formula 2 or Formula 3, as defined herein, or a pharmaceutically acceptable salt thereof and a second pharmaceutically active ingredient, as defined herein, or a pharmaceutically acceptable salt thereof, for treating a disorder or condition relating to dysregulation of an androgen receptor.

This invention also relates to a pharmaceutical composition comprising a combination of a compound of Formula 1, Formula 2 or Formula 3, or a pharmaceutically acceptable salt thereof and a second pharmaceutically active ingredient, as defined herein, or a pharmaceutically acceptable salt thereof, for treating a disorder or condition wherein the disorder or condition is selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy and stress urinary incontinence.

This invention also relates to a kit comprising:
(i) a pharmaceutical dosage form comprising a compound of Formula 1, Formula 2 or Formula 3, as defined herein, or pharmaceutically acceptable salt thereof, and a pharmaceutically acceptable excipient; and
(ii) a pharmaceutical dosage form comprising a second pharmaceutically active ingredient, as defined herein, and a pharmaceutically acceptable excipient for use in the treatment of a disorder or condition selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy and stress urinary incontinence.

For administration to human patients, the total daily dose of a compound of Formula 1, 2 or 3, or pharmaceutically acceptable salt thereof, is typically in the range of about 0.01 mg to about 500 mg depending, of course, on the mode of administration. In another embodiment of the present invention, the total daily dose of a compound of Formula 1, 2 or 3, or pharmaceutically acceptable salt thereof, is typically in the range of about 0.1 mg to about 300 mg. In yet another embodiment of the present invention, the total daily dose of a compound of Formula 1, 2 or 3, or pharmaceutically acceptable salt thereof, is typically in the range of about 1 mg to about 30 mg. Similarly, for administration to human patients, the total daily dose of the second pharmaceutically active ingredient, or pharmaceutically acceptable salt thereof, is typically in the range of about 0.01 mg to about 500 mg depending, of course, on the mode of administration. In another embodiment of the present invention, the total daily dose of a compound of the second pharmaceutically active ingredient, or pharmaceutically acceptable salt thereof, is typically in the range of about 0.1 mg to about 300 mg. In yet another embodiment of the present invention, the total daily dose of the second pharmaceutically active ingredient, or pharmaceutically acceptable salt thereof, is typically in the range of about 1 mg to about 30 mg. The total daily dose of one or both of the pharmaceutically active compounds may be administered in single or divided doses and may, at the physician's discretion, fall outside of the typical range given herein e.g., in order to cope with the needs of a patient subpopulation to be treated or the needs of the single patient which different needs can be due to the particular disease, severity of the disease, age, sex, or body weight as can be readily determined by a person skilled in the art. The dosage indicated are based on an average human subject having a weight of about 65 kg to 70 kg. The physician will readily be able to determine doses for subjects whose weight falls outside this range, such as infants and the elderly.

The novel combinations of the present invention are also useful in the field of veterinary medicine. In addition to use in non-human animals for the uses described hereinabove for human subjects, the compounds of the present invention are also particularly useful in treating non-human animals that are being raised for human food consumption. The dosages and dosage forms described hereinabove for human subjects can be adjusted to accommodate the varying size of animals, as is well known to those of ordinary skill in the veterinary art.

This invention also relates to a crystalline form of 6-[(4R)-4-methyl-1,1-dioxido-1,2,6-thiadiazinan-2-yl]isoquinoline-1-carbonitrile.

This invention also relates to a crystalline form of 6-[(4R)-4-methyl-1,1-dioxido-1,2,6-thiadiazinan-2-yl]isoquinoline-1-carbonitrile Form (1).

According to the present invention, 6-[(4R)-4-methyl-1,1-dioxido-1,2,6-thiadiazinan-2-yl]isoquinoline-1-carbonitrile is in its free base form.

There are a number of analytical methods one of ordinary skill in the art can use to analyze solid forms, in particular crystalline solid forms. The term "analyze" as used herein shall be taken to mean to obtain information about the solid state structure of solid forms. For example, X-ray powder diffraction is one such suitable technique for differentiating amorphous solid forms from crystalline solid forms and for characterizing and identifying crystalline solid forms since different crystalline forms exhibit different X-ray powder patterns. A discussion of the theory of X-ray powder diffraction patterns can be found in Clearfield, Reibenspies and Bhuvanesh (Editors), Principles and Applications of Powder Diffraction: Edition 1, Wiley, John & Sons, Incorporated (2008), which is incorporated by reference in its entirety.

Due to differences in instruments, samples and sample preparation, minor variation in peak values in spectroscopic techniques can occur. In an X-ray powder diffraction pattern typical precision of a 2-theta x-axis value of an x-ray powder pattern is of the order of plus or minus 0.2° 2-theta. As such, a peak value reported to be at 9.2° 2-theta could occur at any where between 9.0° 2-theta and 9.4° 2-theta when measured on most x-ray diffractometers under most conditions. In a FT-Raman spectra typical precision of a Raman shift is of the order of plus or minus 2 cm$^{-1}$. In a solid state NMR the typical precision of a $^{13}$C peak shift is of the order of plus or minus 0.2 ppm.

In a further preferred embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9 and 15.2.

In a yet further preferred embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, and 15.2 and one or more additional characteristic peaks expressed in degrees 2-theta (±0.2° 2-theta) selected from the group consisting of 17.1, 17.3, and 18.5.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2 and 17.1.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2 and 17.3.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2 and 18.5.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2, 17.1 and 17.3.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2, 17.1, and 18.5.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2, 17.3, and 18.5.

In a still further preferred embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9, 15.2, 17.1, 17.3, and 18.5.

In an even further preferred embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) as depicted in Table 1.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in cm$^{-1}$ (±2 cm$^{-1}$) at 708, 1555 and 2230.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in cm$^{-1}$ (±2 cm$^{-1}$) as depicted in Table 2.

In another embodiment of the present invention, the crystalline form of 6-[(4R)-4-methyl-1,1-dioxido-1,2,6-thiadiazinan-2-yl]isoquinoline-1-carbonitrile Form (1) exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a solid state NMR spectra having characteristic peaks expressed in ppm (±0.2 ppm) at 15.3, 136.6 and 143.2.

In another embodiment of the present invention, the crystalline form of 6-[(4R)-4-methyl-1,1-dioxido-1,2,6-thiadiazinan-2-yl]isoquinoline-1-carbonitrile Form (1) exhibits a solid state NMR spectra having characteristic peaks expressed in ppm (±0.2 ppm) as depicted in Table 3.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9 and exhibits a FT-Raman spectra having one or more characteristic peaks expressed in cm$^{-1}$ (±2 cm$^{-1}$) selected from the group consisting of 708, 1555 and 2230.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9 and exhibits a FT-Raman spectra having a characteristic peak expressed in cm$^{-1}$ (±2 cm$^{-1}$) at 708.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9 and 15.2 and exhibits a FT-Raman spectra having characteristic peaks expressed in cm$^{-1}$ (±2 cm$^{-1}$) at 708, 1555 and 2230.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9 and exhibits a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9 and 15.2 and exhibits a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9 and 15.2 and exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in cm$^{-1}$ (±2 cm$^{-1}$) at 708 and 2230 and exhibits a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in cm$^{-1}$ (±2 cm$^{-1}$) at 708 and 2230 and exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in cm$^{-1}$ (±2 cm$^{-1}$) at 708, 1555 and 2230 and exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9, a FT-Raman spectra having characteristic peaks expressed in cm$^{-1}$ (±2 cm$^{-1}$) at 708 and 2230 and exhibits a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9, a FT-Raman spectra having characteristic peaks expressed in cm$^{-1}$ (±2 cm$^{-1}$) at 708 and 2230 and exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8, 10.9 and 15.2, a FT-Raman spectra having characteristic peaks expressed in cm$^{-1}$ (±2 cm$^{-1}$) at 708, 1555 and 2230 and exhibits a solid state NMR spectra having characteristic peaks expressed in ppm (±0.2 ppm) at 15.3 and 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits an X-ray powder diffraction pattern having characteristic peaks expressed in degrees 2-theta (±0.2° 2-theta) at 7.8 and 10.9 and exhibits either a FT-Raman spectra having one or more characteristic peaks expressed in cm$^{-1}$ (±2 cm$^{-1}$) selected from the group consisting of 708, 1555 and 2230; and/or a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a FT-Raman spectra having characteristic peaks expressed in cm$^{-1}$ (±2 cm$^{-1}$) at 708 and 2230 and exhibits either an X-ray powder diffraction pattern having one or more characteristic peaks expressed in degrees 2-theta (±0.2° 2-theta) selected from the group consisting of 7.8, 10.9, 15.2, 17.1, 17.3, and 18.5; and/or a solid state NMR spectra having a characteristic peak expressed in ppm (±0.2 ppm) at 136.6.

In another embodiment of the present invention, the crystalline form of 6-[(4R)-4-methyl-1,1-dioxido-1,2,6-thiadiazinan-2-yl]isoquinoline-1-carbonitrile Form (1) exhibits a solid state NMR spectra having a characteristic peak expressed in ppm (±0.2 ppm) at 136.6 and exhibits either an X-ray powder diffraction pattern having one or more characteristic peaks expressed in degrees 2-theta (±0.2° 2-theta) selected from the group consisting of 7.8, 10.9, 15.2, 17.1, 17.3, and 18.5; and/or exhibits a FT-Raman spectra having one or more characteristic peaks expressed in cm$^{-1}$ (±2 cm$^{-1}$) selected from the group consisting of 708, 1555 and 2230.

In a preferred embodiment of the present invention, the crystalline form of 6-[(4R)-4-methyl-1,1-dioxido-1,2,6-thiadiazinan-2-yl]isoquinoline-1-carbonitrile is anhydrous.

This invention also relates to a process for preparing a crystalline form of 6-[(4R)-4-methyl-1,1-dioxido-1,2,6-thiadiazinan-2-yl]isoquinoline-1-carbonitrile, which process comprises the step of crystallization of 6-[(4R)-4-methyl-1,1-dioxido-1,2,6-thiadiazinan-2-yl]isoquinoline-1-carbonitrile from a solvent, wherein the solvent preferably comprises acetone. In an alternative embodiment the solvent comprises acetone and water. In one embodiment the solvent is acetone. In another embodiment the solvent is acetone and water.

The present invention also relates to a pharmaceutical composition comprising a crystalline form of 6-[(4R)-4-methyl-1,1-dioxido-1,2,6-thiadiazinan-2-yl]isoquinoline-1-carbonitrile and a pharmaceutically acceptable carrier or excipient, and to methods for preparing such pharmaceutical compositions.

In another embodiment, the present invention also relates to a pharmaceutical composition comprising crystalline 6-[(4R)-4-methyl-1,1-dioxido-1,2,6-thiadiazinan-2-yl]isoquinoline-1-carbonitrile Form (1) and a pharmaceutically acceptable carrier or excipient, and to methods for preparing such pharmaceutical compositions Preferred pharmaceutical compositions of the present invention of the crystalline form are those which are suitable for oral administration. More preferably pharmaceutical compositions of the present invention are suitable for oral administration and are in the form of a tablet or a capsule.

In another aspect this invention relates to a method for modulating an activity of an androgen receptor in a subject in need thereof, comprising contacting said androgen receptor with an effective amount of a crystalline form of 6-[(4R)-4-methyl-1,1-dioxido-1,2,6-thiadiazinan-2-yl]isoquinoline-1-carbonitrile, or a pharmaceutical composition thereof, thereby modulating the activity of said androgen receptor.

In another aspect this invention relates to a method for modulating an activity of an androgen receptor in a subject in need thereof, comprising contacting said androgen receptor with an effective amount of crystalline 6-[(4R)-4-methyl-1,1-dioxido-1,2,6-thiadiazinan-2-yl]isoquinoline-1-carbonitrile Form (1), or a pharmaceutical composition thereof, thereby modulating the activity of said androgen receptor.

This invention also relates to a method of treating a disorder or condition relating to dysregulation of an androgen receptor in a subject, comprising administering to the subject a therapeutically effective amount of a crystalline form of 6-[(4R)-4-methyl-1,1-dioxido-1,2,6-thiadiazinan-2-yl]isoquinoline-1-carbonitrile, or a pharmaceutical composition thereof.

This invention also relates to a method of treating a disorder or condition relating to dysregulation of an androgen receptor in a subject, comprising administering to the subject a therapeutically effective amount of crystalline 6-[(4R)-4-methyl-1,1-dioxido-1,2,6-thiadiazinan-2-yl]isoquinoline-1-carbonitrile Form (1), or a pharmaceutical composition thereof.

In yet another aspect, this invention relates to a method for treating a disorder or condition in a subject, wherein the disorder or condition is selected from among anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and muscle wasting comprising administering to said subject an effective amount of a crystalline form of 6-[(4R)-4-methyl-1,1-dioxido-1,2,6-thiadiazinan-2-yl]isoquinoline-1-carbonitrile, or a pharmaceutical composition thereof, thereby treating said disease or condition.

In yet another aspect, this invention relates to a method for treating a disorder or condition in a subject, wherein the disorder or condition is selected from among anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and muscle wasting comprising administering to said subject an effective amount of crystalline 6-[(4R)-4-methyl-1,1-dioxido-1,2,6-thiadiazinan-2-yl]isoquinoline-1-carbonitrile Form (1), or a pharmaceutical composition thereof, thereby treating said disease or condition.

In a further aspect, this invention relates to a method for treating and/or preventing a disorder or condition in a subject, wherein the disorder or condition is selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy and stress urinary incontinence, comprising administering to said subject, an effective amount of a crystalline form of 6-[(4R)-4-methyl-1,1-dioxido-1,2,6-thiadiazinan-2-yl]isoquinoline-1-carbonitrile, or a pharmaceutical composition thereof, thereby treating said disease or condition.

In a further aspect, this invention relates to a method for treating and/or preventing a disorder or condition in a subject, wherein the disorder or condition is selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy and stress urinary incontinence, comprising administering to said subject, an effective amount of crystalline 6-[(4R)-4-methyl-1,1-dioxido-1,2,6-thiadiazinan-2-yl]isoquinoline-1-carbonitrile Form (1), or a pharmaceutical composition thereof, thereby treating said disease or condition.

This invention also relates to a crystalline form of 6-[(4R)-4-methyl-1,1-dioxido-1,2,6-thiadiazinan-2-yl]isoquinoline-1-carbonitrile, or a pharmaceutical composition thereof, for use as a medicament.

This invention also relates to crystalline 6-[(4R)-4-methyl-1,1-dioxido-1,2,6-thiadiazinan-2-yl]isoquinoline-1-carbonitrile Form (1), or a pharmaceutical composition thereof, for use as a medicament.

This invention also relates to a crystalline form of 6-[(4R)-4-methyl-1,1-dioxido-1,2,6-thiadiazinan-2-yl]isoquinoline-1-carbonitrile, or a pharmaceutical composition thereof, for use in the treatment of a disorder or condition relating to dysregulation of an androgen receptor.

This invention also relates to crystalline 6-[(4R)-4-methyl-1,1-dioxido-1,2,6-thiadiazinan-2-yl]isoquinoline-1-carbonitrile Form (1), or a pharmaceutical composition thereof, for use in the treatment of a disorder or condition relating to dysregulation of an androgen receptor.

This invention also relates to a crystalline form of 6-[(4R)-4-methyl-1,1-dioxido-1,2,6-thiadiazinan-2-yl]isoquinoline-1-carbonitrile, or a pharmaceutical composition thereof, for use in the treatment of a disorder or condition selected from the group consisting of anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and muscle wasting.

This invention also relates to crystalline 6-[(4R)-4-methyl-1,1-dioxido-1,2,6-thiadiazinan-2-yl]isoquinoline-1-carbonitrile Form (1), or a pharmaceutical composition thereof, for use in the treatment of a disorder or condition selected from the group consisting of anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and muscle wasting.

In a further aspect, this invention relates to a crystalline form of 6-[(4R)-4-methyl-1,1-dioxido-1,2,6-thiadiazinan-2-yl]isoquinoline-1-carbonitrile, or a pharmaceutical composition thereof, for use in the treatment of a disorder or condition selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy and stress urinary incontinence.

In a further aspect, this invention relates to crystalline 6-[(4R)-4-methyl-1,1-dioxido-1,2,6-thiadiazinan-2-yl]isoquinoline-1-carbonitrile Form (1), or a pharmaceutical composition thereof, for use in the treatment of a disorder or condition selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy and stress urinary incontinence.

This invention also relates to the use of a crystalline form of 6-[(4R)-4-methyl-1,1-dioxido-1,2,6-thiadiazinan-2-yl]isoquinoline-1-carbonitrile, or a pharmaceutical composition thereof, for the manufacture of a medicament for the treatment of a disorder or condition relating to dysregulation of an androgen receptor.

This invention also relates to the use of crystalline 6-[(4R)-4-methyl-1,1-dioxido-1,2,6-thiadiazinan-2-yl]isoquinoline-1-carbonitrile Form (1), or a pharmaceutical composition thereof, for the manufacture of a medicament for the treatment of a disorder or condition relating to dysregulation of an androgen receptor.

This invention also relates to the use of a crystalline form of 6-[(4R)-4-methyl-1,1-dioxido-1,2,6-thiadiazinan-2-yl]isoquinoline-1-carbonitrile, or a pharmaceutical composition thereof, for the manufacture of a medicament for the treatment of a disorder or condition selected from the group consisting of anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and, muscle wasting.

This invention also relates to the use of crystalline 6-[(4R)-4-methyl-1,1-dioxido-1,2,6-thiadiazinan-2-yl]isoquinoline-1-carbonitrile Form (1), or a pharmaceutical composition thereof, for the manufacture of a medicament for the treatment of a disorder or condition selected from the group consisting of anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and, muscle wasting.

In a further aspect, this invention relates to the use of a crystalline form of 6-[(4R)-4-methyl-1,1-dioxido-1,2,6-thiadiazinan-2-yl]isoquinoline-1-carbonitrile, or a pharmaceutical composition thereof, for the manufacture of a medicament for the treatment of a disorder or condition selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy and stress urinary incontinence.

In a further aspect, this invention relates to the use of crystalline 6-[(4R)-4-methyl-1,1-dioxido-1,2,6-thiadiazinan-2-yl]isoquinoline-1-carbonitrile Form (1), or a pharmaceutical composition thereof, for the manufacture of a medicament for the treatment of a disorder or condition selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy and stress urinary incontinence.

This invention also relates to a pharmaceutical composition comprising a crystalline form of 6-[(4R)-4-methyl-1,1-dioxido-1,2,6-thiadiazinan-2-yl]isoquinoline-1-carbonitrile for treating a disorder or condition relating to dysregulation of an androgen receptor.

This invention also relates to a pharmaceutical composition comprising crystalline 6-[(4R)-4-methyl-1,1-dioxido-1,2,6-thiadiazinan-2-yl]isoquinoline-1-carbonitrile Form (1) for treating a disorder or condition relating to dysregulation of an androgen receptor.

This invention also relates to a pharmaceutical composition comprising a crystalline form of 6-[(4R)-4-methyl-1,1-dioxido-1,2,6-thiadiazinan-2-yl]isoquinoline-1-carbonitrile for treating a disorder or condition selected from the group consisting of anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and, muscle wasting.

This invention also relates to a pharmaceutical composition comprising crystalline 6-[(4R)-4-methyl-1,1-dioxido-1,2,6-thiadiazinan-2-yl]isoquinoline-1-carbonitrile Form (1) for treating a disorder or condition selected from the group consisting of anemia; anorexia; arthritis; bone disease; musculoskeletal impairment; cachexia; frailty; age-related functional decline in the elderly; growth hormone deficiency; hematopoietic disorders; hormone replacement; hypogonadism; loss of muscle strength and/or function; muscular dystrophies; muscle loss following surgery; muscular atrophy; neurodegenerative disease; neuromuscular disease; obesity; osteoporosis; sarcopenia, including sarcopenia in chronic obstructive pulmonary disease; and, muscle wasting.

In a further aspect, this invention relates to a pharmaceutical composition comprising a crystalline form of 6-[(4R)-4-methyl-1,1-dioxido-1,2,6-thiadiazinan-2-yl]isoquinoline-1-carbonitrile, for treating a disorder or condition selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy and stress urinary incontinence.

In a further aspect, this invention relates to a pharmaceutical composition comprising crystalline 6-[(4R)-4-methyl-1,1-dioxido-1,2,6-thiadiazinan-2-yl]isoquinoline-1-carbonitrile Form (1), for treating a disorder or condition selected from the group consisting of anemia; anorexia; arthritis; bone disease; benign prostate hyperplasia; musculoskeletal impairment; cachexia; cachexia associated with cancer; cancer; frailty; age-related functional decline in the elderly; growth hormone deficiency; hematopoietic disorders; hormone replacement; hypergonadism; loss of muscle strength and/or function; muscular dystrophies; muscle loss following surgery; muscular atrophy; neurodegenerative diseases; neuromuscular disease; obesity; osteoporosis; sarcopenia, including sarcopenia in chronic obstructive pulmonary disease; a method of improving dexterity and movement in a subject; atherosclerosis and its associated diseases; dysmenorrhea; dysspermtogenic sterility; muscle wasting; respiratory tract disease; otorhinolaryngologic disease; hormonal disorder/disruption or imbalance; androgen deprivation therapy; injuries of the central nervous system; hair loss; an infection; digestive system disease; urologic or male genital disease; dermatological disorder; endocrine disorder; hemic or lymphatic disorder; congenital/hereditary or neonatal disease; connective tissue disease; metabolic disease; disorder of environmental origin; a behavior mechanism; a mental disorder; a cognitive disorder; liver disease; kidney disease and diabetic nephropathy and stress urinary incontinence.

The crystalline form of 6-[(4R)-4-methyl-1,1-dioxido-1,2,6-thiadiazinan-2-yl]isoquinoline-1-carbonitrile, or a pharmaceutical composition thereof, of the present invention may also be useful in the field of veterinary medicine. The dosages and dosage forms described hereinabove for human subjects can be adjusted to accommodate the varying size of animals, as is well known to those of ordinary skill in the veterinary art. In another aspect, this invention also provides a method of affecting carcass composition, increasing lean mass, reducing fat mass, reducing percent fat mass, increasing lean:fat, increasing average daily gain (ADG), or decreasing feed to gain ratio (F:G) of an animal, or increasing feed efficiency in an animal, wherein the method comprises administering to the animal an effective amount of a crystalline form of 6-[(4R)-4-methyl-1,1-dioxido-1,2,6-thiadiazinan-2-yl]isoquinoline-1-carbonitrile, or a pharmaceutical composition thereof. In a preferred embodiment, the animal is a cattle or a swine. The phrase "increasing lean mass" generally refers to increasing muscle in an animal, which is considered in many cases a more desirable carcass for human food consumption. "Reducing fat mass" and "reducing percent fat mass" refer to reduction of fat production in an animal. The phrase "lean:fat", as for example in "increasing lean:fat" refers generally to the ratio of lean mass in an animal relative to fat mass in the animal. An increased lean:fat in an animal is in many cases considered to produce a carcass that is more desirable for human food consumption. The phrase "F:G" refers to the ratio of feed input into an animal relative to weight gain (output) in the animal. A decrease in F:G increases productivity from an economic view point. Dosage forms, the effective amount of active ingredient and suitable compositions will be known to those of ordinary skill can be used for such veterinary applications.

The crystalline form of 6-[(4R)-4-methyl-1,1-dioxido-1,2,6-thiadiazinan-2-yl]isoquinoline-1-carbonitrile, or a pharmaceutical composition thereof, of the present invention may also be usefully combined with other active pharmaceutical ingredients known in the veterinary fields. Such combinations may be accomplished by administering a compound of the present invention to an animal, as described herein, in one dosage form or unit, and administering the second active pharmaceutical ingredient to the animal separately, in a separate dosage form or unit. The administration to the animal of the two separate dosage forms may be at the same time or in any order. In another embodiment, the compound of the present invention and the second pharmaceutical ingredient (or additional pharmaceutical ingredients) are combined together in the same dosage form and are administered to the animal together. Examples of compounds which can be suitably administered with the crystalline compounds of the present invention for veterinary applications include beta adrenergic agonist or beta adrenergic modulator, antibiotics or steroids.

The entire teachings of all of the patents and published patent applications recited hereinabove are incorporated herein by reference.

EXAMPLES

All the compounds of Formula 1, 2 or 3, or pharmaceutically acceptable salts thereof, can be made by the specific and general experimental procedures described below in combination with the common general knowledge of one skilled in the art (see, for example, Comprehensive Organic Chemistry, Ed. Barton and Ollis, Elsevier; Comprehensive Organic Transformations: A Guide to Functional Group Preparations, Larock, John Wiley and Sons).

The following non-limiting Preparations and Examples illustrate the preparation of compounds of the present invention.

Unless otherwise stated, all starting materials and reagents are commercially available, or known from literature sources.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (m/z) were recorded using either electrospray ionization (ESI) or atmospheric pressure chemical ionization (APCI). The following abbreviations have been used for common solvents: CDCl$_3$, deuterochloroform; d$_6$-DMSO, deuterodimethylsulfoxide; CD$_3$OD, deuteromethanol; THF, tetrahydrofuran; DCM, dichloromethane; EtOAc, ethyl acetate; MeOH, methanol; DMF, dimethylformamide. 'Ammonia' refers to a concentrated solution of ammonia in water possessing a specific gravity of 0.88. Where thin layer chromatography (TLC) has been used it refers to silica gel TLC using silica gel 60 F$_{254}$ plates, R$_f$ is the distance travelled by a compound divided by the distance travelled by the solvent front on a TLC plate.

Powder X-Ray Diffraction

Powder X-ray diffraction analysis was conducted using a Bruker AXS D8 ADVANCE diffractometer equipped with a Cu radiation source (K-α average). The system is equipped with a Gobel Mirror and 2.5 axial Soller slits on the primary side. The secondary side utilizes 2.5 axial Soller slits and motorized slits. Diffracted radiation was detected by a Lynx Eye XE detector. The X-ray tube voltage and amperage were set to 40 kV and 40 mA respectively. Data was collected in the Theta-2-Theta configuration with a Cu K-alpha (average) wavelength source scanning from 3.0 to 40.0 degrees 2-Theta using a step size of 0.03 degrees and a step time of 1.0 seconds, at ambient temperature. Samples were prepared by placing them in a silicon low background holder and rotated during collection. Data were collected using Bruker DIFFRAC Plus software (Version 2.0) and analysis was performed by EVA diffract plus software (Version 3.1).

PXRD data file was not processed prior to peak searching. Using the peak search algorithm in the EVA diffract plus software (Version 3.1), peaks were selected with a threshold value of 1 and a width value of 0.3 were used to make preliminary peak assignments. The output of automated assignments was visually checked to ensure validity and adjustments manually made if necessary, in accordance with the routine practice of one of ordinary skill. Peaks with relative intensity of ≥10% were generally chosen. The peaks which were not resolved or were consistent with noise were also discarded. A typical error associated with the peak position from PXRD is +/−0.2° 2-theta.

As used herein the terms "PXRD" and "x-ray powder diffraction pattern" are considered interchangeable and synonymous with the term "powder X-ray diffraction pattern".

Fourier Transform Raman (FT-Raman)

FT-Raman spectra analysis was conducted using a Nicolet NXR FT-Raman accessory attached to the FT-IR bench. The spectrometer was equipped with a 1064 nm Nd:YVO$_4$ laser and a liquid nitrogen cooled Germanium detector. Prior to data acquisition, instrument performance and calibration verifications were conducted using polystyrene. Samples were analyzed in glass NMR tubes that were spun during spectral collection. The spectra were collected using 0.5 W of laser power and 512 co-added scans. The collection range was 3700-50 cm$^{-1}$. The API spectra were recorded using 2 cm$^{-1}$ resolution, and Happ-Genzel apodization was utilized for all of the spectra. A typical error associated with the FT-Raman peak shift is ±2 cm$^{-1}$. It is expected that, due to the similarity of FT-Raman and dispersive Raman spectra techniques, peak positions reported herein obtained using FT-Raman spectroscopy would be likely to be consistent with those which would be observed using dispersive Raman spectroscopy assuming appropriate instrument calibration.

Solid State NMR

Solid State NMR (ssNMR) spectra analysis was conducted at 25° C. on a Varian 4 mm CPMAS probe positioned into a Varian VNMR 400 MHz (1H frequency) NMR spectrometer. The sample was packed into a rotor and the rotor was oriented at the magic angle and spun at 8.0 kHz. The carbon ssNMR spectrum was collected using a proton decoupled cross-polarization magic angle spinning (CP-MAS) experiment with TOSS (Total suppression of spinning sidebands) spinning sideband suppression. The cross-polarization contact time was set to 3 ms and the recycle delay to 30 seconds. The carbon spectrum was referenced using an external standard of crystalline adamantane, setting its downfield resonance to 38.5 ppm (as determined from neat TMS).

The ssNMR data file was processed prior to peak searching. Automatic peak picking was performed using Bruker-BioSpin TopSpin software (Version 3.1). Generally, a threshold value of 5% relative intensity was used for peak selection. A typical error associated with the $^{13}$C chemical shift (ppm) x-axis value for ssNMR is ±0.2 ppm.

DSC

DSC measurements were performed with a Discovery DSC (TA instruments) equipped with a refrigerated cooling accessory. Approximately 2-5 mg of solid sample was weighed into a standard/Tzero aluminum pan and non-hermetically sealed. The sample was placed in a cell with continuous dry nitrogen purge (50 mL/min) and heated from 25° C. to 250° C. at 10° C./min heating rate. The cell constant was determined using indium and temperature calibration was performed using indium and tin as standards. The experimental data were analyzed using commercially available software (TA Universal Analysis 2000/Trios software, TA Instruments).

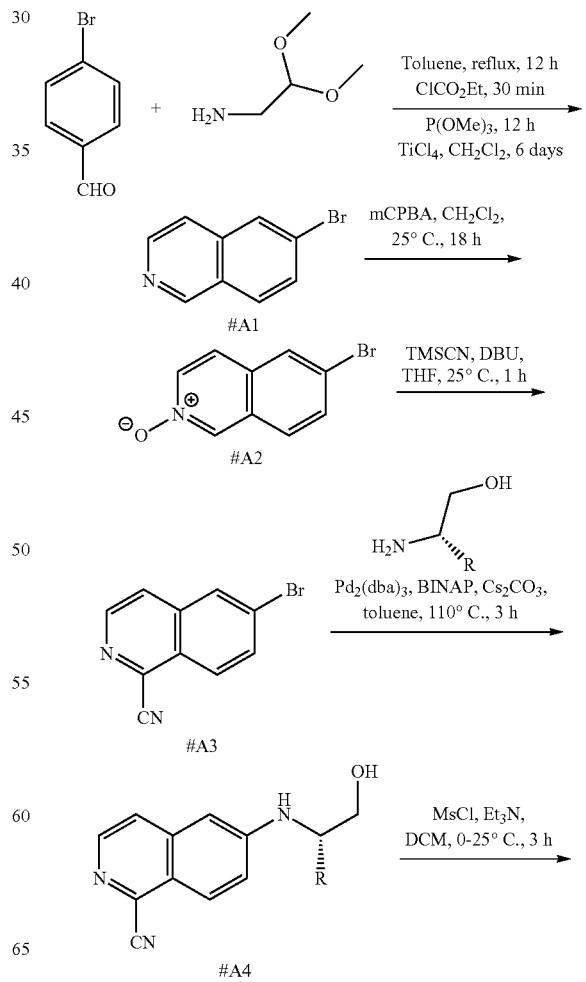

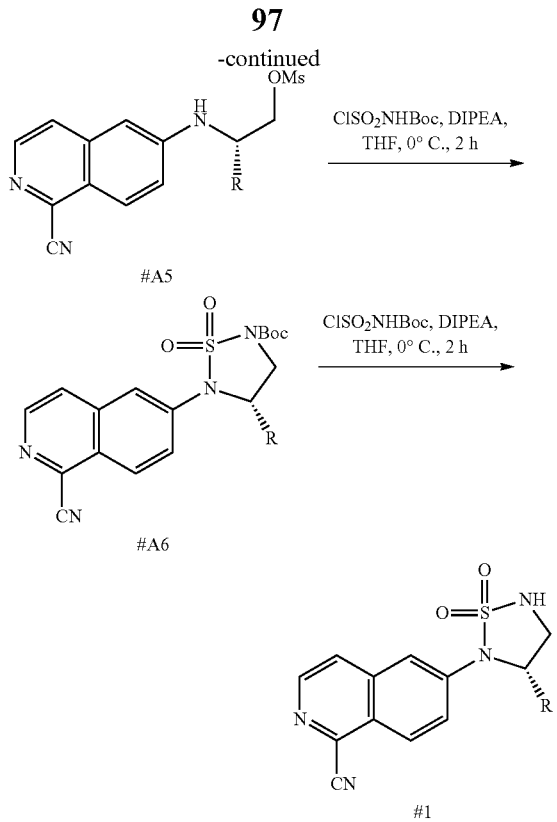

Step 1.

Synthesis of 6-bromoisoquinoline (#A1). A mixture of 4-bromobenzaldehyde (300.0 g, 1620.0 mmol) and amino acetaldehyde dimethyl acetal (170.4 g, 1620 mmol) in anhydrous toluene (1.5 L) was refluxed under a Dean-Stark condenser for 12 h. The solution was concentrated under vacuum. The residue was dissolved in anhydrous THF and cooled to −10° C. Ethyl chloroformate (193.3 mL, 1782 mmol) was added and stirred for 10 min at −10° C., and then allowed to warm to room temperature. Subsequently trimethyl phosphite (249.6 mL, 1782.0 mmol) was added dropwise to the reaction mixture and stirred for 10 h at room temperature. The solvent was evaporated under vacuum and the residue was dissolved in anhydrous DCM (1.5 L) and stirred for 30 minutes. The reaction mixture was cooled to 0° C., and titanium tetrachloride (1.2 L, 6480 mmol) was added dropwise. The reaction mixture was stirred at 40° C. for 6 days. The reaction mixture was poured into ice and pH was adjusted to 8-9 with aqueous 6N NaOH solution. The suspension was extracted three times with EtOAc. The organic layer was extracted with 3 M HCl. The acidic aqueous solution was adjusted to pH to 7-8 with 3N NaOH solutions and extracted two times with EtOAc. The organic layer was dried over anhydrous sodium sulfate and concentrated under reduced pressure to provide the product. Crude compound was dissolved in minimum amount of DCM and mixed with pentane to get compound #A1 as light brown solid. Yield: 90 g (35%). $R_f$: 0.6 (30% EtOAc in petroleum ether).

LCMS m/z=209 (M+1). $^1$H NMR (400 MHz, $d_6$-DMSO): δ 7.82 (m, 2H), 8.11 (d, J=8.8 Hz, 2H), 8.30 (br s, 1H), 8.56 (d, J=6.0 Hz, 1H), 9.35 (s, 1H).

Step 2.

Synthesis of 6-bromoisoquinoline 2-oxide (#A2). m-Chloroperoxybenzoic acid (120.0 g, 720.0 mmol) was added to a solution of #A1 (90.0 g, 480.0 mmol) in DCM (500 mL) at room temperature, and the reaction mixture was stirred for 16 h. 1N NaOH was added to the stirred reaction mixture to adjust the pH to 7-8. The layers were separated and the aqueous layer was extracted with DCM. The organic layer was dried over anhydrous sodium sulfate and concentrated under reduced pressure to render crude product. The solid product was triturated with the mixture of n-pentane and ethanol (8:2) to get the #A2 as white solid. Yield: 65 g (60%). $R_f$: 0.2 (EtOAc).

LCMS m/z=225 (M+1). $^1$H NMR (400 MHz, $d_6$-DMSO): δ 7.83 (m, 2H), 7.91 (d, J=6.8 Hz, 1H), 8.21 (dd, J=8.0, 1.2 Hz, 1H), 8.26 (br s, 1H), 8.97 (s, 1H).

Step 3.

Synthesis of 6-bromoisoquinoline-1-carbonitrile (#A3). Trimethylsilyl cyanide (52.0 mL, 580.0 mmol) was added dropwise to the stirred solution of #A2 (65.0 g, 290.0 mmol) and DBU (50.0 mL, 348.0 mmol) in THF (500 mL) at room temperature over a period of 15 minutes. The reaction mixture was stirred at room temperature for 1 h. Water was added to the reaction mixture, and the solution was extracted with DCM. The organic layer was dried over anhydrous $Na_2SO_4$ and concentrated under reduced pressure to give crude product. The product was purified by column chromatography using silica gel (100-200 mesh) with 0-4% EtOAc in petroleum ether as an eluent to give #A3 as white solid. Yield: 41 g (61%). $R_f$: 0.6 (30% EtOAc in petroleum ether).

LCMS m/z=233 (M+1). $^1$H NMR (400 MHz, $d_6$-DMSO): δ 8.07 (dd, J=11.2, 2.0 Hz, 1H), 8.21 (m, 2H), 8.55 (br s, 1H), 8.77 (d, J=7.6 Hz, 1H).

A General Procedure to Prepare Intermediates of #A4, #A5, #A6 and #1, #2, #3, #4, #6, #7.

Step 4.

A solution of #A3 (1 eq.) in toluene (50 mL) was degassed by bubbling with argon gas for 15 min and then $Pd_2dba_3$ (0.03 eq.), BINAP (0.06 eq.) and $Cs_2CO_3$ (3 eq.) were added to the solution followed by the addition aminoalcohol (2 eq.). The mixture was heated at 100° C. under argon atmosphere for 3 h. Reaction mixture was cooled to room temperature, diluted with EtOAC and washed with water and brine. The organic layer was dried over $Na_2SO_4$ and concentrated to get crude product. The crude compounds were purified by silica gel (100-200 mesh) column chromatography by using 0-5% MeOH in DCM. Yields: 25-45%.

Step 5.

MsCl (1 eq.) was added dropwise to a solution of #A4 (1 eq.) and $Et_3N$ (2 eq.) in DCM (10 mL) at 0° C. and was stirred at room temperature for 3 h. The reaction mixture was diluted with DCM, washed with water and brine. The organic layer was dried over $Na_2SO_4$ and concentrated. Crude products were used in next step without further purification.

Step 6.

t-Butanol (2 eq.) was slowly added to a solution of chloro sulfonyl isocyanate (2 eq.) in toluene (1 mL/1 mmol) at 0° C. The reaction mixture was stirred at room temperature for 45 min. This solution (t-butyl chlorosulfonylcarbamate) was then added to a solution of #A5 (1 eq.) and DIPEA (4 eq.) in THF and stirred for 12 h. Reaction mixture was diluted with water and extracted with EtOAc. Organic layer was washed with water, brine, then dried over anhydrous $Na_2SO_4$ and concentrated. Crude products were purified by silica gel (100-200 mesh) column chromatography using 0-40% EtOAc in petroleum ether.

Step 7.

TFA was added to a solution of #A6 (1 eq.) in DCM (8 mL) at 0° C. and stirred at room temperature for 2 h. Reaction mixture was concentrated, diluted with water, neutralized with sat. aq. NaHCO$_3$ soln. then extracted with DCM. The organic layer was washed with water and dried over Na$_2$SO$_4$ then concentrated. The crude products were purified by triturating with DCM and pentane to provide the compound. In the case of racemic materials, the enantiomers were separated by chiral preparative HPLC.

Column: CHIRALPAK IA, 4.6 mm×250, 5 μm; Mobile phase: n-Hexane: EtOH (65:35) (For X3: 35:65; For X2: 70:30); Flow rate: 1 mL/min; Eluent: EtOH.

Example 1

6-[(3S)-3-methyl-1,1-dioxido-1,2,5-thiadiazolidin-2-yl]isoquinoline-1-carbonitrile (#1; R=CH$_3$)

LCMS m/z=289.1 (M+1). $^1$H NMR (400 MHz, d$_6$-DMSO): δ 1.37 (d, J=6.3 Hz, 3H), 3.27 (m, 1H), 3.74 (m, 1H), 4.63 (m, 1H), 7.17 (d, J=5.7 Hz, 1H), 7.72 (m, 1H), 7.89 (dd, J=10.7, 2.1 Hz, 1H), 8.26 (m, 2H), 8.62 (d, J=5.7 Hz, 1H).

Example 2

6-[(3S)-3-ethyl-1,1-dioxido-1,2,5-thiadiazolidin-2-yl]isoquinoline-1-carbonitrile (Stereochemistry Arbitrarily Assigned) (#2; R=CH$_2$CH$_3$)

LCMS m/z=303.1 (M+1). $^1$H NMR (400 MHz, d$_6$-DMSO): δ 0.92 (t, J=7.4 Hz, 3H), 1.61-1.86 (m, 2H), 3.36 (dd, J=12.6, 4.0 Hz, 1H), 3.67 (dd, J=12.5, 6.5 Hz, 1H), 4.40-4.54 (m, 1H), 7.73 (d, J=2.2 Hz, 1H), 7.89 (dd, J=9.2, 2.3 Hz, 1H), 8.11 (br. s., 1H), 8.17 (d, J=5.7 Hz, 1H), 8.27 (d, J=9.3 Hz, 1H) 8.62 (d, J=5.7 Hz, 1H).

Example 3

6-[(3R)-1,1-dioxido-3-(2,2,2-trifluoroethyl)-1,2,5-thiadiazolidin-2-yl]isoquinoline-1-carbonitrile (Stereochemistry Arbitrarily Assigned) (#3; R=CH$_2$CF$_3$)

LCMS m/z=357.1 (M+1). $^1$H NMR (400 MHz, d$_6$-DMSO): δ 2.72-3.02 (m, 2H), 3.72-3.87 (m, 1H), 4.94-5.06 (m, 1H), 7.76 (d, J=2.2 Hz, 1H), 7.89 (dd, J=9.2, 2.2 Hz, 1H), 8.19 (d, J=5.7 Hz, 1H), 8.28-8.36 (m, 2H), 8.65 (d, J=5.7 Hz, 1H) (additional peak under water peak).

Example 4

6-[(3R)-1,1-dioxido-3-(2-phenylethyl)-1,2,5-thiadiazolidin-2-yl]isoquinoline-1-carbonitrile (Stereochemistry Arbitrarily Assigned) (#4; R=CH$_2$CH$_2$C$_6$H$_5$)

LCMS m/z=379.2 (M+1). $^1$H NMR (400 MHz, d$_6$-DMSO): δ 2.01 (br. s., 2H), 2.63-2.81 (m, 2H), 3.51 (br. s., 1H), 3.71 (d, J=5.4 Hz, 1H), 4.52 (br. s., 1H), 7.10-7.39 (m, 5H), 7.51 (br. s., 1H), 7.85 (d, J=9.1 Hz, 1H), 8.05 (d, J=4.8 Hz, 1H), 8.17-8.33 (m, 2H), 8.62 (d, J=5.1 Hz, 1H).

Example 5

6-[1-methyl-(3S)-3-methyl-1,1-dioxido-1,2,5-thiadiazolidin-2-yl]isoquinoline-1-carbonitrile (#5, R=CH$_3$, N—CH$_3$)

K$_2$CO$_3$ (2 eq.) and MeI (2 eq.) were added to a solution of #1 (1 eq.) in DMF (3 mL) at 0° C. and stirred at room temperature for 2 h. Reaction mixture was diluted with water. The resulting solid was filtered, washed with water and dried. The crude products were purified by triturating with DCM and pentane to get the pure compound.

LCMS m/z=303.1 (M+1). $^1$H NMR (400 MHz, d$_6$-DMSO): δ 1.34 (d, J=6.1 Hz, 3H), 2.78 (s, 3H), 3.20 (dd, J=10.1, 6.5 Hz, 1H) 3.77 (dd, J=10.2, 6.44 Hz, 1H) 4.68 (q, J=6.3 Hz, 1H) 7.85 (d, J=2.2 Hz, 1H) 7.90 (dd, J=9.2, 2.3 Hz, 1H) 8.21 (d, J=5.6 Hz, 1H) 8.31 (d, J=9.1 Hz, 1H) 8.66 (d, J=5.7 Hz, 1H).

Example 6

6-{(3R)-1,1-dioxido-3-[3-(trifluoromethyl)phenyl]-1,2,5-thiadiazolidin-2-yl}isoquinoline-1-carbonitrile (Stereochemistry Arbitrarily Assigned) (#6; R=m-CF$_3$—C$_6$H$_5$)

LCMS m/z=419.1 (M+1). $^1$H NMR (400 MHz, d$_6$-DMSO): δ 3.41 (dd, J=12.7, 4.8 Hz, 1H), 4.11 (dd, J=12.7, 6.9 Hz, 1H), 5.84 (t, J=5.9 Hz, 1H), 7.61-7.66 (m, 2H), 7.66-7.76 (m, 2H), 7.81 (dd, J=9.2, 2.4 Hz, 1H), 7.88 (s, 1H), 8.07 (d, J=5.8 Hz, 1H), 8.22 (d, J=9.2 Hz, 1H), 8.51 (s, 1H), 8.57 (d, J=5.8 Hz, 1H).

Example 7

6-[(3S)-3-(4-chlorophenyl)-1,1-dioxido-1,2,5-thiadiazolidin-2-yl]isoquinoline-1-carbonitrile (Stereochemistry Arbitrarily Assigned) (#7; R=p-Cl—C$_6$H$_5$)

LCMS m/z=385.6 (M+1). $^1$H NMR (400 MHz, d$_6$-DMSO): δ 4.06 (dd, J=12.5, 6.9 Hz, 1H), 5.70 (t, J=6.1 Hz, 1H), 7.41-7.52 (m, 4H), 7.57 (d, J=2.2 Hz, 1H), 7.78 (dd, J=9.2, 2.3 Hz, 1H), 8.06 (d, J=5.6 Hz, 1H), 8.20 (d, J=9.2 Hz, 1H), 8.43 (br. s., 1H), 8.56 (d, J=5.8 Hz, 1H) (additional peak under water peak).

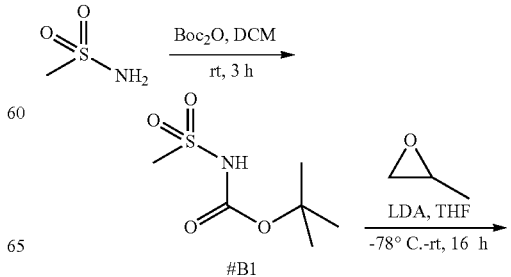

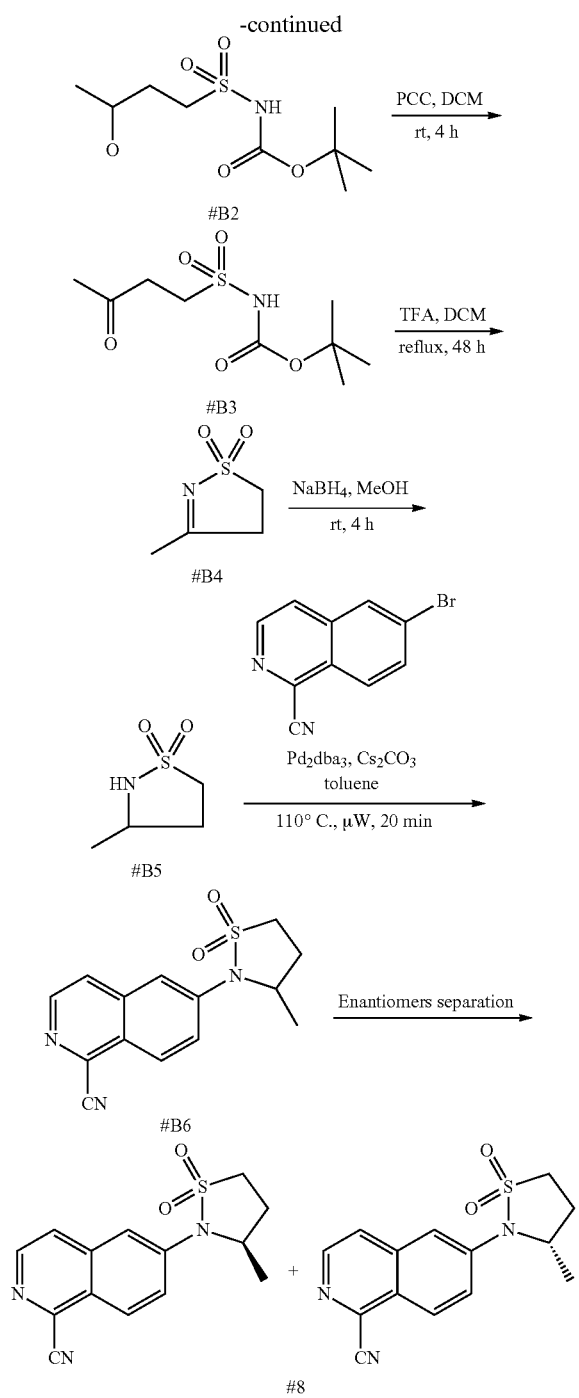

Step 1.

Synthesis of tert-butyl methylsulfonylcarbamate (#B1). A solution of Boc$_2$O (41.2 g, 189.2 mmol) in DCM (200 mL) was added dropwise to a stirred suspension of methane sulfonamide (15.0 g, 157.7 mmol), Et$_3$N (23.6 mL, 173.5 mmol) and DMAP (1.9 g, 15.8 mmol) in DCM (200 mL). The resulting suspension was stirred for 3 h at room temperature and concentrated under vacuum. The resulting residue was diluted with EtOAc (300 mL) and acidified with 1 N HCl (200 mL). The organic layer was washed with water followed by brine, dried over Na$_2$SO$_4$ and concentrated under reduced pressure to obtain a crude mixture, which was triturated with 10% EtOAc in petroleum ether to obtain #B1 as a white solid (25.0 g, 81%). R$_f$: 0.6 (50% EtOAc in petroleum ether).

LCMS m/z=194.3 (M−H). $^1$H NMR (400 MHz, CDCl$_3$): δ 1.44 (s, 9H), 3.19 (s, 3H), 7.19 (s, 1H).

Step 2.

Synthesis of tert-butyl 3-hydroxybutylsulfonylcarbamate (#B2). Freitag, D., Metz, P. *Tetrahedron* 2006, 62(8), 1799-1805.

n-BuLi (10.2 mL, 1M in hexane, 10.2 mmol) was added to a solution of diisopropylamine (1.7 mL, 10.2 mmol) in THF (20 mL) at −78° C., and the resulting mixture was stirred for 10 minutes at −78° C. and then 30 minutes at −5° C. The reaction mixture was again cooled to −78° C., then a solution of #B1 (1.0 g, 5.1 mmol) in THF (10 mL) was added dropwise to this reaction mixture (maintaining the reaction mixture temperature at −78° C.) and the stirring was continued for 20 minutes. A solution of propylene oxide (0.47 mL, 6.7 mmol) in THF (15 mL) was added dropwise to this reaction mixture at −78° C. and stirring was continued for 30 minutes. The reaction mixture was slowly warmed to room temperature and stirring was continued for 16 h. The mixture was poured onto an ice-cold saturated aqueous NH$_4$Cl solution. The resulting precipitate was dissolved by addition of water, and the mixture was acidified with 1N HCl to pH=3. The aqueous layer was extracted with DCM. The organic layer was washed with brine, dried over anhydrous Na$_2$SO$_4$, concentrated to get residue which was chromatographed on silica gel (230-400 mesh) using diethyl ether as eluent to obtain #B2 as a colorless oil (0.3 g, 25%). R$_f$: 0.3 (Et$_2$O).

LCMS m/z=252.1 (M−1)

Step 3.

Synthesis of Boc-protected sulfonamide ketone (#B3). Pyridinium chlorochromate (0.53 g, 2.5 mmol) was added to a solution of #B2 (0.30 g, 1.2 mmol) in DCM (15 mL) and the resulting dark-brown solution was stirred for 4 h at ambient temperature. The reaction mixture was diluted with Et$_2$O (10 mL) and stirring was continued for 15 minutes. It was filtered through silica gel (230-400 mesh) and washed with Et$_2$O and the filtrate was concentrated under reduced pressure to afford #B3 as brown oil (0.2 g, 68%). R$_f$: 0.4 (Et$_2$O).

LCMS m/z=250.1 (M−H). $^1$H NMR (300 MHz, CDCl$_3$): δ 1.51 (s, 9H), 2.23 (s, 3H), 3.02 (t, J=7.2 Hz, 2H), 3.68 (t, J=6.9 Hz, 2H), 7.00 (s, 1H).

Step 4.

Synthesis of unsaturated heterocycle (#B4). TFA (4.2 mL, 55.7 mmol) was added to a solution of #B3 (3.5 g, 13.9 mmol) in DCM (50 mL) and the resulting solution was heated to reflux for 48 h. After cooling, EtOH (40 mL) was added to this solution and the solution was concentrated under vacuum to one third of the original volume and subsequent crystallization was done at −20° C. to afford #B4 as an off-white solid (1.1 g, 61%). R$_f$: 0.3 (1:1 EtOAc/DCM).

GCMS m/z=133.0 (M). $^1$H NMR (400 MHz, CDCl$_3$): δ 2.34 (s, 3H), 3.18-3.29 (m, 4H).

Step 5.

Synthesis of saturated heterocycle (#B5). NaBH$_4$ (0.46 g, 12.4 mmol) was added in small portions to a solution of #B4 (1.1 g, 8.3 mmol) in dry MeOH (40 mL) at 0° C. and the reaction mixture was stirred at room temperature for 4 h. The reaction mixture was quenched with ice water and extracted with DCM. The organic layers were dried over Na$_2$SO$_4$ and concentrated to provide the pure #B5 as colorless oil (0.85 g, 77%). R$_f$: 0.4 (1:1 EtOAc/DCM).

GCMS m/z=135.1 (M). ¹H NMR (400 MHz, CDCl₃): δ 1.30 (d, J=6 Hz, 3H), 2.00-2.10 (m, 1H), 2.40-2.56 (m, 1H), 3.09-3.17 (m, 1H), 3.20-3.27 (m, 1H), 3.70-3.77 (m, 1H), 4.12 (br s, 1H).

Step 6.

Synthesis of coupling product (#B6). Pd₂dba₃ (0.094 g, 0.10 mmol), BINAP (0.19 g, 0.31 mmol) and Cs₂CO₃ (3.3 g, 10.3 mmol) were added to a degassed solution of 6-bromoisoquinoline-1-carbonitrile (0.8 g, 3.4 mmol) in toluene (10 mL) followed by the addition of #B5 (0.52 g, 3.8 mmol) under nitrogen atmosphere. The resulting reaction mixture was irradiated in a microwave at 110° C. for 20 minutes. The reaction mixture was cooled to room temperature, diluted with EtOAc, filtered and the filtrate was washed with water. The organic layer was separated and the aqueous layer was extracted with EtOAc. The organic layers were combined, dried over Na₂SO₄ and evaporated under reduced pressure to afford the crude mixture which was chromatographed on silica gel (100-200 mesh) using 25% EtOAc in petroleum ether to give #B6 as a light brown solid (0.25 g, 25%). R$_f$: 0.4 (25% EtOAc/petroleum ether).

Racemic: LCMS m/z=288.1 (M+H). ¹H NMR (300 MHz, CDCl₃): δ 1.41 (d, J=6.3 Hz, 3H), 2.27-2.38 (m, 1H), 2.71-2.79 (m, 1H), 3.30-3.38 (m, 1H), 3.50-3.58 (m, 1H), 4.38-4.44 (m, 1H), 7.67 (d, J=2.1 Hz, 1H), 7.71 (dd, J=2.1, 9.3 Hz, 1H), 7.83 (d, J=5.7 Hz, 1H), 8.35 (d, J=9 Hz, 1H), 8.61 (d, J=5.7 Hz, 1H).

The racemic compound was chromatographed for enantiomeric separation. Conditions: Column: CHIRAL PAK IA, 4.6×250 mm, 5 μm; Column ID: ANL_CHIR IA_145; Mobile Phase: A=hexane, B=isopropyl alcohol; ISOCRATIC: 60:40; FLOW: 0.8 mL/min; Column Temp: 25° C.; Eluent: EtOH Enantiomer of #8: Chiral HPLC purity: 99.38% (retention time 12.55 minutes)

LCMS m/z=287.9 (M+H). ¹H NMR (300 MHz, d₆-DMSO): δ 1.30 (d, J=6.3 Hz, 3H), 2.10-2.17 (m, 1H), 2.65-2.76 (m, 1H), 3.51-3.55 (m, 1H), 3.70-3.79 (m, 1H), 4.50-4.57 (m, 1H), 7.81 (d, J=2.1 Hz, 1H), 7.87 (dd, J=2.7, 9.0 Hz, 1H), 8.20 (d, J=5.4 Hz, 1H), 8.28 (d, J=9.0 Hz, 1H), 8.64 (d, J=5.7 Hz, 1H).

Example 8

6-[(3S)-3-methyl-1,1-dioxido-1,2-thiazolidin-2-yl]isoquinoline-1-carbonitrile

LCMS m/z=287.9 (M+1). ¹H NMR (400 MHz, d₆-DMSO): δ 1.31 (d, J=5.7 Hz, 3H), 2.08-2.27 (m, 1H), 2.67-2.74 (m, 1H), 3.49-3.59 (m, 1H), 3.71-3.79 (m, 1H), 4.50-4.57 (m, 1H), 7.81 (s, 1H), 7.87 (d, J=9.3 Hz, 1H), 8.21 (d, J=5.4 Hz, 1H), 8.29 (d, J=9.0 Hz, 1H), 8.64 (d, J=5.7 Hz, 1H). Chiral HPLC purity: 98.9% (retention time 20.42 minutes)

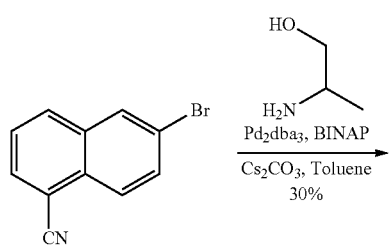

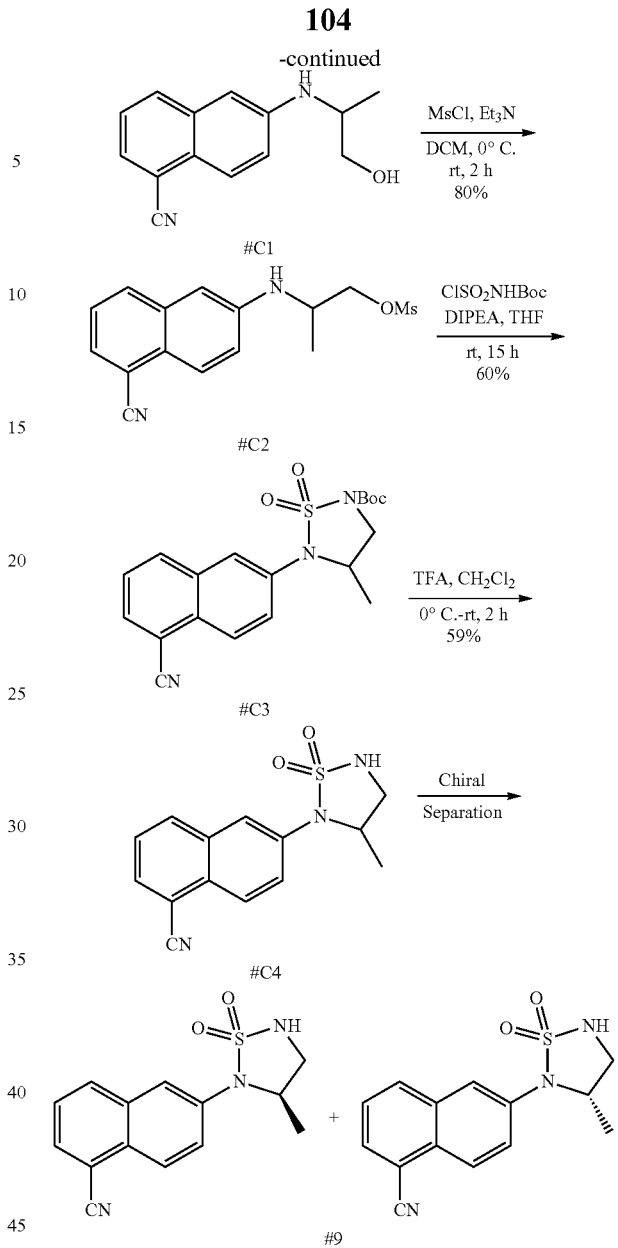

Step 1.

Synthesis of coupling product (#C1). A solution of #A3 (1.0 g, 4.3 mmol) in toluene (100 mL) was bubbled with argon gas for 15 minutes. Pd₂dba₃ (0.12 g, 0.13 mmol), BINAP (0.24 g, 0.39 mmol) and Cs₂CO₃ (4.7 g, 14.6 mmol) were added to the solution followed by the addition of racemic 2-aminopropan-1-ol (0.66 mL, 8.6 mmol). The mixture was heated at 100° C. under argon atmosphere for 3 h. The reaction mixture cooled to room temperature, diluted with EtOAc and washed with water. The organic layer was washed with brine, dried over Na₂SO₄ and concentrated under reduced pressure. The crude compound was purified by silica gel column chromatography using 25% EtOAc in petroleum ether as an eluent to yield product #C1 as yellow solid (0.3 g, 30%). R$_f$: 0.3 (40% EtOAc in petroleum ether).

LCMS m/z=227.0 (M+H).

Step 2.

Synthesis of mesylate product (#C2). Mesyl chloride (0.80 mL, 10.6 mmol) was added to a solution of #C1 (0.60 g, 2.7 mmol) and Et₃N (1.4 mL, 10.6 mmol) in DCM (40 mL) at 0° C., and the mixture was stirred at room temperature for 2 h. The reaction mixture diluted with DCM and, washed with water. The organic layer was washed with brine, dried over Na₂SO₄ and concentrated under reduce pressure. The crude product #C2 (0.65 g of oily solid) was used for the next step without purification. R$_f$: 0.4 (40% EtOAc in petroleum ether).

LCMS m/z=305.0 (M+H).

Step 3.

Synthesis of cyclized Boc-protected product (#C3). ClSO₂NCO (1 mL, 10.6 mmol) was added dropwise over 5 minutes to a mixture of t-butanol (1 mL) and toluene (2.5 mL), and the reaction mixture was stirred at room temperature for 45 minutes. The mixture (t-butyl chlorosulfonylcarbamate) was added to a solution of #C2 (0.65 g, 2.1 mmol) and DIPEA (1.8 mL, 10.6 mmol) in THF (10 mL), and the mixture was stirred at room temperature for 15 h. The reaction mixture was diluted with DCM and extracted with water. The organic layer dried over Na₂SO₄ and concentrated in vacuo. Product was purified by passing through silica gel column (100-200 mesh) using 25% EtOAc in petroleum ether to yield 0.5 g (60%) of #C3 as off-white solid. R$_f$: 0.5 (50% EtOAc in petroleum ether).

¹H NMR (400 MHz, d₆-DMSO): δ 1.29 (d, J=6.2 Hz, 3H), 1.59 (s, 9H), 3.62 (m, 1H), 4.19 (m, 1H), 4.26 (m, 1H), 7.75 (t, J=7.8 Hz, 1H), 7.83 (m, 1H), 8.17 (d, J=6.6 Hz, 1H), 8.21 (d, J=6.6 Hz, 1H), 8.24 (d, J=8.4 Hz, 1H), 8.40 (d, J=8.9 Hz, 1H).

Step 4.

Synthesis of racemic mixture (#C4) and final product #9. TFA (10 mL) was added to a solution of #C3 (0.50 g, 0.82 mmol) in DCM (10 mL) at 0° C., and the mixture was stirred at room temperature for 2 h. The reaction mixture was concentrated, diluted with water, neutralized with NaHCO₃, extracted with DCM and washed with water. The organic layer was dried over Na₂SO₄ and concentrated. Crude compound was purified by treating with DCM and n-pentane to yield 0.22 g (59%) of #C4 as white solid. R$_f$: 0.3 (60% EtOAc in petroleum ether). #C4 (racemic, 220 mg) was subjected to chiral preparative HPLC to obtain two enantiomers as off-white solids (65 mg of #9 and 35 mg of the other enantiomer). Chiral preparative HPLC conditions:

Column: CHIRALPAK IC, 250×30 mm, 5 μm; Mobile phase: n-Hexane/EtOH (60%/40%); Flow rate: 30 mL/min.

Enantiomer of #9: Chiral HPLC purity: 98.60% (retention time 10.93 minutes)

Example 9

6-[(3S)-3-methyl-1,1-dioxido-1,2,5-thiadiazolidin-2-yl]naphthalene-1-carbonitrile (Stereochemistry is Arbitrarily Assigned)

LCMS m/z=286.0 (M−H). ¹H NMR (400 MHz, d₆-DMSO): δ 1.31 (d, J=6.2 Hz, 3H), 3.13-3.25 (m, 1H), 3.71 (dt, J=12.5, 6.8 Hz, 1H), 4.49-4.62 (m, 1H), 7.62-7.70 (m, 1H), 7.75-7.83 (m, 2H), 7.99 (t, J=7.8 Hz, 1H), 8.07 (d, J=6.6 Hz, 1H), 8.14 (d, J=8.9 Hz, 1H), 8.28 (d, J=8.4 Hz, 1H). Chiral HPLC purity: 99.1% (retention time 17.12 minutes)

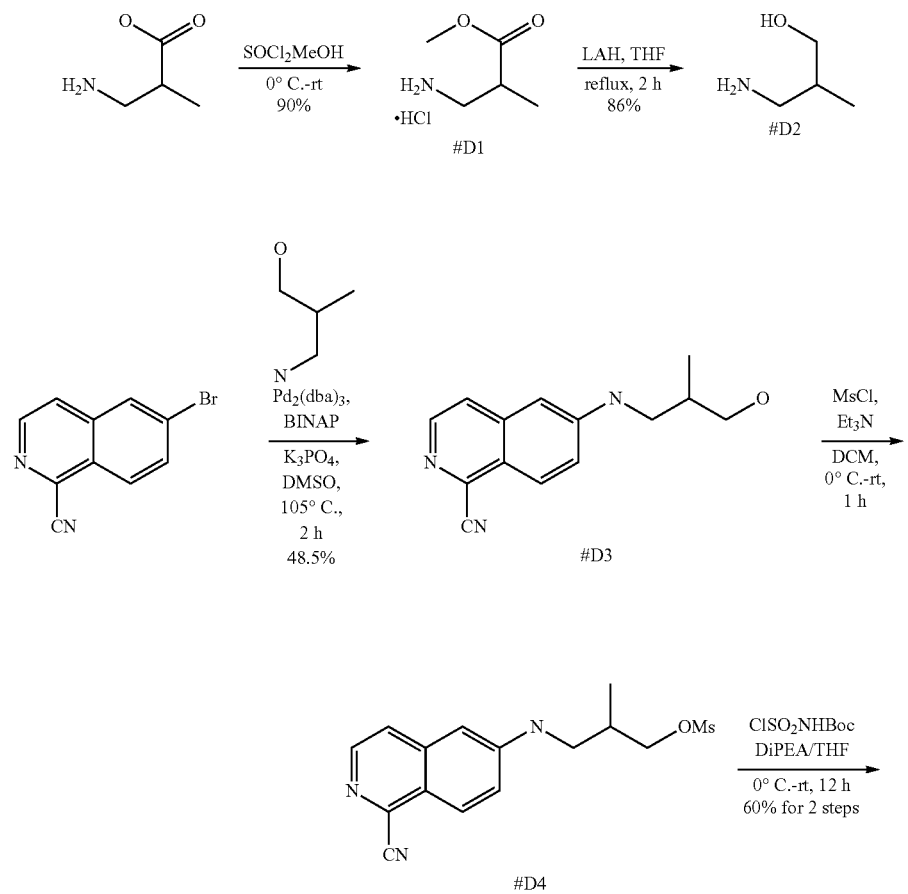

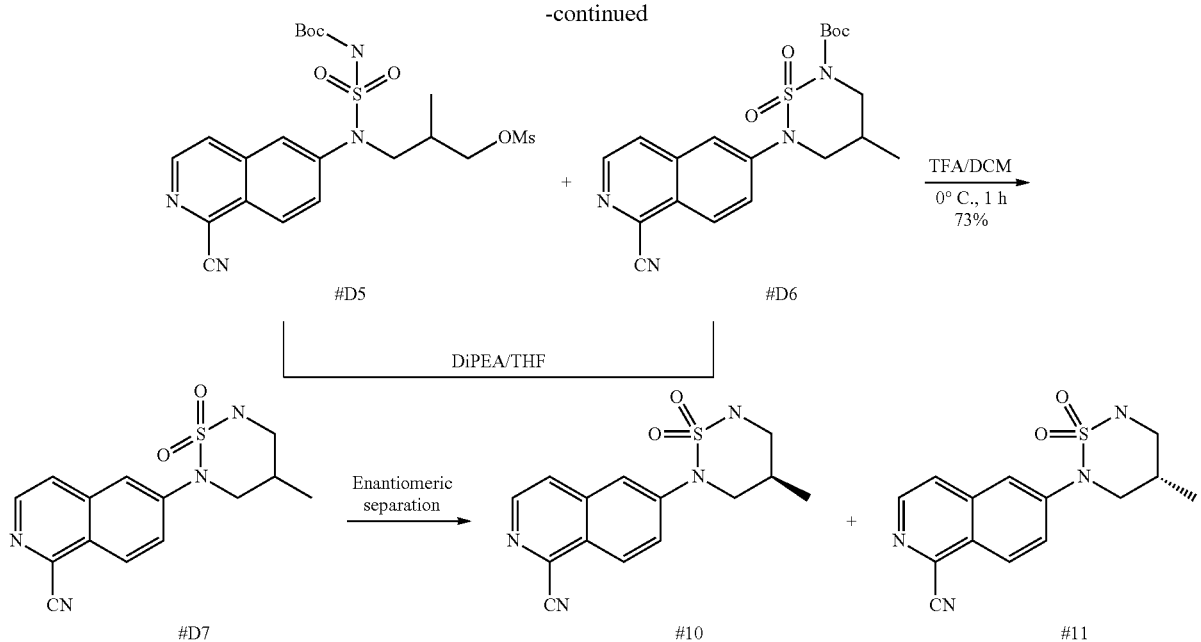

-continued

Step 1.
Synthesis of aminoester (#D1). Thionylchlride (8.5 mL, 116.5 mmol) was added to the solution of amino acid (4.0 g, 38.8 mmol) in MeOH (170 mL) at 0° C., and the reaction mixture was stirred for 6 h at room temperature. The reaction was monitored by TLC, and after disappearance of the starting material it was cooled to room temperature and solid $NaHCO_3$ was added. The reaction mixture was filtered, concentrated in vacuo and the resulting residue was triturated with diethyl ether to obtain crude #D1 (4 g, 90%) as a white solid. $R_f$: 0.4 (t-BuOH:AcOH:$H_2O$ (4:0.5:0.5)).

GCMS m/z=117.1 (M). $^1$H NMR (400 MHz, $d_6$-DMSO): δ 1.17 (d, J=6.8 Hz, 3H), 2.83-2.88 (m, 2H), 3.03-3.05 (m, 1H), 3.65 (s, 3H), 8.02-8.30 (br s, 3H).

Step 2.
Synthesis of aminoalcohol (#D2). #D1 (2.0 g, 13.0 mmol) was added portionwise to a suspension of $LiAlH_4$ (1.4 g, 39.2 mmol) in THF (75 mL) under nitrogen atmosphere at 0° C. The reaction mixture was stirred for 30 minutes and then allowed to stir at room temperature for another 30 minutes. The reaction mixture was refluxed for 2 h, and then it was cooled to −10° C. and quenched carefully with ice cold water (1.4 mL). 10% NaOH solution (2.8 mL) and ice cold water (4.2 mL) were added, and the mixture was stirred for 15 minutes. It was filtered, and the filtrate washed with EtOAc (3×100 mL), dried over anhydrous $Na_2SO_4$ and concentrated under vacuum to obtain #D2 (1.2 g, 86%) as a pale yellow liquid. $R_f$: 0.2 (20% MeOH in DCM).

$^1$H NMR (400 MHz, $d_6$-DMSO): δ 0.78 (d, J=6.8 Hz, 3H), 1.46-1.54 (m, 1H), 2.41-2.45 (m, 2H), 2.50-2.54 (m, 1H), 3.22-3.34 (m, 4H).

Step 3.
Synthesis of coupling product (#D3). $K_3PO_4$ (6.1 g, 28.8 mmol), BINAP (0.44 g, 0.72 mmol) and $Pd_2(dba)_3$ (0.32.0 g, 0.36 mmol) was added to the degassed suspension of 6-bromo-1-cyanoisoquinoline #A3 (1.7 g, 7.2 mmol), #D2 (1.2 g, 14.5 mmol) in DMSO at room temperature. The reaction mixture was heated at 105° C. for 2 h. The reaction was cooled to room temperature, water (500 mL) followed by EtOAc (100 mL) were added, and the mixture was stirred for 10 minutes. The biphasic mixture was filtered through a Celite™ pad and washed with EtOAc (100 mL). The organic layer was separated, and the aqueous layer was extracted with EtOAc (3×100 mL). The combined organic layers were dried over anhydrous $Na_2SO_4$, concentrated under reduced pressure to get a crude material. This was purified by column chromatography on 100-200 mesh silica gel, using 50-70% EtOAc in petroleum ether as the eluent to obtain #D3 (0.5 g, 48.5%) as a yellow solid. $R_f$: 0.4 (60% EtOAC in petroleum ether).

LCMS m/z=242.0 (M+H). $^1$H NMR (400 MHz, $d_6$-DMSO): δ 0.97 (d, J=6.4 Hz, 3H), 1.87-1.99 (m, 1H), 2.92-2.99 (m, 1H), 3.20-3.27 (m, 1H), 3.38-3.42 (m, 2H), 4.59 (t, J=5.2 Hz, 1H), 6.77 (d, J=2.0, 1H), 7.01 (t, J=5.6 Hz, 1H), 7.34 (dd, J=9.2 Hz, J=2.0 Hz, 1H), 7.73 (d, J=6.0 Hz, 1H), 7.88 (d, J=8.8 Hz, 1H), 8.312 (d, J=6.0 Hz, 1H).

Step 4.
Methanesulfonated coupling product (#D4). Triethylamine (0.44 mL, 3.1 mmol) was added to a solution of #D3 (0.50 g, 2.0 mmol) in DCM at 0° C. Methanesulfonylchloride (0.25 mL, 3.1 mmol) was added over 10 minutes, and the reaction mixture was stirred for 1 h at room temperature. After disappearance of the starting material by TLC, it was diluted with DCM and washed with water. The organic layer was separated, dried over $Na_2SO_4$, concentrated under reduced pressure to obtain crude #D4 (0.6 g, crude) as yellow solid. This was used for next step without any purification. $R_f$: 0.6 (50% EtOAc in petroleum ether).

LCMS m/z=320.0 (M+H). $^1$H NMR (400 MHz, $CDCl_3$): δ 1.17 (d, J=6.8 Hz, 3H), 2.32-2.37 (m, 1H), 3.06 (s, 3H), 3.26-3.41 (m, 2H), 4.16-4.20 (m, 1H), 4.33-4.37 (m, 1H), 4.75 (br s, 1H), 6.70 (d, J=2.4, 1H), 7.09 (dd, J=9.2 Hz, 2.4 Hz, 1H), 7.57 (d, J=6.0 Hz, 1H), 8.05 (d, J=9.2 Hz, 1H), 8.39 (d, J=5.6 Hz, 1H).

Step 5.
Cyclized and uncyclized intermediates (#D5, #D6). Chlorosulfonylisocyanate (1.2 mL, 13.1 mmol) was added dropwise to a solution t-BuOH (1.4 mL, 13.1 mmol) in toluene (4.0 mL) at −5° C. The reaction mixture was stirred at room temperature for 20 minutes, and then THF (1 mL) was added to the resulting suspension to obtain clear solution. In another flask, DIPEA (2.3 mL, 13.1 mmol) was added to a solution of #D4 (0.6 g, crude 2.6 mmol) in dry THF (3 mL). The above prepared reagent (ClSO$_2$NH-Boc) was added to this reaction mixture dropwise at room temperature over a period of 20 minutes. The resulting reaction mixture was then stirred for 16 h at room temperature. The mixture was diluted with EtOAc (100 mL) and washed with water (100 mL). The aqueous layer was washed with EtOAc (2×100 mL), combined all the organic layers, dried over Na$_2$SO$_4$, concentrated under reduced pressure to obtain the crude product (LCMS shows desired #D6 and uncyclized #D5. This crude was purified by column chromatography on 100-200 mesh silica gel, using 10-30% EtOAc in petroleum ether as an eluent to obtain desired #D6 (0.35 g, 47.8%), and uncyclized #D5 (0.22 g, crude).

The uncyclized #D5 (0.22 g, crude) was dissolved in THF (1 mL) and DIPEA (0.6 mL) was added to the solution. The reaction mixture was stirred for another 12 h at room temperature. After which time, it was diluted with EtOAc (100 mL) and washed with water (100 mL). The aqueous layer was washed with EtOAc (2×100 mL), combined all the organic layers, dried over Na$_2$SO$_4$, concentrated under reduced pressure to obtain crude product. This crude was purified by column chromatography on 100-200 mesh silica gel, using 10-30% EtOAc in petroleum ether as an eluent to obtain desired #D6 (1.1 g, 13.2%). Total amount of #D6 was (0.5 g, 60% for two steps, 82% LCMS purity). R$_f$: 0.8 (60% EtOAc in petroleum ether).

LCMS m/z=403.1 (M+H). $^1$H NMR (400 MHz, CDCl3): δ 1.04 (d, J=6.8 Hz, 3H), 1.50 (s, 9H), 2.38-2.48 (m, 1H), 3.65-3.82 (m, 2H), 3.92-4.02 (m, 1H), 4.30-4.38 (m, 1H), 7.79-7.81 (m, 1H), 7.86-7.88 (m, 2H), 8.34-8.37 (d, J=9.2 Hz, 1H), 8.67 (d, J=6.0 Hz, 1H).

Step 6.

Racemate #D7 and final products (#10, #11). TFA (5 mL) was added to a solution of #D6 (0.15 g, 0.37 mmol) in DCM (100 mL) at 0° C. The reaction mixture was stirred for 1 h at 0° C. The solution was neutralized with saturated aqueous NaHCO$_3$ solution at 0° C. The mixture was diluted with water, extracted with DCM (3×100 mL). The combined organic layers were dried over anhydrous Na$_2$SO$_4$ and concentrated under reduced pressure to obtain racemic #D7 (0.10 mg, 73%).

LCMS m/z=303.0 (M+H). R$_f$: 0.3 (60% EtOAc in petroleum ether).

Enantiomeric separation: #D7 was submitted for chiral separation to obtain final compounds #10 (0.015 mg) and #11 (0.016 mg).

Column: CHIRALPAK IA, 4.6×250 mm, 5 µm; Mobile phase: n-Hexane/i-PrOH/DCM (60%/15%/15%); Flow rate: 0.8 mL/min.

Example 10

6-[(4R)-4-methyl-1,1-dioxido-1,2,6-thiadiazinan-2-yl]isoquinoline-1-carbonitrile (#10; R=(R)—CH$_3$)

LCMS m/z=303.0 (M+1). $^1$H NMR (400 MHz, d$_6$-DMSO): δ 0.98 (d, J=6.4 Hz, 3H), 2.22-2.26 (m, 1H), 3.16-3.22 (m, 1H), 3.34-3.39 (m, 1H), 3.59-3.65 (m, 1H), 3.77-3.81 (m, 1H), 7.75-7.79 (m, 1H, disappeared in D20 exchange), 7.95 (dd, J=8.8 Hz, J=2.0 Hz, 1H), 8.06 (d, J=1.6 Hz, 1H), 8.23-8.27 (m, 2H), 8.703 (d, J=5.2 Hz, 1H). R$_f$: 0.3 (60% EtOAc in petroleum ether). Chiral HPLC purity: 98.2% (retention time 11.43 minutes).

Example 11

6-[(4S)-4-methyl-1,1-dioxido-1,2,6-thiadiazinan-2-yl]isoquinoline-1-carbonitrile (#11; R=(S)—CH$_3$)

LCMS m/z=301.0 (M−1). $^1$H NMR (400 MHz, d$_6$-DMSO): δ 0.98 (d, J=7.2 Hz, 3H), 2.22-2.27 (m, 1H), 3.13-3.22 (m, 1H), 3.32-3.39 (m, 1H), 3.59-3.65 (m, 1H), 3.77-3.81 (m, 1H), 7.76-7.79 (m, 1H, disappeared in D$_2$O exchange), 7.96 (dd, J=9.2 Hz, J=2.0 Hz, 1H), 8.06 (d, J=2.0 Hz, 1H), 8.23-8.27 (m, 2H), 8.70 (d, J=5.2 Hz, 1H). R$_f$: 0.3 (60% EtOAc in petroleum ether). Chiral HPLC purity: 97.5% (retention time 12.81 minutes).

Targets #12, #13, #14, #15, #17, #18, #19, #20, #21, #22 of the general formula below were prepared according to a similar procedure outlined above for targets #10, #11.

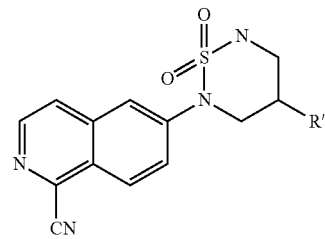

Example 12

6-{(3R)-1,1-dioxido-3-(3-phenyl)-1,2,5-thiadiazolidin-2-yl}isoquinoline-1-carbonitrile (Stereochemistry Arbitrarily Assigned) (#12; R=C$_6$H$_5$)

LCMS m/z=365.1 (M+1). $^1$H NMR (400 MHz, d$_6$-DMSO): δ 3.39-3.57 (m, 2H), 3.67-3.81 (m, 1H), 3.87 (d, J=11.2 Hz, 1H), 4.14 (t, J=11.9 Hz, 1H), 7.26-7.48 (m, 5H), 8.02 (d, J=9.37 Hz, 2H), 8.13 (br. s., 1H), 8.25 (d, J=7.0 Hz, 2H) 8.69 (d, J=5.4 Hz, 1H).

Example 13

6-(4,4-dimethyl-1,1-dioxido-1,2,6-thiadiazinan-2-yl)isoquinoline-1-carbonitrile (#13; R'=(gem-(CH$_3$)$_2$)

LCMS m/z=317.0 (M+1). $^1$H NMR (400 MHz, d$_6$-DMSO): δ 1.10 (s, 6H), 3.16 (d, J=7.3 Hz, 2H), 3.55 (s, 2H), 7.92 (dd, J=9.1, 2.1 Hz, 1H), 7.97-8.04 (m, 2H), 8.21-8.28 (m, 2H), 8.69 (d, J=5.6 Hz, 1H).

Example 14

6-(6,6-dioxido-6-thia-5,7-diazaspiro[2.5]oct-5-yl)isoquinoline-1-carbonitrile (#14; R'=cyclopropyl)

LCMS m/z=315.2 (M+1). $^1$H NMR (400 MHz, d$_6$-DMSO): δ 0.66 (d, J=6.2 Hz, 4H), 3.24 (d, J=7.1 Hz, 2H), 3.64 (s, 2H), 7.89-8.00 (m, 2H), 8.03 (d, J=2.1 Hz, 1H), 8.21-8.27 (m, 2H), 8.69 (d, J=5.6 Hz, 1H).

Example 15

6-[(4R)-4-(3-methylbenzyl)-1,1-dioxido-1,2,6-thiadiazinan-2-yl]isoquinoline-1-carbonitrile (Stereochemistry Arbitrarily Assigned) (#15; R'=CH$_2$-[m-CH$_3$—C$_6$H$_4$])

LCMS m/z=393.0 (M+1). $^1$H NMR (400 MHz, d$_6$-DMSO): δ 2.26 (s, 3H), 2.58-2.69 (m, 1H), 2.69-2.78 (m, 1H), 3.63-3.81 (m, 2H), 6.98-7.11 (m, 3H), 7.18 (t, J=7.5 Hz, 1H), 7.69-7.78 (m, 1H), 7.93 (dd, J=9.1, 2.0 Hz, 1H), 8.03 (d, J=2.1 Hz, 1H), 8.21-8.28 (m, 2H), 8.70 (d, J=5.6 Hz, 1H) (Additional protons under water peak and cannot be integrated).

Targets #16 was prepared according to a similar procedure outlined above for target #5.

Example 16

6-[(4R)-6-ethyl-4-methyl-1,1-dioxido-1,2,6-thiadiazinan-2-yl]isoquinoline-1-carbonitrile (Stereochemistry Arbitrarily Assigned) (#16; R'=CH$_3$, N—C$_2$H$_5$)

LCMS m/z=303.0 (M+1). $^1$H NMR (400 MHz, d$_6$-DMSO): δ 0.95 (d, J=6.3 Hz, 3H), 1.15 (t, 3H), one proton under DMSO peak, 3.09-3.14 (m, 1H), 3.20-3.26 (m, 3H), 3.64-3.69 (m, 2H), 7.96 (dd, J=8.8 Hz, J=2.1 Hz, 1H), 8.05 (m, 1H), 8.21-8.25 (m, 2H), 8.703 (m, 1H).

Example 17

6-(5-methyl-1,1-dioxido-1,2,6-thiadiazinan-2-yl)isoquinoline-1-carbonitrile (Racemic Mixture)

LCMS m/z=303.1 (M+1). $^1$H NMR (400 MHz, CDCl3): δ 1.39 (d, J=6.3 Hz, 3H), 1.79-1.94 (m, 1H), 2.05 (dd, J=14.1, 2.5 Hz, 1H), 3.66-3.77 (m, 1H), 4.03-4.18 (m, 2H), 7.78-7.91 (m, 3H), 8.34 (d, J=9.0 Hz, 1H), 8.66 (d, J=5.7 Hz, 1H) (NH proton exchanged).

Example 18

6-[(4S)-4-(4-methylphenyl)-1,1-dioxido-1,2,6-thiadiazinan-2-yl]isoquinoline-1-carbonitrile (Stereochemistry Arbitrarily Assigned) (#18; R'=(S)-p-CH$_3$—C$_6$H$_4$)

LCMS m/z=379.1 (M+1). $^1$H NMR (400 MHz, d$_6$-DMSO): δ 2.29 (s, 3H), 3.36-3.52 (m, 2H), 3.71 (d, J=12.0 Hz, 1H), 3.83 (d, J=11.0 Hz, 1H), 4.05-4.16 (m, 1H), 7.19 (m, J=7.9 Hz, 2H), 7.30 (m, J=7.9 Hz, 2H), 7.95-8.05 (m, 2H), 8.09-8.14 (m, 1H), 8.21-8.28 (m, 2H), 8.69 (d, J=5.6 Hz, 1H).

Example 19

6-[(4R)-4-(4-methylphenyl)-1,1-dioxido-1,2,6-thiadiazinan-2-yl]isoquinoline-1-carbonitrile (Stereochemistry Arbitrarily Assigned) (#19; R'=(R)-p-CH$_3$—C$_6$H$_4$])

LCMS m/z=379.1 (M+1). $^1$H NMR (400 MHz, d$_6$-DMSO): δ 2.29 (s, 3H), 3.36-3.53 (m, 2H), 3.63-3.77 (m, 1H), 3.83 (d, J=11.0 Hz, 1H), 4.03-4.16 (m, 1H), 7.19 (m, J=7.9 Hz, 2H), 7.30 (m, J=8.0 Hz, 2H), 7.94-8.05 (m, 2H), 8.12 (d, J=1.9 Hz, 1H), 8.21-8.30 (m, 2H), 8.69 (d, J=5.5 Hz, 1H).

Example 20

6-[(4S)-4-(3-methylphenyl)-1,1-dioxido-1,2,6-thiadiazinan-2-yl]isoquinoline-1-carbonitrile (Stereochemistry Arbitrarily Assigned) (#20; R'=(S)—C$_2$H$_5$)

LCMS m/z=317.1 (M+1). $^1$H NMR (400 MHz, d$_6$-DMSO): δ 0.94 (t, J=7.5 Hz, 3H), 1.31-1.44 (m, 2H), 1.91-2.07 (m, 1H), 3.19 (dd, J=14.0, 10.4 Hz, 1H), 3.37-3.48 (m, 1H), 3.63 (dd, J=12.4, 10.3 Hz, 1H), 3.74-3.84 (m, 1H), 7.73 (s, 1H), 7.95 (dd, J=9.1, 2.2 Hz, 1H), 8.06 (d, J=2.1 Hz, 1H), 8.20-8.30 (m, 2H), 8.70 (d, J=5.6 Hz, 1H).

Example 21

6-[(4S)-4-ethyl-1,1-dioxido-1,2,6-thiadiazinan-2-yl]isoquinoline-1-carbonitrile (Stereochemistry Arbitrarily Assigned) (#21; R'=(S)-m-CH$_3$—C$_6$H$_4$)

LCMS m/z=379.1 (M+1). $^1$H NMR (400 MHz, d$_6$-DMSO): δ 2.32 (s, 3H), 3.35-3.54 (m, 2H), 3.66-3.79 (m, 1H), 3.84 (d, J=10.7 Hz, 1H), 4.06-4.19 (m, 1H), 7.12 (d, J=7.3 Hz, 1H), 7.17-7.22 (m, 1H), 7.22-7.31 (m, 2H), 7.96-8.05 (m, 2H), 8.12 (d, J=2.1 Hz, 1H), 8.21-8.28 (m, 2H), 8.69 (d, J=5.7 Hz, 1H).

Example 22

6-(1,1-dioxido-4-propyl-1,2,6-thiadiazinan-2-yl)isoquinoline-1-carbonitrile (Racemic Mixture) (#22; R'=C$_3$H$_7$)

LCMS m/z=331.2 (M+1). $^1$H NMR (400 MHz, d$_6$-DMSO): δ 0.81-0.96 (m, 3H), 1.33 (br. s., 4H), 2.09 (br. s., 1H), 3.12-3.25 (m, 1H), 3.41 (d, J=13.5 Hz, 1H), 3.56-3.68 (m, 1H), 3.77 (d, J=10.4 Hz, 1H), 7.73 (dd, J=9.0, 4.6 Hz, 1H), 7.95 (d, J=9.1 Hz, 1H), 8.06 (s, 1H), 8.20-8.30 (m, 2H), 8.70 (d, J=5.6 Hz, 1H).

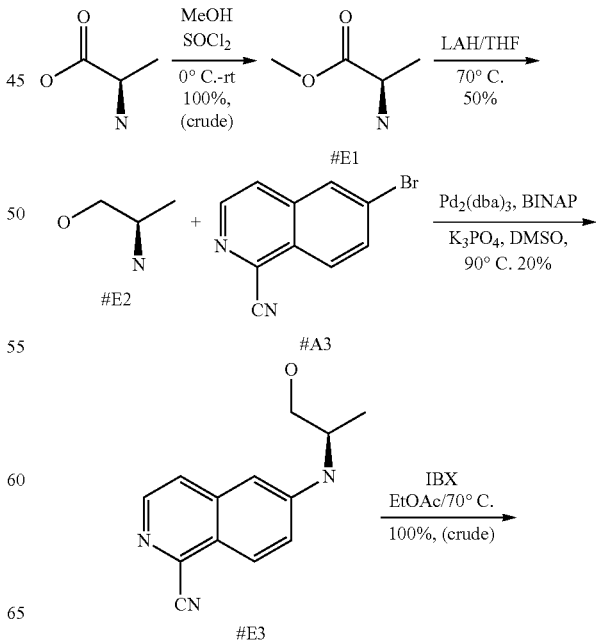

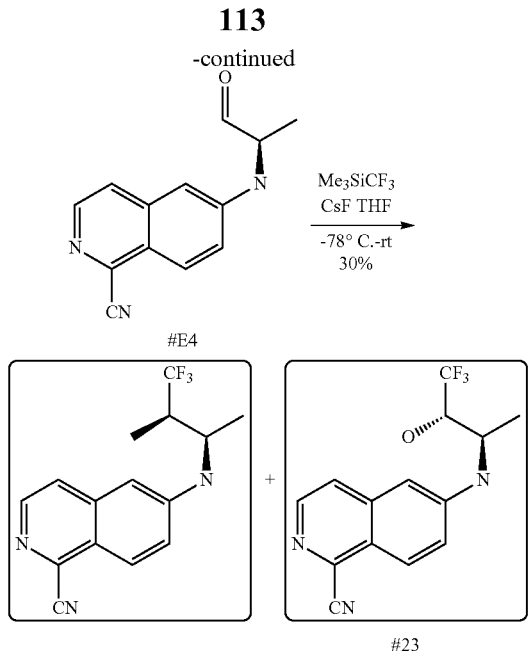

Step 1.

Synthesis of methyl alanine (#E1). Thionyl chloride (18.4 mL, 252.8 mmol) was added to a solution of alanine (15.0 g, 168.5 mmol) in methanol at 0° C. Then, the reaction mixture was stirred at room temperature for 3 h. After the depletion of the starting material, the reaction was cooled to 0° C. and treated with solid $NaHCO_3$. The slurry was filtered through Celite™ pad, and rinsed with MeOH (100 mL). The filtrate was concentrated under reduced pressure to provide a residue that was diluted with DCM, washed with water, brine, dried and concentrated to give #E1 (19.0 g, crude). This was used for the next step without further purification. $R_f$: 0.6 (20% methanol in DCM).

$^1$H NMR (400 MHz, $d_6$-DMSO): δ 1.36 (d, J=7.2 Hz, 3H), 3.11 (s, 1H), 3.68 (s, 3H), 3.90 (q, J=7.2 Hz, 1H), 6.50 (br s, 3H).

Step 2.

Synthesis of aminoalcohol (#E2). A solution of #E1 (19.0 g, 184.5 mmol) in THF (300 mL) was cooled to 0° C., and $LiAlH_4$ (21.0 g, 553.4 mmol) was added portionwise over 30 minutes. The reaction mixture was stirred at room temperature till the reaction mixture become slurry, and then refluxed for 2 h. The reaction mixture was cooled to room temperature, quenched with 2N NaOH solution to pH 7. The solids were filtered through a Celite™ pad and washed with THF (100 mL×3). The filtrate was concentrated under reduced pressure to give crude material. The product was purified by neutral alumina column chromatography with 100% MeOH as an eluting system to give #E2 as a brown liquid (6.0 g, 43%). $R_f$: 0.1 (20% MeOH in DCM).

$^1$H NMR (400 MHz, $d_6$-DMSO): δ 0.89 (d, J=6.4 Hz, 3H), 2.71-2.78 (m, 1H), 3.06-3.10 (m, 1H), 3.17-3.23 (m, 1H).

Step 3.

Synthesis of 6-amino isoquinoline (#E3). A solution of #A2 (4.0 g, 51.7 mmol), 6-bromoisoquinoline-1-carbonitrile #A3 (6.0 g, 25.9 mmol), BINAP (3.2 g, 5.2 mmol), $Pd_2$(dba)$_3$ (2.3 g, 2.6 mmol) and potassium phosphate (11.0 g, 51.7 mmol) in anhydrous DMSO (35 mL) was heated at 80° C. for 2 h. The complete disappearance of the 6-bromoisoquinoline-1-carbonitrile #A3 was observed on TLC. The reaction mixture was cooled to room temperature, filtered through Celite™ pad and the filtrate was diluted with water (100 mL). The mixture was extracted with EtOAc (100 mL×3). The combined organic layers were dried over anhydrous sodium sulfate and concentrated under reduced pressure to give crude material which was purified by silica gel (100-200 mesh) column chromatography using 40% EtOAc in petroleum ether as an eluting system to give #E3 as yellow solid (1.5 g, 25.4%). $R_f$: 0.4 (60% EtOAc in petroleum ether).

LCMS m/z=227.9 (M+H); $^1$H NMR (400 MHz, $d_6$-DMSO): δ 1.18 (d, J=6.8 Hz, 3H), 3.36-3.47 (m, 1H), 3.48-3.53 (m, 1H), 3.60-3.66 (m, 1H), 6.80-6.82 (m, 2H), 7.32 (dd, J=2.4 Hz, 8.8 Hz, 1H), 7.72 (d, J=5.6 Hz, 1H), 7.87 (d, J=9.6 Hz, 1H), 8.30 (d, J=5.6 Hz, 1H).

Step 4.

Synthesis of aldehyde product (#E4). A solution of #E3 (0.70 g, 3.1 mmol) in EtOAc (15 mL) was cooled to 0° C., and IBX (1.7 g, 6.2 mmol) was added portionwise. The reaction mixture was stirred at 80° C. for 2 h and was cooled to room temperature. Then the reaction mixture was filtered through Celite™ pad and rinsed with EtOAc. The filtrate was washed with aqueous saturated $NaHCO_3$ solution (50 mL). The organic layer was collected, washed with water, brine, dried over anhydrous sodium sulfate and concentrated under reduced pressure to give #E4 (0.7 g, crude). This was used as such in next step without any further purification. $R_f$: 0.7 (60% EtOAc in petroleum ether).

LCMS m/z=225.9 (M+H).

Step 5.

Synthesis of product (#23). A solution of #E4 (0.70 g crude, 3.1 mmol), cesium fluoride (2.3 g, 15.5 mmol), in THF (15 mL) was cooled at −78° C., and $Me_3SiCF_3$ (0.7 mL, 4.7 mmol) was added dropwise over 10 minutes. After stirring 1 h, the reaction mixture was stirred at room temperature for 16 h. Water (50 mL) was added, and the reaction mixture was extracted with EtOAc (50 mL×3). The combined organic layers were dried over anhydrous sodium sulfate and concentrated under reduced pressure to give crude material. The stereoisomers were separated by chromatography on silica gel (230-400 mesh) using 30% EtOAc in petroleum ether as the eluent to provide compound #23 (55 mg, 6%) and its stereoisomer (130 mg, 14%). Total yield (185 mg, 20%). $R_f$: 0.5 (50% EtOAc in petroleum ether). Chiral HPLC purity: 95.9% purity. The absolute stereochemistry was assigned using crystallography.

Example 23

6-{[(2R,3S)-4,4,4-trifluoro-3-hydroxybutan-2-yl]amino}isoquinoline-1-carbonitrile (#23)

LCMS m/z=296.3 (M+1). $^1$H NMR (400 MHz, $d_6$-DMSO): δ 1.27 (d, J=8.0 Hz, 3H), 4.01-4.04 (m, 1H), 4.11-4.15 (m, 1H), 6.69 (d, J=6.8 Hz, 1H), 6.76 (d, J=9.2 Hz, 1H), 6.89 (d, J=2.0 Hz, 1H), 7.44 (dd, J=2.0 Hz, 1H), 7.74 (d, J=5.6 Hz, 1H), 7.88 (d, J=9.6 Hz, 1H), 8.33 (d, J=6.0 Hz, 1H).

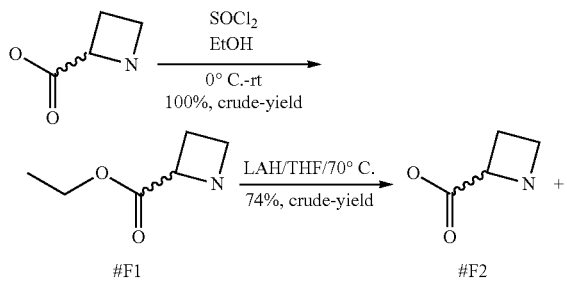

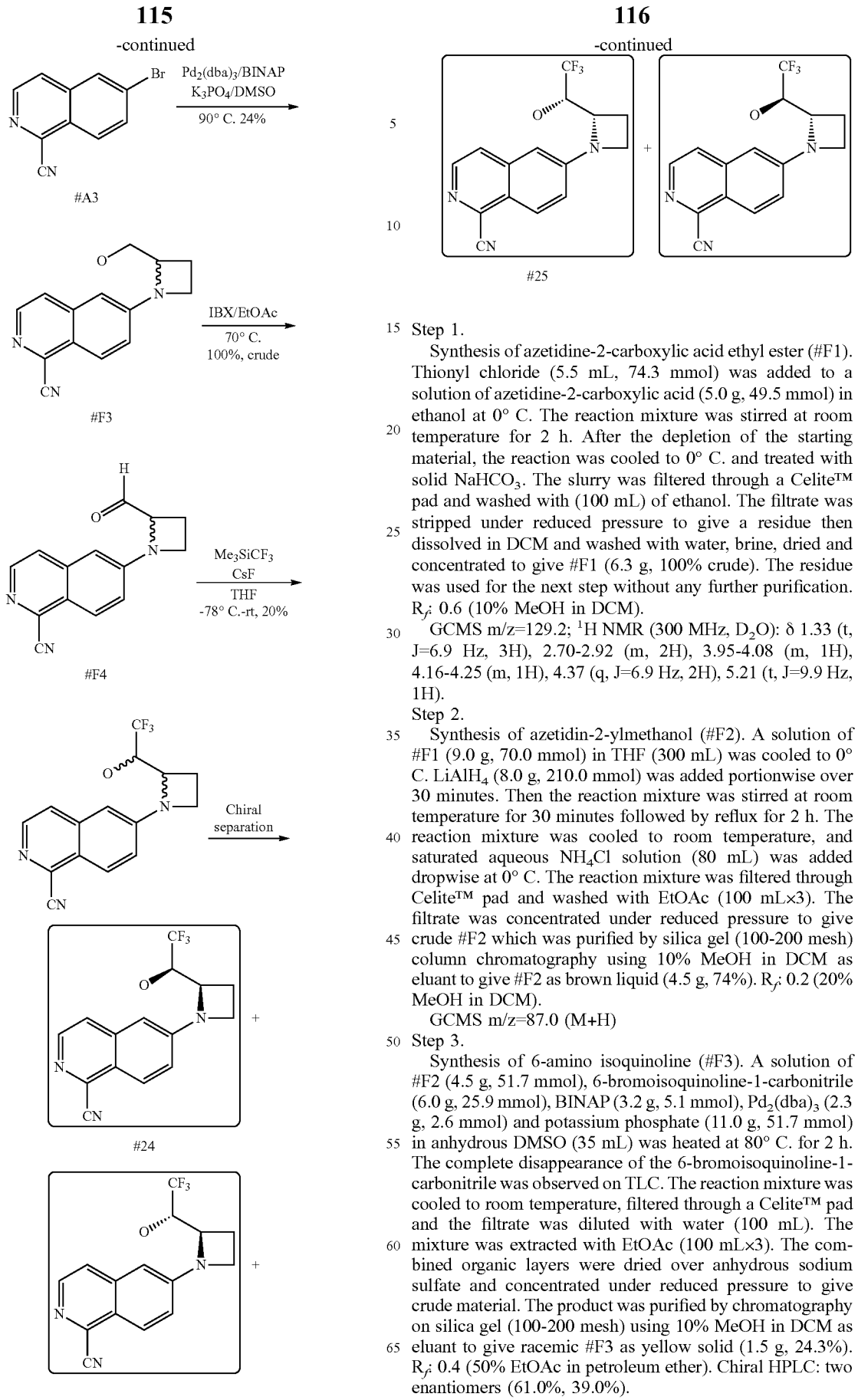

Step 1.

Synthesis of azetidine-2-carboxylic acid ethyl ester (#F1). Thionyl chloride (5.5 mL, 74.3 mmol) was added to a solution of azetidine-2-carboxylic acid (5.0 g, 49.5 mmol) in ethanol at 0° C. The reaction mixture was stirred at room temperature for 2 h. After the depletion of the starting material, the reaction was cooled to 0° C. and treated with solid NaHCO$_3$. The slurry was filtered through a Celite™ pad and washed with (100 mL) of ethanol. The filtrate was stripped under reduced pressure to give a residue then dissolved in DCM and washed with water, brine, dried and concentrated to give #F1 (6.3 g, 100% crude). The residue was used for the next step without any further purification. R$_f$: 0.6 (10% MeOH in DCM).

GCMS m/z=129.2; $^1$H NMR (300 MHz, D$_2$O): δ 1.33 (t, J=6.9 Hz, 3H), 2.70-2.92 (m, 2H), 3.95-4.08 (m, 1H), 4.16-4.25 (m, 1H), 4.37 (q, J=6.9 Hz, 2H), 5.21 (t, J=9.9 Hz, 1H).

Step 2.

Synthesis of azetidin-2-ylmethanol (#F2). A solution of #F1 (9.0 g, 70.0 mmol) in THF (300 mL) was cooled to 0° C. LiAlH$_4$ (8.0 g, 210.0 mmol) was added portionwise over 30 minutes. Then the reaction mixture was stirred at room temperature for 30 minutes followed by reflux for 2 h. The reaction mixture was cooled to room temperature, and saturated aqueous NH$_4$Cl solution (80 mL) was added dropwise at 0° C. The reaction mixture was filtered through Celite™ pad and washed with EtOAc (100 mL×3). The filtrate was concentrated under reduced pressure to give crude #F2 which was purified by silica gel (100-200 mesh) column chromatography using 10% MeOH in DCM as eluant to give #F2 as brown liquid (4.5 g, 74%). R$_f$: 0.2 (20% MeOH in DCM).

GCMS m/z=87.0 (M+H)

Step 3.

Synthesis of 6-amino isoquinoline (#F3). A solution of #F2 (4.5 g, 51.7 mmol), 6-bromoisoquinoline-1-carbonitrile (6.0 g, 25.9 mmol), BINAP (3.2 g, 5.1 mmol), Pd$_2$(dba)$_3$ (2.3 g, 2.6 mmol) and potassium phosphate (11.0 g, 51.7 mmol) in anhydrous DMSO (35 mL) was heated at 80° C. for 2 h. The complete disappearance of the 6-bromoisoquinoline-1-carbonitrile was observed on TLC. The reaction mixture was cooled to room temperature, filtered through a Celite™ pad and the filtrate was diluted with water (100 mL). The mixture was extracted with EtOAc (100 mL×3). The combined organic layers were dried over anhydrous sodium sulfate and concentrated under reduced pressure to give crude material. The product was purified by chromatography on silica gel (100-200 mesh) using 10% MeOH in DCM as eluant to give racemic #F3 as yellow solid (1.5 g, 24.3%). R$_f$: 0.4 (50% EtOAc in petroleum ether). Chiral HPLC: two enantiomers (61.0%, 39.0%).

LCMS m/z=240.1 (M+H). $^1$H NMR (400 MHz, d$_6$-DMSO): δ 2.19-2.27 (m, 1H), 2.36-2.45 (m, 1H), 3.67-3.84 (m, 3H), 4.02-4.07 (m, 1H), 4.33-4.39 (m, 1H), 5.09 (t, J=4.8 Hz, 1H), 6.83 (d, J=1.6 Hz, 1H), 7.33 (dd, J=8.8 Hz, J=2.0 Hz, 1H), 7.78 (d, J=6.4 Hz, 1H), 7.97 (d, J=8.8 Hz, 1H), 8.36 (d, J=5.6 Hz, 1H).

Step 4.

Synthesis of aldehyde (#F4). A solution of #F3 (1.5 g, 6.3 mmol) in EtOAc (45 mL) was cooled to 0° C., and IBX (3.5 g, 12.6 mmol) was added portionwise over 10 minutes. The reaction mixture was stirred at 80° C. for 2 h. The reaction mixture was cooled to room temperature, filtered through a Celite™ pad, and the filtrate was washed with saturated aqueous NaHCO$_3$ solution (100 mL). The organic layer was separated, washed with water, brine, dried over anhydrous sodium sulfate and concentrated under reduced pressure to give #F4 (1.5 g, crude). This was used for the next step without any further purification. R$_f$: 0.5 (60% EtOAc in petroleum ether).

LCMS m/z=238.1 (M+H).

Step 5.

Synthesis of products (#24, #25). A solution of #F4 (1.5 g crude material as above, ~6.3 mmol) and cesium fluoride (5.1 g, 34.2 mmol) in THF (30 mL) was cooled to −78° C. Me$_3$SiCF$_3$ (1.5 mL, 9.5 mmol) was added to the mixture dropwise over 10 minutes. The reaction mixture was allowed to warm to room temperature and stirred for 16 h. The reaction mixture was diluted with water (100 mL) and extracted with EtOAc (100 mL×3). The combined organic layers were dried over anhydrous sodium sulfate and concentrated under reduced pressure to give crude material. This was purified by chromatography on silica gel (230-400) using 40% EtOAc in petroleum ether as eluant to provide an inseparable mixture of diastereoisomers (650 mg, 33% yield) which were further separated by chiral preparative HPLC to give target compounds #24 (92 mg, 5%) and #25 (44 mg, 2%) and two other diastereomers.

Final target #24. R$_f$: 0.3 (50% EtOAc in petroleum ether). Chiral HPLC purity: 98.2%.

Final target #25. R$_f$: 0.4 (50% EtOAc in petroleum ether). Chiral HPLC purity: 99.0%.

Example 24

6-{(2R)-2-[(1R)-2,2,2-trifluoro-1-hydroxyethyl]azetidin-1-yl}isoquinoline-1-carbonitrile (#2) (Stereochemistry Arbitrarily Assigned)

LCMS m/z=308.0 (M+1). $^1$H NMR (300 MHz, CDCl$_3$): δ 2.39-2.50 (m, 1H), 2.91-2.97 (m, 1H), 3.83 (q, J=7.8 Hz, 1H), 4.27-4.34 (m, 1H), 4.52-4.66 (m, 1H), 5.29 (br s, 1H, disappeared in D$_2$O exchange), 6.16 (d, J=2.1 Hz, 1H), 6.88 (dd, J=6.3 Hz, J=3.0 Hz, 1H), 7.33 (d, J=5.7 Hz, 1H), 7.81 (d, J=9.0 Hz, 1H), 8.17 (d, J=5.7 Hz, 1H).

Example 25

6-{(2S)-2-[(1S)-2,2,2-trifluoro-1-hydroxyethyl]azetidin-1-yl}isoquinoline-1-carbonitrile (Stereochemistry Arbitrarily Assigned)

LCMS m/z=308.0 (M+1). $^1$H NMR (300 MHz, CDCl$_3$): δ 2.32-2.50 (m, 1H), 2.85-2.30 (m, 1H), 3.87-3.95 (m, 1H), 4.27-4.32 (m, 1H), 4.54-4.67 (m, 2H), 5.29 (br s, 1H, disappeared in D20 exchange), 6.19 (d, J=2.1 Hz, 1H), 6.89 (dd, J=9.0 Hz, J=2.1 Hz, 1H), 7.35 (d, J=5.7 Hz, 1H), 7.83 (d, J=9.0 Hz, 1H), 8.19 (d, J=6.3 Hz, 1H).

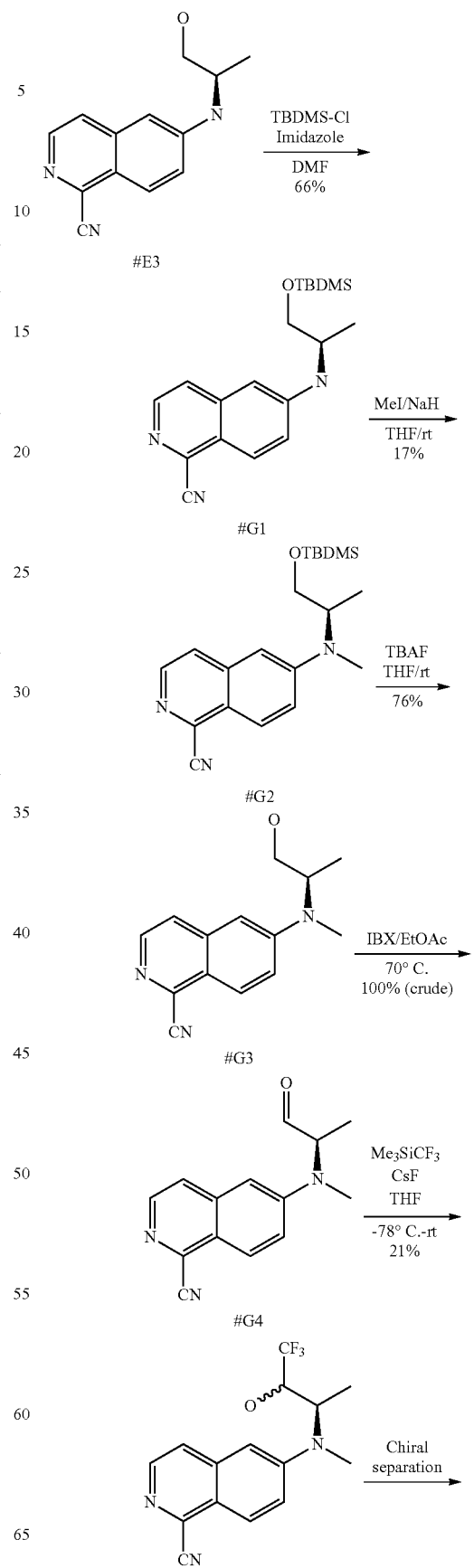

-continued

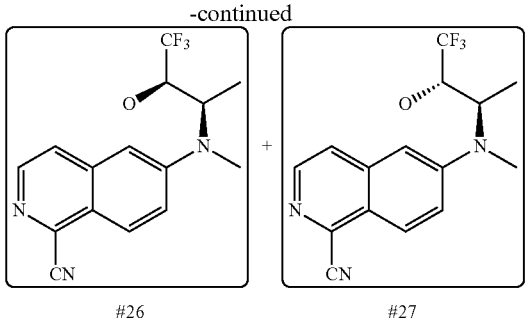

Step 1.

Synthesis of t-butyldimethylsilyl alcohol (#G1). t-Butyldimethylsilyl chloride (0.9 g, 6.2 mmol) was added to a solution of #E3 (0.7 g, 3.1 mmol) and imidazole (0.6 g, 9.2 mmol) in DMF (10 mL) at 0° C. The reaction mixture was stirred at room temperature for 12 h. After consumption of the starting material, the reaction mixture was diluted with water (50 mL) and extracted with EtOAc (50 mL×3). The combined organic layers were dried and concentrated under reduced pressure to give crude #G1. The product was purified by chromatography on silica gel (100-200 mesh) using 20% EtOAc in petroleum ether as eluant to give #G1 as brown solid (0.7 g, 66.5%). $R_f$: 0.5 (30% EtOAc in petroleum ether).

$^1$H NMR (400 MHz, CDCl$_3$): δ 0.07 (s, 6H), 0.91 (s, 9H), 1.29 (d, J=6.0 Hz, 3H), 3.65-3.75 (m, 3H), 4.59 (d, J=6.8 Hz, 1H), 6.70 (d, J=2.4 Hz, 1H), 7.05 (dd, J=1.6 Hz, 8.8 Hz, 1H), 7.53 (d, J=6.0 Hz, 1H), 8.04 (d, J=8.8 Hz, 1H), 8.36 (d, J=6.0 Hz, 1H).

Step 2.

Synthesis of methyl t-butyldimethylsilyl alcohol (#G2). #G1 (0.70 g, 2.1 mmol) was added dropwise to a solution of NaH (0.20 g, 8.2 mmol) in THF (15 mL) at 0° C. The reaction mixture was stirred for 15 minutes at room temperature then MeI (0.40 mL, 6.2 mmol) was added. The reaction mixture was stirred for 2 h at room temperature and then at 50° C. for 12 h. The reaction mixture was cooled, quenched with ice-cold water (10 mL) and extracted with EtOAc (25 mL×2). All the organic layers were combined, dried over anhydrous Na$_2$SO$_4$ and concentrated under reduced pressure to give crude #G2 as oily solid. The product was purified by chromatography on silica gel (100-200 mesh) using 20% EtOAc in petroleum ether as eluant to give #G2 as yellow solid (0.13 g, 17.3%). $R_f$: 0.6 (30% EtOAc in petroleum ether).

LCMS m/z=356.1 (M+H). $^1$H NMR (400 MHz, CDCl$_3$): δ 0.002 (s, 6H), 0.78 (s, 9H), 1.26 (d, J=6.8 Hz, 3H), 2.94 (s, 3H), 3.65-3.75 (m, 2H), 4.24-4.29 (m, 1H), 6.82 (d, J=2.0 Hz, 1H), 7.45 (dd, J=2.8 Hz, 9.6 Hz, 1H), 7.54 (d, J=5.6 Hz, 1H), 8.08 (d, J=9.2 Hz, 1H), 8.35 (d, J=6.0 Hz, 1H).

Step 3.

Synthesis of N-methyl amino alcohol (#G3). A solution of 1M TBAF (2 mL in THF, 2.1 mmol) was added to a solution of #G2 (0.25 g, 1.0 mmol) in THF (10 mL) at room temperature. The reaction mixture was diluted with EtOAc (50 mL), and the organic layer was washed with water and brine. The combined organic layer was dried over anhydrous Na$_2$SO$_4$, filtered and concentrated under reduced pressure to give crude #G3. This was purified by chromatography on silica gel (100-200 mesh) using 100% EtOAc as eluant to give #G3 as a yellow oily liquid (0.13 g, 75.4%). $R_f$: 0.3 (40% EtOAc in petroleum ether).

LCMS m/z=242.0 (M+H). $^1$H NMR (400 MHz, CDCl$_3$): δ 3.05 (s, 3H), 3.68-3.81 (m, 3H), 3.36-3.63 (m, 1H), 6.93 (d, J=2.4 Hz, 1H), 7.50 (dd, J=2.4 Hz, 9.2 Hz, 1H), 7.58 (d, J=5.6 Hz, 1H), 8.12 (d, J=1.2 Hz, 1H), 8.38 (q, 1H).

Step 4.

Synthesis of N-methyl amino aldehyde (#G4). A solution of #G3 (0.13 g, 0.54 mmol) in EtOAc (5 mL) was cooled to 0° C., and IBX (0.38 g, 1.3 mmol) was added portionwise. The reaction mixture was stirred at 70° C. for 2 h, and then it was cooled to room temperature, filtered through a Celite™ pad and washed with EtOAc (25 mL). The filtrate was washed with aqueous saturated NaHCO$_3$ solution (10 mL), water and brine. The organic layer was separated, dried over anhydrous sodium sulfate and concentrated under reduced pressure to give #G4 (0.13 g, crude). The product was used for the next step without further purification. $R_f$: 0.5 (60% EtOAc in petroleum ether).

LCMS m/z=240.0 (M+H).

Step 5.

Synthesis of products (#26, #27). A solution of #G4 (0.13 g, crude, 0.54 mmol), cesium fluoride (0.40 g, 2.7 mmol) in THF (5 mL) was cooled to −78° C., and Me$_3$SiCF$_3$ (0.12 mL, 0.80 mmol) was added dropwise over 10 minutes. The reaction mixture was allowed to warm and stirred at room temperature for 16 h. Water (2 mL) was added, and the mixture was diluted with EtOAc (100 mL), washed with water, brine, dried over anhydrous sodium sulfate and concentrated under reduced pressure to get crude mixture of products. The isomers were separated by chiral preparative HPLC to give compounds #26 (23 mg, 13.6%) and #27 (11 mg, 6.5%). Total yield (34 mg, 21%).

26. $R_f$: 0.6 (50% EtOAc in petroleum ether). Chiral HPLC purity: 97.9%.

27. $R_f$: 0.6 (50% EtOAc in petroleum ether). Chiral HPLC purity: 98.5%.

Example 26

6-{methyl[(2R,3R)-4,4,4-trifluoro-3-hydroxybutan-2-yl]amino}isoquinoline-1-carbonitrile (Stereochemistry Arbitrarily Assigned)

LCMS m/z=310.1 (M+1). $^1$H NMR (300 MHz, d$_6$-DMSO): δ 1.32 (d, J=6.3 Hz, 3H), 2.94 (s, 3H), 4.20-4.26 (m, 1H), 4.40-4.45 (m, 1H), 6.67 (d, J=6.9 Hz, 1H), 7.10 (s, 1H), 7.64 (d, J=9.9 Hz, 1H), 7.85 (d, J=5.7 Hz, 1H), 8.02 (d, J=9.0 Hz, 1H), 8.38 (d, J=5.4 Hz, 1H).

Example 27

6-{methyl[(2R,3S)-4,4,4-trifluoro-3-hydroxybutan-2-yl]amino}isoquinoline-1-carbonitrile (Stereochemistry Arbitrarily Assigned)

LCMS m/z=310.1 (M+1). $^1$H NMR (300 MHz, d$_6$-DMSO): δ 1.30 (d, J=6.3 Hz, 3H), 2.97 (s, 3H), 4.22-4.25 (m, 1H), 4.49-4.53 (m, 1H), 6.55 (d, J=6.3 Hz, 1H), 7.07 (s, 1H), 7.65 (d, J=7.5 Hz, 1H), 7.83 (d, J=7.6 Hz, 1H), 8.04 (d, J=9.0 Hz, 1H), 8.37 (d, J=9.2 Hz, 1H).

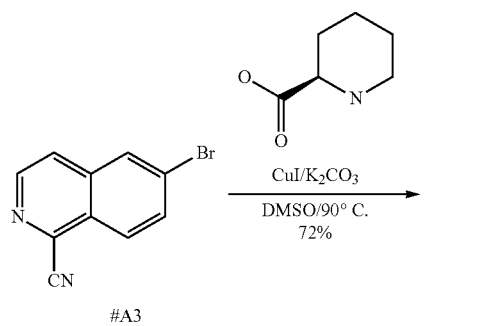

A3

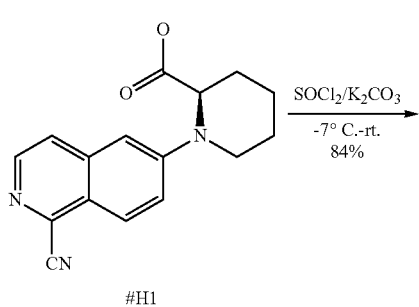

H1

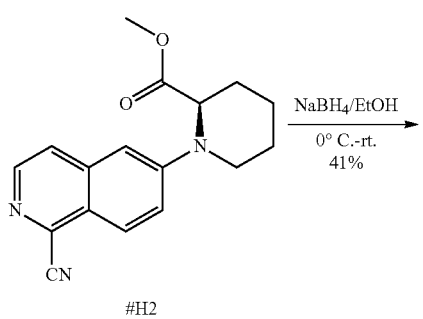

H2

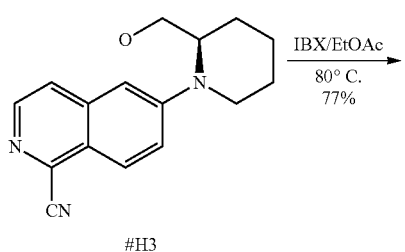

H3

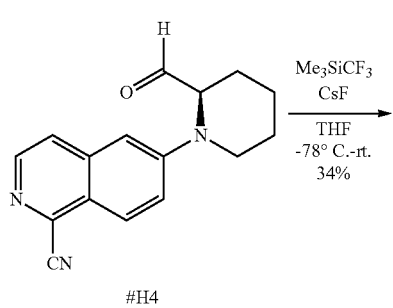

H4

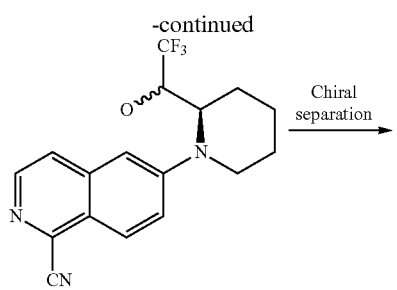

H5

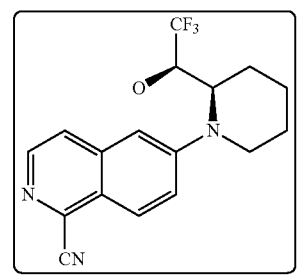

26

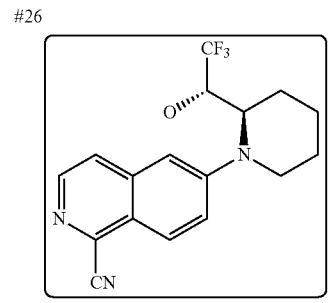

29

Step 1.

Synthesis of product (#H1). A mixture of 6-bromoisoquinoline-1-carbonitrile #A3 (4.5 g, 19.3 mmol), (R)-piperidine carboxylic acid (2.7 g, 20.9 mmol), CuI (3.2 g, 1.9 mmol) and $K_2CO_3$ (5.4 g, 39.1 mmol) in DMSO (15 mL) was heated at 90° C. for 5 h. The consumption of 6-bromoisoquinoline-1-carbonitrile was observed on TLC. The reaction mixture was cooled to room temperature, filtered through a Celite™ pad, rinsed with EtOAc and the filtrate was diluted with water (200 mL). The filtrate was washed with EtOAc (100 mL×3). The combined organic layers were dried over anhydrous sodium sulfate, filtered and concentrated under reduced pressure to give crude material. This was triturated with pentane to give #H1 as a pure yellow solid (4 g, 72%). $R_f$: 0.1 (EtOAc).

LCMS m/z=281.9 (M+H). $^1$H NMR (300 MHz, $d_6$-DMSO): δ 1.56-1.89 (m, 3H), 2.26 (d, J=12.6 Hz, 1H), 2.71 (dd, J=15.3 Hz, 17.4 Hz, 1H), 3.16 (td, J=12.6 Hz, 3.6 Hz, 1H), 3.90 (d, J=11.7 Hz, 1H), 4.99 (d, J=3.3 Hz, 1H), 7.26 (d, J=2.7 Hz, 1H), 7.75 (dd, J=9.2 Hz, J=2.4 Hz, 1H), 7.86 (d, J=5.4 Hz, 1H), 7.98 (d, J=9.0 Hz, 1H), 8.41 (d, J=6.3 Hz, 1H), 12.60 (br s, 1H).

Step 2.

Synthesis of methyl ester product (#H2). Thionyl chloride (2.0 mL, 28.6 mmol) was added to a solution of #H1 (4.0 g, 14.3 mmol) in methanol at 0° C. The reaction mixture was stirred at room temperature for 16 h. After the depletion of the starting material, the reaction was cooled to 0° C. and treated with solid $NaHCO_3$. The mixture was filtered to remove solids, and the filtrate was concentrated under reduced pressure. The residue was diluted with EtOAc, washed with water and brine. The organic layer was dried over anhydrous Na$_2$SO$_4$ and concentrated under reduced pressure to give crude material. This was purified by column chromatography on silica gel (100-200) using 20% EtOAc in petroleum ether as eluent to give #H2 (3.5 g, 84%). R$_f$: 0.6 (50% EtOAc in petroleum ether).

LCMS m/z=296.0 (M+H). $^1$H NMR (400 MHz, d$_6$-DMSO): δ 1.56-1.61 (m, 1H), 1.71-1.89 (m, 3H), 2.24 (d, J=12 Hz, 1H), 2.73 (d, J=15.2 Hz, 1H), 2.87 (d, J=15.2 Hz, 1H), 3.57 (s, 3H), 3.91 (d, J=11.2 Hz, 1H), 5.14 (d, J=3.6 Hz, 1H), 7.29 (d, J=2.4 Hz, 1H), 7.76 (dd, J=2.8 Hz, 9.6 Hz, 1H), 7.87 (d, J=5.6 Hz, 1H), 7.99 (d, J=9.6 Hz, 1H), 8.43 (d, J=6.0 Hz, 1H).

Step 3.

Synthesis of alcohol (#H3). A solution of #D2 (3.5 g, 11.9 mmol) in ethanol (35 mL) was cooled to 0° C., and NaBH$_4$ (0.90 g, 23.7 mmol) was added portionwise over 30 minutes. The reaction mixture was stirred at room temperature for 16 h. Water (10 mL) was added to the reaction mixture at 0° C., and ethanol was removed under reduced pressure. The resulting crude material was diluted with EtOAc (300 mL), and washed with water. The organic layer was dried over Na$_2$SO$_4$ and concentrated under reduced pressure to give crude material. This was purified by chromatography on silica gel (100-200) using 30% EtOAc in petroleum ether as eluent to give #H3 (1.3 g, 41%). R$_f$: 0.5 (50% EtOAc in petroleum ether).

LCMS m/z=268.0 (M+H). $^1$H NMR (300 MHz, d$_6$-DMSO): δ 1.51-1.64 (m, 4H), 1.77 (d, J=10.5, 1H), 1.94 (d, J=5.7 Hz, 1H), 3.04-3.12 (m, 1H), 3.48-3.66 (m, 2H), 3.81 (d, J=13.2 Hz, 1H), 4.22 (br s, 1H), 4.74 (t, 1H), 7.19 (s, 1H), 7.73 (dd, J=2.1 Hz, 9.9 Hz, 1H), 7.79 (d, J=5.7 Hz, 1H), 7.94 (d, J=9.9 Hz, 1H) 8.36 (d, J=5.4 Hz, 1H).

Step 4.

Synthesis of aldehyde (#H4). A solution of #H3 (1.3 g, 4.9 mmol) in EtOAc (10 mL) was cooled to 0° C., and IBX (2.7 g, 9.7 mmol) was added portionwise over 10 minutes. The reaction mixture was stirred at 80° C. for 2 h, cooled to room temperature, and filtered through Celite™ pad. The filtrate was washed with saturated aqueous NaHCO$_3$ solution (30 mL). The organic layer was separated, washed with water, brine, dried over anhydrous Na$_2$SO$_4$ and concentrated under reduced pressure to provide #H4 (1 g, crude). This material was used for the next step without any further purification. R$_f$: 0.6 (50% EtOAc in petroleum ether).

$^1$H NMR (300 MHz, d$_6$-DMSO): δ 1.48-1.52 (m, 1H), 1.53-1.74 (m, 3H), 3.01-3.20 (m, 1H), 3.97-4.12 (m, 1H), 5.07 (d, J=4.8 Hz, 1H), 7.32 (s, 1H), 7.75 (d, J=9.6 Hz, 1H), 7.84 (d, J=5.4 Hz, 1H), 7.99 (d, J=9.0 Hz, 1H), 8.42 (d, J=5.4 Hz, 1H), 9.67 (s, 1H).

Step 5.

Synthesis of products (#28, #29). A solution of #D4 (1.0 g, crude, 3.8 mmol), CsF (3.1 g, 20.5 mmol) in THF (10 mL) was cooled to −78° C. Me$_3$SiCF$_3$ (0.47 mL, 6.0 mmol) was added dropwise over 10 minutes. The reaction mixture was stirred at room temperature for 16 hour. Water (20 mL) was added at 0° C. The mixture was washed with EtOAc (100 mL×3). The combined organic layer was dried over anhydrous sodium sulfate and concentrated under reduced pressure to give crude material. It was purified by chromatography on silica gel (230-400 mesh) using 20% EtOAc in petroleum ether as eluent to give a mixture of final compounds (500 mg, 94% LCMS purity). This was again purified by chiral preparative HPLC to get target compounds #28 (303 mg, 24%) and #29 (104 mg, 8%). Total yield (407 mg, 32%). Final target GCSW#193966:

28. R$_f$: 0.5 (40% EtOAc in petroleum ether). Chiral HPLC purity: (99.1%).

29. R$_f$: 0.5 (40% EtOAc in petroleum ether). Chiral HPLC purity: (98.7%)

Example 28

6-{(2R)-2-[(1R)-2,2,2-trifluoro-1-hydroxyethyl]piperidin-1-yl}isoquinoline-1-carbonitrile (Stereochemistry Arbitrarily Assigned)

LCMS m/z=336.1 (M+1). $^1$H NMR (300 MHz, d$_6$-DMSO): δ 1.61-1.77 (m, 6H), 3.24 (d, J=11.1 Hz, 1H), 3.90 (d, J=13.5 Hz, 1H), 4.43 (d, J=9.0 Hz, 1H), 4.56 (m, 1H), 6.37 (d, J=6.3 Hz, 1H), 7.21 (d, J=2.1 Hz, 1H), 7.70 (dd, J=2.4 Hz, 9.2 Hz, 1H), 7.81 (d, J=5.7 Hz, 1H), 7.95 (d, J=9.0 Hz, 1H), 8.36 (d, J=5.4 Hz, 1H).

Example 29

6-{(2R)-2-[(1S)-2,2,2-trifluoro-1-hydroxyethyl]piperidin-1-yl}isoquinoline-1-carbonitrile (Stereochemistry Arbitrarily Assigned)

LCMS m/z=336.1 (M+1). $^1$H NMR (300 MHz, d$_6$-DMSO): δ 1.49-1.68 (m, 4H), 1.76-1.85 (m, 1H), 2.08 (d, J=13.5 Hz, 1H), 3.25-3.29 (m, 1H), 3.92 (d, J=13.8 Hz, 1H), 4.36 (br s, 1H), 4.55-4.60 (m, 1H), 6.64 (d, J=7.2 Hz, 1H), 7.24 (d, J=2.1 Hz, 1H), 7.65 (d, J=2.1 Hz, 9.6 Hz, 1H), 7.83 (d, J=5.4 Hz, 1H), 7.99 (d, J=9.6 Hz, 1H), 8.38 (d, J=5.4 Hz, 1H).

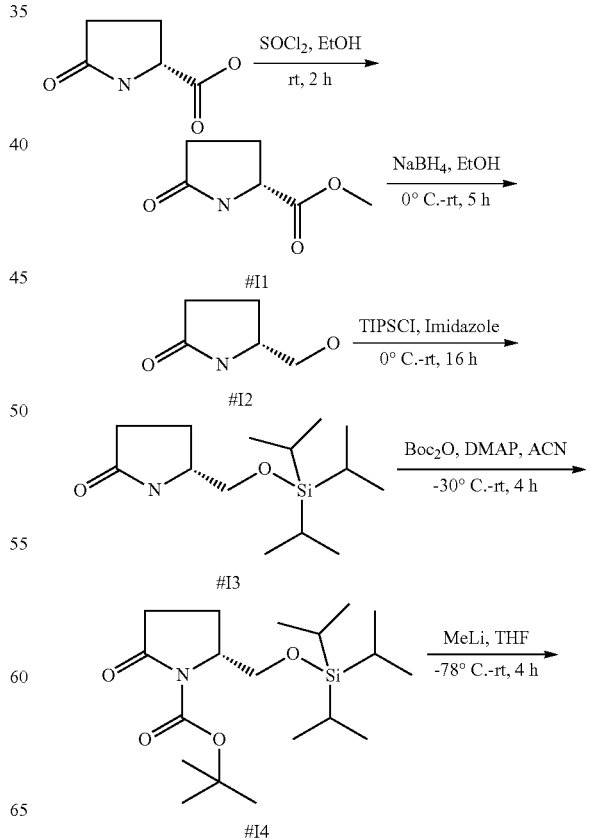

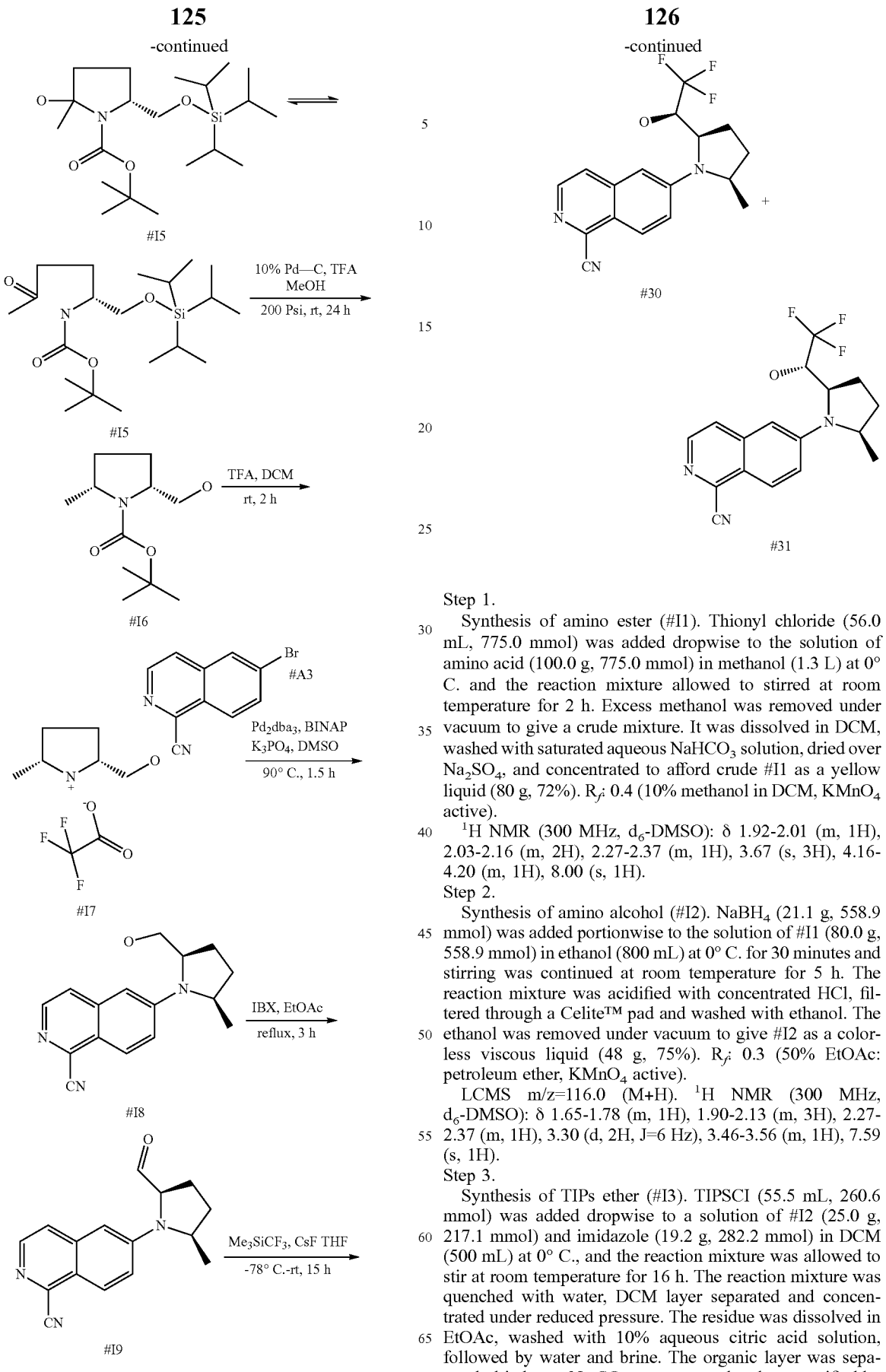

Step 1.

Synthesis of amino ester (#I1). Thionyl chloride (56.0 mL, 775.0 mmol) was added dropwise to the solution of amino acid (100.0 g, 775.0 mmol) in methanol (1.3 L) at 0° C. and the reaction mixture allowed to stirred at room temperature for 2 h. Excess methanol was removed under vacuum to give a crude mixture. It was dissolved in DCM, washed with saturated aqueous NaHCO₃ solution, dried over Na₂SO₄, and concentrated to afford crude #I1 as a yellow liquid (80 g, 72%). R$_f$: 0.4 (10% methanol in DCM, KMnO₄ active).

$^1$H NMR (300 MHz, d$_6$-DMSO): δ 1.92-2.01 (m, 1H), 2.03-2.16 (m, 2H), 2.27-2.37 (m, 1H), 3.67 (s, 3H), 4.16-4.20 (m, 1H), 8.00 (s, 1H).

Step 2.

Synthesis of amino alcohol (#I2). NaBH₄ (21.1 g, 558.9 mmol) was added portionwise to the solution of #I1 (80.0 g, 558.9 mmol) in ethanol (800 mL) at 0° C. for 30 minutes and stirring was continued at room temperature for 5 h. The reaction mixture was acidified with concentrated HCl, filtered through a Celite™ pad and washed with ethanol. The ethanol was removed under vacuum to give #I2 as a colorless viscous liquid (48 g, 75%). R$_f$: 0.3 (50% EtOAc: petroleum ether, KMnO₄ active).

LCMS m/z=116.0 (M+H). $^1$H NMR (300 MHz, d$_6$-DMSO): δ 1.65-1.78 (m, 1H), 1.90-2.13 (m, 3H), 2.27-2.37 (m, 1H), 3.30 (d, 2H, J=6 Hz), 3.46-3.56 (m, 1H), 7.59 (s, 1H).

Step 3.

Synthesis of TIPs ether (#I3). TIPSCI (55.5 mL, 260.6 mmol) was added dropwise to a solution of #I2 (25.0 g, 217.1 mmol) and imidazole (19.2 g, 282.2 mmol) in DCM (500 mL) at 0° C., and the reaction mixture was allowed to stir at room temperature for 16 h. The reaction mixture was quenched with water, DCM layer separated and concentrated under reduced pressure. The residue was dissolved in EtOAc, washed with 10% aqueous citric acid solution, followed by water and brine. The organic layer was separated, dried over Na₂SO₄, concentrated and was purified by chromatography on silica gel (100-200 mesh) using 20-40% EtOAc and petroleum ether to afford #I3 as a pale yellow liquid (20 g, 37%). $R_f$: 0.4 (50% EtOAc/petroleum ether, KMnO$_4$ active)

$^1$H NMR (300 MHz, d$_6$-DMSO): δ 1.00-1.05 (m, 21H), 1.77-1.84 (m, 1H), 2.03-2.17 (m, 3H), 3.31-3.62 (m, 3H), 7.50 (s, 1H).

Step 4.

Synthesis of N-Boc TIPs ether (#I4). (Boc)$_2$O (16.80 mL, 73.67 mmol) was added to a stirred solution of #I3 (20.0 g, 73.7 mmol) and DMAP (0.90 g, 7.4 mmol) in acetonitrile (200 mL) at −30° C. and the reaction mixture was stirred for 30 minutes and then stirring was continued at room temperature for 16 h. The reaction mixture was concentrated under reduced pressure to give crude material, which was purified by column chromatography on silica gel (100-200 mesh) using 10% EtOAc in petroleum ether to afford #I4 as a light brown liquid (18 g, 66%). $R_f$: 0.5 (20% EtOAc in petroleum ether, KMnO$_4$ active).

$^1$H NMR (400 MHz, d$_6$-DMSO): δ 1.00-1.05 (m, 21H), 1.43 (s, 9H), 1.84-1.90 (m, 1H), 2.08-2.16 (m, 1H), 2.24-2.32 (m, 1H), 2.53-2.58 (m, 1H), 3.73 (dd, 1H, J=2.0, 10.0 Hz), 4.00 (dd, 1H, J=3.2, 10.0 Hz), 4.13 (d, 1H, J=8.8 Hz).

Step 5.

Methyl addition adduct N-Boc TIPs protected alcohol (#I5). MeLi in DCM (20.0 mL, 2M, 60.0 mmol) was added dropwise to a solution of #I4 (20.0 g, 53.8 mmol) in dry THF (100 mL) at −78° C. and stirring was continued for 4 h. The reaction mixture was quenched with NH$_4$Cl solution, extracted with EtOAc, dried over Na$_2$SO$_4$, concentrated to give #I5 as a light brown liquid (20 g, 95%) which was used for the next step without further purification. $R_f$: 0.6 (30% EtOAc/petroleum ether, KMnO$_4$ active).

$^1$H NMR (300 MHz, d$_6$-DMSO): δ 0.97-1.02 (m, 21H), 1.17 (s, 9H), 1.73-1.75 (m, 2H), 2.05 (s, 3H), 2.40-2.45 (m, 2H), 3.45-3.55 (m, 3H), 6.52-6.54 (m, 1H).

Step 6.

Dehydroxylation product of N-Boc alcohol (#I6). A mixture of #I5 (7.0 g, 18.1 mmol) and 10% Pd/C (1.8 g) in 10% trifluoroacetic acid/MeOH (80 mL) was shaken in a Parr apparatus under hydrogen atmosphere at 200 psi at room temperature for 24 h. The reaction mixture was filtered through a Celite™ pad, washed with EtOAc and concentrated under reduced pressure to give crude mixture. This was purified by chromatography on silica gel (100-200 mesh) using 10-30% EtOAc in petroleum ether to give #I6 as a yellow liquid (2.3 g, 63%). $R_f$: 0.4 (30% EtOAc/petroleum ether, KMnO$_4$ active).

$^1$H NMR (300 MHz, d$_6$-DMSO) δ 1.11 (d, J=6 Hz, 3H), 1.39 (s, 9H), 1.45-1.51 (m, 1H), 1.76-1.98 (m, 3H), 3.18-3.34 (m, 1H), 3.46-3.49 (m, 2H), 3.65-3.74 (m, 2H).

Step 7.

Synthesis of amino alcohol trifluoroacetic acid salt (#I7). Trifluoroacetic acid (40 mL) was added dropwise to a solution of #I6 (6.5 g, 30.2 mmol) in DCM (40 mL) at room temperature and the reaction mixture was stirred for 2 h. The solvents were evaporated under reduced pressure to get residue mixture which was co-distilled with methanol to afford #I7 as a pale yellow liquid (6.5 g, 94%). $R_f$: 0.2 (20% MeOH in DCM, KMnO$_4$ active).

LCMS m/z=116.1 (M+H) (free base). $^1$H NMR (300 MHz, d$_6$-DMSO): δ 1.28 (d, 3H, J=6.3 Hz), 1.48-1.68 (m, 2H), 1.92-2.11 (m, 2H), 3.49-3.64 (m, 4H), 8.15 (br s, 1H), 9.3 (br s, 1H).

Step 8.

Synthesis of coupling product (#I8). #I7 (3.4 g, 29.9 mmol) was added to degassed DMSO. K$_3$PO$_4$ (7.3 g, 34.5 mmol) was added to the solution and stirring was continued for 5 minutes, followed by the addition of Pd$_2$(dba$_3$) (0.27 g, 0.30 mmol), BINAP (0.55 g, 0.88 mmol) and 6-bromoisoquinoline-1-carbonitrile #A3 (2.3 g, 9.9 mmol) under an argon atmosphere. The resulting reaction mixture was heated at 90° C. under argon atmosphere for 1.5 h. The reaction mixture was cooled to room temperature, diluted with EtOAc, and filtered through a Celite™ pad. The filtrate was washed with water followed by brine. The organic layer was dried over Na$_2$SO$_4$, evaporated under reduced pressure to get the crude mixture which was chromatographed on silica gel (100-200 mesh) using 20-80% EtOAc in petroleum ether as eluent to give #I8 as a yellow solid (3.8 g, 48%). $R_f$: 0.2 (50% EtOAc in petroleum ether, UV active)

LCMS m/z=268.4 (M+H). $^1$H NMR (400 MHz, d$_6$-DMSO): δ 1.27 (d, J=6 Hz, 3H), 1.72-1.79 (m, 1H), 1.91-2.03 (m, 2H), 2.11-2.19 (m, 1H), 3.38-3.44 (m, 1H), 3.58-3.63 (m, 1H), 3.93-4.03 (m, 2H), 4.94 (t, J=5.6 Hz, 1H), 6.94 (d, J=2 Hz, 1H), 7.47 (dd, J=2.4, 9.2 Hz, 1H), 7.80 (d, J=5.6 Hz, 1H), 7.94 (d, J=9.6 Hz, 1H), 8.33 (d, J=6.4 Hz, 1H).

Step 9.

Synthesis of aldehyde (#I9). Mixture of #I8 (3.8 g, 14.0 mmol) and IBX (7.8 g, 28.0 mmol) in EtOAc (150 mL) was refluxed for 3 h. The reaction mixture was cooled to room temperature, filtered through a Celite™ pad and washed with EtOAc. The organic layer was washed with saturated aqueous NaHCO$_3$ solution, dried over Na$_2$SO$_4$ and evaporated in vacuo to obtain crude mixture. This was triturated with pentane to afford #I9 as light yellow solid (3.1 g, 82%) which was used for the next step without further purification. $R_f$: 0.4 (50% EtOAc/petroleum ether, UV active).

LCMS m/z=266.2 (M+H). $^1$H NMR (300 MHz, d$_6$-DMSO): δ 1.28 (d, J=6.3 Hz, 3H), 1.66-1.68 (m, 1H), 2.16-2.26 (m, 3H), 4.20-4.22 (m, 1H), 4.52-4.55 (m, 1H), 6.89 (d, J=2.1 Hz, 1H), 7.35 (dd, J=2.7, 9.6 Hz, 1H), 7.82 (d, J=5.7 Hz, 1H), 8.00 (d J=9 Hz, 1H), 8.37 (d, J=5.7 Hz, 1H), 9.59 (s, 1H).

Step 10.

Synthesis of products (#30, #31). Me$_3$SiCF$_3$ (2.30 g, 16.35 mmol) was added to a solution of #I9 (3.1 g, 16.4 mmol) and CsF (16.7 g, 109.8 mmol) in THF (100 mL) at −78° C. and the reaction mixture was allowed to warm and stirred at room temperature for 15 h. Ethanol (25 mL) was added to the reaction mixture and stirring was continued at room temperature for 3 h. The reaction mixture was poured into water, extracted with EtOAc, dried over Na$_2$SO$_4$, concentrated under reduced pressure to give a crude product mixture (3.8 g) which was purified by preparative HPLC to afford diastereomers #30 (1.1 g) and #31 (1.1 g). $R_f$: 0.3 and 0.4 in 30% EtOAc in petroleum ether simultaneously. The absolute stereochemistry was established using crystallography.

Example 30

6-{(2R,5R)-2-methyl-5-[(1R)-2,2,2-trifluoro-1-hydroxyethyl]pyrrolidin-1-yl}isoquinoline-1-carbonitrile LCMS m/z=336.3 (M+1). $^1$H NMR (400 MHz, d$_6$-DMSO): δ 1.32 (d, J=6.3 Hz, 3H), 1.75-1.83 (m, 1H), 1.91-1.96 (m, 1H), 1.97-2.08 (m, 1H), 2.34-2.39 (m, 1H), 4.05-4.10 (m, 1H), 4.22-4.27 (m, 1H), 4.33-4.38 (m, 1H), 6.62 (d, J=6.6 Hz, 1H), 6.86 (d, J=2.1 Hz, 1H), 7.42 (dd, J=2.7, 9.6 Hz, 1H), 7.87 (d, J=5.4 Hz, 1H), 8.05 (d, J=9.3 Hz, 1H), 8.37 (d, J=5.7 Hz, 1H). Chiral HPLC purity: 97.9%.

Example 31

6-{(2R,5R)-2-[(1R)-1-hydroxyethyl]-5-methylpyrrolidin-1-yl}isoquinoline-1-carbonitrile (Stereochemistry Arbitrarily Assigned)

LCMS m/z=336.3 (M+1). $^1$H NMR (400 MHz, d$_6$-DMSO): δ 1.35 (d, J=6.3 Hz, 3H), 1.79-1.88 (m, 1H), 1.93-1.98 (m, 2H), 2.34-2.37 (m, 1H), 3.96-4.01 (m, 1H), 4.03-4.13 (m, 1H), 4.22-4.27 (m, 1H), 6.64 (d, J=6.6 Hz, 1H), 7.03 (d, J=2.1 Hz, 1H), 7.55 (dd, J=2.3, 9.3 Hz, 1H), 7.83 (d, J=5.7 Hz, 1H), 7.97 (d, J=9 Hz, 1H), 8.35 (d, J=6 Hz, 1H). Chiral HPLC purity: 99.2%.

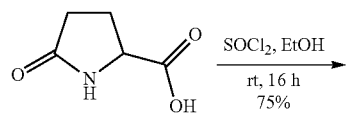

SOCl$_2$, EtOH
rt, 16 h
75%

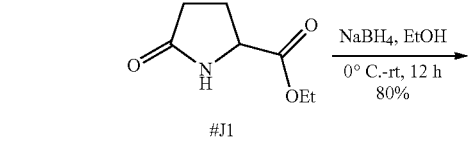
J1

NaBH$_4$, EtOH
0° C.-rt, 12 h
80%

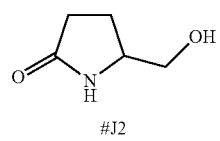
J2

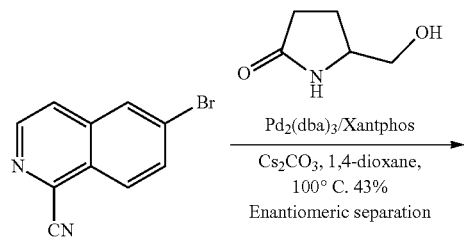

Pd$_2$(dba)$_3$/Xantphos
Cs$_2$CO$_3$, 1,4-dioxane,
100° C. 43%
Enantiomeric separation

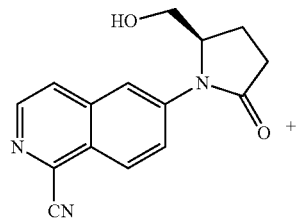
J3

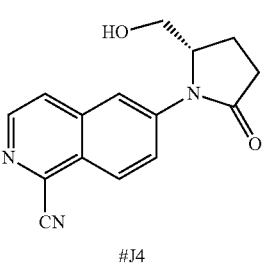
J4

-continued

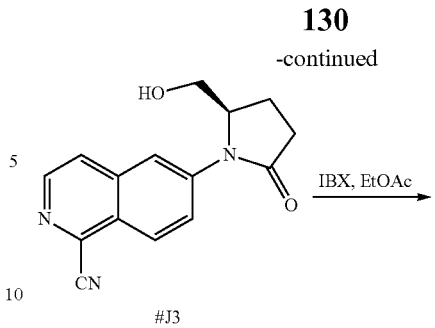
J3

IBX, EtOAc

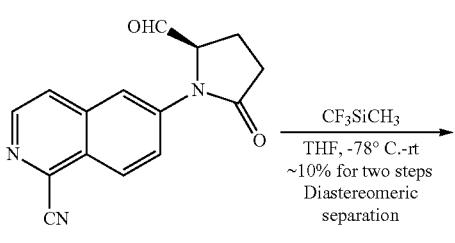
J5

CF$_3$SiCH$_3$
THF, -78° C.-rt
~10% for two steps
Diastereomeric separation

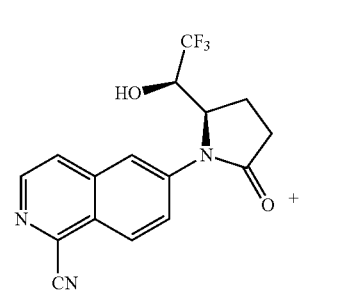
+

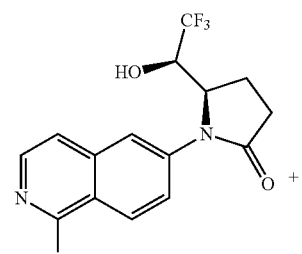
32

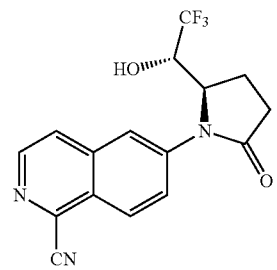
J4

IBX, EtOAc

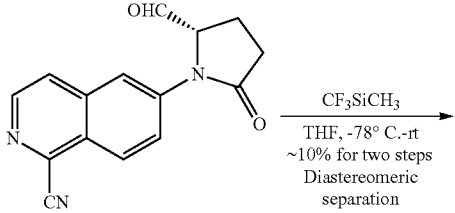
J6

CF$_3$SiCH$_3$
THF, -78° C.-rt
~10% for two steps
Diastereomeric separation

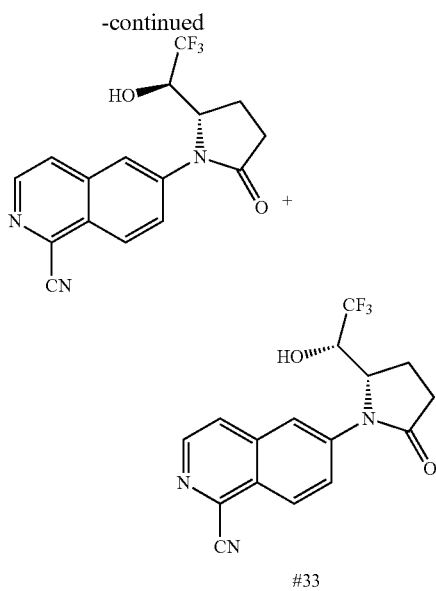

33

Step 1.

Synthesis of ester (#J1). Thionyl chloride (5.6 mL, 77.0 mmol) was slowly added to a solution of acid (10.0 g, 77.0 mmol) in ethanol (130 mL) at 0° C. The reaction mixture was allowed to stir at room temperature overnight. The mixture was concentrated in vacuo to remove ethanol. The crude residue was diluted with DCM washed with saturated aqueous NaHCO₃ solution, water and brine. The organic layer was dried over Na₂SO₄ and concentrated to give #J1 (9 g, 75%) as yellow liquid. $R_f$: 0.3 EtOAc (KMnO₄ active).

GCMS m/z=157.1 (M).

Step 2.

Synthesis of lactam carbinol (#J2). NaBH₄ (1.2 g, 30.0 mmol) was added slowly to a solution of #J1 (8.0 g, 50.0 mmol) in ethanol (60 mL) at 0° C. portionwise. The reaction mixture was allowed to stir at room temperature for 6 h. The mixture was quenched with concentrated HCl and the precipitated solid was filtered and purified by column chromatography on 100-200 silica gel with 8% methanol in DCM as eluent to give pure #J2 (4.7 g, 80%) as pale yellow thick liquid. $R_f$: 0.1 (20% MeOH in DCM, KMnO₄ active).

¹H NMR (400 MHz, d₆-DMSO) δ 1.65-1.78 (m, 1H); 1.96-2.15 (m, 3H); 3.25 (m, 2H); 3.46 (m, 1H); 3.92 (br. s., 1H); 7.58 (br. s., 1H).

Step 3.

Synthesis of carbinol products (#J3, #J4). Pd₂(dba)₃ (55.0 mg, 0.06 mmol), xanthphos (110.0 mg, 0.19 mmol) and Cs₂CO₃ (2.0 g, 6.4 mmol) were added to a mixture of #J2 (0.50 g, 2.1 mmol) and 6-bromoisoquinoline-1-carbonitrile (0.50 g, 4.3 mmol) in 1,4-dioxane (10 mL) under nitrogen atmosphere. The reaction mixture was heated to 110° C. for 2.5 h. After the consumption of the starting material, the mixture was diluted with EtOAc, washed with water and brine. The organic layer was dried over Na₂SO₄ and concentrated in vacuo to get crude material. This was purified by column chromatography using 100-200 silica gel and eluted with 70% EtOAc in petroleum ether to get pure #J3 and #J4 as a racemic mixture. The reaction was repeated three times. The combined crude products were separated by chiral prep HPLC to give #J3 (350 mg) and #J4 (350 mg) as pale brown solids. Absolute configuration was arbitrarily assigned as shown. $R_f$: 0.2 (EtOAc).

LCMS m/z=268.1 (M+H). ¹H NMR (400 MHz, CDCl₃): δ 2.22 (m, 1H), 2.39 (m, 1H), 2.62 (m, 1H), 2.84 (m, 1H), 3.73 (m, 1H), 3.83 (m, 1H), 4.60 (m, 1H), 7.85 (d, J=5.6 Hz, 1H), 8.00 (dd, J=1.6, 9.2 Hz, 1H), 8.20 (d, J=2.0 Hz, 1H), 8.34 (d, J=9.2 Hz, 1H), 8.61 (d, J=5.6 Hz, 1H).

Step 4.

Synthesis of aldehyde (#J5). IBX (587.0 mg, 2.1 mmol) was added to a stirred solution of #J3 (280.0 mg, 1.0 mmol) in EtOAc (10 mL) at room temperature. The reaction mixture was heated to 80° C. for 3 h. After completion of the reaction, the mixture was filtered through a Celite™ pad and was washed with EtOAc. The filtrate was washed with saturated aqueous NaHCO₃ solution, dried over Na₂SO₄, filtered and concentrated to give #J5 (300 mg crude) as a pale yellow liquid used in the next step without further purification. $R_f$: 0.3 (EtOAc).

LCMS m/z=266.1 (M+H).

Step 5.

Synthesis of product (#32). Me₃SiCF₃ (224 mg, 1.58 mmol) was added dropwise to a stirred suspension of compound #J5 (300.0 mg, 1.1 mmol) and CsF (950.0 mg, 5.9 mmol) in THF (10 mL) at −78° C. very slowly. Then, the reaction mixture was allowed to warm to room temperature and stir overnight. The mixture was quenched with water and extracted with EtOAc. The organic layer was dried over Na₂SO₄, filtered and concentrated in vacuo to give crude compound (diastereomeric mixture). This was purified by column chromatography on silica gel (100-200 mesh). Elution with 15% EtOAc in petroleum ether provides the first eluting hydroxyl center diastereomer and 40% EtOAc in petroleum ether gave the other diastereomer, target #32 (45 mg, 12%). Hydroxyl center diastereomer (10 mg, 3%). $R_f$: 0.7 (other diastereomer) and 0.5 (#32) (EtOAc).

Example 32

6-{(5R)-2-oxo-5-[(1S)-2,2,2-trifluoro-1-hydroxyethyl]pyrrolidin-1-yl}isoquinoline-1-carbonitrile (Stereochemistry Arbitrarily Assigned)

LCMS m/z=336.0 (M+1). ¹H NMR (400 MHz, d₆-DMSO) δ 2.42-2.50 (m, 2H); 2.72-2.73 (m, 1H); 4.28-4.30 (m, 1H); 4.97-5.03 (m, 1H); 6.68 (d, J=6.9 Hz, 1H); 8.11-8.28 (m, 4H); 8.65 (d, J=5.4 Hz, 1H).

Step 6.

Synthesis of aldehyde (#J6). IBX (730.0 mg, 2.6 mmol) was added to a stirred solution of #J4 (350 mg, 1.3 mmol) in EtOAc (10 mL) at room temperature. The reaction mixture was heated to 80° C. for 3 h. After completion of reaction, the mixture was filtered through a Celite™ pad and washed with EtOAc. The filtrate was washed with saturated aqueous NaHCO₃ solution, dried over Na₂SO₄, filtered and concentrated to give crude #J6 (400 mg crude) as a pale yellow liquid. The crude compound was used without further purification in the next step. $R_f$: 0.3 (EtOAc).

LCMS m/z=266.1 (M+H).

Step 7.

Synthesis of product (#33). Me₃SiCF₃ (297.0 mg, 2.1 mmol) was added dropwise to a stirred suspension of #J6 (400.0 mg, 1.5 mmol) and CsF (1.2 g, 7.9 mmol) in THF (10 mL) at −78° C. very slowly. The reaction mixture was allowed to warm to room temperature and stirred overnight. The mixture was quenched with water and extracted with EtOAc. Organic layer was dried over Na₂SO₄, filtered and concentrated to give a crude diastereomeric mixture. This was purified by column chromatography on silica gel (100-200 mesh). Elution with 15% EtOAc in petroleum ether provides the first eluting hydroxyl center diastereomer and 40% EtOAc in petroleum ether gave the other diastereomer, target #33 (72 mg, 14%) and hydroxy center diastereomer (17 mg, 3%). R$_f$: 0.5 (other diastereomer) and 0.7 (#33) (EtOAc).

Example 33

6-{(5S)-2-oxo-5-[(1S)-2,2,2-trifluoro-1-hydroxy-ethyl]pyrrolidin-1-yl}isoquinoline-1-carbonitrile (Stereochemistry Arbitrarily Assigned)

LCMS m/z=336.0 (M+1). $^1$H NMR (400 MHz, d$_6$-DMSO) δ 1.98-2.17 (m, 1H); 2.39-2.46 (m, 2H); 2.5-2.77 (m, 1H); 4.23-4.30 (m, 1H); 4.99 (t, J=7.2 Hz, 1H); 6.70 (d, J=6.3 Hz, 1H); 8.11-8.25 (m, 3H); 8.29 (d, J=2.1 Hz, 1H); 8.65 (d, J=5.7 Hz, 1H).

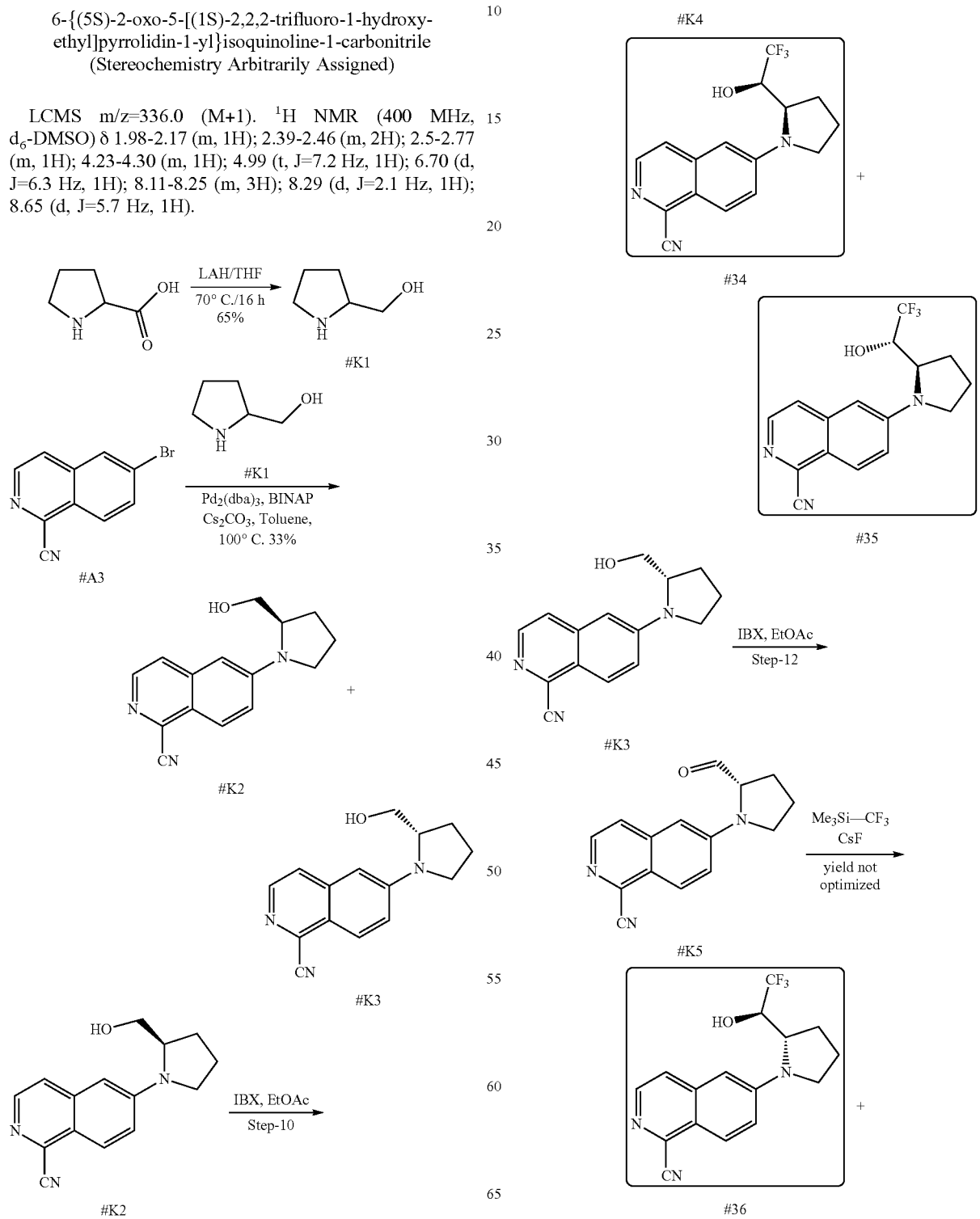

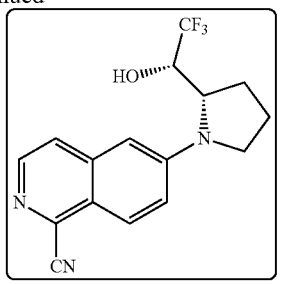

37

Step 1.

Preparation of amino alcohol (#K1). DL-Proline (6.0 g, 52.0 mmol) was added slowly and portion wise to a stirred suspension of LiAlH$_4$ (3.0 g, 78.0 mmol) in THF (80 mL) at 0° C. under nitrogen atmosphere carefully over a period of 30 minutes. The reaction mixture was warmed to room temperature and then heated to reflux for 3 h. The mixture was quenched with 20% KOH solution at 0° C. slowly (18-20 mL). The mixture was filtered through a Celite™ pad and washed with THF. The filtered precipitate was again refluxed with THF for 30 minutes and filtered. The combined filtrates were concentrated to give #K1 as pale yellow liquid which is slowly converts to dark brown liquid (3.2 g, 65%). R$_f$: 0.1 (10% MeOH in DCM & 1 drop AcOH, ninhydrin active).

Step 2.

Synthesis of coupling products (#K2, #K3). Pd$_2$(dba)$_3$ (350 mg, 0.06 mmol), BINAP (790.0 mg, 0.2 mmol), Cs$_2$CO$_3$ (6.2 g, 3.0 mmol) were added to a mixture of 6-bromoisoquinoline-1-carbonitrile #A3 (1.5 g, 6.4 mmol) and #K1 (1.3 g, 12.8 mmol) in toluene (10 mL) under nitrogen atmosphere. The reaction mixture was heated to 110° C. for 3 h. The mixture was diluted with EtOAc and washed with water and brine solution. Organic layer was dried over Na$_2$SO$_4$ and concentrated to give crude material. The crude material was purified by column chromatography on silica gel (100-200 mesh) eluted with 40% EtOAc in petroleum ether to give racemic material (#K2, #K3, 1 g, 33%). The isomers were separated by chiral preparative HPLC to give #K2 (500 mg) and #K3 (450 mg). R$_f$: 0.2 (EtOAc).

Step 3.

Synthesis of aldehyde (#K4). IBX (1.5 g, 5.5 mmol) was added to a stirred solution of #K2 (0.7 g, 2.7 mmol) in EtOAc (15 mL) at room temperature. The reaction mixture was heated to 80° C. for 3 h. The mixture was filtered through a Celite™ pad and washed with EtOAc. The collected organic layers were washed with saturated aqueous NaHCO$_3$ solution, dried over Na$_2$SO$_4$, filtered and concentrated to get crude #K4 (1 g crude) as a yellow liquid. The crude compound was used for next step without further purification. R$_f$: 0.7 (EtOAc).

Step 4.

Synthesis of products (#34, #35). Me$_3$SiCF$_3$ (0.6 g, 4.7 mmol) was added dropwise to a stirred suspension of #K4 (1.0 g, 4.0 mmol) and CsF (3.0 g, 19.7 mmol) in THF at −78° C. very slowly. The reaction mixture was allowed to warm to room temperature and stirred overnight. The mixture was quenched with water and extracted with EtOAc. Organic layer was dried over Na$_2$SO$_4$, filtered and concentrated to give the crude diastereomeric mixture. This was purified by column chromatography on) silica gel (100-200 mesh eluting with 15% EtOAc in petroleum ether to give diastereomer #34 and 30% EtOAc in pet ether to give diastereomer #35. Yield of #34 (66 mg, 6%) and #35 (72 mg, 7%) as pale yellow solids. R$_f$: 0.5 (#34) and 0.7 (#35) (EtOAc).

Example 34

6-{(2R)-2-[(1R)-2,2,2-trifluoro-1-hydroxyethyl]pyrrolidin-1-yl}isoquinoline-1-carbonitrile (Stereochemistry Arbitrarily Assigned)

LCMS m/z=322.0 (M+1). $^1$H NMR (300 MHz, d$_6$-DMSO): δ 1.90-2.10 (m, 2H); 2.18-2.43 (m, 2H); 3.43-3.53 (m, 1H); 3.57-3.65 (m, 1H); 4.32 (t, 2H); 6.50 (d, J=9.6 Hz, 1H); 6.89 (d, J=3.6 Hz, 1H); 7.41 (d, J=6.8 Hz, 1H); 7.85 (d, J=6.0 Hz, 1H); 8.06 (d, J=9.6 Hz, 1H); 8.38 (d, J=6.0 Hz, 1H).

Example 35

6-{(2R)-2-[(1S)-2,2,2-trifluoro-1-hydroxyethyl]pyrrolidin-1-yl}isoquinoline-1-carbonitrile (Stereochemistry Arbitrarily Assigned)

LCMS m/z=322.0 (M+1). $^1$H NMR (300 MHz, d$_6$-DMSO): δ 1.96-2.15 (m, 1H); 3.30 (t, J=12.4 Hz, 1H); 3.56 (t, J=7.6 Hz, 1H); 4.05-4.15 (m, 1H); 4.33 (d, J=5.2 Hz, 1H); 6.53 (d, J=6.4 Hz, 1H); 6.95 (d, J=2.0 Hz, 1H); 7.51 (d, J=7.2 Hz, 1H); 7.80 (d, J=6.0 Hz, 1H); 7.96 (d, J=9.6 Hz, 1H); 8.35 (d, J=6.0 Hz, 1H).

Step 5.

Synthesis of aldehyde (#K5). IBX (1.1 g, 3.8 mmol) was added to a stirred solution of #K3 (0.5 g, 1.9 mmol) in EtOAc (10 mL) at room temperature. The reaction mixture was heated to reflux for 3 h. The mixture was filtered through a Celite™ pad and washed with EtOAc. The collected organic layers were washed with saturated aqueous NaHCO$_3$ solution, dried over Na$_2$SO$_4$, filtered and concentrated to give crude #K5 (0.5 g crude) as a pale yellow liquid. The crude compound was used in the next step without further purification. R$_f$: 0.7 (EtOAc).

Step 6.

Synthesis of final compounds (#36, #37). Me$_3$SiCF$_3$ (0.34 g, 2.4 mmol) was added dropwise to a stirred suspension of aldehyde #K5 (0.5 g, 1.4 mmol) and CsF (1.5 g, 10.0 mmol) in THF (15 mL) at −78° C. very slowly. The reaction mixture was allowed to warm to room temperature and stirred overnight. The mixture was quenched with water and extracted with EtOAc. The organic layer was dried over Na$_2$SO$_4$ and concentrated to give crude diastereomeric mixture. This was purified by column chromatography on silica gel (100-200 mesh) eluted with 15% EtOAc in petroleum ether to give diastereomer #36 (22 mg, 4%) and 30% EtOAc in petroleum ether to give diastereomer #37 (33 mg, 6%) as pale brown solids. R$_f$: 0.5 (#36) and & 0.7 (#37) (EtOAc).

Example 36

6-{(2S)-2-[(1S)-2,2,2-trifluoro-1-hydroxyethyl]pyrrolidin-1-yl}isoquinoline-1-carbonitrile (Stereochemistry Arbitrarily Assigned)

LCMS m/z=322.0 (M+1). $^1$H NMR (300 MHz, d$_6$-DMSO) δ 2.05 (m, 4H); 3.29-3.30 (m, 1H); 3.57 (m, 1H); 4.07-4.09 (m, 1H); 4.34 (s, 1H); 6.53 (d, J=1.8 Hz, 1H); 7.52

(dd, J=9.0 Hz, 1H); 7.80 (d, J=6.0 Hz, 1H); 7.96 (d, J=9.6 Hz, 1H); 8.36 (d, J=5.4 Hz, 1H).

Example 37

6-{(2S)-2-[(1R)-2,2,2-trifluoro-1-hydroxyethyl]pyrrolidin-1-yl}isoquinoline-1-carbonitrile (Stereochemistry Arbitrarily Assigned)

LCMS m/z=322.0 (M+1). $^1$H NMR (300 MHz, d$_6$-DMSO) δ 1.95-2.04 (m, 2H), 2.18-2.32 (m, 2H); 3.36-3.40 (m, 1H); 3.58-3.61 (m, 1H); 4.29-4.38 (m, 2H); 6.5 (d, J=5.1 Hz, 1H); 6.89 (d, J=1.5 Hz, 1H); 7.40-7.43 (d, J=7.2 Hz, 1H); 7.85 (d, J=4.2 Hz, 1H); 8.06 (d, J=6.9 Hz; 1H); 8.38 (d, J=4.5 Hz, 1H).

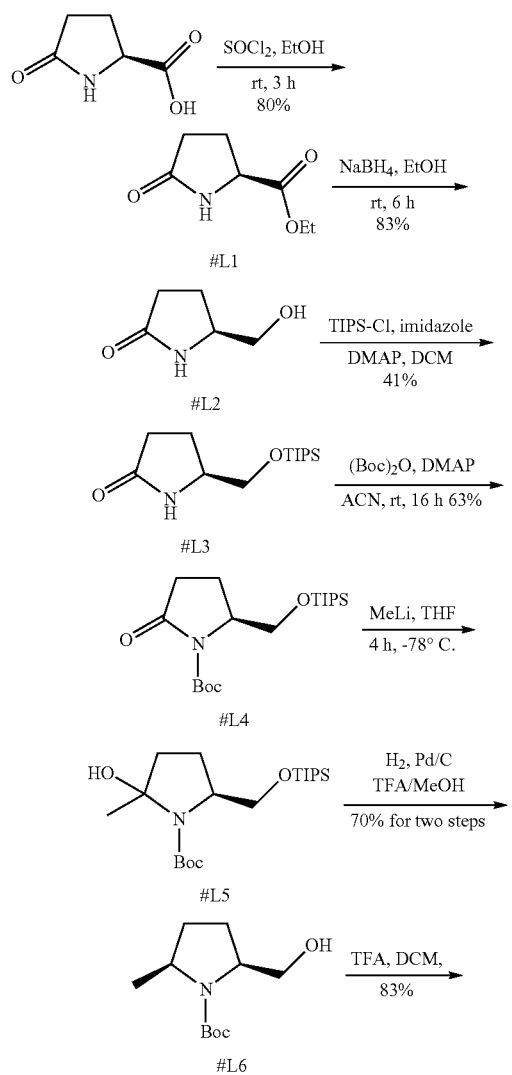

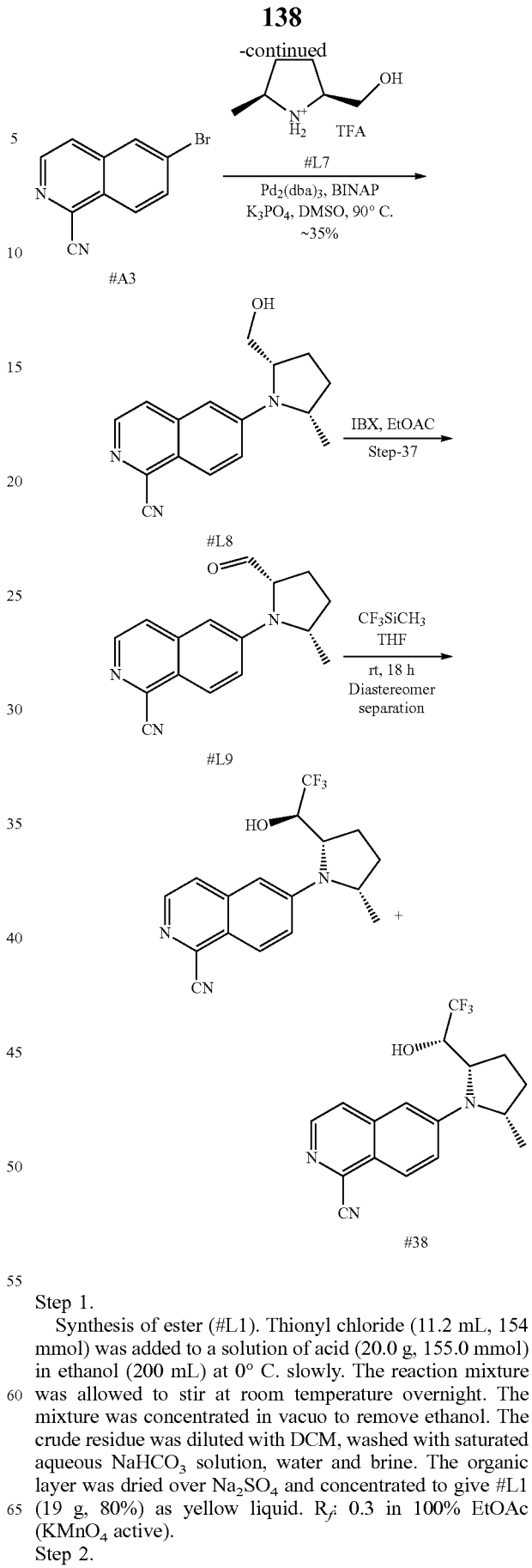

Step 1.

Synthesis of ester (#L1). Thionyl chloride (11.2 mL, 154 mmol) was added to a solution of acid (20.0 g, 155.0 mmol) in ethanol (200 mL) at 0° C. slowly. The reaction mixture was allowed to stir at room temperature overnight. The mixture was concentrated in vacuo to remove ethanol. The crude residue was diluted with DCM, washed with saturated aqueous NaHCO$_3$ solution, water and brine. The organic layer was dried over Na$_2$SO$_4$ and concentrated to give #L1 (19 g, 80%) as yellow liquid. R$_f$: 0.3 in 100% EtOAc (KMnO$_4$ active).

Step 2.

Synthesis of alcohol (#L2). NaBH$_4$ (1.7 g, 45.0 mmol) was added slowly to a solution of #L1 (12.0 g, 76.0 mmol) in ethanol (120 mL) at 0° C. portionwise. The reaction mixture was allowed to stir at room temperature for 6 h. After the reaction completion, the mixture was quenched with concentrated HCl and the precipitated solid was filtered. The crude compound was purified by column chromatography using silica gel (100-200 mesh) and eluted with 8% methanol in DCM to give pure #L2 (7.3 g, 83%) as pale yellow thick liquid. R$_f$: 0.1 (20% MeOH in DCM, KMnO$_4$ active).

Step 3.

Synthesis of TIPS protected alcohol (#L3). Imidazole (11.8 g, 173.0 mmol) and DMAP (3.1 g, 26.0 mmol) were added to a stirred solution of #L2 (10.0 g, 87.0 mmol) in DCM at 0° C. followed by TIPS-Cl (27.8 mL, 130.0 mmol). The mixture was allowed to stir at room temperature for 16 h. After the starting material was consumed, the mixture was quenched with ice water and extracted with EtOAc. The organic layer was washed with brine, dried over Na$_2$SO$_4$, filtered and concentrated to give crude product which was purified by column chromatography on silica gel (100-200 mesh) eluted with 20% EtOAc in petroleum ether to give pure #L3 (10.0 g, 31%) as pale yellow liquid. R$_f$: 0.3 (50% EtOAc in petroleum ether, KMnO$_4$ active).

Step 4.

Synthesis of N-Boc TIPS protected alcohol (#L4). (Boc)$_2$O (4.5 mL, 20.5 mmol) was added to a stirred solution of #L3 (5.0 g, 18.0 mmol) and DMAP (0.5 g, 4.0 mmol) in acetonitrile (40 mL) at −30° C. The reaction mixture was stirred for 30 minutes and then continued at room temperature for 16 h. The reaction mixture was concentrated under reduced pressure to give a crude product which was purified by column chromatography on silica gel (100-200 mesh) using 10% EtOAc and petroleum ether to afford #H4 (4.5 g, 66%) as a light brown liquid. R$_f$: 0.6 (30% EtOAc/petroleum ether, KMnO$_4$ active).

Step 5.

Synthesis of methylated N-Boc TIPS protected alcohol (#L5). MeLi (3 M in diethylamine, 2.6 mL, 8.1 mmol) was added dropwise to a solution of #L4 (3.0 g, 8.1 mmol) in dry THF (20 mL) at −78° C. and stirring was continued at same at temperature for 4 h. The reaction mixture was quenched with saturated aqueous NH$_4$Cl solution, extracted with EtOAc, dried over Na$_2$SO$_4$ and concentrated to give #L5 (3 g, 96%) as a light brown liquid which was used in next step without further purification. R$_f$: 0.2 (30% EtOAc in petroleum ether, KMnO$_4$ active).

Step 6.

Synthesis of N-Boc alcohol (#H6). A mixture of #L5 (3.5 g, 9.0 mmol) and 10% Pd/C (1.2 g) in 10% trifluoroacetic acid in methanol (80 mL) was shaken in a Parr apparatus under a hydrogen atmosphere at 200 psi at room temperature for 24 h. The reaction mixture was filtered through a Celite™ pad, washed with EtOAc, concentrated under reduced pressure to provide crude product. This was purified by column chromatography on silica gel (100-200 mesh) using 15% EtOAc/petroleum ether to get #L6 (2 g, 60%) as a yellow liquid. R$_f$: 0.4 (30% EtOAc: petroleum ether, KMnO$_4$ active).

Step 7.

Synthesis of amino alcohol trifluoroacetic acid salt (#L7). Trifluoroacetic acid (10.0 mL) was added dropwise to a solution of #H6 (1.0 g, 4.6 mmol) in DCM (10 mL) at room temperature, and the reaction mixture was stirred for 2 h. The solvents were evaporated under reduced pressure to get residue mixture which was co-distilled with methanol and concentrated under reduced pressure to afford #L7 (1 g, 94%) as a pale yellow liquid. R$_f$: 0.2 (20% methanol in DCM, KMnO$_4$ active).

Step 8.

Synthesis of product (#L8). Pd$_2$(dba)$_3$ (235.0 mg, 0.25 mmol), BINAP (480.0 mg, 0.77 mmol), K$_3$PO$_4$ (1.9 g, 9.0 mmol) were added to a mixture of 6-bromoisoquinoline-1-carbonitrile (600.0 mg, 2.57 mmol) and #L7 (1 g, 4.1 mmol) in DMSO (5 mL) under nitrogen atmosphere. The reaction mixture was heated to 110° C. for 3 h. The mixture was diluted with EtOAc and washed with water and brine. Organic layer was dried over Na$_2$SO$_4$ and concentrated to give crude compound. The crude material was purified by column chromatography using silica gel (100-200 mesh) eluted with 40% EtOAc in petroleum ether to get pure #L8 (400 mg, 58%) as pale yellow solid. R$_f$: 0.4 (50% EtOAc in petroleum ether).

LCMS m/z=268.2 (M+1).

Step 9.

Synthesis of aldehyde (#L9). IBX (800.0 mg, 2.9 mmol) was added to a stirred solution #L8 (400 mg, 1.45 mmol) in EtOAc (10 mL) at room temperature. The reaction mixture was heated to 80° C. for 3 h. The mixture was filtered through a Celite™ pad and washed with EtOAc. The filtrate was washed with saturated aqueous NaHCO$_3$ solution, dried over Na$_2$SO$_4$, filtered and concentrated to give #L9 (400 mg crude) as a pale yellow solid. The crude compound was used in the next step without further purification. R$_f$: 0.5 (50% EtOAc in petroleum ether).

Step 10.

Synthesis of product (#38). Me$_3$SiCF$_3$ (300.0 mg, 2.1 mmol) was added dropwise to a stirred suspension of #L9 (400 mg, 1.5 mmol) and CsF (1.2 g, 8 mmol) in THF (10 mL) at −78° C. very slowly. The reaction mixture was stirred at room temperature overnight. The mixture was quenched with water and extracted with EtOAc. The organic layer was dried over Na$_2$SO$_4$, filtered and concentrated to give a crude diastereomeric mixture. Purification by column chromatography on silica gel (230-400 mesh) and elution with 10% EtOAc in petroleum ether provided hydroxy center diastereomer (75 mg, 15%) as a pale brown solid. Further elution with 20% EtOAc in petroleum ether gave hydroxy center diastereomer #38 (60 mg, 12%) as off white solids. R$_f$: 0.6 (hydroxyl center diastereomer) and 0.7 (#38) (50% EtOAc in pet ether).

Example 38

6-{(2S,5S)-2-methyl-5-[(1S)-2,2,2-trifluoro-1-hydroxyethyl]pyrrolidin-1-yl}isoquinoline-1-carbonitrile (Stereochemistry Arbitrarily Assigned)

LCMS m/z=336.2 (M+1). $^1$H NMR (400 MHz, d$_6$-DMSO) δ 1.36 (d, J=6.3 Hz, 3H); 1.79-1.93 (m, 3H); 2.27 (s, 1H); 3.97-4.03 (m, 2H); 4.29-4.26 (m, 1H); 6.64 (d, J=6.3 Hz; 1H); 7.04 (d, J=2.1 Hz; 1H); 7.56 (q, J=9.0 Hz, 9.9 Hz, 1H); 7.84 (d, J=5.4 Hz; 1H); 7.98 (d, J=9 Hz; 1H); 8.36 (d, J=5.4 Hz; 1H).

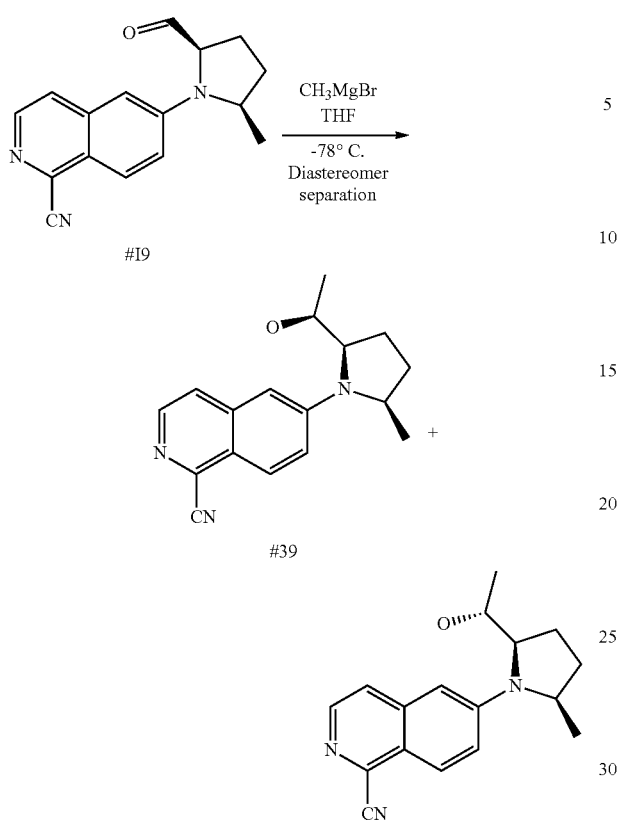

Step 1.

Synthesis of final product (#39). Step 1. Synthesis of product (#17). [125536-36-1,4]. Methylmagnesium bromide (1.2 mL, 1.2 mmol) was added to #I9 (0.30 g, 1.1 mmol) in dry THF (8 mL) at −78° C. The mixture warmed to −30° C. and stirred for 4 h. After consumption of starting material the mixture was quenched with saturated aqueous NH₄Cl solution and extracted with EtOAc. The organic layer was washed with brine, dried over Na₂SO₄, filtered and concentrated. This crude material was purified by column chromatography on silica gel (230-400 mesh). Elution with 20% EtOAc in pet ether gave (#39) (37 mg, 11%) as a pale brown solid. Further elution with 30% EtOAc in petroleum ether gave hydroxy center diastereomer (18 mg, 5%) as a pale brown solid. $R_f$: 0.4 (#39) and 0.2 (hydroxyl center diastereomer) (60% EtOAc in petroleum ether).

Example 39

6-{(2R,5R)-2-[(1S)-1-hydroxyethyl]-5-methylpyrrolidin-1-yl}isoquinoline-1-carbonitrile (Stereochemistry Arbitrarily Assigned)

LCMS m/z=282.1 (M+1). ¹H NMR (300 MHz, d₆-DMSO) δ 1.14 (d, J=6.3 Hz, 3H); 1.30 (d, J=6.3 Hz, 3H); 1.17-1.83 (m, 2H); 2.01-2.07 (m, 1H); 2.07-2.27 (m, 1H); 3.82-3.85 (m, 1H); 3.97-4.04 (m, 2H); 4.73 (d, J=3.3 Hz, 1H); 6.9 (d, J=2.1 Hz, 1H); 7.43 (m, 1H); 7.82 (d, J=5.4 Hz, 1H); 7.96 (d, J=9.0 Hz, 1H); 8.30 (d, J=5.7 Hz, 1H).

The following examples are prepared using 2-bromo-5-cyanonaphthalene instead of 1-cyano-6-bromoisoquinoline:

Example 40

6-((2R,3S)-4,4,4-trifluoro-3-hydroxybutan-2-ylamino)-1-naphthonitrile

Example 41

6-((R)-2-((R)-2,2,2-trifluoro-1-hydroxyethyl)azetidin-1-yl)-1-naphthonitrile

Example 42

6-((S)-2-((S)-2,2,2-trifluoro-1-hydroxyethyl)azetidin-1-yl)-1-naphthonitrile

Example 43

6-(methyl((2R,3R)-4,4,4-trifluoro-3-hydroxybutan-2-yl)amino)-1-naphthonitrile

Example 44

6-(methyl((2R,3S)-4,4,4-trifluoro-3-hydroxybutan-2-yl)amino)-1-naphthonitrile

Example 45

6-((R)-2-((R)-2,2,2-trifluoro-1-hydroxyethyl)piperidin-1-yl)-1-naphthonitrile

Example 46

6-((R)-2-((S)-2,2,2-trifluoro-1-hydroxyethyl)piperidin-1-yl)-1-naphthonitrile

Example 47

6-((2R,5R)-2-methyl-5-((R)-2,2,2-trifluoro-1-hydroxyethyl)pyrrolidin-1-yl)-1-naphthonitrile Example 48

6-((2R,5R)-2-((R)-1-hydroxyethyl)-5-methylpyrrolidin-1-yl)-1-naphthonitrile

Example 49

6-((R)-2-oxo-5-((S)-2,2,2-trifluoro-1-hydroxyethyl)pyrrolidin-1-yl)-1-naphthonitrile Example 50

6-((S)-2-oxo-5-((S)-2,2,2-trifluoro-1-hydroxyethyl)pyrrolidin-1-yl)-1-naphthonitrile Example 51

6-((R)-2-((R)-2,2,2-trifluoro-1-hydroxyethyl)pyrrolidin-1-yl)-1-naphthonitrile

Example 52

6-((R)-2-((S)-2,2,2-trifluoro-1-hydroxyethyl)pyrrolidin-1-yl)-1-naphthonitrile

Example 53

6-((S)-2-((S)-2,2,2-trifluoro-1-hydroxyethyl)pyrrolidin-1-yl)-1-naphthonitrile

Example 54

6-((S)-2-((R)-2,2,2-trifluoro-1-hydroxyethyl)pyrrolidin-1-yl)-1-naphthonitrile

Example 55

6-((2S,5S)-2-methyl-5-((S)-2,2,2-trifluoro-1-hydroxyethyl)pyrrolidin-1-yl)-1-naphthonitrile

Example 56

6-((2R,5R)-2-((S)-1-hydroxyethyl)-5-methylpyrrolidin-1-yl)-1-naphthonitrile

Example 57

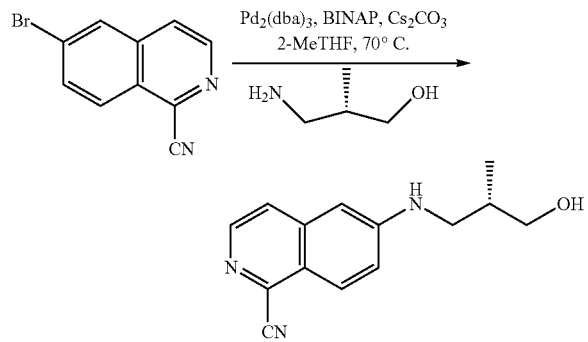

Procedure:

Into a 2 L 3-neck round bottom flask equipped with a mechanical stirrer, reflux condenser and thermocouple with heating mantle was placed 2-methyltetrahydrofuran (2-MeTHF) (10 mL/g; 8.15 moles; 817 mL; 702 g) followed by racemic-2,2'-bis(diphenylphosphino)-1,1'-binaphthyl (BINAP) (0.04 equiv (molar); 14.0 mmol; 8.74 g) and bis(dibenzylideneacetone)palladium ($Pd_2(dba)_3$) (0.04 equiv (molar); 14.0 mmol; 8.07 g). The mixture was degassed by pulling vacuum and refilling with nitrogen three times then heated to 75° C. for 15 minutes and cooled to ambient temperature. In a separate flask, (S)-3-amino-2-methylpropan-1-ol (1.60 equiv; 561 mmol; 50.0 g, prepared using literature methods for example as disclosed in EP-A-0,089,139 published on 21 Sep. 1983) was dissolved in 2-methyltetrahydrofuran (5 mL/g; 4.08 moles; 409 mL; 351 g) and degassed by pulling vacuum and refilling with nitrogen three times. Into the pot containing the catalyst was added 6-(bromoisoquinoline-1-carbonitrile) (1.00 equiv; 351 mmol; 81.75 g) and cesium carbonate (1.6 equiv (molar); 561 mmol; 185 g) in single portions followed by the solution of the aminoalcohol via addition funnel. The reaction mixture was again degassed by pulling vacuum and refilling with nitrogen three times. The reaction was heated to 70° C. for 3 hours. The reaction was cooled to ambient temperature and filtered through a pad of Celite. The contents of the flask were rinsed out with three 100 mL portions of 2-methyltetrahydrofuran. The filtrate was transferred into a 2 L round bottom flask equipped with a thermocouple and mechanical stirrer under nitrogen. Silica Gel (Silicylate SiliaMet® Thiol) (0.4 g/g-pure-LR; 544 mmol; 32.7 g) was charged and the flask was stirred at 40° C. overnight. The following morning, the reaction was cooled to <30° C. and filtered again through Celite. The pad was washed with 100 mL of 2-methyltetrahydrofuran (or until no yellow color persisted in the filtrate). The filtrate was placed into a 3 L round bottom flask equipped with a magnetic stir bar, distillation head (with condenser and receiving flask), and thermocouple. The mixture was heated to 60° C. and placed under vacuum (~450-500 mbar) to distil out 1.3 L total of 2-methyltetrahydrofuran. 500 mL of toluene was added to precipitate the desired product. The heating mantle was removed and the reaction was allowed to reach ambient temperature. The mixture was stirred for 1 hour at ambient temperature and then the solids were collected by vacuum filtration on a sintered glass funnel. The cake was dried overnight on the funnel under vacuum. The following morning, the solids were transferred into an amber bottle and weighed (71.9 g; 298 mmol). The product was used in the next step without further purification.

Example 58

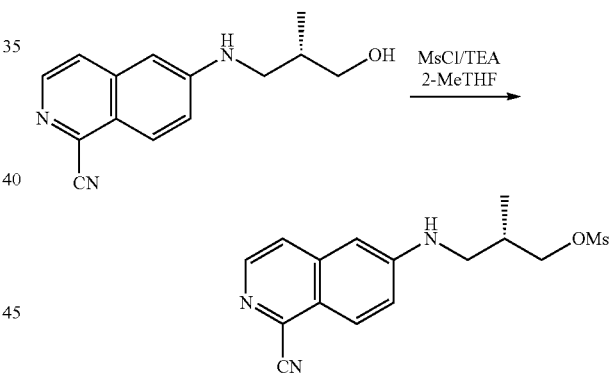

Procedure:

In a 1 L reactor equipped with a temperature probe and overhead stirring was added the product of Example 1 (20.0 g; 1.00 equiv; 82.9 mmol) and 2-methyltetrahydrofuran (2-MeTHF) (30 mL/g-pure-LR; 5.98 moles; 600 mL; 515 g). The reaction mixture was gently warmed to 40° C. to achieve partial solubility. The reaction was cooled to 0° C. Once the reaction reached 0° C. methanesulfonyl chloride (MsCl) (1.4 equiv (molar); 116 mmol; 8.98 mL; 13.3 g) was added in a single portion followed immediately by triethylamine (TEA) (1.4 equiv (molar); 116 mmol; 16.2 mL; 11.7 g) dropwise via syringe over a period of 15 minutes. The reaction mixture was further stirred for 30 min at 0° C. and then warmed to 23° C. for 60 minutes. The product (26.47 g; 1.00 equiv; 82.88 mmol; 26.47 g; 100% assumed yield) was then used without purification for the sulfonylation reaction.

Example 59

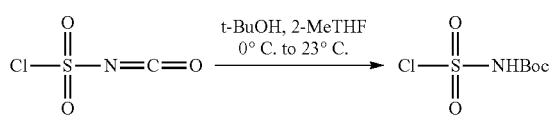

Procedure:

To a solution of t-butyl alcohol (t-BuOH) (1 equiv (molar); 116 mmol; 11.0 mL; 8.60 g) in 2-methyltetrahydrofuran (2-MeTHF) (1 M; 1.16 moles; 116 mL; 99.6 g) at 0° C. was added chlorosulfonyl isocyanate (116 mmol; 1.00 equiv; 10.1 mL; 16.4 g) dropwise. The homogeneous solution was stirred for 30 minutes at ambient temperature and then used directly in the sulfonylation reaction.

Example 60

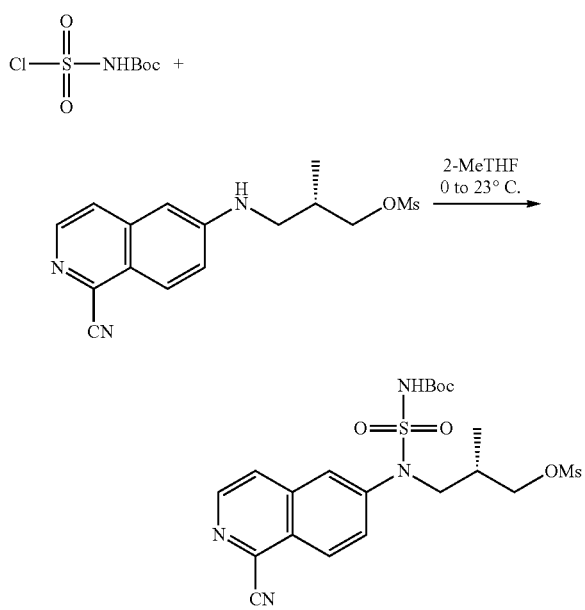

Sulfonylation Reaction Procedure:

A previously prepared solution of the product of Example 3 (1.4 equiv (molar); 116 mmol; 116 g) in 2-methyltetrahydrofuran was added to a suspension of the product of Example 2 (1.00 equiv; 82.89 mmol; 26.5 g) at 0° C. The mixture was warmed to ambient temperature over 30 minutes. HPLC analysis revealed the reaction was complete. The reaction was quenched with a 10% sodium carbonate solution (2 equiv (molar); 165 mmol; 101 mL; 117 g) and water (to dissolve salts) (5 L/kg; 7.35 moles; 132 mL; 132 g). The top organic layer was removed and passed through a plug of Carbon (Darco G60) (0.5 g/g) on a filter. A significant improvement in color (dark orange to yellow) was observed. The solution was concentrated to 10 total volumes and used in the next step without purification.

Example 61

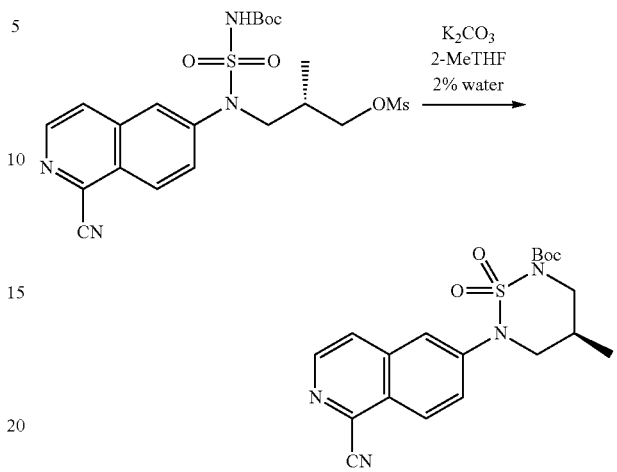

Procedure:

A solution of the product of Example 4 (1.00 equiv; 82.9 mmol; 41.3 g) in 2-methyltetrahydrofuran (2-MeTHF) (10 mL/g; 4.12 moles; 413 mL; 355 g) was placed into a 1 L reactor equipped with an overhead stirrer and temperature probe. Next, potassium carbonate ($K_2CO_3$) (325 mesh) (6 equiv (molar); 497 mmol; 69.4 g) and water (0.0 L/100-g-bulk-LR; 459 mmol; 8.26 mL; 8.26 g) were added and the mixture heated to 40° C. (jacket temperature) and stirred overnight. The reaction was cooled to ambient temperature and water (4 L/kg-pure-LR; 9.17 moles; 165 mL; 165 g]) was added. The biphasic reaction was stirred for 1 hour at 23° C. The aqueous layer was extracted and removed. The organic layer was passed through a plug of Carbon (Darco G60) (0.5 g/g-pure-LR; 20.7 g) in a disposable filter. The 2-methyltetrahydrofuran solution was switched to a 10 volume solution of toluene via a constant strip-and-replace distillation to no more than 1% 2-methyltetrahydrofuran. The toluene solution of the reaction product (1.00 equiv; 82.9 mmol; 33.4 g; 100% assumed yield) was used as-is in the next step without further purification.

Example 62

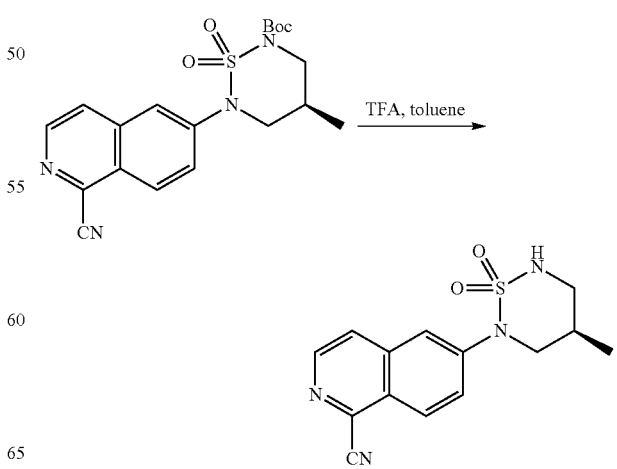

147

Procedure:

To a 1 L reactor under nitrogen and equipped with overhead stirring and a temperature probe was added the product of Example 5 (1.00 equiv; 78.7 mmol; 33.4 g) as a solution in toluene (10 mL/g-pure-LR; 3.00 moles; 317 mL; 276 g). Next, trifluoroacetic acid (TFA) (10 equiv (molar); 787 mmol; 59.5 mL; 89.8 g) was added to the reaction over a period of 1 hour keeping the internal temperature below 30° C. The dark red mixture was stirred for 1 hour. The reaction was quenched at 23° C. by the addition of sodium carbonate (5 equiv (molar); 394 mmol; 240 mL; 278 g). The reaction was quenched slowly, over a period of 1 hour to form the TFA salt of the product. Once the charge was complete, the mixture was cooled to 0° C., held for 1 hour and filtered. The next morning, the solid product (6-[(4R)-4-methyl-1,1-dioxido-1,2,6-thiadiazinan-2-yl]isoquinoline-1-carbonitrile in its free base form) was weighed (0.89 equiv; 70.0 mmol; 21.2 g; 89.0% yield) and used in the next step without further purification.

Example 63

Crystalline 6-[(4R)-4-methyl-1,1-dioxido-1,2,6-thiadiazinan-2-yl]isoquinoline-1-carbonitrile (Form (1)) free base was prepared as follows.

In a 1 L 3-neck round bottom flask was added 6-[(4R)-4-methyl-1,1-dioxido-1,2,6-thiadiazinan-2-yl]isoquinoline-1-carbonitrile free base (1.00 equiv; 70.0 mmol; 21.2 g) a magnetic stir bar and acetone (40 mL/g; 11.5 moles; 847 mL; 669 g). The mixture was heated to reflux (approximately 57° C.) and stirred for 1 hour. The mixture was concentrated by atmospheric distillation (heating mantle set at 65° C.) and 40 mL of acetone was collected into a graduated cylinder. Next, water (25 mL/g; 29.4 moles; 530 mL; 530 g) was charged over a period of one hour. The mixture was stirred at ambient temperature for 60 min before being cooled to 0° C. at 1° C./min for 1 hour. The solids were collected by filtration in a disposable funnel. Crystalline 6-[(4R)-4-methyl-1,1-dioxido-1,2,6-thiadiazinan-2-yl]isoquinoline-1-carbonitrile (Form (1), 0.88 equiv; 61.9 mmol; 18.7 g; 88.3% yield) was dried under vacuum overnight at 40° C. Typical purity after crystallization is 98%.

Example 64

The powder X-ray diffraction pattern of crystalline 6-[(4R)-4-methyl-1,1-dioxido-1,2,6-thiadiazinan-2-yl]isoquinoline-1-carbonitrile was collected using a Bruker AXS D8 ADVANCE diffractometer equipped with a Cu radiation source and then processed as set out above. The results are shown in FIG. 1 and are summarised in Table 1 below.

TABLE 1

PXRD Peak list for crystalline 6-[(4R)-4-methyl-1,1-dioxido-1,2,6-thiadiazinan-2-yl]isoquinoline-1-carbonitrile free base (Form (1))

| Angle degrees 2-Theta (±0.2° 2-theta) | Intensity %* |
|---|---|
| 7.8 | 54 |
| 10.9 | 69 |
| 15.2 | 22 |
| 15.6 | 17 |
| 16.8 | 30 |
| 17.1 | 92 |
| 17.3 | 100 |
| 18.5 | 82 |
| 20.1 | 65 |
| 21.8 | 23 |
| 22.8 | 40 |

TABLE 1-continued

PXRD Peak list for crystalline 6-[(4R)-4-methyl-1,1-dioxido-1,2,6-thiadiazinan-2-yl]isoquinoline-1-carbonitrile free base (Form (1))

| Angle degrees 2-Theta (±0.2° 2-theta) | Intensity %* |
|---|---|
| 23.0 | 76 |
| 23.4 | 26 |
| 24.3 | 44 |
| 27.7 | 17 |
| 28.1 | 24 |
| 29.0 | 23 |
| 29.6 | 15 |
| 30.0 | 10 |
| 31.4 | 13 |
| 39.5 | 10 |

*Relative intensities may vary depending on sample orientation, crystal size and/or morphology.

Example 65

Figure 2:
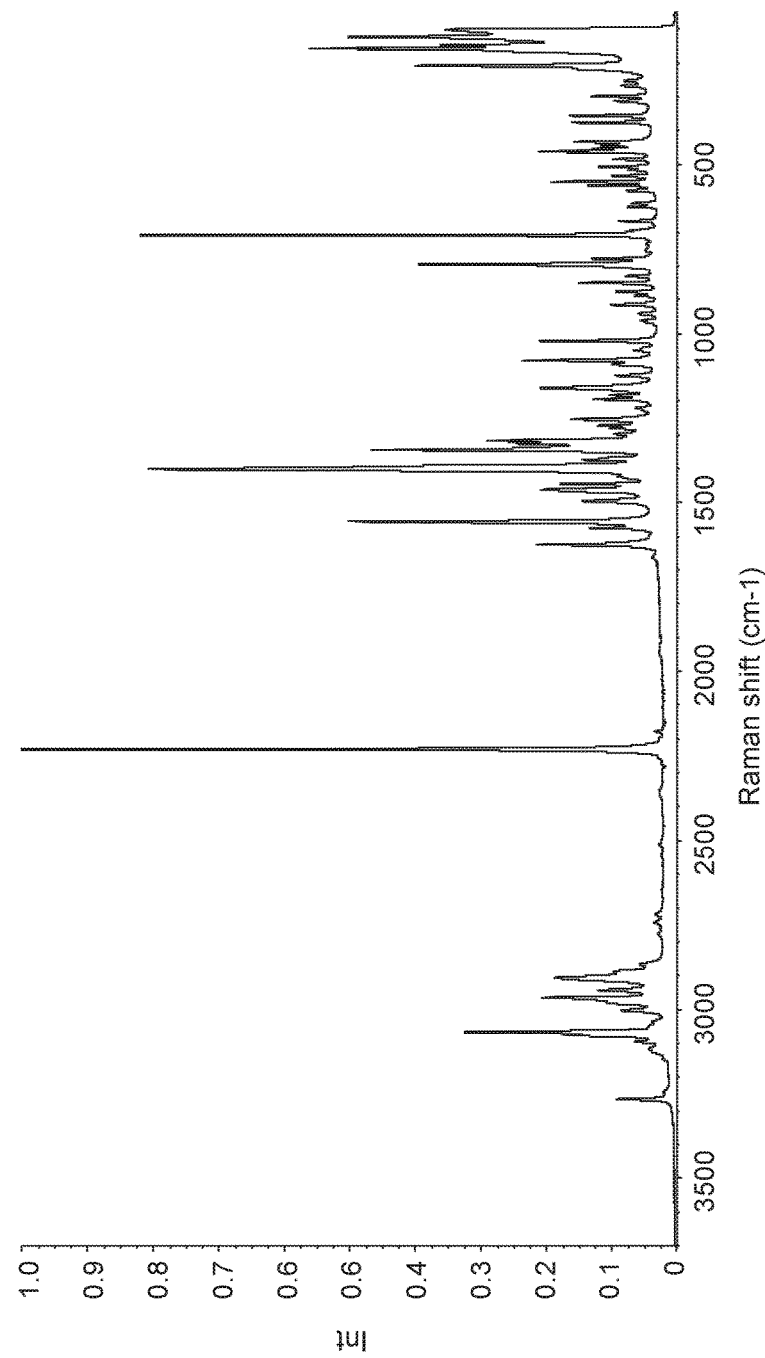
FIG. 2 is a characteristic Raman spectrum of crystalline 6-[(4R)-4-methyl-1,1-dioxido-1,2,6-thiadiazinan-2-yl]isoquinoline-1-carbonitrile free base (Form (1)). (Vertical axis intensity (counts), horizontal axis: Raman shift ($cm^{-1}$)).

The Raman spectra of crystalline 6-[(4R)-4-methyl-1,1-dioxido-1,2,6-thiadiazinan-2-yl]isoquinoline-1-carbonitrile (Form (1)) was collected using a Nicolet NXR FT-Raman accessory attached to the FT-IR bench, equipped with a 1064 nm Nd:YVO$_4$ laser and a liquid nitrogen cooled Germanium detector in accordance with the experimental details and data processing details set out above. The results are shown in FIG. 2 and are summarised in Table 2 below.

TABLE 2

Raman spectra peak list for crystalline 6-[(4R)-4-methyl-1,1-dioxido-1,2,6-thiadiazinan-2-yl]isoquinoline-1-carbonitrile free base (Form (1))

| Position (cm$^{-1}$) | Intensity (W = weak, M = medium, S = strong) |
|---|---|
| 207 | M |
| 667 | W |
| 708 | S |
| 795 | M |
| 1496 | W |
| 1555 | M |
| 1575 | W |
| 1624 | W |
| 2230 | S |
| 3067 | M |
| 3077 | W |
| 3095 | W |
| 3116 | W |
| 3265 | W |

Example 66

Figure 3:
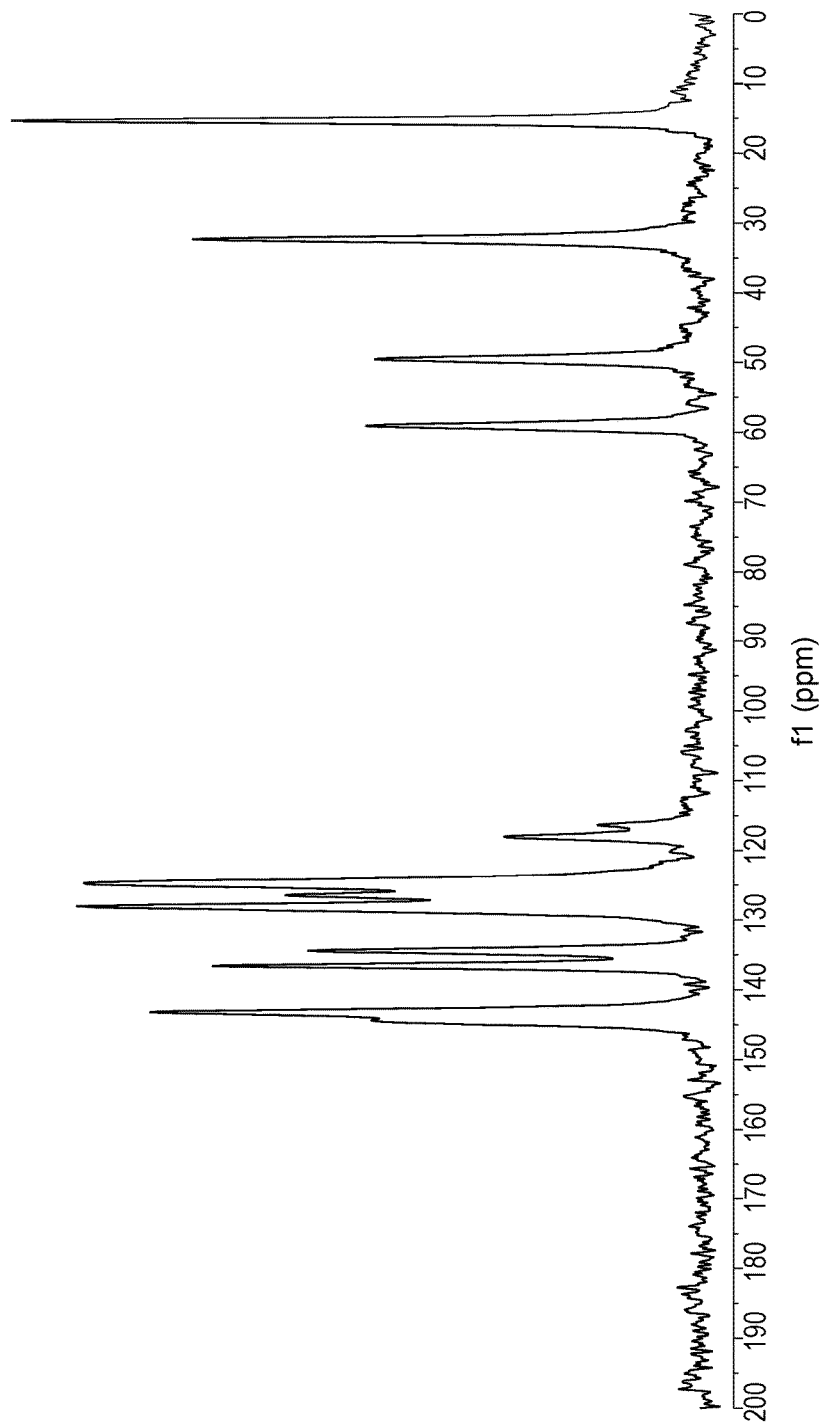
FIG. 3 is a characteristic solid state NMR spectrum of crystalline 6-[(4R)-4-methyl-1,1-dioxido-1,2,6-thiadiazinan-2-yl]isoquinoline-1-carbonitrile free base (Form (1)). (Horizontal axis peak shift (ppm)).
Figure 4:
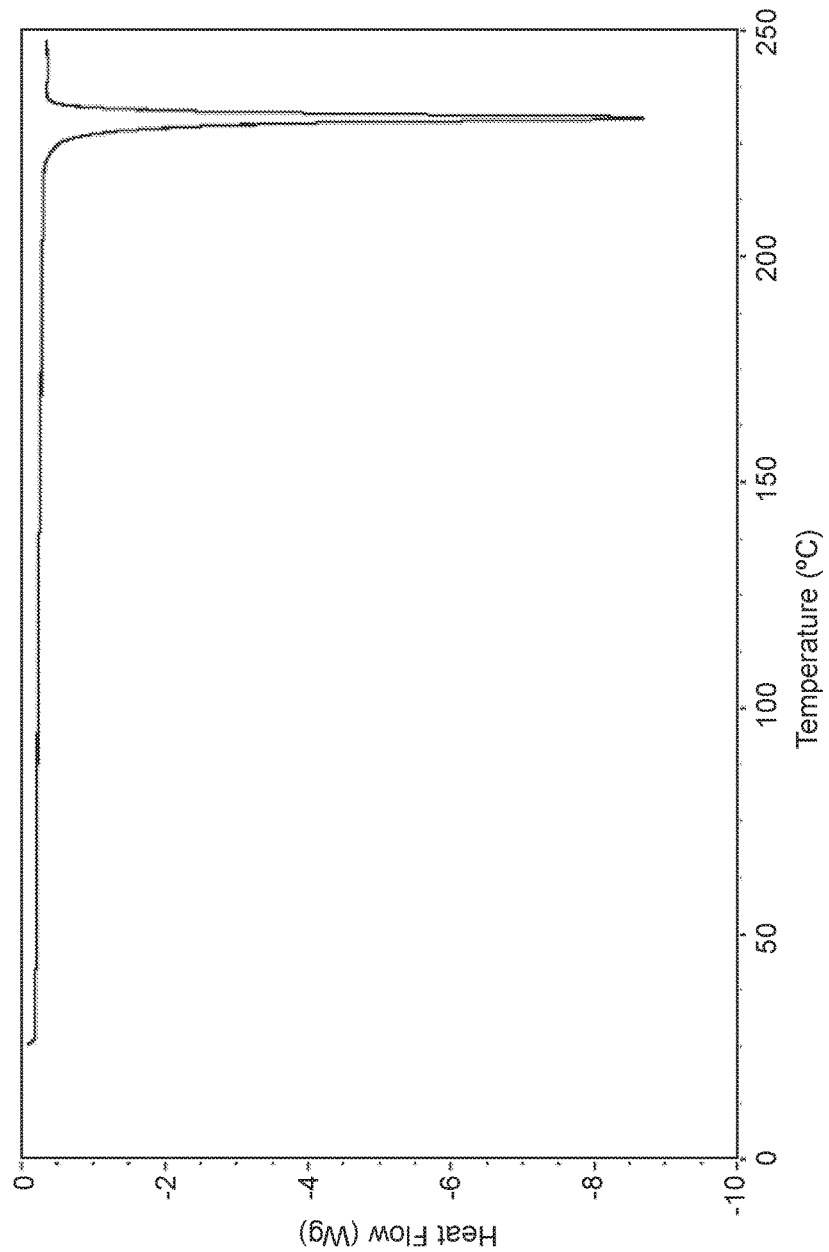
FIG. 4 is a characteristic DSC diffractogram of crystalline 6-[(4R)-4-methyl-1,1-dioxido-1,2,6-thiadiazinan-2-yl]isoquinoline-1-carbonitrile free base (Form (1)). (Vertical axis heat flow (W/g), horizontal axis temperature (° C.)).

The solid state NMR (ssNMR) spectra of crystalline 6-[(4R)-4-methyl-1,1-dioxido-1,2,6-thiadiazinan-2-yl]isoquinoline-1-carbonitrile (Form (1)) was collected at 25° C. using a Varian 4 mm CPMAS probe positioned into a Varian VNMR 400 MHz (1H frequency) NMR spectrometer in accordance with the experimental details and data processing details set out above. The results are shown in FIG. 3 and are summarised in Table 3 below.

TABLE 3

Solid state NMR (ssNMR) peak list for crystalline
6-[(4R)-4-methyl-1,1-dioxido-1,2,6-
thiadiazinan-2-yl]isoquinoline-1-carbonitrile free base
(Form (1))

| $^{13}$C Chemical Shifts [ppm] |
| --- |
| 15.3 |
| 32.3 |
| 49.6 |
| 59.1 |
| 116.4 |
| 118.0 |
| 124.7 |
| 124.9 |
| 126.5 |
| 128.1 |
| 128.6 |
| 134.4 |
| 136.6 |
| 143.2 |
| 144.4 |

Example 67—Immediate Release Tablet

An immediate release tablet formulation comprising crystalline 6-[(4R)-4-methyl-1,1-dioxido-1,2,6-thiadiazinan-2-yl]isoquinoline-1-carbonitrile (Form (1)) can be prepared as shown. Tablets can be prepared using three different strengths of active ingredient (A).

| Ingredient | Tablet 1 (1 mgA Dose) | | Tablet 2 (5 mgA Dose) | | Tablet 3 (25 mgA Dose) | |
| --- | --- | --- | --- | --- | --- | --- |
| | mg/tablet | % w/w | mg/tablet | % w/w | mg/tablet | % w/w |
| Active (SARM)[1] | 1 | 1% | 5 | 5% | 25 | 5% |
| Microcrystalline cellulose, NF[2] | 63.3 | 63% | 60.7 | 61% | 303.5 | 61% |
| Lactose monohydrate, NF[3] | 31.7 | 32% | 30.3 | 30% | 151.5 | 30% |
| Sodium starch glycolate, NF[4] | 3 | 3% | 3 | 3% | 15 | 3% |
| Magnesium stearate, NF[5] | 1 | 1% | 1 | 1% | 5 | 1% |
| Total | 100 | 100% | 100 | 100% | 500 | 100% |

[1]Assumes 100% purity and no salt form. When a potency adjustment is required the amounts of microcrystalline cellulose and lactose monohydrate may be adjusted
[2]Avicel PH102, FMC Corporation
[3]Fast Flo, Foremost Farms
[4]Explotab, Penwest Pharmaceuticals
[5]Vegetable derived; Malinkrodt The tablet formulation may be prepared using direct compression or wet or dry granulation processes. Alternatively, the formulation may be used for filling hard-shell capsules or other dosage forms.

In this case, direct compression can be used to manufacture the tablet and a standard blend-mill-blend process can be used to prepare the blend. For example, first, all of the ingredients except magnesium stearate would be added to a bin. The material would then be mixed until well blended. The material would then be passed through a mill. The material would then be mixed again until well blended. The magnesium stearate would then be added to the mixture and mixed again. Finally, the resulting mixture would then be compressed into a tablet.

Example 68—Immediate Release Tablet Formulation

An immediate release tablet formulation comprising crystalline 6-[(4R)-4-methyl-1,1-dioxido-1,2,6-thiadiazinan-2-yl]isoquinoline-1-carbonitrile (Form (1)) can be prepared as shown. Tablets can be prepared using three different strengths of active ingredient (A).

| Ingredient | Tablet 1 (1 mgA Dose) | | Tablet 2 (5 mgA Dose) | | Tablet 3 (25 mgA Dose) | |
| --- | --- | --- | --- | --- | --- | --- |
| | mg/tablet | % w/w | mg/tablet | % w/w | mg/tablet | % w/w |
| Active (SARM)[1] | 1 | 1% | 5 | 5% | 25 | 5% |
| Microcrystalline cellulose, NF[2] | 47.5 | 48% | 45.5 | 46% | 227.5 | 46% |

-continued

| Ingredient | Tablet 1 (1 mgA Dose) | | Tablet 2 (5 mgA Dose) | | Tablet 3 (25 mgA Dose) | |
|---|---|---|---|---|---|---|
| | mg/tablet | % w/w | mg/tablet | % w/w | mg/tablet | % w/w |
| Lactose monohydrate, NF[3] | 47.5 | 48% | 45.5 | 46% | 227.5 | 46% |
| Sodium starch glycolate, NF[4] | 3 | 3% | 3 | 3% | 15 | 3% |
| Magnesium stearate, NF[5] | 1 | 1% | 1 | 1% | 5 | 1% |
| Total | 100 | 100% | 100 | 100% | 500 | 100% |

[1]Assumes 100% purity and no salt form. When a potency adjustment is required the amounts of microcrystalline cellulose and lactose monohydrate may be adjusted
[2]Avicel PH102, FMC Corporation
[3]Fast Flo, Foremost Farms
[4]Explotab, Penwest Pharmaceuticals
[5]Vegetable derived; Malinkrodt Tablets containing the ingredients shown can be prepared by the direct compression method described in Example 67. Alternatively, the formulation may be used for filling hard-shell capsules or tableted using a wet or dry granulation process.

Example 69—Immediate Release Tablet Formulation

An immediate release tablet formulation comprising crystalline 6-[(4R)-4-methyl-1,1-dioxido-1,2,6-thiadiazinan-2-yl]isoquinoline-1-carbonitrile Form (1) can be prepared as shown. Tablets can be prepared using three different strengths of active ingredient (A).

| Ingredient | Tablet 1 (1 mgA Dose) | | Tablet 2 (5 mgA Dose) | | Tablet 3 (25 mgA Dose) | |
|---|---|---|---|---|---|---|
| | mg/tablet | % w/w | mg/tablet | % w/w | mg/tablet | % w/w |
| Active (SARM)[1] | 1 | 1% | 5 | 5% | 25 | 5% |
| Microcrystalline cellulose, NF[2] | 63.3 | 63% | 60.7 | 61% | 303.5 | 61% |
| Calcium phosphate, dibasic anhydrous[3] | 31.7 | 32% | 30.3 | 30% | 151.5 | 30% |
| Sodium starch glycolate, NF[4] | 3 | 3% | 3 | 3% | 15 | 3% |
| Magnesium stearate, NF[5] | 1 | 1% | 1 | 1% | 5 | 1% |
| Total | 100 | 100% | 100 | 100% | 500 | 100% |

[1]Assumes 100% purity and no salt form. When a potency adjustment is required the amounts of microcrystalline cellulose and lactose monohydrate may be adjusted
[2]Avicel PH102, FMC Corporation
[3]A-tab, Rhodia Incorporated
[4]Explotab, Penwest Pharmaceuticals
[5]Vegetable derived; Malinkrodt Tablets containing the ingredients shown can be prepared by the direct compression method described in Example 67. Alternatively, the formulation may be used for filling hard-shell capsules or tableted using a wet or dry granulation process.

Example 70—Immediate Release Tablet Formulation

An immediate release tablet formulation comprising crystalline 6-[(4R)-4-methyl-1,1-dioxido-1,2,6-thiadiazinan-2-yl]isoquinoline-1-carbonitrile Form (1) can be prepared as shown. Tablets can be prepared using three different strengths of active ingredient (A).

|  | Tablet 1 (1 mgA Dose) | | Tablet 2 (5 mgA Dose) | | Tablet 3 (25 mgA Dose) | |
|---|---|---|---|---|---|---|
| Ingredient | mg/tablet | % w/w | mg/tablet | % w/w | mg/tablet | % w/w |
| Active (SARM)[1] | 1 | 1% | 5 | 5% | 25 | 5% |
| Microcrystalline cellulose, NF[2] | 47.5 | 48% | 45.5 | 46% | 227.5 | 46% |
| Calcium phosphate, dibasic anhydrous[3] | 47.5 | 48% | 45.5 | 46% | 227.5 | 46% |
| Sodium starch glycolate, NF[4] | 3 | 3% | 3 | 3% | 15 | 3% |
| Magnesium stearate, NF[5] | 1 | 1% | 1 | 1% | 5 | 1% |
| Total | 100 | 100% | 100 | 100% | 500 | 100% |

[1] Assumes 100% purity and no salt form. When a potency adjustment is required the amounts of microcrystalline cellulose and lactose monohydrate may be adjusted
[2] Avicel PH102, FMC Corporation
[3] A-tab, Rhodia Incorporated
[4] Explotab, Penwest Pharmaceuticals
[5] Vegetable derived; Malinkrodt Tablets containing the ingredients shown can be prepared by the direct compression method described in Example 67. Alternatively, the formulation may be used for filling hard-shell capsules or tableted using a wet or dry granulation process.

The characterization data disclosed herein confirms the crystalline nature of the 6-[(4R)-4-methyl-1,1-dioxido-1,2,6-thiadiazinan-2-yl]isoquinoline-1-carbonitrile free base Form (1) material and, as such, that it is a useful form for pharmaceutical development. For example, crystalline materials are generally considered to be an advantageous form for drug substance manufacturing because, for example, they are more easily purified, can be prepared with higher yields, have improved filtration and drying characteristics and improved flow and handling characteristics. Crystalline 6-[(4R)-4-methyl-1,1-dioxido-1,2,6-thiadiazinan-2-yl]isoquinoline-1-carbonitrile Form (1) also demonstrates physicochemical properties which render it useful for drug product manufacturing such as its thermal stability and non-hygroscopic nature demonstrated by the high DSC melting point and DSC profile.

Androgen Receptor-Mediated Transcriptional Assay Summary

CV-1 cells (American Tissue Culture Collection cat# CCL-70) were expanded in Growth Media and transiently transfected in T225 cm² flasks with a full length human Androgen Receptor (AR) cDNA in the pcDNA3 expression vector and a human Androgen Response Element (ARE)-luciferase cDNA in the pGL3 vector (both from Invitrogen). DNA (µg) and Lipofectamine (µl) at a ratio of 1:3 were incubated with the cells in a total volume of 55 mL Basal Media for 4 hours. Cells were harvested by trypsinization and frozen back (−150° C. cryomed) at a concentration of 4.3 million cells/mL.

On the day of the assay, frozen cells were thawed and re-suspended in Re-suspension Media and plated at 40,000 cells/well (in 100 µL volume) in 96 well white plates and were incubated for at least 4 h at 37° C., 5% $CO_2$. After incubation, cells were treated with the compounds to be screened. 10 mM stocks of the compounds were serially diluted 1:10 in 100% DMSO followed by an additional 1:100 dilution in Assay Media. These dilution series were added to the cell plates resulting in a further 1:10 dilution and a final % DMSO of 0.1%. The vehicle control wells also contained this dilution of DMSO and the positive control wells contained Dihydroxytestosterone (DHT) as an AR agonist at final concentration of 0.3 nM in 0.1% DMSO. Cells were incubated for 16-18 hours at 37° C. and 5% $CO_2$.

Then the culture media was removed from and the cells were lysed in 20 µL of cell lysis reagent for 5 minutes at room temperature. 50 µL of luciferase reagent was added to each well and luminescence, over 5 seconds, was measured. The $EC_{50}$ for each compound was calculated using the formulas shown below.

Formulas $EC_{50}$ (half maximal effective concentration) was calculated from concentration series plots which generated sigmoidal curves. Xlfit software was used to plot the best fit of the % effect vs concentration and to calculate the $EC_{50}$. Using this protocol, the results set forth in the Tables below were generated for the title compounds 1-39. The $EC_{50}$ values obtained suggest that the compounds of Formula 1, Formula 2 and Formula 3 as defined herein have activity in modulating androgenic receptors, a key feature in many diseases affected by SARMs.

Reagents and Materials used in the Androgen Receptor-Mediated Transcriptional Assay include the following:
Growth Media—DMEM/high glucose—10% FBS: 500 ml phenol red DMEM/high glucose (Gibco, Grand Island N.Y., cat#10569-010), 10% non heat-inactivated Fetal Bovine Serum (FBS) (Atlanta Biologicals, Norcross Ga., cat# S-12450), 1% Nonessential Amino Acids (Gibco, cat#11140-050), 1% Penicillin-Streptomycin (Gibco, cat#15140-122)
Basal Media—phenol red free DMEM/high glucose (Gibco, cat#31053-028)+1% Na Pyruvate (Gibco, cat#11360-070), 1% Nonessential Amino Acids (Gibco, cat#11140-050), 1% GlutaMAX-I (Gibco, cat#35050-061)
Re-suspension Media—basal media+1% Penicillin-Streptomycin (Gibco, cat#15140-122)
Assay Media—basal media+5% charcoal stripped FBS (Hy-Clone, Logan Utah, Cat#SH30068)+1% Penicillin-Streptomycin (Gibco, cat#15140-122)
Cell Lysis Reagent—Promega, Cat# PAE1531
Luciferase Reagent—Promega, Cat# PAE1483

TABLE 1

$EC_{50}$ Values for Compounds 1-22 from Androgen Receptor-Mediated Transcriptional Assay

| Compound # | $EC_{50}$, nM |
|---|---|
| 1 | 15 |
| 2 | 18 |
| 3 | 79 |
| 4 | 22 |
| 5 | 5 |

TABLE 1-continued

EC$_{50}$ Values for Compounds 1-22 from Androgen Receptor-Mediated Transcriptional Assay

| Compound # | EC$_{50}$, nM |
|---|---|
| 6 | 10 |
| 7 | 22 |
| 8 | 271 |
| 9 | 4 |
| 10 | 0.4 |
| 11 | 687 |
| 12 | 217 |
| 13 | 0.7 |
| 14 | 22 |
| 15 | 195 |
| 16 | 262 |
| 17 | 16 |
| 18 | 20 |
| 19 | 177 |
| 20 | 8 |
| 21 | 8 |
| 22 | 569 |

TABLE 2

EC$_{50}$ Values for Compounds 23-39 from Androgen Receptor-Mediated Transcriptional Assay

| Compound # | EC$_{50}$, nM |
|---|---|
| 23 | 5.1 |
| 24 | 9.6 |
| 24 | 383.2 |
| 26 | 0.1 |
| 27 | 12.9 |
| 28 | 61.5 |
| 29 | 0.02 |
| 30 | 0.1 |
| 31 | 473.9 |
| 32 | 84.3 |
| 33 | 231.3 |
| 34 | 0.1 |
| 35 | 7.4 |
| 36 | 120.2 |
| 37 | 9.1 |
| 38 | 187.0 |
| 39 | 37.3 |

What is claimed is:

1. A method for treating and/or preventing a disorder or condition in a subject, wherein the disorder or condition is selected from the group consisting of cachexia; and cachexia associated with cancer, comprising administering to said subject an effective amount of a compound of Formula 1, Formula 2 or Formula 3,

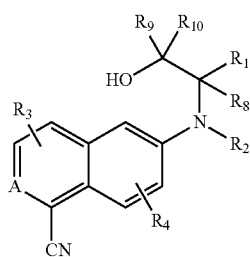

Formula 1

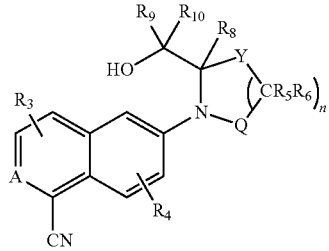

Formula 2

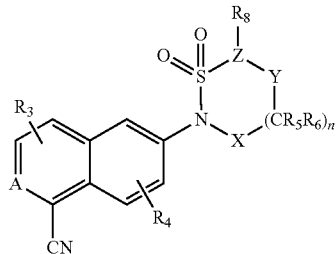

Formula 3 wherein A is N or —CR$_0$—, where R$_0$ is hydrogen, C$_1$-C$_6$ linear or branched chain alkyl, C$_1$-C$_6$ linear or branched chain perfluoroalkyl, aryl, perfluoroaryl, alkylaryl, heteroaryl; or, alkylheteroaryl; X and Y are independently —CH$_2$—, —CHR$_a$—, or, —CR$_a$R$_b$—, where R$_a$ and R$_b$ are independently C$_1$-C$_6$ linear or branched chain alkyl, aryl, alkylaryl, heteroaryl or, alkylheteroaryl; or, R$_a$ and R$_b$ together form a chain comprising —(CH$_2$)$_j$—, —(CHR$_c$)$_j$—, or —(CR$_c$R$_d$)$_j$—, where R$_c$ and R$_d$ are independently C$_1$-C$_6$ linear or branched chain alkyl, C$_1$-C$_6$ linear or branched chain perfluoroalkyl, aryl, alkylaryl, heteroaryl or alkylheteroaryl; where j is 2; 3, 4 or 5; Z is —CR$_e$—, or, —N—, where R$_e$ is hydrogen, C$_1$-C$_6$ linear or branched chain alkyl, C$_1$-C$_6$ linear or branched chain perfluoroalkyl, aryl, alkylaryl, heteroaryl or, alkylheteroaryl; R$_1$ is hydrogen, C$_1$-C$_6$ linear or branched chain alkyl, aryl, C$_1$-C$_6$ linear or branched chain perfluoroalkyl, alkylaryl, heteroaryl, alkylheteroaryl, C$_1$-C$_6$ linear or branched chain alkoxylcarbonyl, C$_1$-C$_6$ linear or branched chain alkylamino-carbonylamino, C$_1$-C$_6$ linear or branched chain alkyloxycarbonylamino, C$_1$-C$_6$ linear or branched chain alkylcarbonylamino, or, C$_1$-C$_6$ linear or branched chain alkylaminocarbonyl; R$_2$ are independently hydrogen or C$_1$-C$_6$ linear or branched chain alkyl; R$_3$ and R$_4$ are independently hydrogen, C$_1$-C$_6$ linear or branched chain alkyl, C$_1$-C$_6$ linear or branched chain perfluoroalkyl, C$_1$-C$_6$ linear or branched chain perfluoroalkoxy, halogen, cyano, hydroxyl, amino, carboxy, hydroxyl, aryl, heteroaryl, C$_1$-C$_6$ linear or branched chain alkoxylcarbonyl, C$_1$-C$_6$ linear or branched chain alkylaminocarbonylamino, or, C$_1$-C$_6$ linear or branched chain alkylaminocarbonyl; R$_5$ and R$_6$ are independently hydrogen or C$_1$-C$_6$ linear or branched chain alkyl, C$_1$-C$_6$ linear or branched chain perfluoroalkyl, cyano, hydroxyl, amino, carboxy, hydroxyl, aryl, heteroaryl, or, R$_5$ and R$_6$ together form a chain comprising —(CH$_2$)$_k$—, —(CHR$_7$)$_k$—, or —(CR$_{7a}$R$_{7b}$)$_k$—, where R$_7$, R$_{7a}$, and R$_{7b}$ are independently C$_1$-C$_6$ linear or branched chain alkyl, C$_1$-C$_6$ linear or branched chain perfluoroalkyl, aryl, alkylaryl, heteroaryl or alkylheteroaryl; where k is 2; 3, 4 or 5; R$_8$ is hydrogen, C$_1$-C$_6$ linear or branched chain alkyl, C$_1$-C$_6$ linear or branched chain perfluoroalkyl, aryl, aryl substituted with one, two or three fluorine atoms, perfluoroaryl, alkylaryl, heteroaryl; or, alkylheteroaryl; or, $R_1$ and $R_8$ together form a chain comprising —$(CH_2)_m$—, —$(CHR_f)_m$—, or —$(CR_fR_g)_m$—, where $R_f$ and $R_g$ are independently $C_1$-$C_6$ linear or branched chain alkyl, aryl, alkylaryl, heteroaryl or alkylheteroaryl; where m is 2; 3, 4 or 5; $R_9$ and $R_{10}$ are independently hydrogen or $C_1$-$C_6$ linear or branched chain alkyl, $C_1$-$C_6$ linear or branched chain perfluoroalkyl, cyano, hydroxyl, amino, carboxy, hydroxyl, aryl, heteroaryl, or, $R_9$ and $R_{10}$ together form a chain comprising —$(CH_2)_p$—, —$(CHR_h)_p$—, or —$(CR_hR_i)_p$—, where $R_h$ and $R_i$ are independently $C_1$-$C_6$ linear or branched chain alkyl, aryl, alkylaryl, heteroaryl or alkylheteroaryl; where p is 2; 3, 4 or 5; Q is —CO—, —$(CH_2)_q$—, —$(CHR_s)_q$—, or —$(CR_sR_t)_q$—, where $R_s$ and $R_t$ are independently $C_1$-$C_6$ linear or branched chain alkyl, aryl, alkylaryl, heteroaryl or alkylheteroaryl; where q is 0, 1, 2, or 3; and, where n is 0, 1, 2, 3, 4 or 5; or, a pharmaceutically acceptable salt thereof.

2. The method of claim 1, wherein the disorder to condition is selected from the group consisting of cachexia associated with cancer.

3. The method of claim 1 or claim 2, wherein, for a compound of Formula 3 X and Y are independently —$CH_2$—, —$CHR_a$—, or, —$CR_aR_b$—, $R_a$ and $R_b$ are independently $C_1$-$C_6$ linear or branched chain alkyl, aryl, alkylaryl, heteroaryl or, alkylheteroaryl.

4. The method of claim 3, wherein X and Y are independently —$CH_2$—, —$CHR_a$—, or,
—$CR_aR_b$—, where $R_a$ and $R_b$ are independently methyl, ethyl.

5. The method of claim 1 or claim 2, wherein the compound is 6-[(4R)-4-methyl-1,1-dioxido-1,2,6-thiadiazinan-2-yl]isoquinoline-1-carbonitrile, or a pharmaceutically acceptable salt thereof.

6. The method of claim 1 or claim 2, wherein the compound is crystalline 6-[(4R)-4-methyl-1,1-dioxido-1,2,6-thiadiazinan-2-yl]isoquinoline-1-carbonitrile (Form (1)).

* * * * *